United States Patent
Jung et al.

(10) Patent No.: US 12,304,977 B2
(45) Date of Patent: May 20, 2025

(54) POLYMER, MONOMER, COATING COMPOSITION COMPRISING SAME, ORGANIC LIGHT EMITTING DEVICE USING SAME, AND METHOD FOR MANUFACTURING ORGANIC LIGHT EMITTING DEVICE BY USING SAME

(71) Applicant: LG Chem, Ltd., Seoul (KR)

(72) Inventors: Min Suk Jung, Daejeon (KR); Jaesoon Bae, Daejeon (KR); Youngju Park, Daejeon (KR); Esder Kang, Daejeon (KR); Byeong Yun Lim, Daejeon (KR); Dowon Lim, Daejeon (KR); Jaechol Lee, Daejeon (KR); Hyunju Choi, Daejeon (KR)

(73) Assignee: LG Chem, Ltd., Seoul (KR)

( * ) Notice: Subject to any disclaimer, the term of this patent is extended or adjusted under 35 U.S.C. 154(b) by 777 days.

(21) Appl. No.: 17/621,007

(22) PCT Filed: Sep. 18, 2020

(86) PCT No.: PCT/KR2020/012624
§ 371 (c)(1),
(2) Date: Dec. 20, 2021

(87) PCT Pub. No.: WO2021/054764
PCT Pub. Date: Mar. 25, 2021

(65) Prior Publication Data
US 2022/0389127 A1    Dec. 8, 2022

(30) Foreign Application Priority Data

Sep. 19, 2019    (KR) .................. 10-2019-0115460
Sep. 27, 2019    (KR) .................. 10-2019-0119623

(51) Int. Cl.
*C09D 125/18*    (2006.01)
*C07C 211/54*    (2006.01)
(Continued)

(52) U.S. Cl.
CPC ............ *C08F 12/32* (2013.01); *C07C 211/54* (2013.01); *C07D 209/82* (2013.01); *C07D 307/91* (2013.01); *C09D 125/18* (2013.01); *H10K 71/00* (2023.02); *H10K 85/111* (2023.02); *H10K 85/615* (2023.02); *H10K 85/624* (2023.02);
(Continued)

(58) Field of Classification Search
None
See application file for complete search history.

(56) References Cited

U.S. PATENT DOCUMENTS 10,954,218 B2 *    3/2021    Bae ................ C07D 487/14
11,706,970 B2 *    7/2023    Jung ............... C07C 211/54
(Continued)

FOREIGN PATENT DOCUMENTS

CN    108947902 A      12/2018
CN    109516923 A *    3/2019    ........... C07C 211/61
(Continued)

OTHER PUBLICATIONS

Machine translation of CN-109516923-A, translation generated Oct. 2024, 24 pages. (Year: 2024).*
(Continued)

*Primary Examiner* — Robert S Loewe
(74) *Attorney, Agent, or Firm* — Lerner David LLP

(57) ABSTRACT

The present specification relates to a polymer comprising a unit represented by Chemical Formula 1, a monomer represented by Chemical Formula 2, a coating composition comprising the same, an organic light emitting device formed using the same, and a method for manufacturing an organic light emitting device using the same:

[Chemical Formula 1]

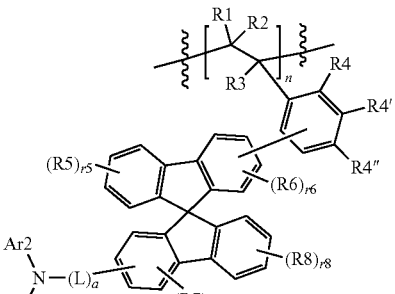

[Chemical Formula 2]

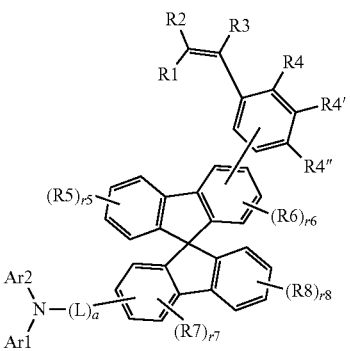

wherein the variables are described herein.

18 Claims, 1 Drawing Sheet

(51) Int. Cl.
    *C07D 209/82*     (2006.01)
    *C07D 307/91*     (2006.01)
    *C08F 12/32*     (2006.01)
    *H10K 71/00*     (2023.01)
    *H10K 85/10*     (2023.01)
    *H10K 85/60*     (2023.01)

(52) U.S. Cl.
    CPC ....... *H10K 85/631* (2023.02); *H10K 85/6572* (2023.02); *H10K 85/6574* (2023.02)

(56) References Cited

U.S. PATENT DOCUMENTS

| | | | |
|---|---|---|---|
| 11,889,746 B2 * | 1/2024 | Lim | ................ H10K 85/151 |
| 2016/0181535 A1 | 6/2016 | Tsuji et al. | |
| 2016/0329501 A1 | 11/2016 | Kim et al. | |
| 2019/0109284 A1 * | 4/2019 | Xia | ................ H10K 85/6572 |
| 2019/0225581 A1 * | 7/2019 | Scheible | ............ H10K 85/633 |
| 2019/0334106 A1 | 10/2019 | Sokolov et al. | |
| 2020/0235301 A1 | 7/2020 | Seo et al. | |
| 2020/0280001 A1 | 9/2020 | Kang et al. | |
| 2021/0147358 A1 * | 5/2021 | Kim | ................ C09D 7/63 |
| 2021/0151681 A1 * | 5/2021 | Kang | ................ H10K 85/636 |
| 2021/0175427 A1 | 6/2021 | Jung et al. | |
| 2021/0210691 A1 | 7/2021 | Zhu et al. | |

FOREIGN PATENT DOCUMENTS

| | | |
|---|---|---|
| JP | H11273863 A | 10/1999 |
| KR | 20160074382 A | 6/2016 |
| KR | 20160129191 A | 11/2016 |
| KR | 20190020072 A | 2/2019 |
| KR | 20190103994 A | 9/2019 |
| WO | 2017107117 A1 | 6/2017 |
| WO | 2018005318 A1 | 1/2018 |
| WO | 2019146967 A1 | 8/2019 |
| WO | 2019168322 A1 | 9/2019 |
| WO | 2020036459 A1 | 2/2020 |

OTHER PUBLICATIONS

International Search Report for PCT/KR2020/012624 dated Jan. 13, 2021. 4 pgs.

* cited by examiner

| 701 |
|---|
| 601 |
| 501 |
| 401 |
| 301 |
| 201 |
| 101 |

POLYMER, MONOMER, COATING COMPOSITION COMPRISING SAME, ORGANIC LIGHT EMITTING DEVICE USING SAME, AND METHOD FOR MANUFACTURING ORGANIC LIGHT EMITTING DEVICE BY USING SAME

CROSS-REFERENCE TO RELATED APPLICATION(S)

The present application is a national stage entry under 35 U.S.C. § 371 of International Application No. PCT/KR2020/012624 filed on Sep. 18, 2020, which claims priority from Korean Patent Application No. 10-2019-0115460 filed on Sep. 19, 2019, and Korean Patent Application No. 10-2019-0119623 filed on Sep. 27, 2019, all the disclosures of which are incorporated herein by reference.

TECHNICAL FIELD

The present specification relates to a polymer, a monomer, a coating composition comprising the same, an organic light emitting device formed using the same, and a method for manufacturing an organic light emitting device using the same.

BACKGROUND ART

An organic light emission phenomenon is one of examples converting a current to visible light by an internal process of specific organic molecules. A principle of an organic light emission phenomenon is as follows. When an organic material layer is placed between an anode and a cathode and a current is applied between the two electrodes, electrons and holes are injected to the organic material layer from the cathode and the anode, respectively. The holes and the electrons injected to the organic material layer recombine to form excitons, and light emits when these excitons fall back to the ground state.

An organic electroluminescent device using such a principle may be generally formed with a cathode, an anode, and an organic material layer placed therebetween, for example, an organic material layer comprising a hole injection layer, a hole transfer layer, a light emitting layer, an electron transfer layer and an electron injection layer.

Materials used in an organic light emitting device are mostly pure organic materials or complex compounds in which organic materials and metals form complexes, and may be divided into a hole injection material, a hole transfer material, a light emitting material, an electron transfer material, an electron injection material and the like depending on the application. Herein, as the hole injection material or the hole transfer material, organic materials having a p-type property, that is, organic materials readily oxidized and having an electrochemically stable state when oxidized, are generally used. Meanwhile, as the electron injection material or the electron transfer material, organic materials having an n-type property, that is, organic materials readily reduced and having an electrochemically stable state when reduced, are generally used. As the light emitting material, materials having both a p-type property and an n-type property, that is, materials having a stable form in both oxidized and reduced states, are preferred, and materials having high light emission efficiency converting, when excitons are formed, the excitons to light are preferred.

In addition to the properties described above, it is preferred that materials used in an organic light emitting device additionally have properties as follows.

First, materials used in an organic light emitting device preferably have excellent thermal stability. This is due to joule heating produced by charge migration in the organic light emitting device. N,N'-di(1-naphthyl)-N,N"-diphenyl-(1,1"-biphenyl)-4,4"-diamine (NPB) normally used as a hole transfer layer material currently has a glass transition temperature of 100° C. or lower, and has a problem in that it is difficult to use in organic light emitting devices requiring a high current.

Second, in order to obtain a highly efficient organic light emitting device capable of low voltage driving, holes or electrons injected into the organic light emitting device need to be smoothly transferred to a light emitting layer, and at the same time, the injected holes and electrons need to be kept from escaping out of the light emitting layer. For this, materials used in the organic light emitting device need to have a proper band gap and a highest occupied molecular orbital (HOMO) or lowest unoccupied molecular orbital (LUMO) energy level. Poly(3,4-ethylenedioxythiophene) doped:poly(styrenesulfonic acid) (PEDOT:PSS) currently used as a hole transfer material in an organic light emitting device manufactured using a solution coating method has a lower LUMO energy level compared to a LUMO energy level of organic materials used as a light emitting layer material, and therefore, has a problem in manufacturing an organic light emitting device with high efficiency and long lifetime.

In addition thereto, materials used in an organic light emitting device need to have excellent chemical stability, charge mobility, and interfacial properties with electrodes or adjacent layers. In other words, materials used in an organic light emitting device need to undergo less material deformation caused by moisture or oxygen. In addition, by having proper hole or electron mobility, the materials need to maximize exciton formation through balancing hole and electron density in a light emitting layer of the organic light emitting device. For device stability, the materials also need to improve an interface with electrodes comprising metals or metal oxides.

In addition to the properties described above, materials used in an organic light emitting device for a solution process additionally need to have properties as follows.

First, a storable homogeneous solution needs to be formed. Commercialized materials for a deposition process have favorable crystallinity, and are not favorably dissolved in a solution, or crystals are readily caught when forming a solution. Therefore, a concentration gradient of the solution may vary depending on the time of storage, or possibility of forming a defective device is high.

Second, layers going through a solution process need to have solvent and material tolerance for other layers. For this, materials capable of forming a self-crosslinked polymer on a substrate through heat treatment or ultraviolet (UV) irradiation after coating a solution by introducing a curing group such as N4,N4"-di(naphthalen-1-yl)-N4,N4"-bis(4-vinylphenyl)biphenyl-4,4"-diamine (VNPB) or forming a polymer having sufficient tolerance for a next process are preferred, and materials capable of having solvent tolerance by itself such as hexaazatriphenylene hexacarbonitrile (HATCN) are also preferred. Arylamine-based monomers generally used in an organic light emitting device (OLED) do not have tolerance for a solvent of a next process by themselves, and therefore, arylamine-based monomer compounds usable in an OLED for a solution process need to have a curing group introduced thereto.

Accordingly, development of organic materials fulfilling such requirements has been required in the art.

PRIOR ART DOCUMENTS

Patent Documents (Patent Document 1) KR 10-2016-0129191 A

DISCLOSURE

Technical Problem

The present specification is directed to providing a polymer, a coating composition comprising the same, and an organic light emitting device formed using the same.

Technical Solution

One embodiment of the present specification provides a polymer comprising a unit represented by the following Chemical Formula 1.

[Chemical Formula 1]

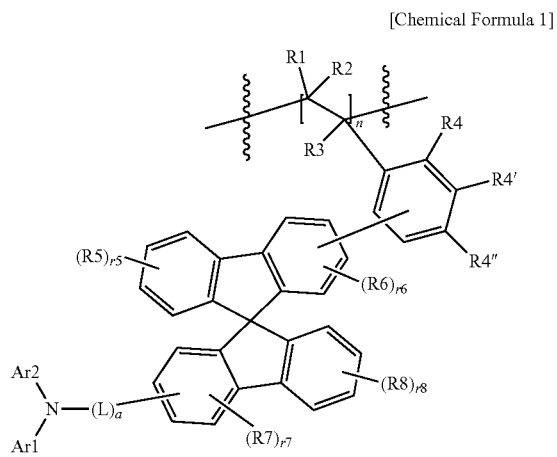

In Chemical Formula 1,
L is a direct bond; a substituted or unsubstituted arylene group; or a substituted or unsubstituted heteroarylene group,
a is an integer of 0 to 3, and when a is 2 or greater, Ls are the same as or different from each other,
Ar1 and Ar2 are the same as or different from each other, and each independently a substituted or unsubstituted aryl group; or a substituted or unsubstituted heteroaryl group,
R1 to R8, R4' and R4" are the same as or different from each other, and each independently hydrogen; deuterium; a halogen group; a hydroxyl group; a cyano group; a substituted or unsubstituted alkyl group; a substituted or unsubstituted cycloalkyl group; a substituted or unsubstituted alkoxy group; a substituted or unsubstituted aryl group; or a substituted or unsubstituted heteroaryl group,
r6 and r7 are the same as or different from each other, and each independently an integer of 0 to 3, and when r6 is 2 or greater, R6s are the same as or different from each other, and when r7 is 2 or greater, R7s are the same as or different from each other,
r5 and r8 are the same as or different from each other, and each independently an integer of 0 to 4, and when r5 is 2 or greater, R5s are the same as or different from each other, and when r8 is 2 or greater, R8s are the same as or different from each other, and
n is, as a repetition number of the unit, an integer of 2 to 10,000.

Another embodiment of the present specification provides a monomer represented by the following Chemical Formula 2.

[Chemical Formula 2]

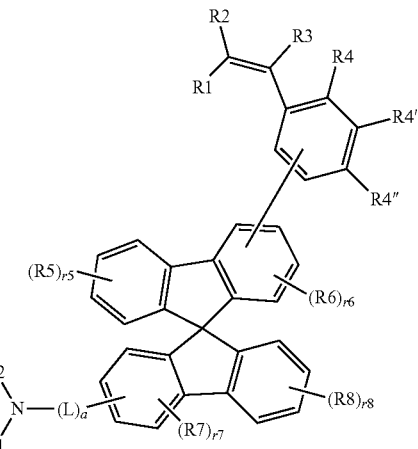

In Chemical Formula 2,
L is a direct bond; a substituted or unsubstituted arylene group; or a substituted or unsubstituted heteroarylene group,
a is an integer of 0 to 3, and when a is 2 or greater, Ls are the same as or different from each other,
Ar1 and Ar2 are the same as or different from each other, and each independently a substituted or unsubstituted aryl group; or a substituted or unsubstituted heteroaryl group,
R1 to R8, R4' and R4" are the same as or different from each other, and each independently hydrogen; deuterium; a halogen group; a hydroxyl group; a cyano group; a substituted or unsubstituted alkyl group; a substituted or unsubstituted cycloalkyl group; a substituted or unsubstituted alkoxy group; a substituted or unsubstituted aryl group; or a substituted or unsubstituted heteroaryl group,
r6 and r7 are the same as or different from each other, and each independently an integer of 0 to 3, and when r6 is 2 or greater, R6s are the same as or different from each other, and when r7 is 2 or greater, R7s are the same as or different from each other, and
r5 and r8 are the same as or different from each other, and each independently an integer of 0 to 4, and when r5 is 2 or greater, R5s are the same as or different from each other, and when r8 is 2 or greater, R8s are the same as or different from each other.

Another embodiment of the present specification provides a coating composition comprising the polymer comprising the unit represented by Chemical Formula 1 described above.

Still another embodiment of the present specification provides a coating composition comprising the monomer represented by Chemical Formula 2 described above.

One embodiment of the present specification provides an organic light emitting device comprising a first electrode; a second electrode; and an organic material layer provided between the first electrode and the second electrode, wherein the organic material layer comprises the polymer comprising the unit represented by Chemical Formula 1 described above.

In addition, one embodiment of the present specification provides a method for manufacturing an organic light emitting device, the method comprising preparing a first electrode; forming one or more organic material layers on the first electrode; and forming a second electrode on the organic material layer, wherein the forming of one or more organic material layers comprises forming the organic material layer using the coating composition comprising the polymer comprising the unit represented by Chemical Formula 1 described above or the coating composition comprising the monomer represented by Chemical Formula 2 described above, and the forming of the organic material layer using the coating composition comprises coating the coating composition on the first electrode; and heat treating or light treating the coated coating composition.

Advantageous Effects

An organic material layer formed using a polymer comprising a unit represented by Chemical Formula 1 according to one embodiment of the present specification has very low solubility for some solvents, and therefore, a lamination process can be conducted on the organic material layer formed using the polymer through a solution process.

The polymer comprising the unit represented by Chemical Formula 1 according to one embodiment of the present specification has a high glass transition temperature due to uniqueness of the spirobifluorene structure, and in addition thereto, has low crystallinity due to low π-π stacking, and has excellent solubility for solvents.

In addition, the polymer according to one embodiment of the present specification can be used as a material of an organic material layer of an organic light emitting device to lower a driving voltage of the organic light emitting device.

In addition, the polymer according to one embodiment of the present specification can be used as a material of an organic material layer of an organic light emitting device to enhance light efficiency.

In addition, the polymer according to one embodiment of the present specification can be used as a material of an organic material layer of an organic light emitting device to enhance lifetime properties of the device.

DESCRIPTION OF DRAWINGS

The FIGURE illustrates an example of an organic light emitting device according to one embodiment of the present specification.

REFERENCE NUMERAL

101: Substrate
201: First Electrode
301: Hole Injection Layer
401: Hole Transfer Layer
501: Light Emitting Layer
601: Layer Carrying Out Electron Transfer And Electron Injection At The Same Time
701: Second Electrode Mode for Disclosure Hereinafter, the present specification will be described in more detail.

One embodiment of the present specification provides a polymer comprising a unit represented by the following Chemical Formula 1.

In one embodiment of the present specification, the polymer comprising the unit represented by Chemical Formula 1 is a linear polymer. The linear polymer is polymerized by a monomer having only two functional groups, and means a linear one-dimensional polymer connected in a row. In one embodiment, the polymer comprising the unit represented by Chemical Formula 1 is a polymer in which the unit represented by Chemical Formula 1 is linearly arranged.

In one embodiment of the present specification, the polymer comprising the unit represented by Chemical Formula 1 may comprise two or more types of the unit represented by Chemical Formula 1. In this case, the polymer comprising the unit represented by Chemical Formula 1 may be a random copolymer; or a block copolymer.

In one embodiment of the present specification, the polymer comprising the unit represented by Chemical Formula 1 may be a homopolymer. Herein, the homopolymer means a polymer formed with only one type of monomer.

In the present specification, the polymer comprising the unit represented by Chemical Formula 1 is a polymer formed with 100 mol % of the unit represented by Chemical Formula 1.

In the present specification, the "unit" is a structure in which a monomer is included and repeated in a polymer, and means a structure in which a monomer bonds in a polymer by polymerization.

In the present specification, the meaning of "including a unit" means the corresponding unit being included in a main chain in a polymer.

In the present specification, the "monomer" means a monomer or a unit body becoming a unit forming the polymer.

Materials of an OLED used in a solution process need to have proper solubility for proper solvents. A compound having spirobifluorene connected to a polymer main chain through a p-phenylene group has a high polymerization rate during preparation resulting in an increase in the molecular weight of the polymer, which decreases solubility for solvents causing a problem of having a limit in usable solvents.

In one embodiment of the present specification, the unit represented by Chemical Formula 1 has spirobifluorene connected to a polymer main chain through an o-phenylene group or an m-phenylene group. Compared to the structure having spirobifluorene connected to a polymer main chain through a p-phenylene group, the polymer according to one embodiment of the present disclosure may readily control a molecular weight of the polymer when preparing the polymer, and is effective in improving solubility at the same molecular weight.

Accordingly, when using the polymer comprising the unit represented by Chemical Formula 1 in a hole transfer layer, a hole injection layer, or a layer carrying out hole transfer and hole injection at the same time of an organic light emitting device, the prepared hole transfer layer, hole injection layer, or layer carrying out hole transfer and hole injection at the same time has excellent uniformity and surface properties as well, and therefore, device performance and lifetime properties may be enhanced.

In addition, the organic material layer comprising the polymer comprising the unit represented by Chemical Formula 1 may have the molecular weight readily controlled compared to monomer compounds comprising spirobifluorene, and viscosity of a solution comprising the same may also be readily controlled.

An organic material layer may be formed using a solution process when using the polymer according to one embodiment of the present specification. In one embodiment, the polymer comprising the unit represented by Chemical Formula 1; or the monomer represented by Chemical Formula 2 according to one embodiment of the present disclosure may be dissolved in solvents such as tetrahydrofuran (THF), xylene or toluene, however, the solvent is not limited thereto. In addition, the solvents may be used in one type or as a mixture of two or more types.

The organic material layer comprising the polymer comprising the unit represented by Chemical Formula 1 according to one embodiment of the present specification has solvent tolerance for solvents such as cycloketone; cycloalkane; or dioxane.

In one embodiment, the organic material layer comprising the polymer comprising the unit represented by Chemical Formula 1 has solubility of 0.05 wt % or less for cyclohexanone.

In one embodiment, the organic material layer comprising the polymer comprising the unit represented by Chemical Formula 1 has solubility of 0.05 wt % or less for dioxane.

In one embodiment, the organic material layer comprising the polymer comprising the unit represented by Chemical Formula 1 has solubility of 0.05 wt % or less for cyclohexane.

In one embodiment, the organic material layer comprising the polymer comprising the unit represented by Chemical Formula 1 has solubility of 0 wt % or greater for cyclohexane; cyclohexanone; or dioxane.

In one embodiment, whether or not the organic material layer is dissolved in a specific solvent may be identified by immersing the corresponding organic material layer in a solvent to measure the solubility, taking out the organic material layer, and measuring a difference in the UV absorption values of the organic material layer before and after being exposed to the specific solvent. Herein, the organic material layer exposed to the solvent may have a form of a single layer of the organic material layer, or may be a laminate having a form of providing the corresponding organic material layer on an outermost layer. The laminate having a form of providing the organic material layer on an outermost layer means, in a laminate in which two or more layers are consecutively laminated, a structure having a form of providing the corresponding organic material layer as the last layer in a lamination direction of the layers.

More specifically, when UV absorption intensity of an organic material layer in a maximum absorption wavelength before being exposed to a specific solvent is employed as b1 and UV absorption intensity of the organic material layer in a maximum absorption wavelength after being exposed to the specific solvent is employed as b2, b2/b1*100 being greater than or equal to 97% and less than or equal to 100% may be understood to have solvent tolerance for the specific solvent.

In one embodiment, materials forming a specific organic material layer of an organic light emitting device may be analyzed through MS and NMR analyses after extracting the corresponding organic material layer from the organic light emitting device.

In one embodiment, when forming an organic material layer having a thickness of 20 nm by spin coating a composition obtained by dissolving the polymer comprising the unit represented by Chemical Formula 1 in toluene in 2 wt % on a glass plate and heat treating the result for 30 minutes at 230° C., solubility of the organic material layer for cyclohexanone is 0.05 wt % or less.

In one embodiment, when forming an organic material layer having a thickness of 20 nm by spin coating a composition obtained by dissolving the polymer comprising the unit represented by Chemical Formula 1 in toluene in 2 wt % on a glass plate and heat treating the result for 30 minutes at 230° C., solubility of the organic material layer for dioxane is 0.05 wt % or less.

In one embodiment, when forming an organic material layer having a thickness of 20 nm by spin coating a composition obtained by dissolving the polymer comprising the unit represented by Chemical Formula 1 in toluene in 2 wt % on a glass plate and heat treating the result for 30 minutes at 230° C., solubility of the organic material layer for cyclohexane is 0.05 wt % or less.

In the present specification,

means a site bonding to other substituents or bonding sites.

In the present specification, a description of a certain member being placed "on" another member comprises not only a case of the one member adjoining the another member but a case of still another member being present between the two members.

In the present specification, a description of a certain part "comprising" certain constituents means capable of further comprising other constituents, and does not exclude other constituents unless particularly stated on the contrary.

Examples of substituents in the present specification are described below, however, the substituents are not limited thereto.

The term "substitution" means a hydrogen atom bonding to a carbon atom of a compound being changed to another substituent. The position of substitution is not limited as long as it is a position at which the hydrogen atom is substituted, that is, a position at which a substituent can substitute. When two or more substituents substitute, the two or more substituents may be the same as or different from each other.

The term "substituted or unsubstituted" in the present specification means being substituted with one or more substituents selected from the group consisting of deuterium; a halogen group; a hydroxyl group; a cyano group; an alkyl group; a cycloalkyl group; an alkenyl group; an alkoxy group; an aryloxy group; —N(Rm) (Rn); an aryl group; and a heteroaryl group, or being substituted with a substituent linking two or more substituents among the substituents illustrated above, or having no substituents, and Rm and Rn are the same as or different from each other and each independently hydrogen; an alkyl group; an aryl group; or a heteroaryl group. For example, "a substituent linking two or more substituents" may comprise a biphenyl group. In other words, a biphenyl group may be an aryl group, or interpreted as a substituent linking two phenyl groups.

In the present specification, examples of the halogen group may comprise fluorine, chlorine, bromine or iodine.

In the present specification, the alkyl group may be linear or branched, and although not particularly limited thereto, the number of carbon atoms is preferably from 1 to 30. Specific examples thereof may comprise methyl, ethyl, propyl, n-propyl, isopropyl, butyl, n-butyl, isobutyl, tert-butyl, sec-butyl, 1-methylbutyl, 1-ethylbutyl, pentyl, n-pentyl, isopentyl, neopentyl, tert-pentyl, hexyl, n-hexyl, 1-methylpentyl, 2-methylpentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethylpropyl, 1,1-dimethylpropyl, isohexyl, 2-methylpentyl, 4-methylhexyl, 5-methylhexyl and the like, but are not limited thereto.

In the present specification, the cycloalkyl group is not particularly limited, but preferably has 3 to 30 carbon atoms, and specific examples thereof may comprise cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl and the like, but are not limited thereto.

In the present specification, the alkenyl group may be linear or branched, and although not particularly limited thereto, the number of carbon atoms is preferably from 2 to 30. Specific examples thereof may comprise a vinyl group, a 1-propenyl group, an isopropenyl group, a 1-butenyl group, a 2-butenyl group, a 3-butenyl group, a 1-pentenyl group, a 2-pentenyl group, a 3-pentenyl group, a 3-methyl-1-butenyl group, a 1,3-butadienyl group, an allyl group, a 1-phenylvinyl-1-yl group, a 2-phenylvinyl-1-yl group, a 2,2-diphenylvinyl-1-yl group, a 2-phenyl-2-(naphthyl-1-yl)vinyl-1-yl group, a 2,2-bis(diphenyl-1-yl)vinyl-1-yl group, a stilbenyl group, a styrenyl group and the like, but are not limited thereto.

In the present specification, the alkoxy group may be linear, branched or cyclic. The number of carbon atoms of the alkoxy group is not particularly limited, but is preferably from 1 to 30. Specific examples thereof may comprise a methoxy group, an ethoxy group, an n-propoxy group, an isopropoxy group, an n-butoxy group, an isobutoxy group, a tert-butoxy group, a sec-butoxy group, an n-pentyloxy group, a neopentyloxy group, an isopentyloxy group, an n-hexyloxy group, a 3,3-dimethylbutyloxy group, a 2-ethylbutyloxy group, an n-octyloxy group, an n-nonyloxy group, an n-decyloxy group, a benzyloxy group, a p-methylbenzyloxy group and the like, but are not limited thereto.

In the present specification, the aryl group is not particularly limited, but preferably has 6 to 30 carbon atoms, and the aryl group may be monocyclic or polycyclic.

When the aryl group is a monocyclic aryl group, the number of carbon atoms is not particularly limited, but is preferably from 6 to 30. Specific examples of the monocyclic aryl group may comprise a phenyl group, a biphenyl group, a terphenyl group and the like, but are not limited thereto.

When the aryl group is a polycyclic aryl group, the number of carbon atoms is not particularly limited, but is preferably from 10 to 30. Specific examples of the polycyclic aryl group may comprise a naphthyl group, an anthracenyl group, a phenanthrenyl group, a triphenylenyl group, a pyrenyl group, a phenalenyl group, a perylenyl group, a chrysenyl group, a fluorenyl group and the like, but are not limited thereto.

In the present specification, the fluorenyl group may be substituted, and adjacent groups may bond to each other to form a ring.

When the fluorenyl group is substituted, the substituted fluorenyl group may be, for example, any one selected from among the following compounds, but is not limited thereto.

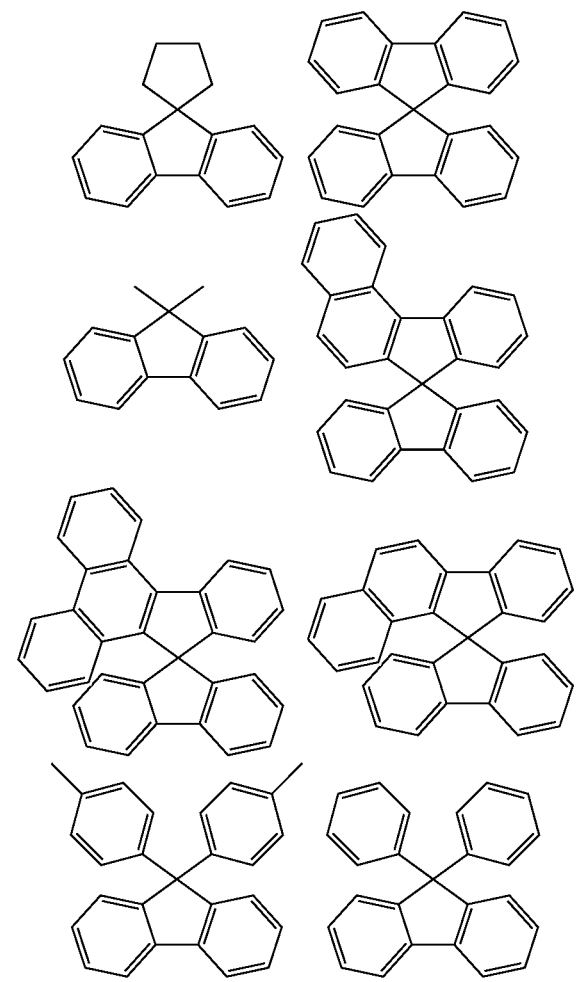

In the present specification, the "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

In the present specification, the heteroaryl group comprises one or more heteroatoms that are not carbon in the ring, and specifically, the heteroatom may comprise one or more atoms selected from the group consisting of O, N, Se and S. The number of carbon atoms of the heteroaryl group is not particularly limited, but is preferably from 2 to 30. The heteroaryl group may be monocyclic or polycyclic. Examples of the heterocyclic group may comprise a thiophenyl group, a furanyl group, a pyrrolyl group, an imidazolyl group, a thiazolyl group, an oxazolyl group, an oxadiazolyl group, a pyridinyl group, a bipyridinyl group, a pyrimidinyl group, a triazinyl group, a triazolyl group, an acridinyl group, a pyridazinyl group, a pyrazinyl group, a quinolinyl group, a quinazolinyl group, a quinoxalinyl group, a phthalazinyl group, a pyridopyrimidinyl group, a pyridopyrazinyl group, a pyrazinopyrazinyl group, an isoquinolinyl group, an indolyl group, a carbazolyl group, a benzoxazolyl group, a benzimidazolyl group, a benzothiazolyl group, a benzocarbazolyl group, a benzothiophenyl group, a dibenzothiophenyl group, a benzofuranyl group, a phenanthridinyl group, a phenanthrolinyl group, an isoxazolyl group, a thiadiazolyl group, a phenothiazinyl group, a dibenzofuranyl group and the like, but are not limited thereto.

In the present specification, the aryl group in the aryloxy group is the same as the examples of the aryl group described above. Specific examples of the aryloxy group may comprise a phenoxy group, a p-tolyloxy group, an m-tolyloxy group, a 3,5-dimethyl-phenoxy group, a 2,4,6-trimethylphenoxy group, a p-tert-butylphenoxy group, a 3-biphenyloxy group, a 4-biphenyloxy group, a 1-naphthyloxy group, a 2-naphthyloxy group, a 4-methyl-1-naphthyloxy group, a 5-methyl-2-naphthyloxy group, a 1-anthracenyloxy group, a 2-anthracenyloxy group, a 9-anthracenyloxy group, a 1-phenanthrenyloxy group, a 3-phenanthrenyloxy group, a 9-phenanthrenyloxy group and the like, but are not limited thereto.

In the present specification, specific examples of —N(Rm) (Rn) may comprise a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, a ditolylamine group, an N,N-(phenyl) (tolyl)amine group, an N,N-(phenyl) (biphenyl)amine group, an N,N-(phenyl) (naphthyl)amine group, an N,N-(biphenyl) (naphthyl)amine group, an N,N-(naphthyl) (fluorenyl)amine group, an N,N-(phenyl) (phenanthrenyl)amine group, an N,N-(biphenyl) (phenanthrenyl)amine group, an N,N-(phenyl) (fluorenyl) amine group, an N,N-(phenyl) (terphenyl)amine group, an N,N-(phenanthrenyl) (fluorenyl)amine group, an N,N-(biphenyl) (fluorenyl)amine group and the like, but are not limited thereto.

In the present specification, the arylene group means an aryl group having two bonding sites, that is, a divalent group. Descriptions on the aryl group provided above may be applied thereto except for those that are each divalent.

In the present specification, the heteroarylene group means a heteroaryl group having two bonding sites, that is, a divalent group. Descriptions on the heteroaryl group provided above may be applied thereto except for those that are each divalent.

According to one embodiment of the present specification, Chemical Formulae 1 and 2 comprise a group represented by the following Chemical Formula A.

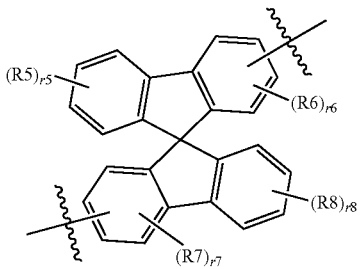

[Chemical Formula A]

In Chemical Formula A,

R5 to R8 and r5 to r8 have the same definitions as in Chemical Formulae 1 and 2.

According to one embodiment of the present specification, Chemical Formula A is represented by the following Chemical Formula a-1.

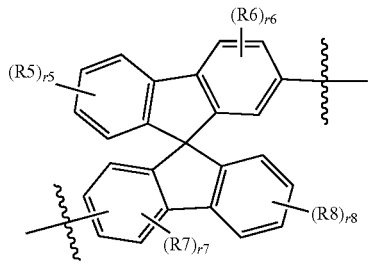

[Chemical Formula a-1]

In Chemical Formula a-1,

R5 to R8 and r5 to r8 have the same definitions as in Chemical Formula A.

According to one embodiment of the present specification, Chemical Formula A is represented by the following Chemical Formula a-2.

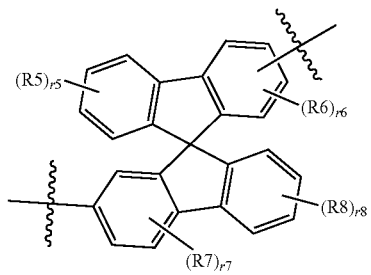

[Chemical Formula a-2]

In Chemical Formula a-2,

R5 to R8 and r5 to r8 have the same definitions as in Chemical Formula A.

According to one embodiment of the present specification, Chemical Formula 1 is represented by the following Chemical Formula 1-1.

[Chemical Formula 1-1]

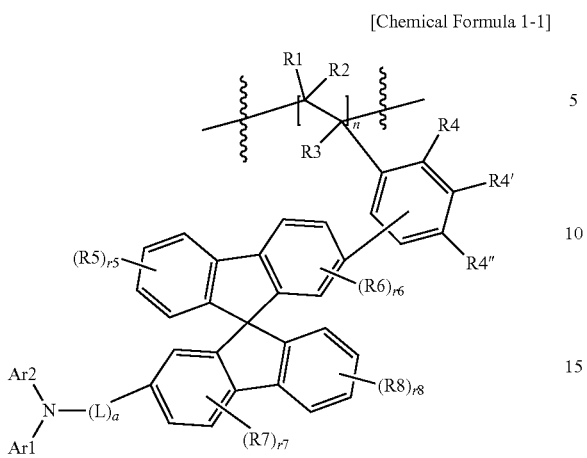

In Chemical Formula 1-1,

R1 to R8, R4', R4", L, Ar, Ar2, r5 to r8, n and a have the same definitions as in Chemical Formula 1.

According to one embodiment of the present specification, R1 is hydrogen; or an alkyl group.

According to one embodiment of the present specification, R1 is hydrogen; or a $C_{1-6}$ alkyl group.

According to one embodiment of the present specification, R1 is hydrogen; or a methyl group.

According to one embodiment of the present specification, R1 is hydrogen.

According to one embodiment of the present specification, R2 is hydrogen; or an alkyl group.

According to one embodiment of the present specification, R2 is hydrogen; or a $C_{1-6}$ alkyl group.

According to one embodiment of the present specification, R2 is hydrogen; or a methyl group.

According to one embodiment of the present specification, R2 is hydrogen.

According to one embodiment of the present specification, R3 is hydrogen; or an alkyl group.

According to one embodiment of the present specification, R3 is hydrogen; or a $C_{1-6}$ alkyl group.

According to one embodiment of the present specification, R3 is hydrogen; or a methyl group.

According to one embodiment of the present specification, R3 is hydrogen.

According to one embodiment of the present specification, R4, R4' and R4" are hydrogen.

According to one embodiment of the present specification, R5 is hydrogen.

According to one embodiment of the present specification, R6 is hydrogen.

According to one embodiment of the present specification, R7 is hydrogen.

According to one embodiment of the present specification, R8 is hydrogen.

According to one embodiment of the present specification, L is a direct bond; or any one selected from among the following structures.

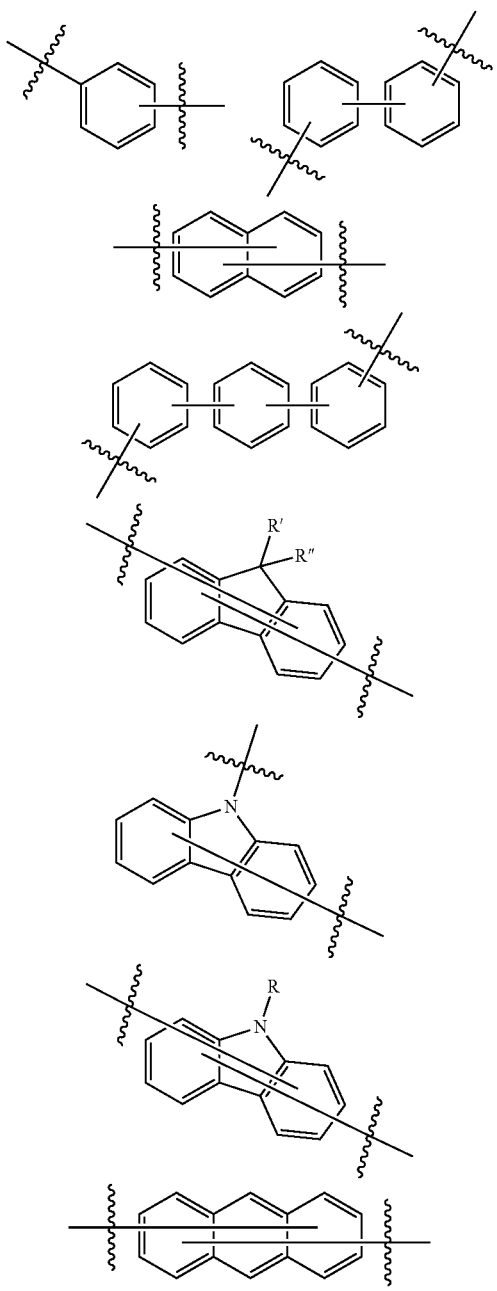

In the structures, R is an aryl group,

R' and R" are the same as or different from each other, and each independently hydrogen; or an alkyl group, and the structures may be further substituted with an alkyl group.

According to one embodiment of the present specification, R is a phenyl group.

According to one embodiment of the present specification, R' and R" are the same as or different from each other, and each independently hydrogen; or a $C_{1-10}$ alkyl group.

According to one embodiment of the present specification, R' and R" are the same as or different from each other, and each independently hydrogen; or a $C_{1-6}$ alkyl group.

In one embodiment, when R' and R" are hydrogen, the fluorene may react with oxygen to form ketone, and forming ketone may have fatal effects on a device, and therefore, R' and R" are the same as or different from each other, and preferably each independently an alkyl group.

According to one embodiment of the present specification, R' and R" are the same as or different from each other, and each independently hydrogen; a methyl group; or a butyl group.

According to one embodiment of the present specification, L is a direct bond; or any one selected from among the following structures, and the following structures may be further substituted with an alkyl group.

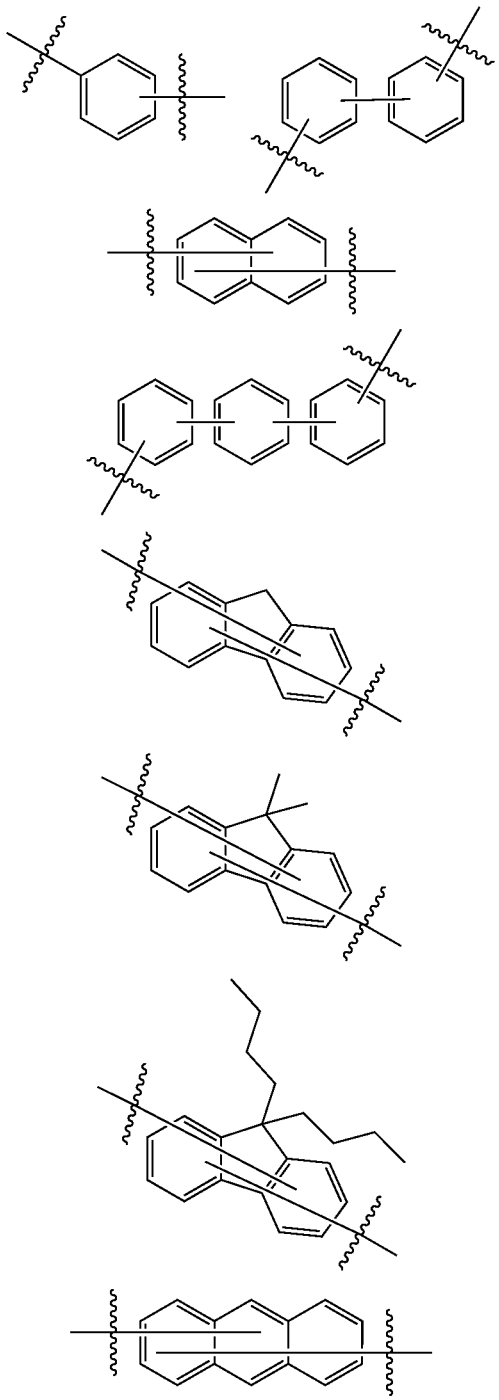

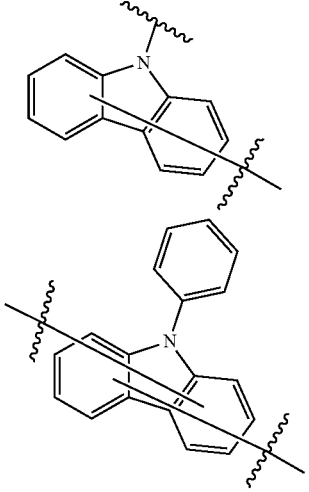

According to one embodiment of the present specification, L is a direct bond; a phenylene group unsubstituted or substituted with a methyl group; a naphthylene group; a divalent anthracenyl group; a divalent fluorenyl group unsubstituted or substituted with a methyl group or a butyl group; or a divalent carbazolyl group unsubstituted or substituted with a phenyl group.

According to one embodiment of the present specification, a is an integer of 0 to 3.

According to one embodiment of the present specification, a is an integer of 1 to 3.

According to one embodiment of the present specification, Ar1 and Ar2 are the same as or different from each other, and each independently an aryl group unsubstituted or substituted with an aryl group; an aryl group substituted with a heteroaryl group; an aryl group substituted with an alkyl group; an aryl group substituted with an aryl group substituted with an alkyl group; an aryl group substituted with a heteroaryl group substituted with an aryl group; or a heteroaryl group unsubstituted or substituted with an aryl group.

According to one embodiment of the present specification, Ar1 and Ar2 are the same as or different from each other, and each independently a phenyl group unsubstituted or substituted with an aryl group; a biphenyl group; a phenyl group substituted with a heteroaryl group; a fluorenyl group substituted with an alkyl group; a phenyl group substituted with an aryl group substituted with an alkyl group; a phenyl group substituted with a heteroaryl group substituted with an aryl group; a carbazolyl group unsubstituted or substituted with an aryl group; or a spirobifluorenyl group.

According to one embodiment of the present specification, Ar1 and Ar2 are the same as or different from each other, and each independently a phenyl group unsubstituted or substituted with a phenyl group; a biphenyl group; a phenyl group substituted with a dibenzofuranyl group; a phenyl group substituted with a dimethylfluorenyl group; a fluorenyl group substituted with a methyl group; a phenyl group substituted with a fluorenyl group substituted with a methyl group; a phenyl group substituted with a carbazolyl group substituted with a phenyl group; a carbazolyl group unsubstituted or substituted with a phenyl group; or a spirobifluorenyl group.

According to one embodiment of the present specification, Ar1 and Ar2 are the same as or different from each other, and each independently a phenyl group; a biphenyl group; a 9,9-dimethylfluorenyl group; a 9-phenylcarbazolyl group; a phenyl group substituted with a 9-phenylcarbazolyl group; a phenyl group substituted with a dibenzofuranyl group; or a 9,9'-spirobifluorenyl group.

According to one embodiment of the present specification, the monomer represented by Chemical Formula 2 is any one selected from among the following structures.

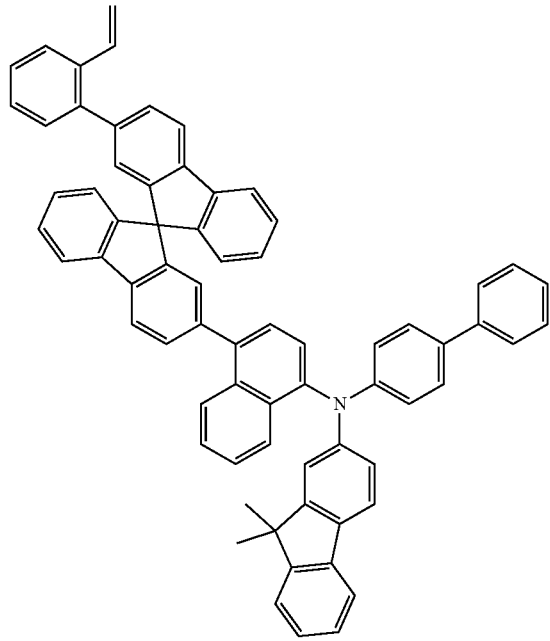

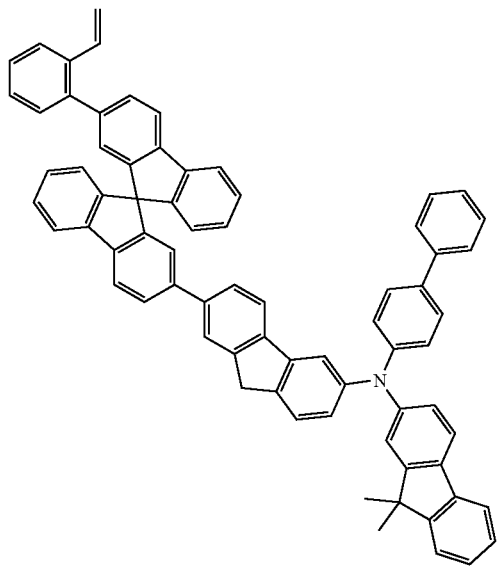

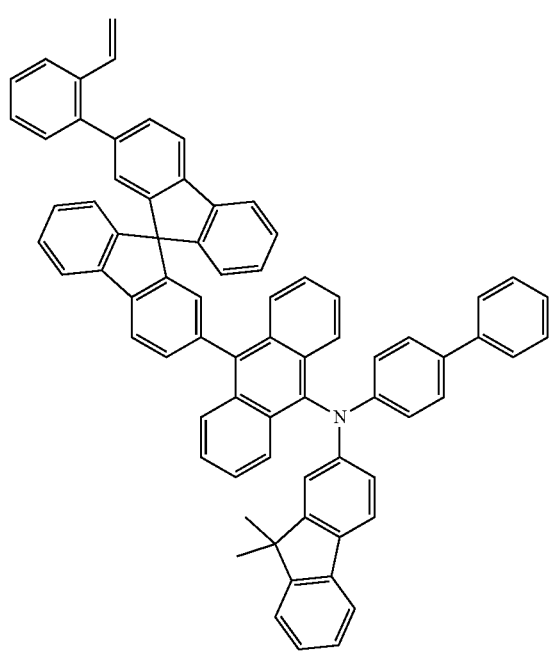

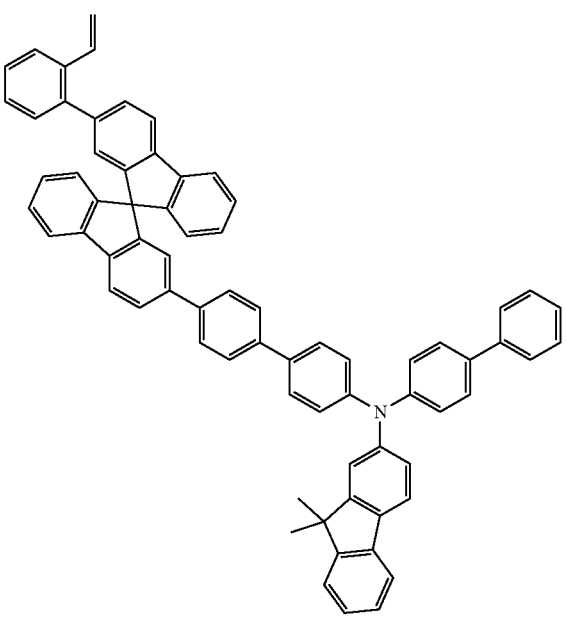

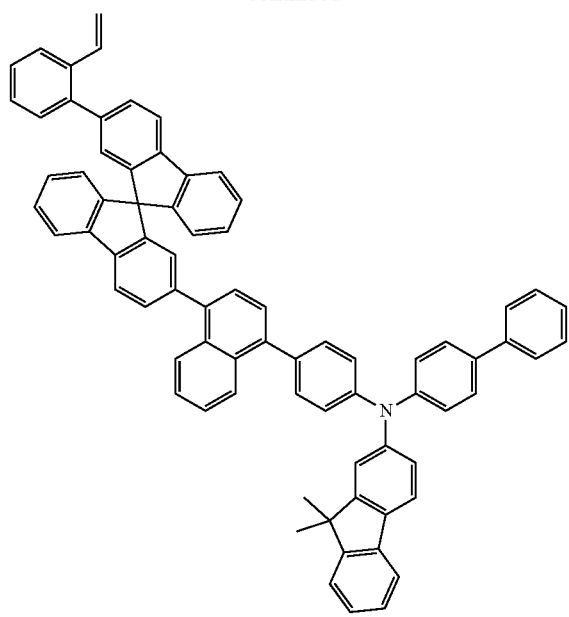
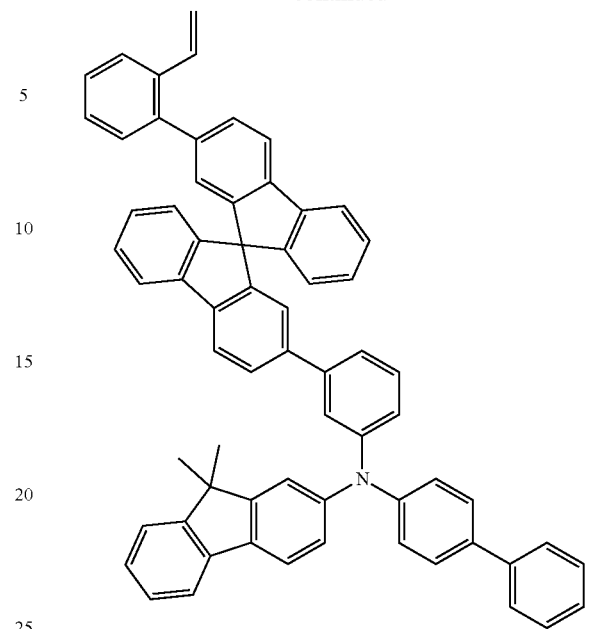
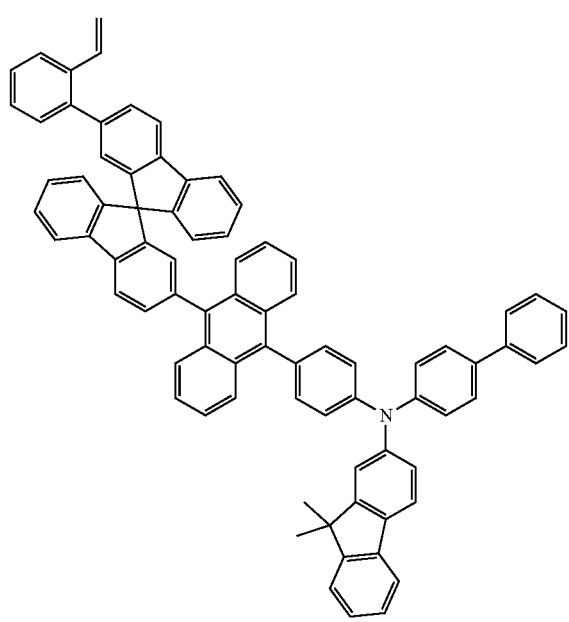
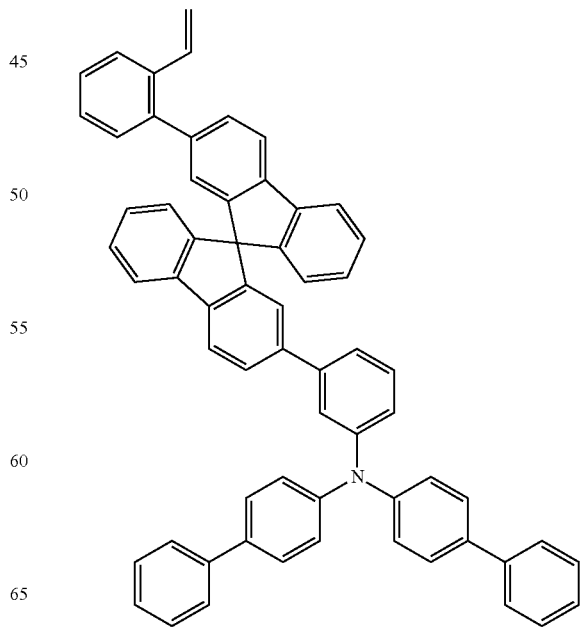

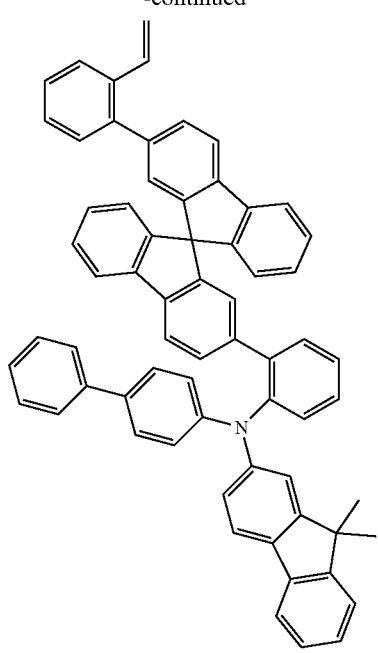
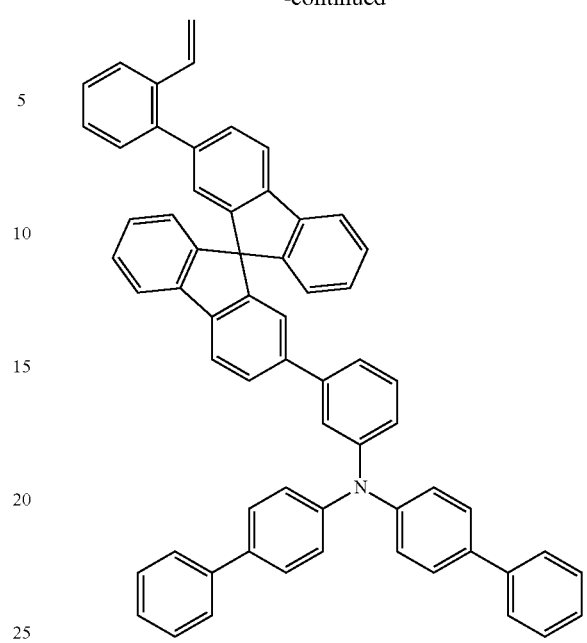
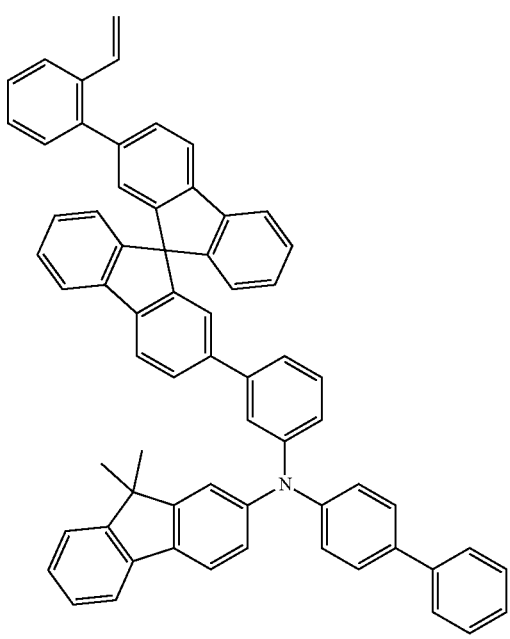
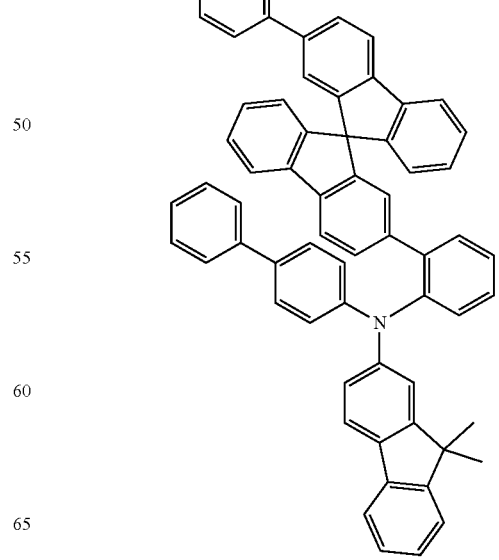

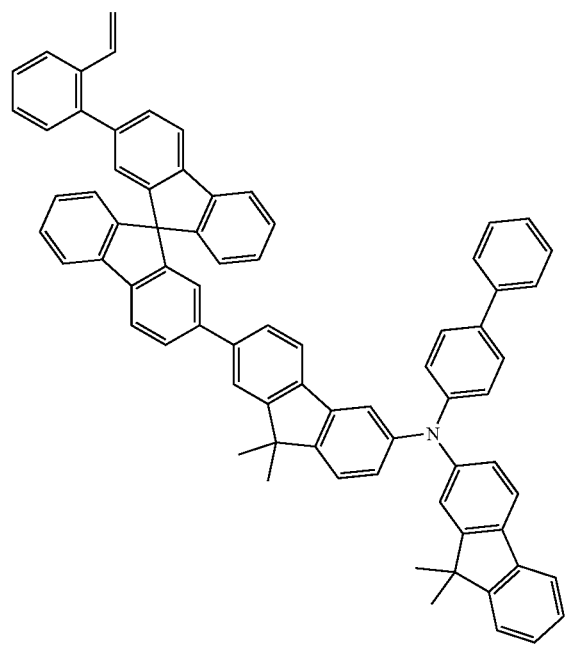
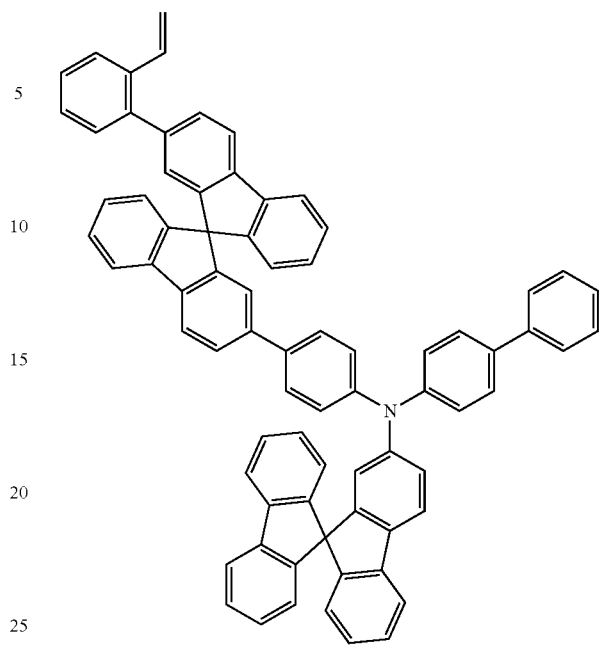
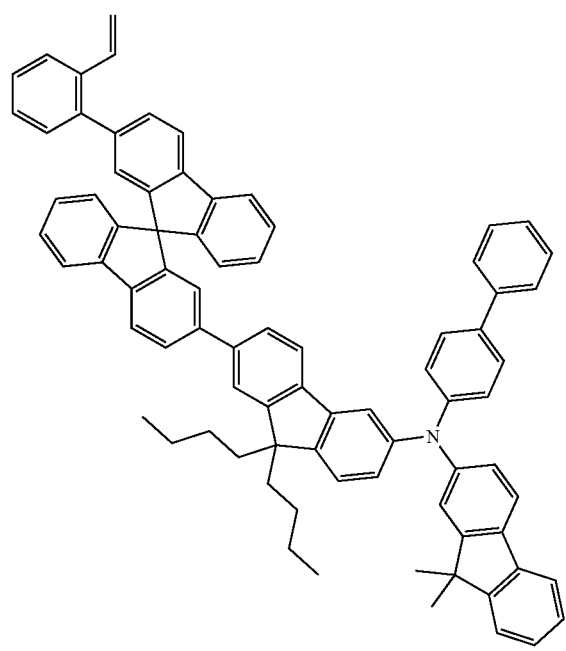
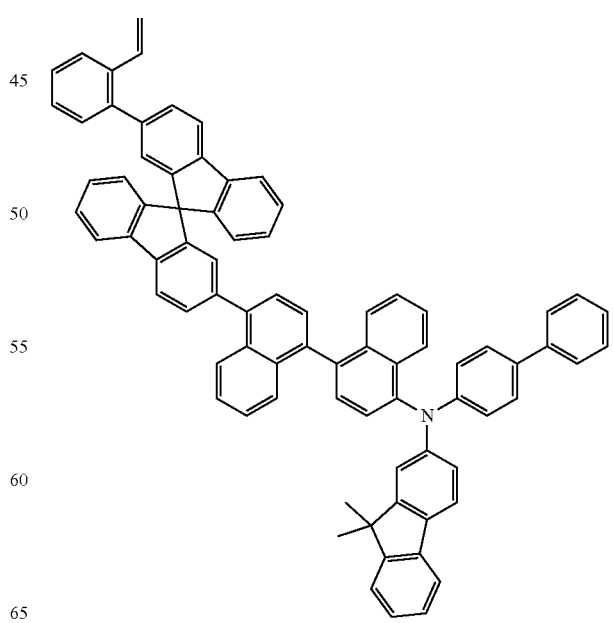

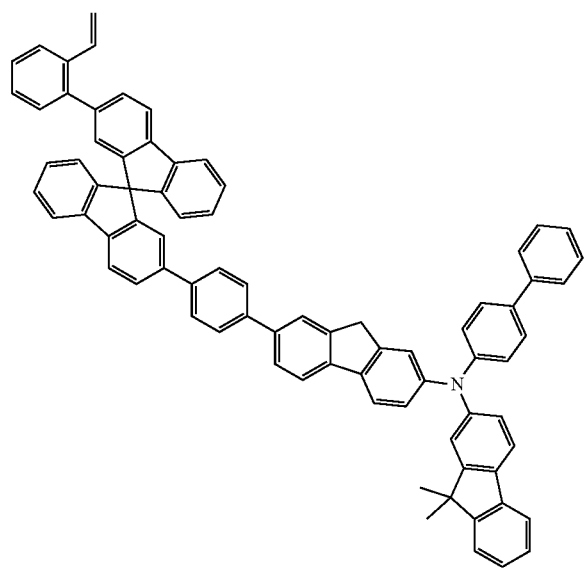
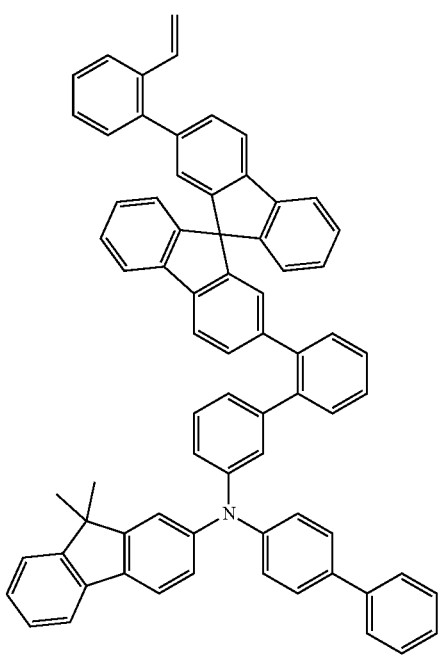
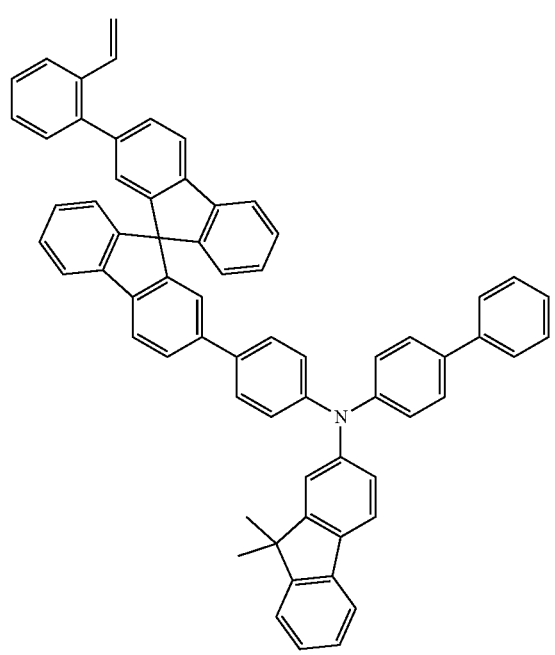
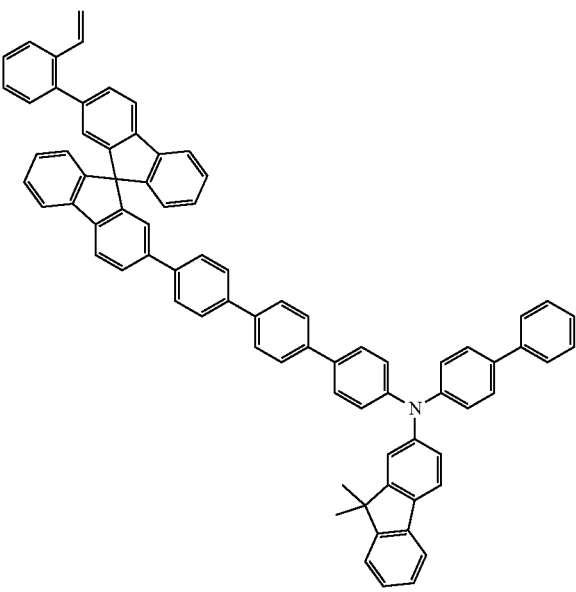

-continued
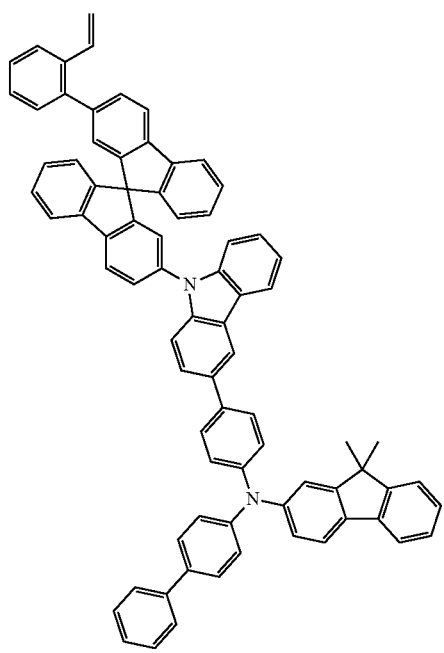
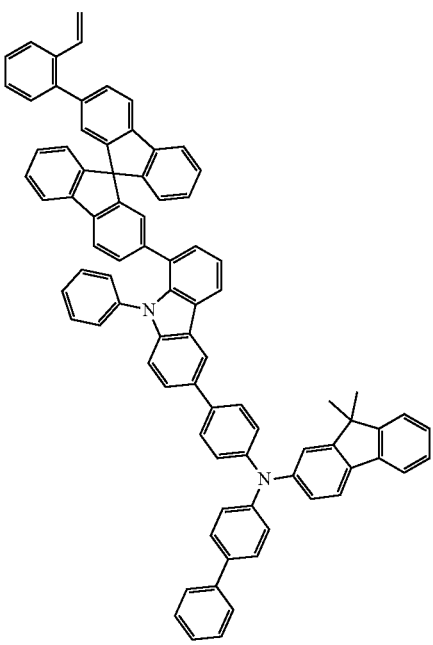

29
-continued
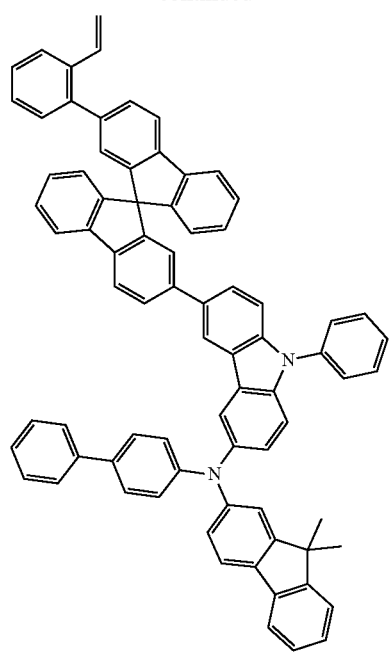
30
-continued
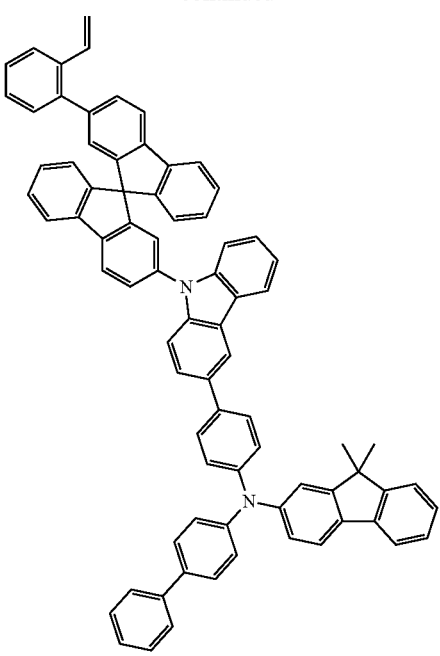
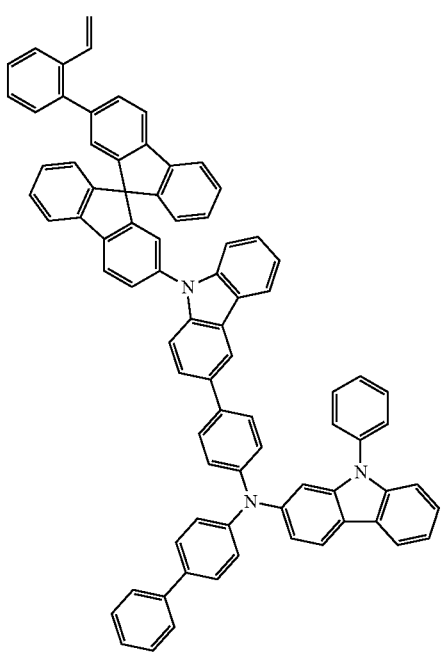
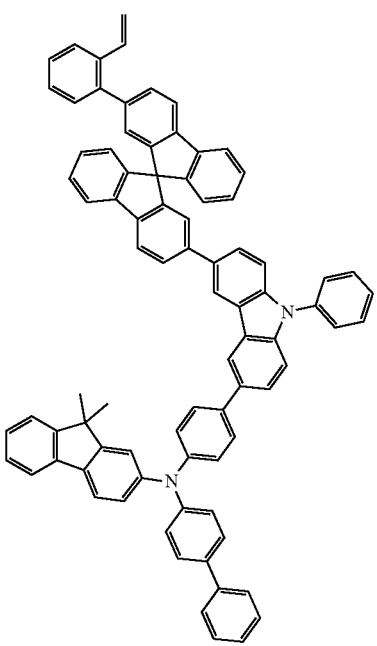

31
-continued
32
-continued
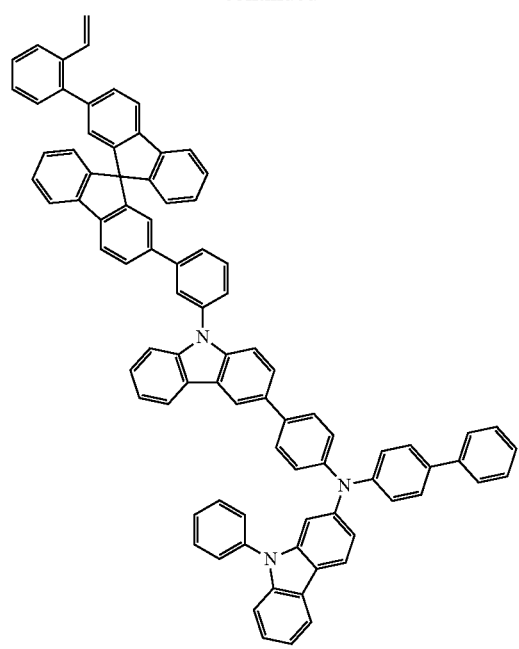
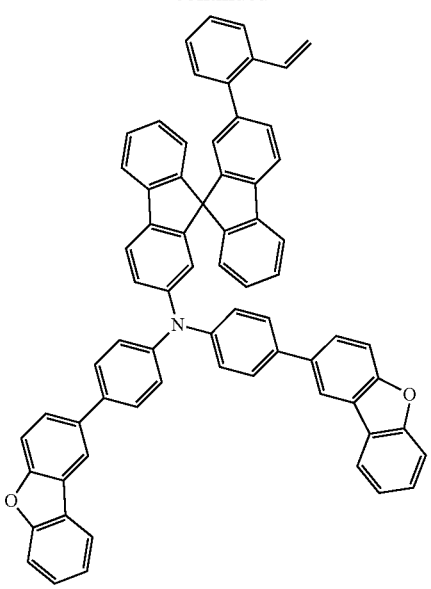
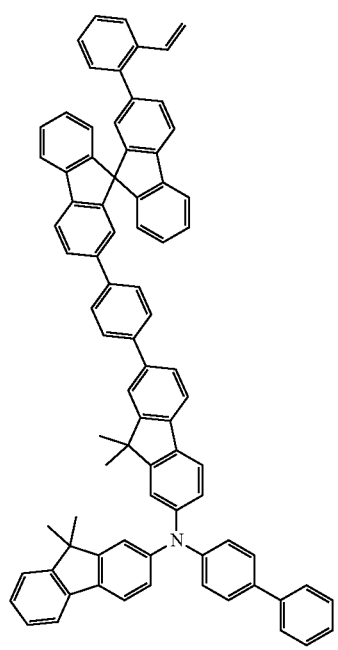

33
-continued
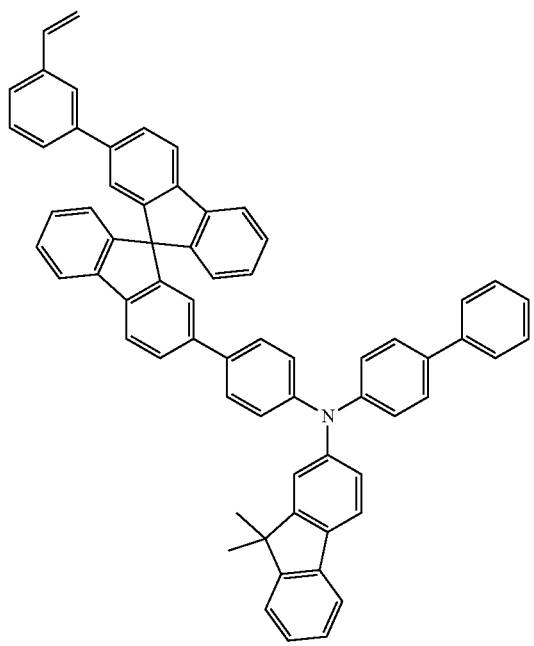
34
-continued
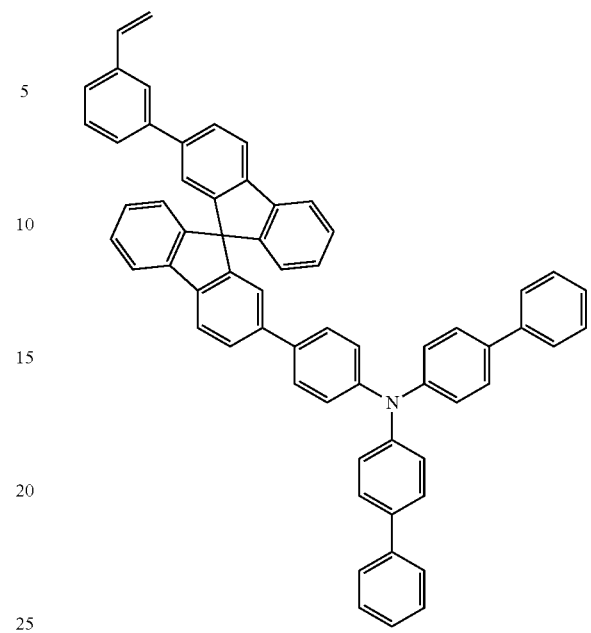
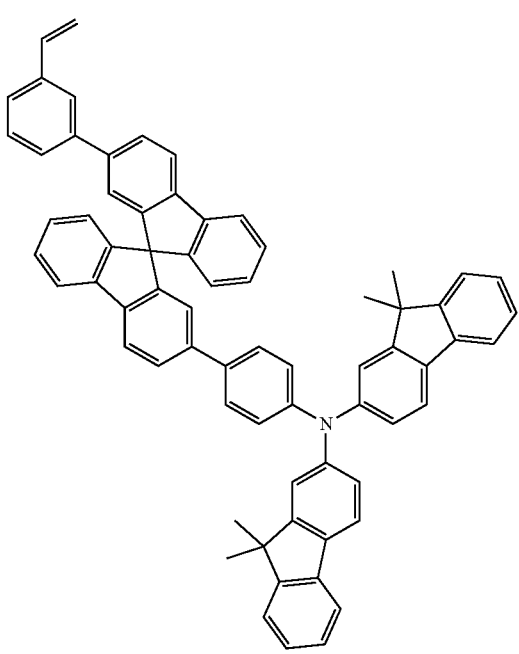

35
-continued
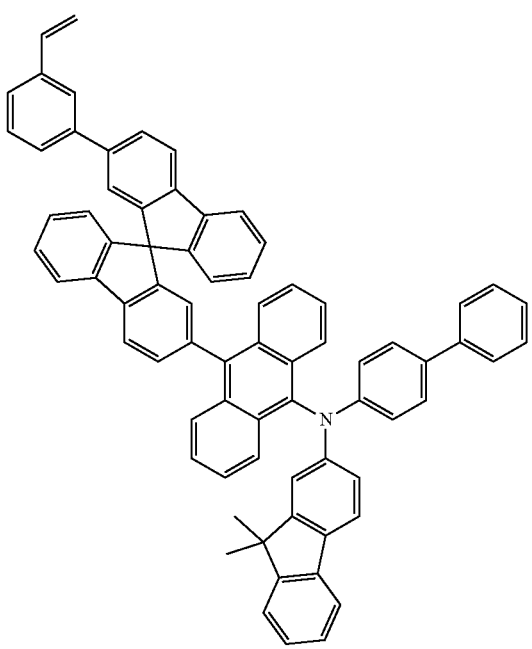
36
-continued
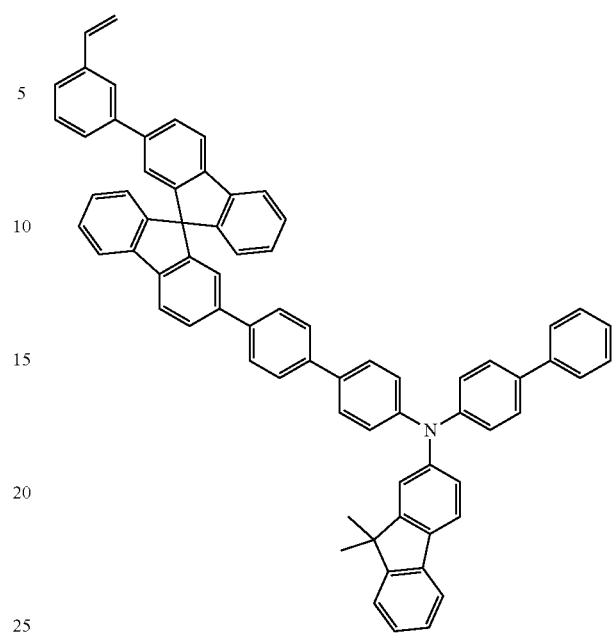
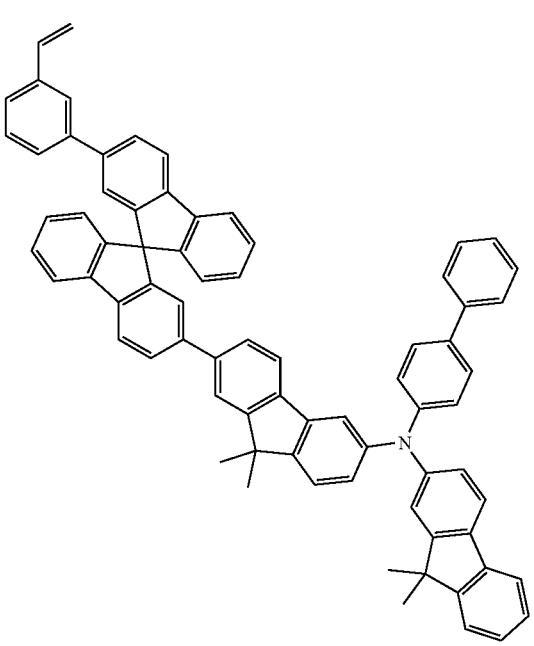
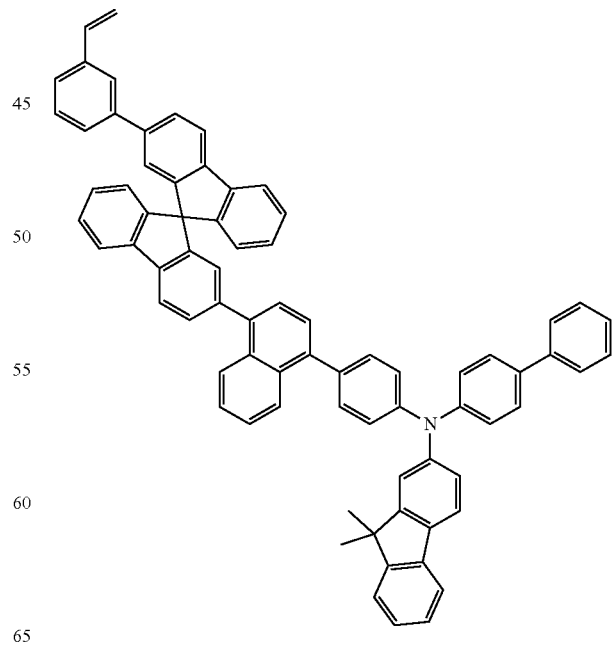

37
-continued
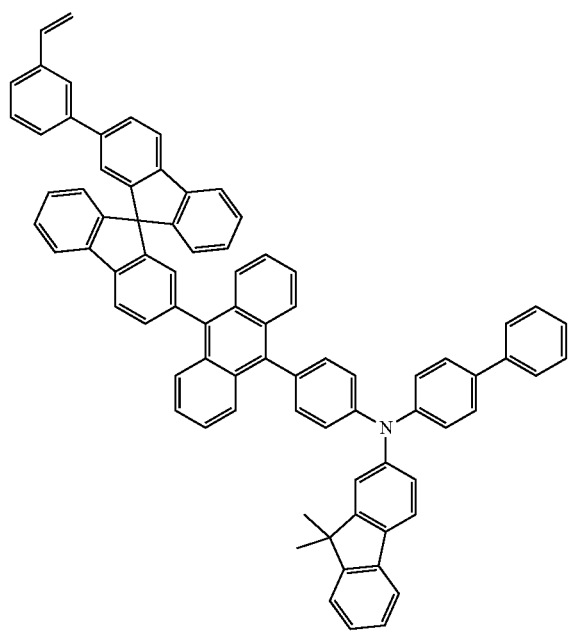
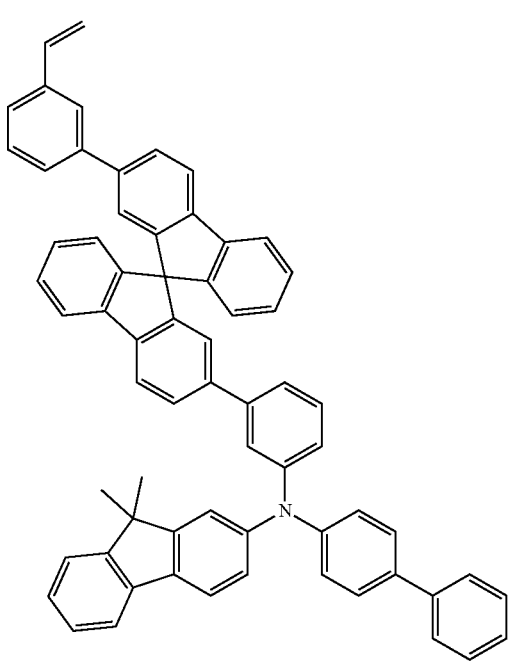
38
-continued
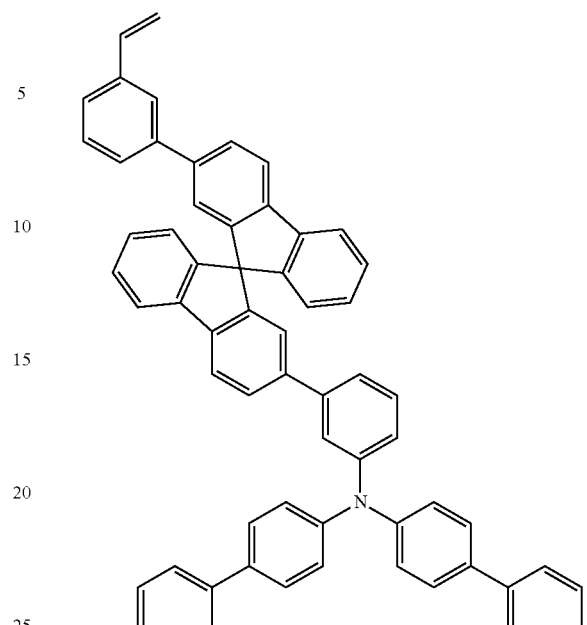
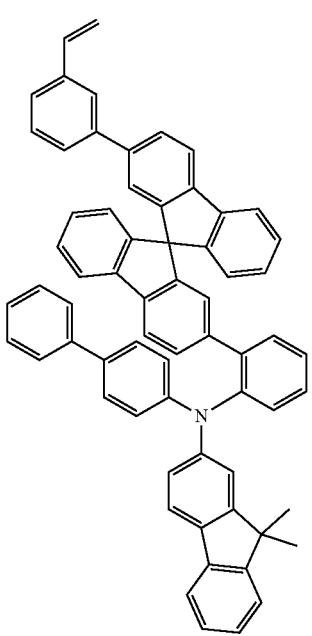

39
-continued
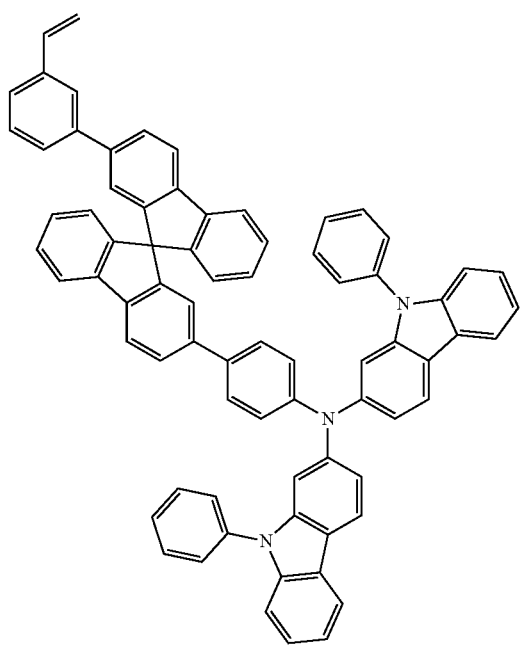
40
-continued
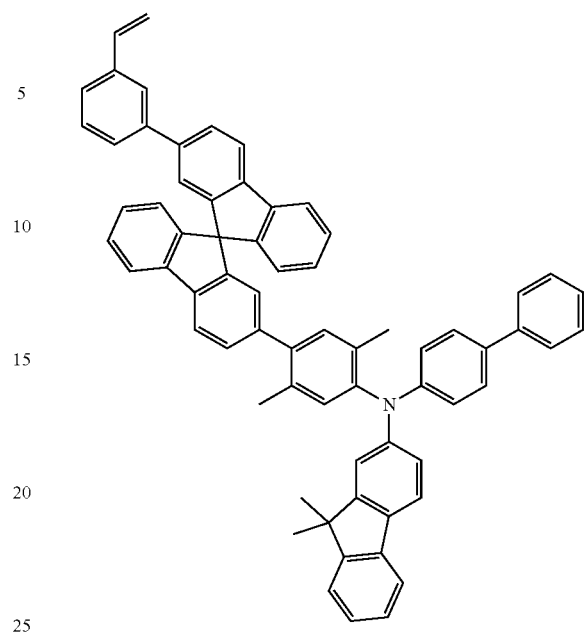
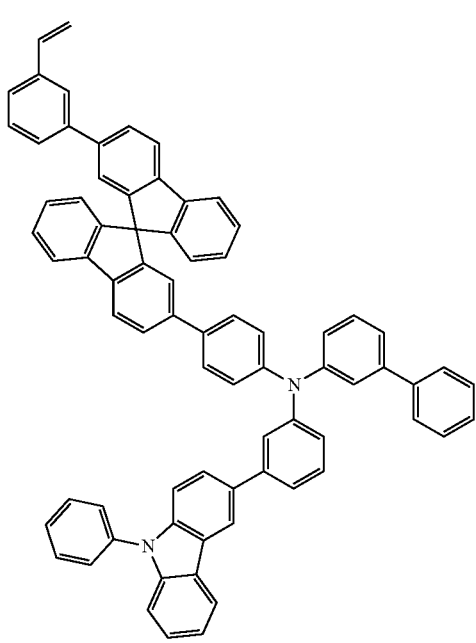

41
-continued
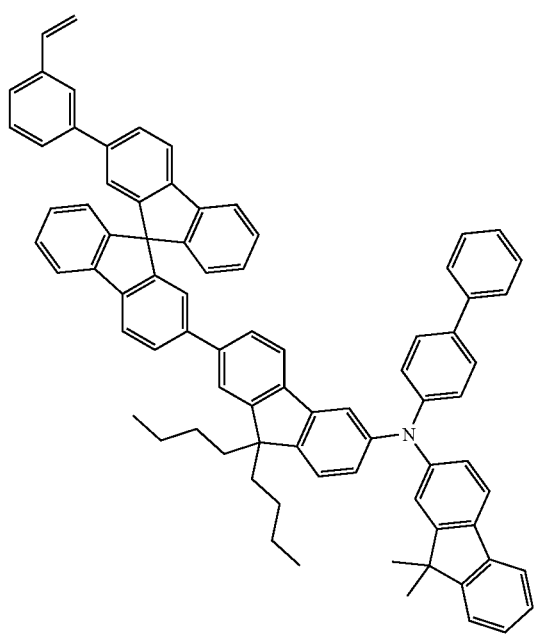
42
-continued
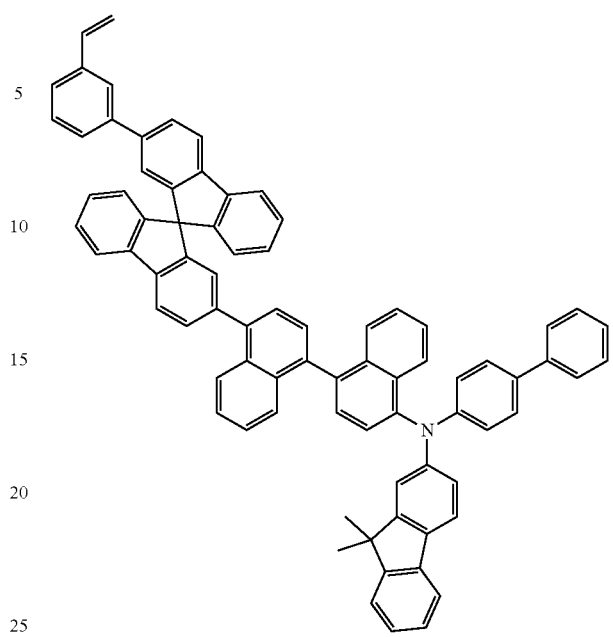
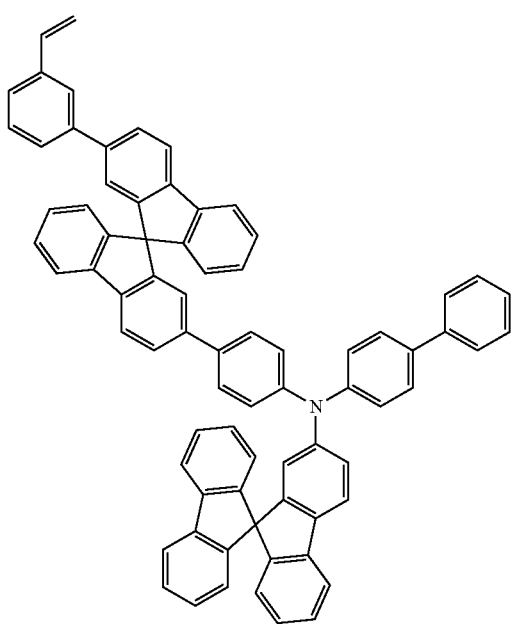
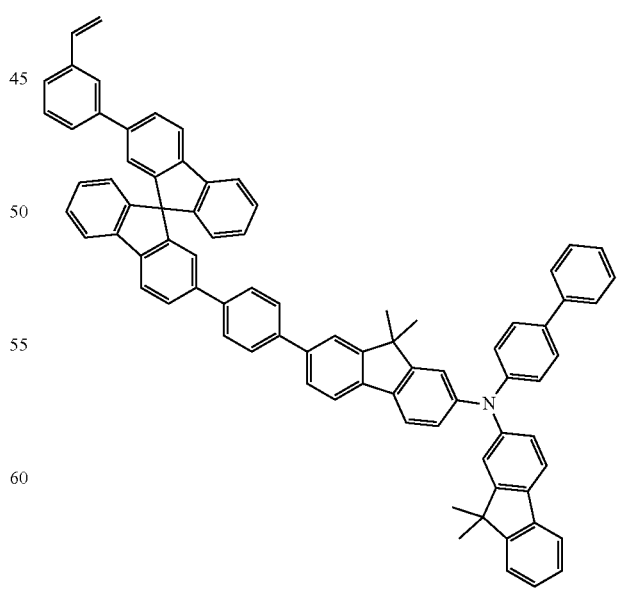

43
-continued
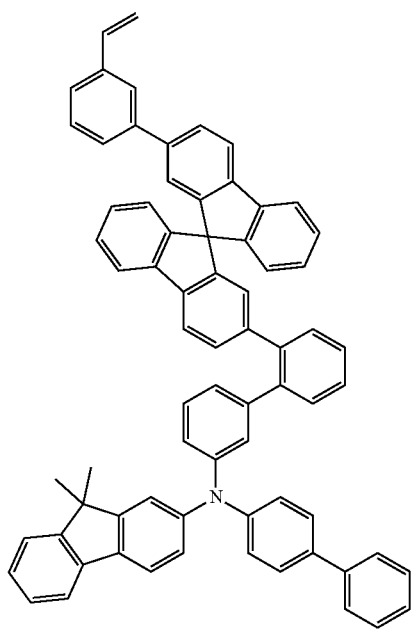
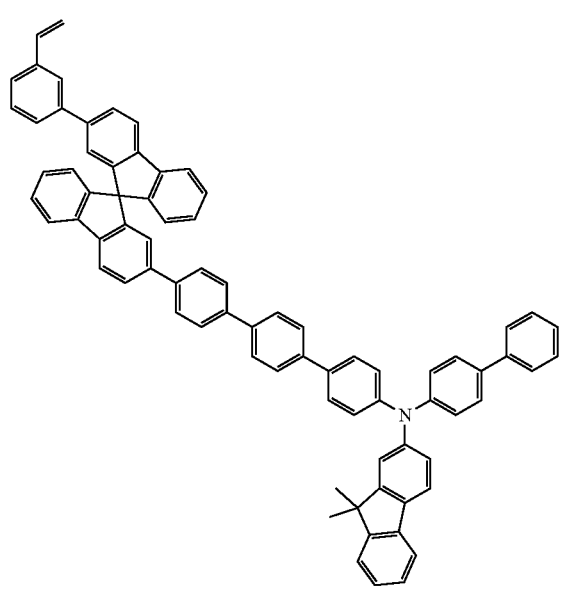
44
-continued
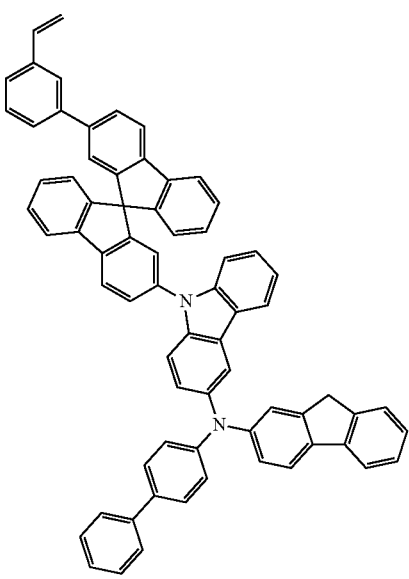
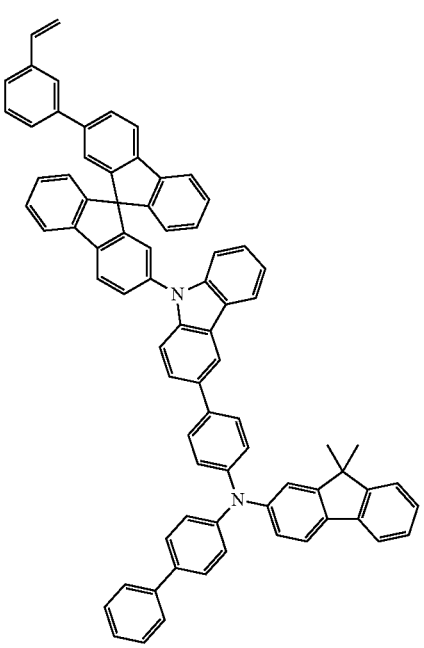

45
-continued
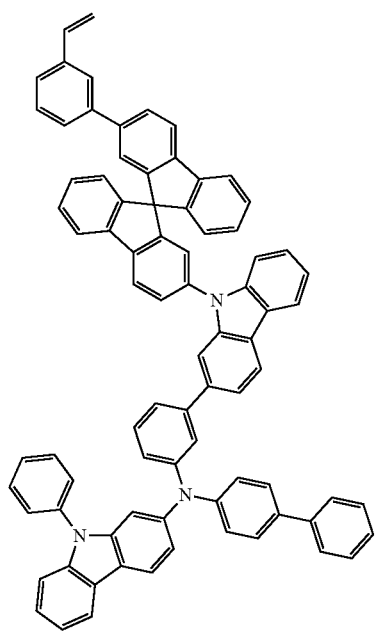
46
-continued
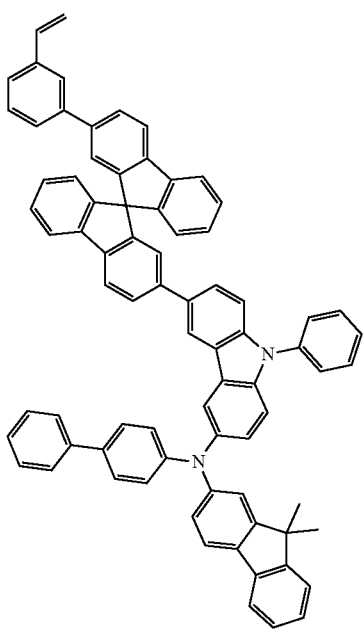
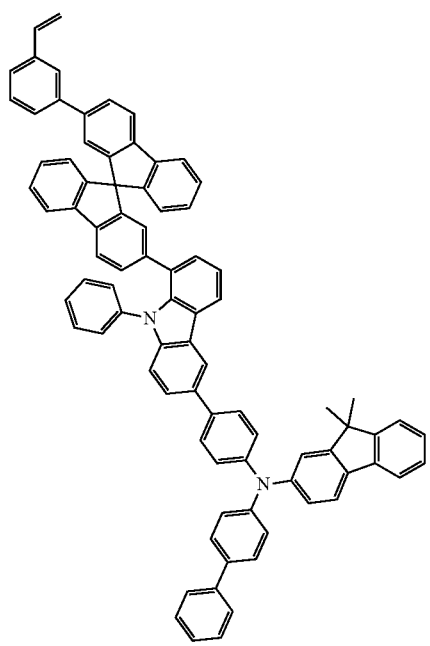
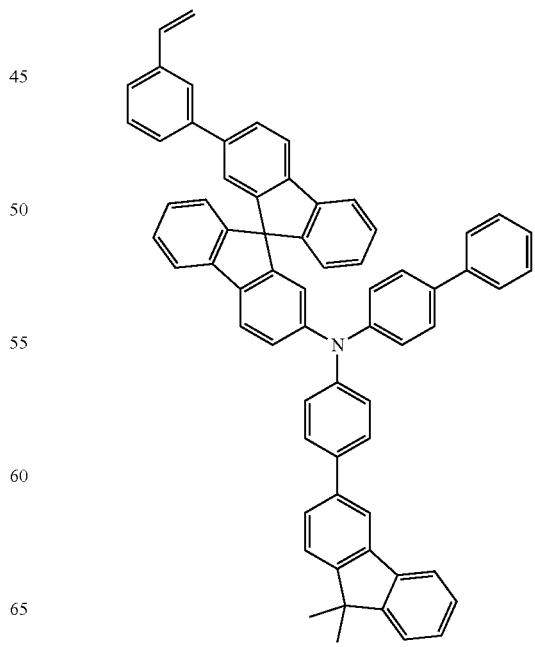

47
-continued
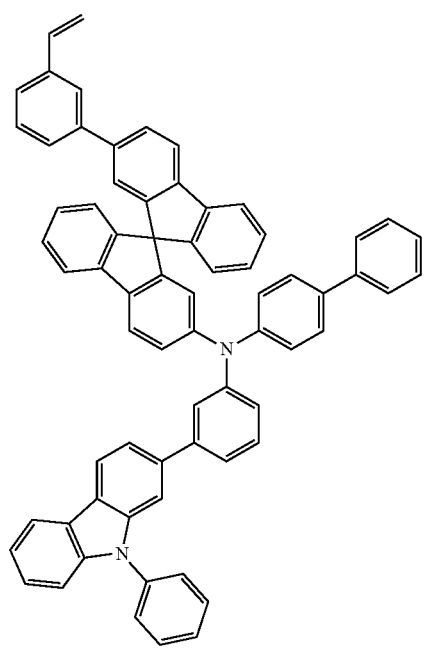
48
-continued
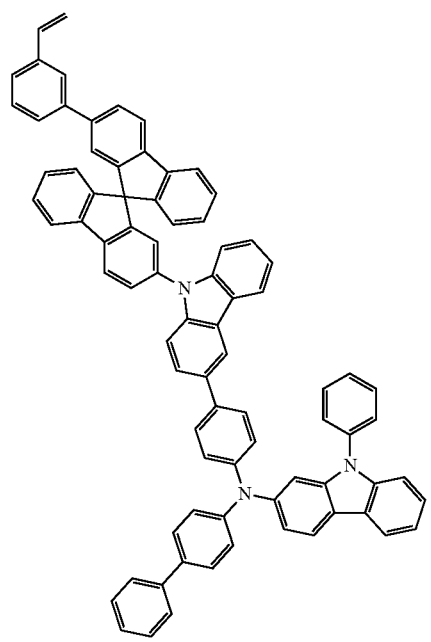
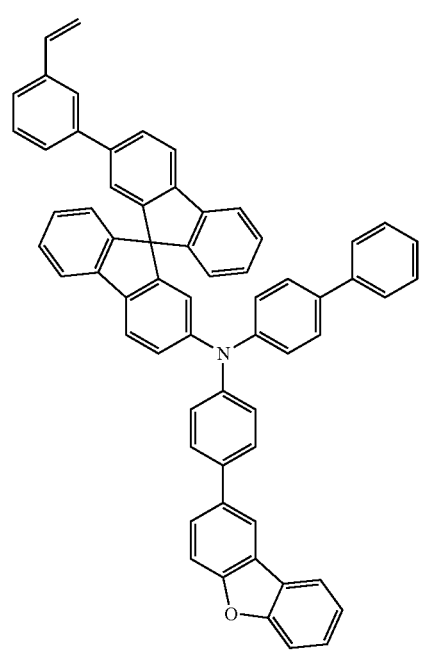
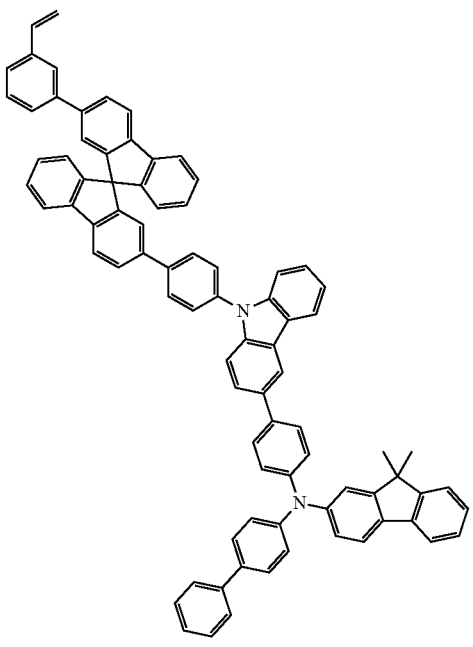

-continued
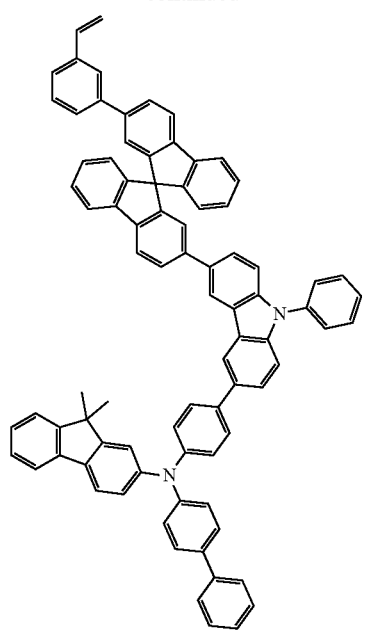
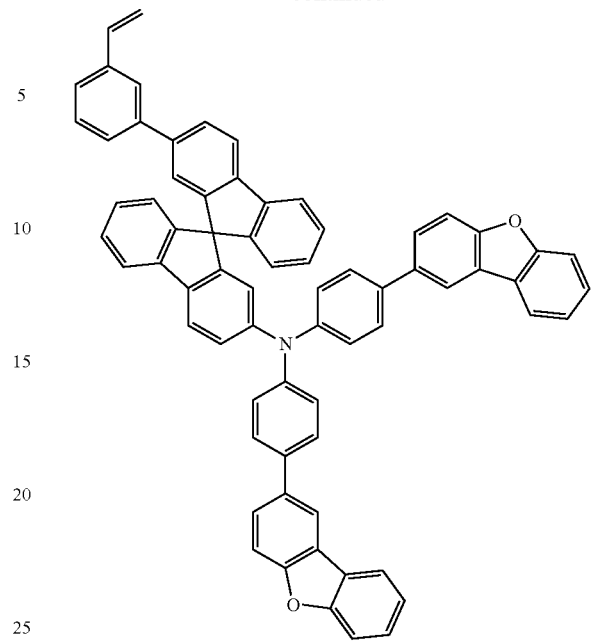
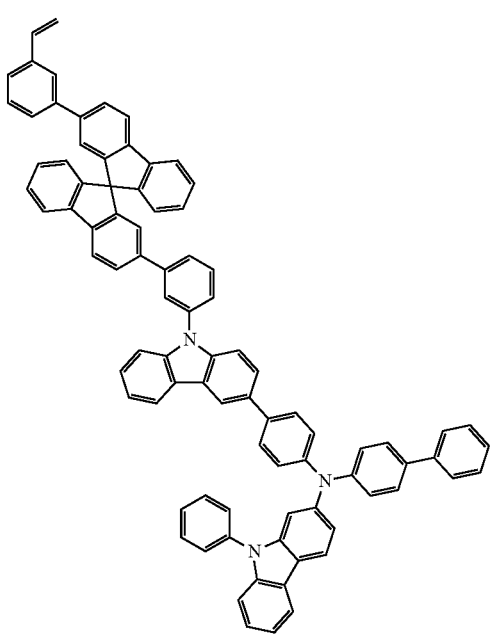
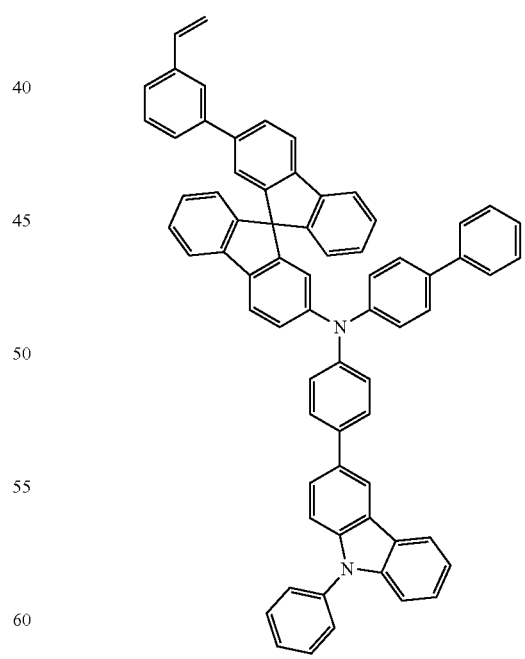
According to one embodiment of the present specification, the polymer comprising the unit represented by Chemical Formula 1 is any one selected from among the following structures.

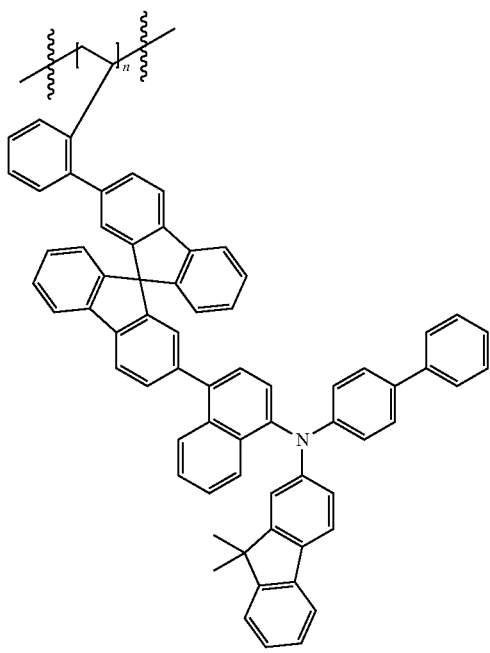
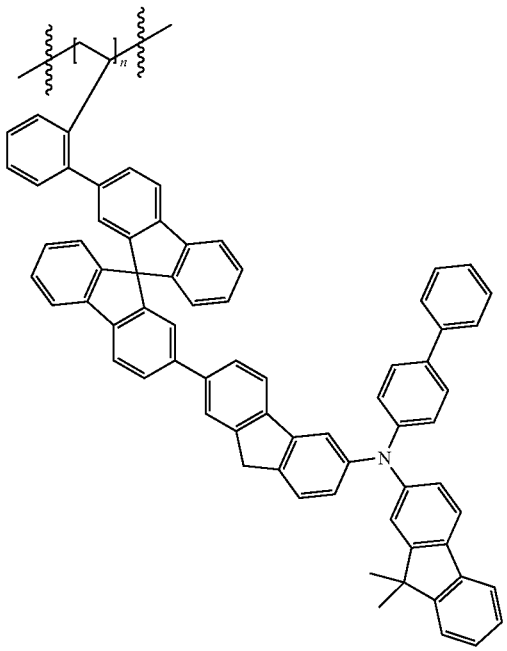
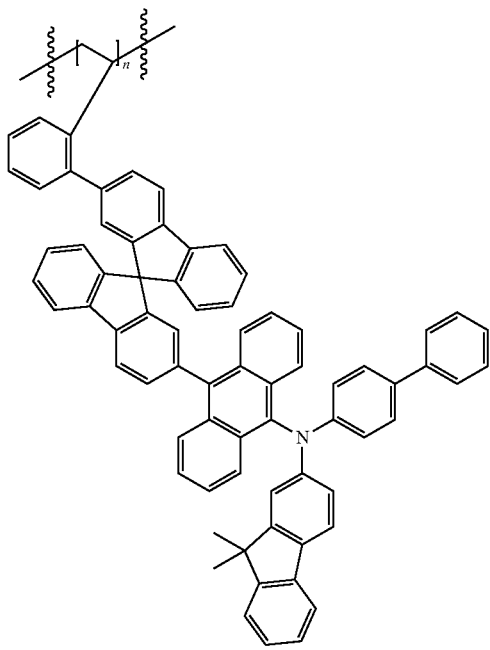
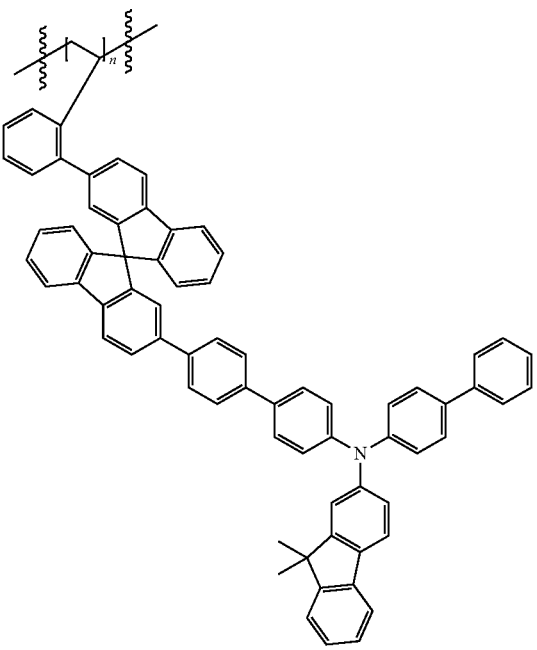

53
-continued
54
-continued
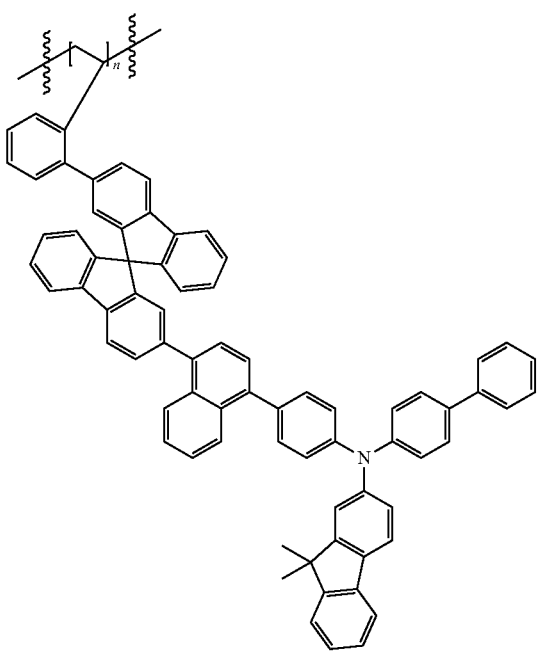
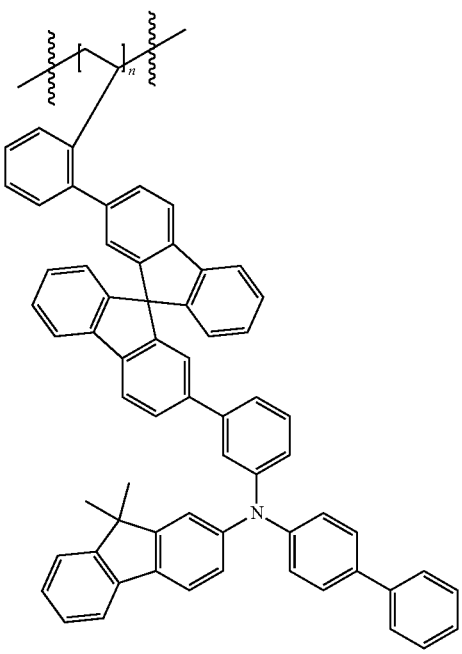

55
-continued
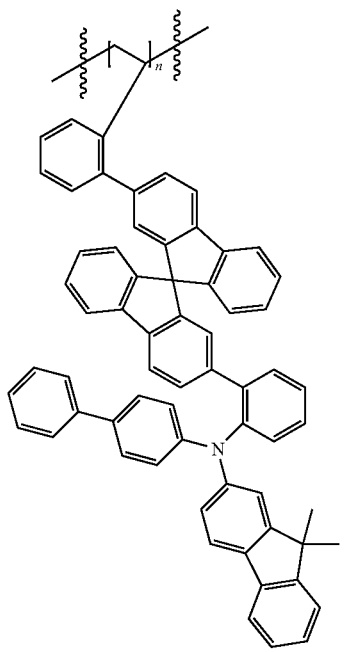
56
-continued
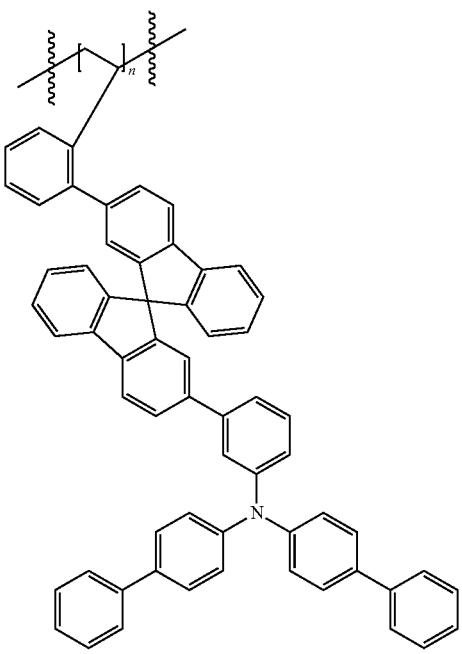
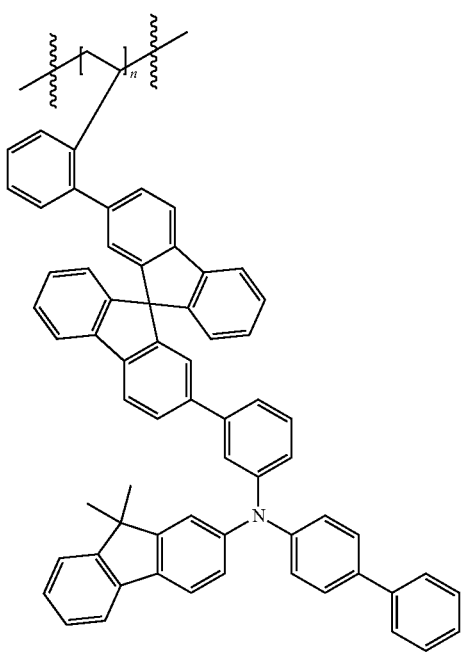
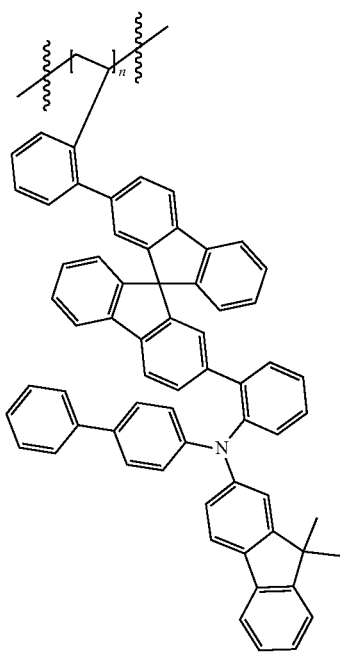

57
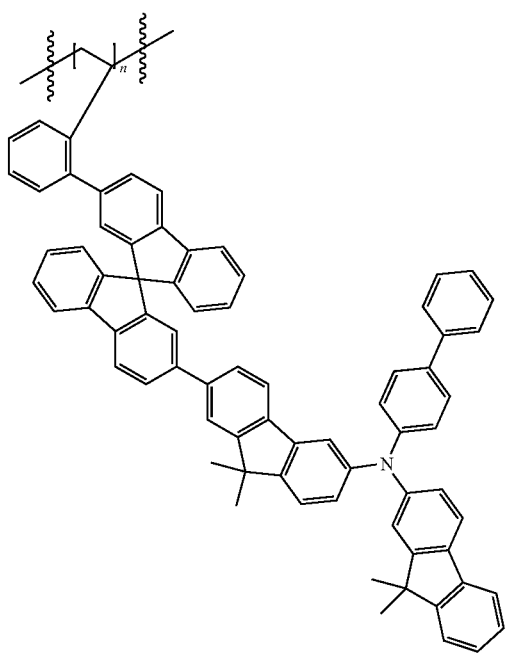
58
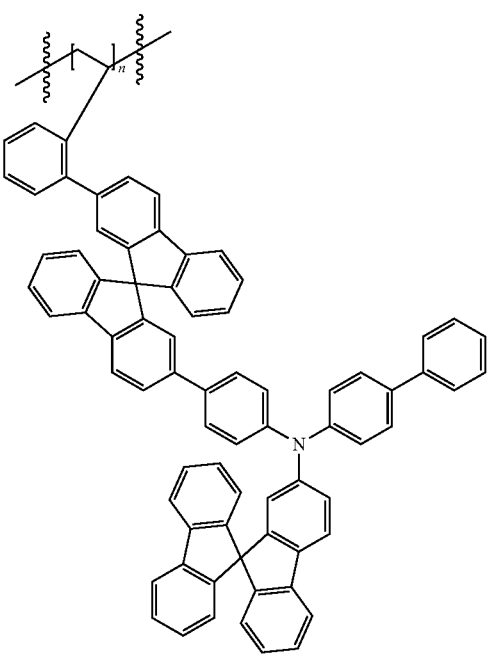
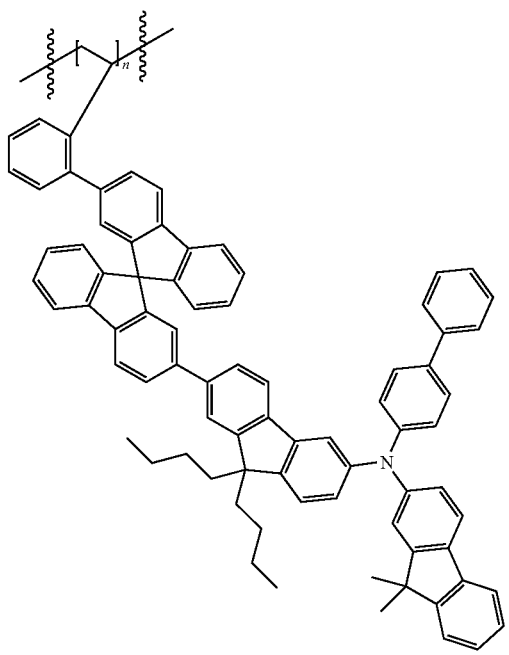
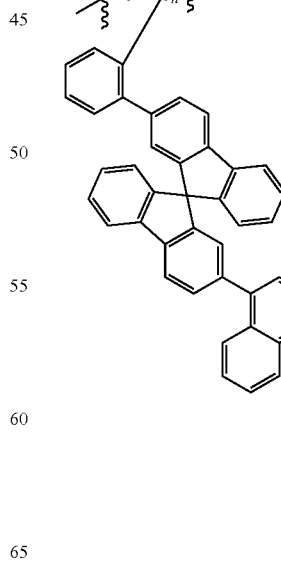

59
-continued
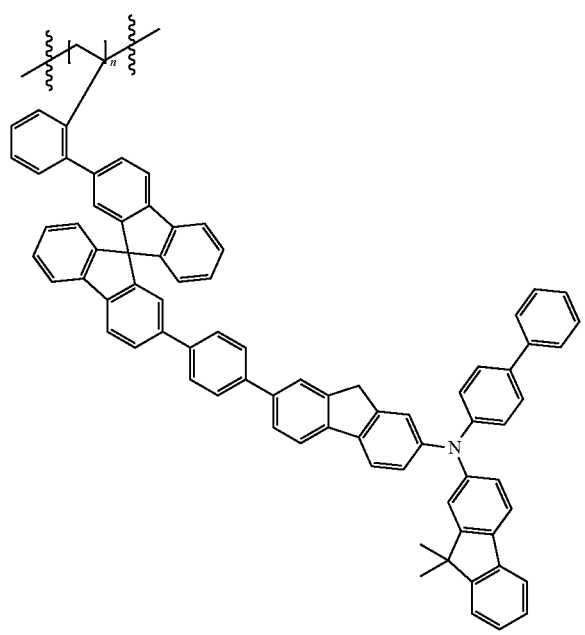
60
-continued
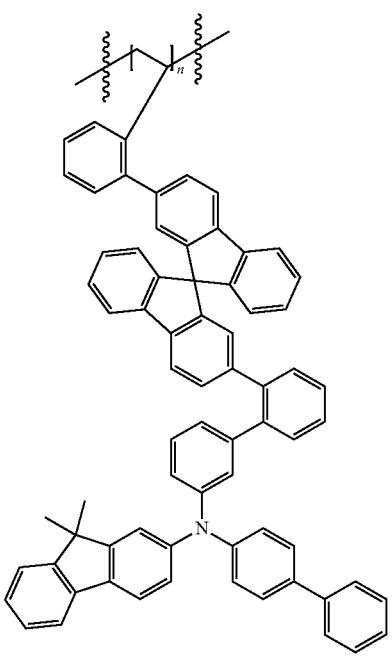
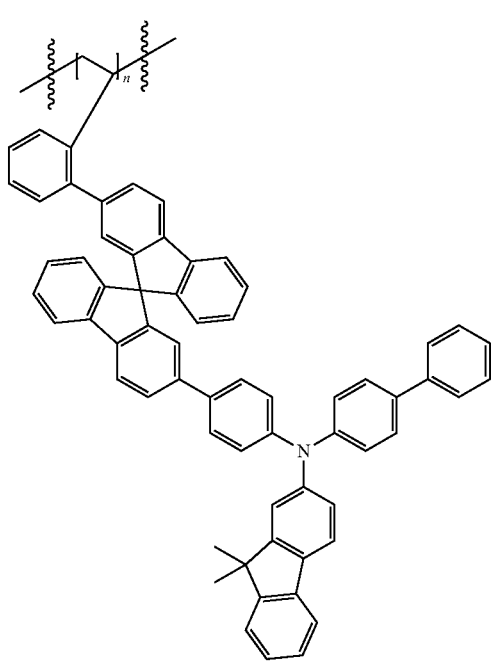
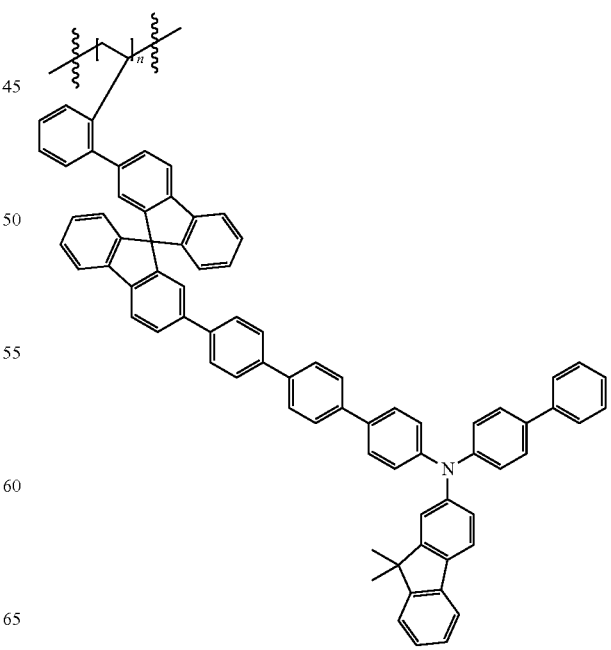

61
-continued
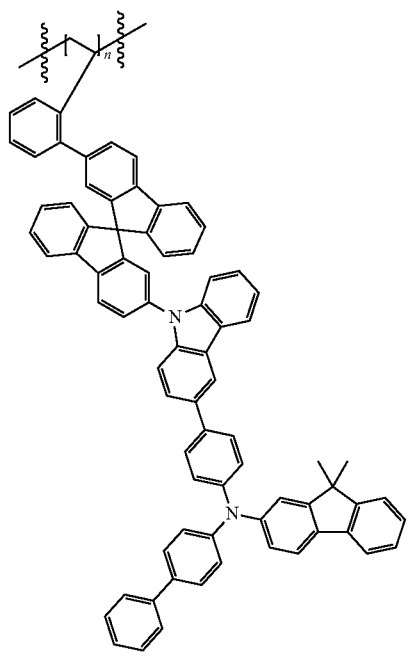
62
-continued
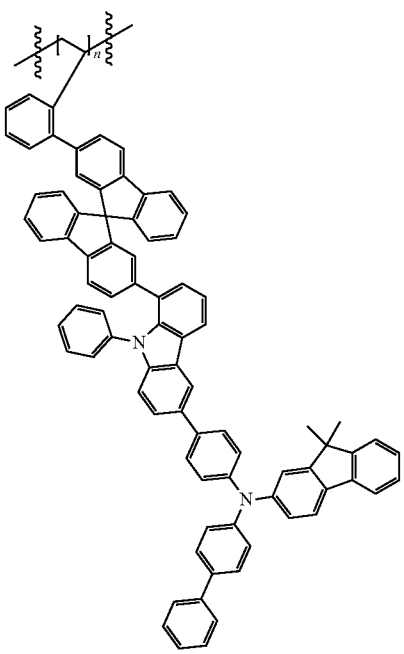
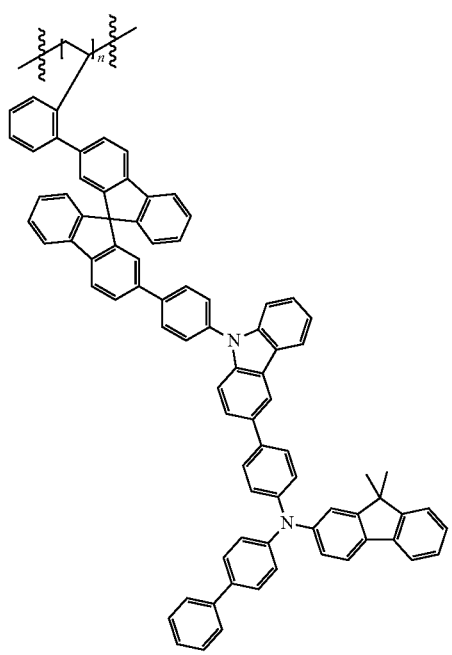
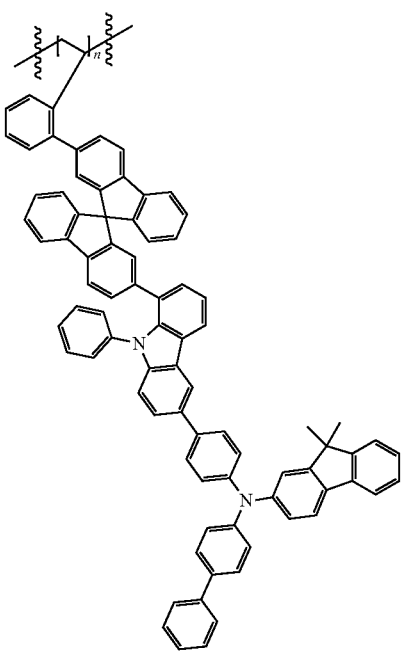

63
-continued
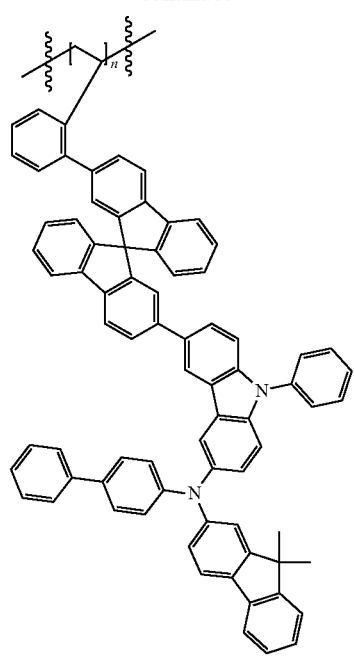
64
-continued
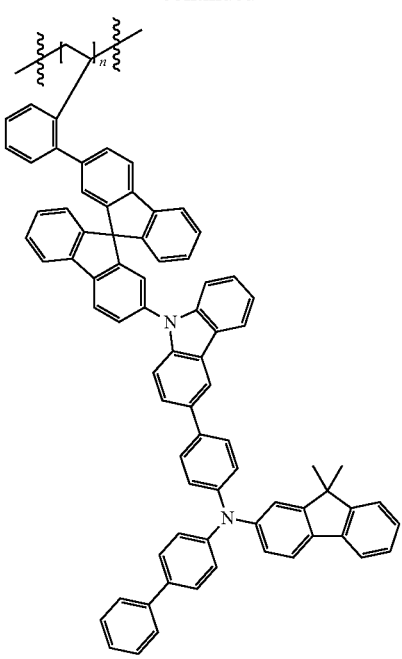
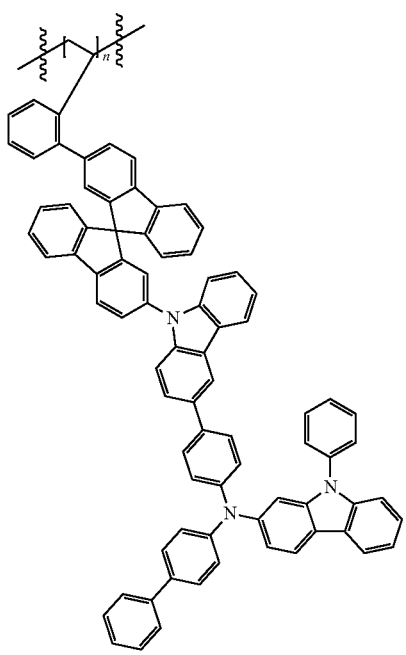
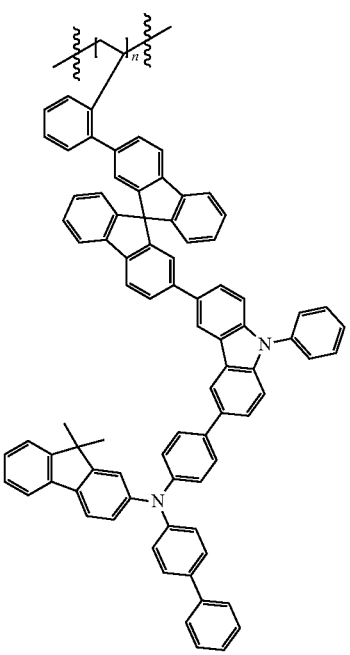

65
-continued
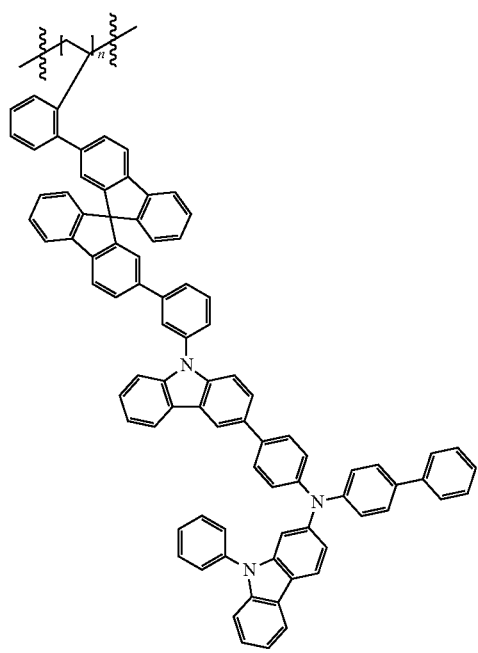
66
-continued
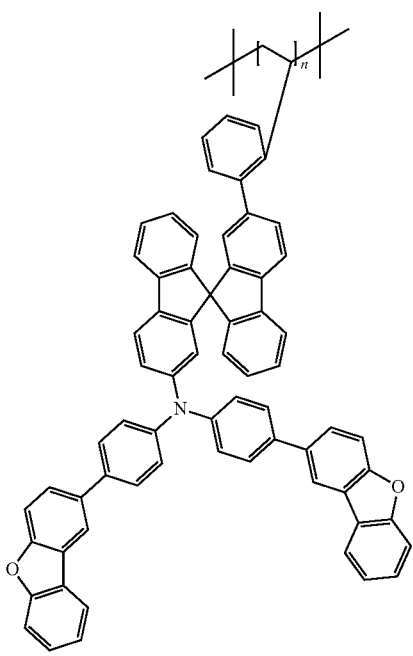
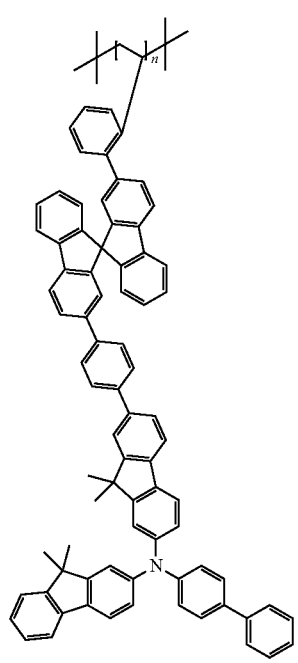
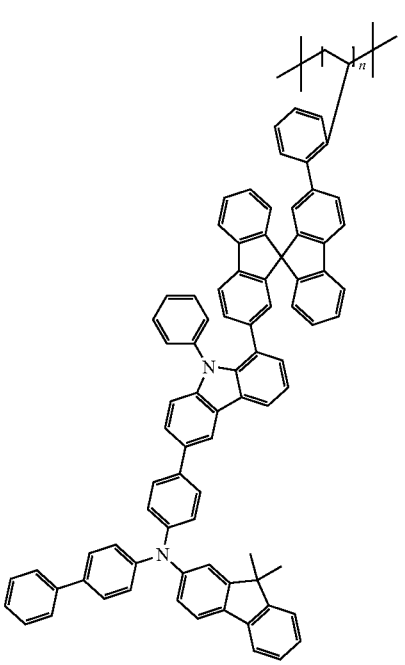

67
-continued
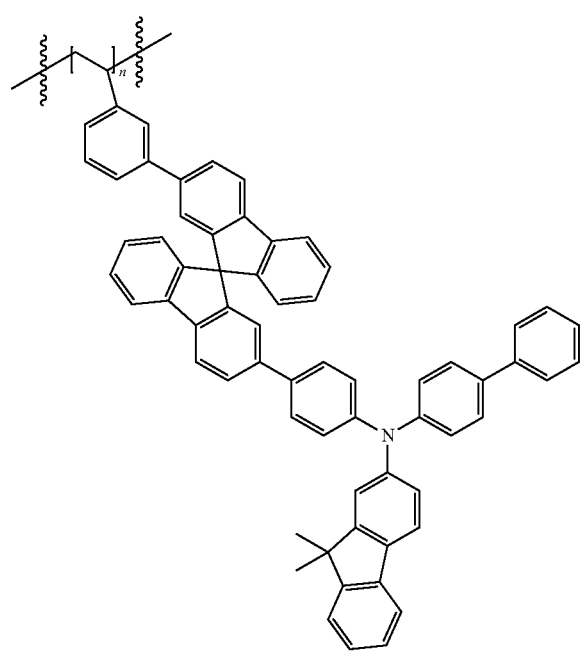
68
-continued
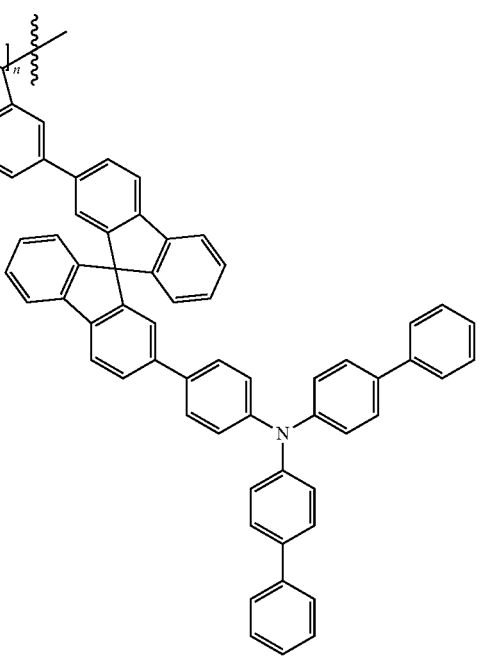
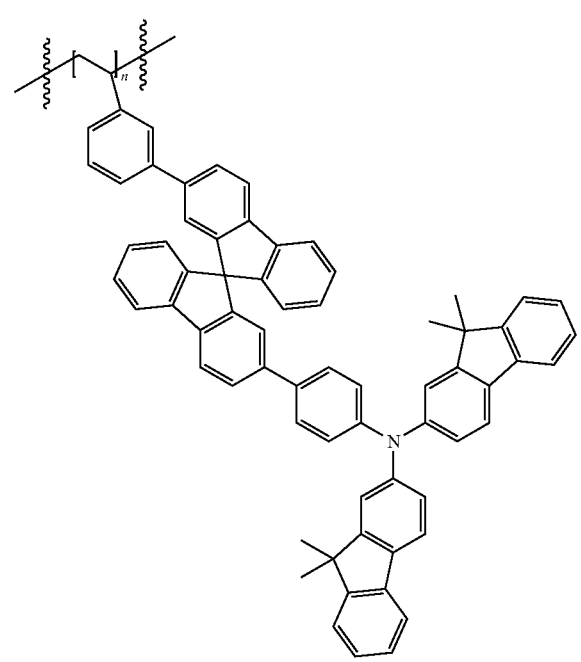
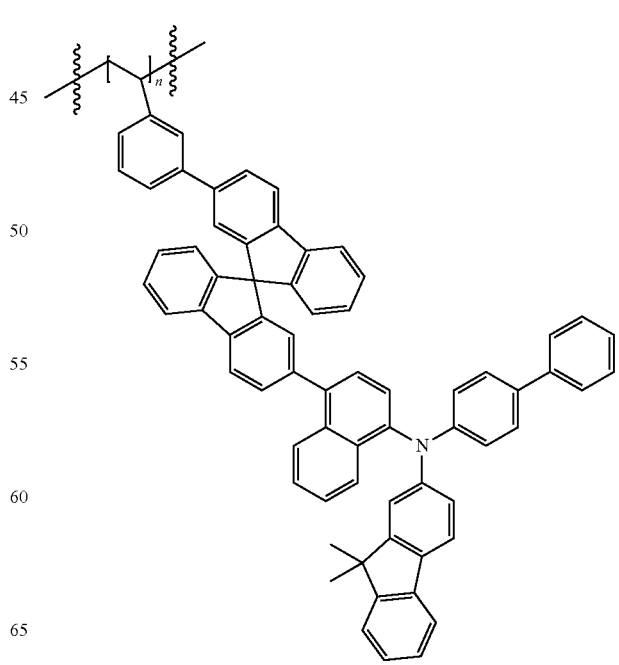

69
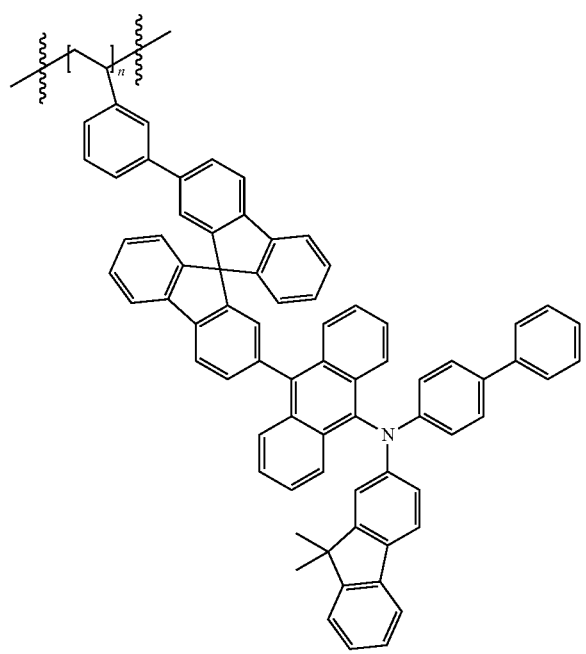
70
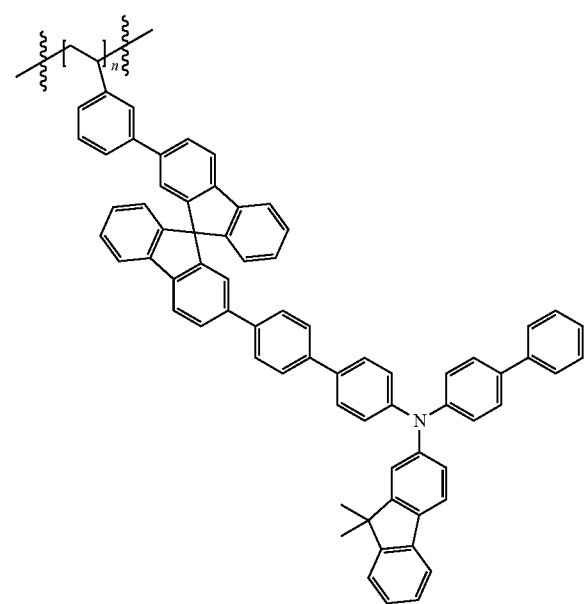
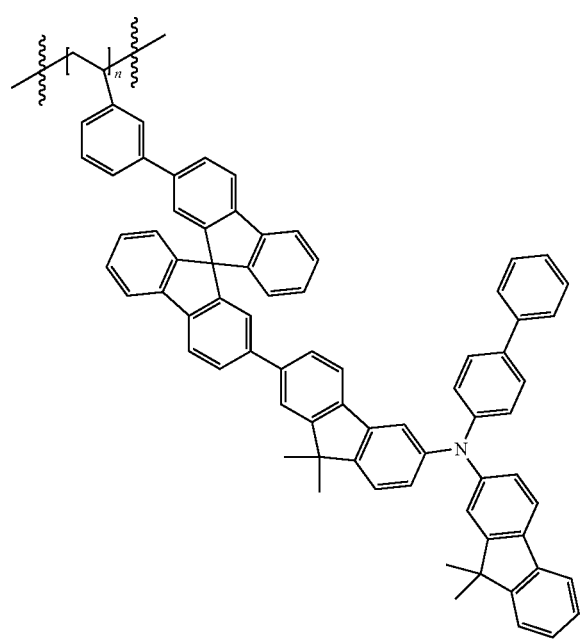
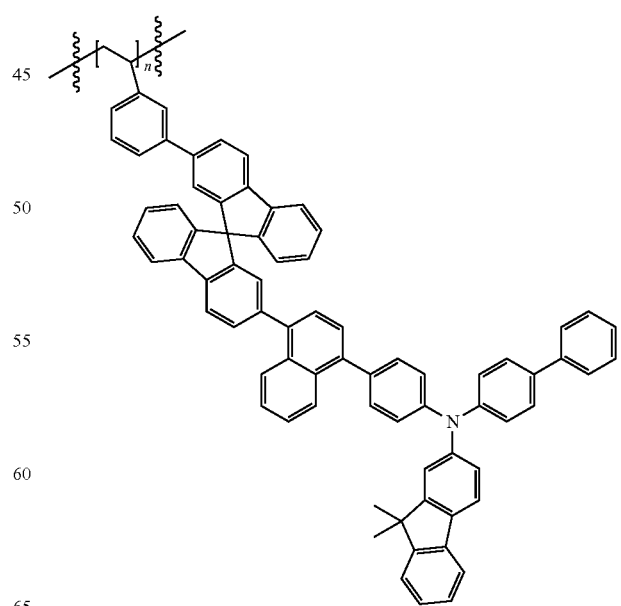

71
-continued
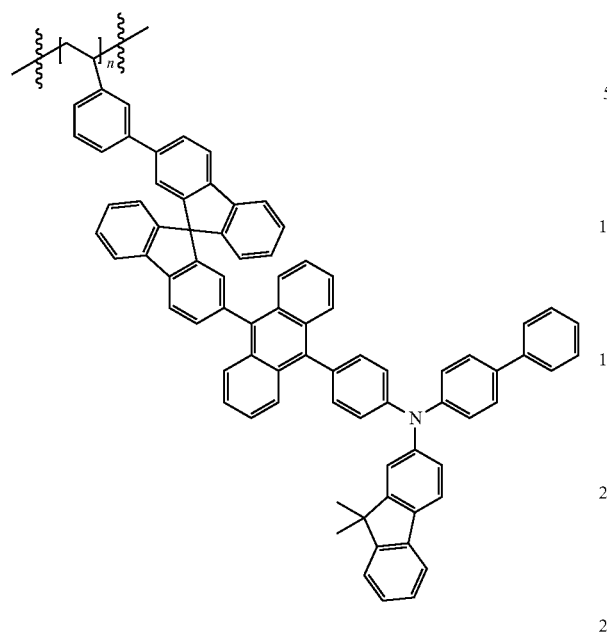
72
-continued
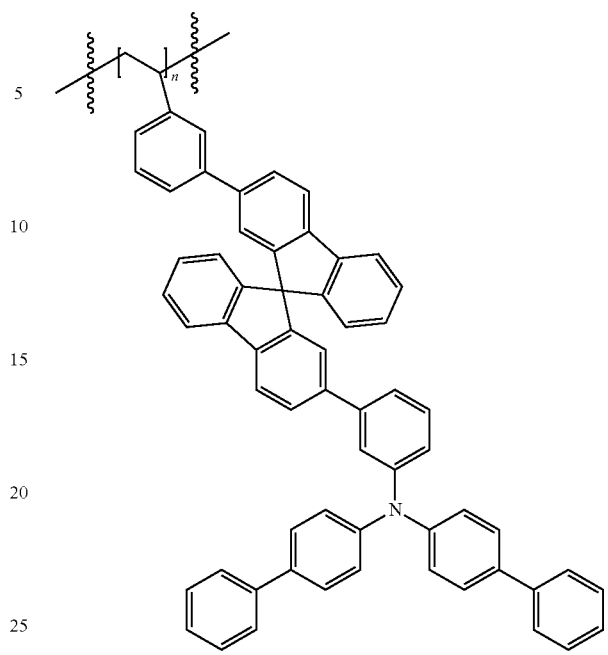
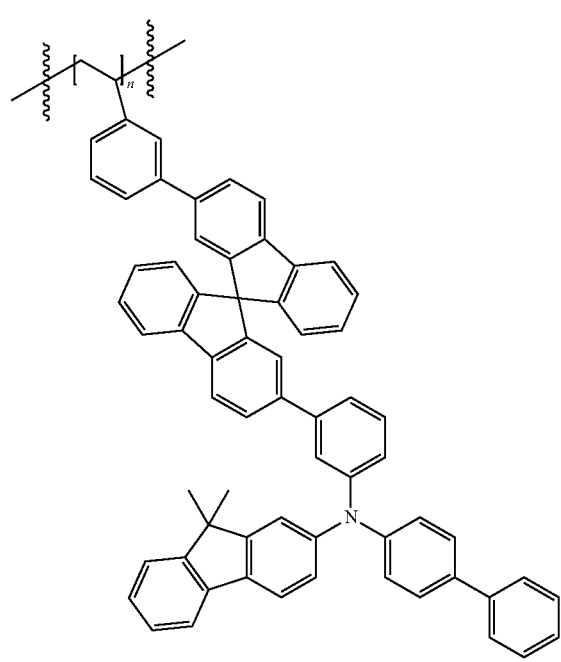
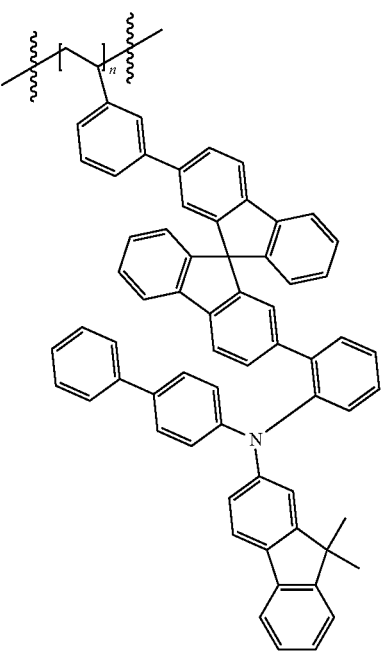

73
-continued
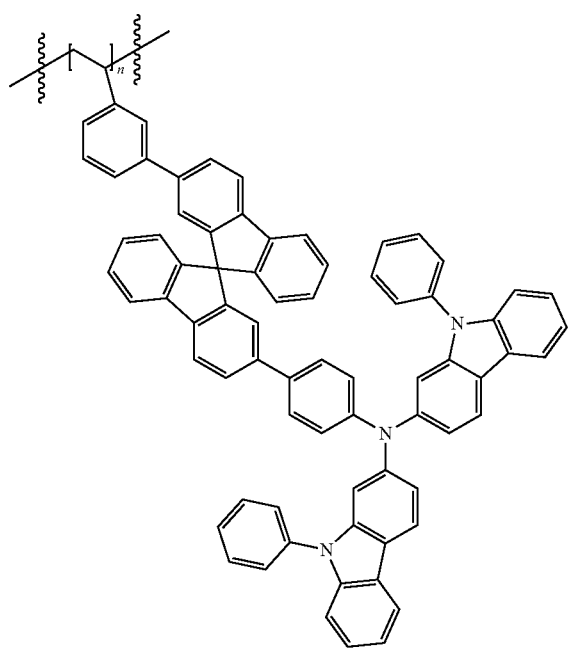
74
-continued
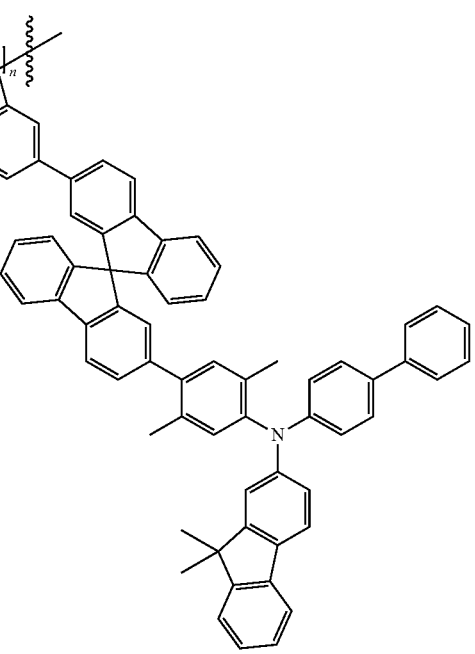
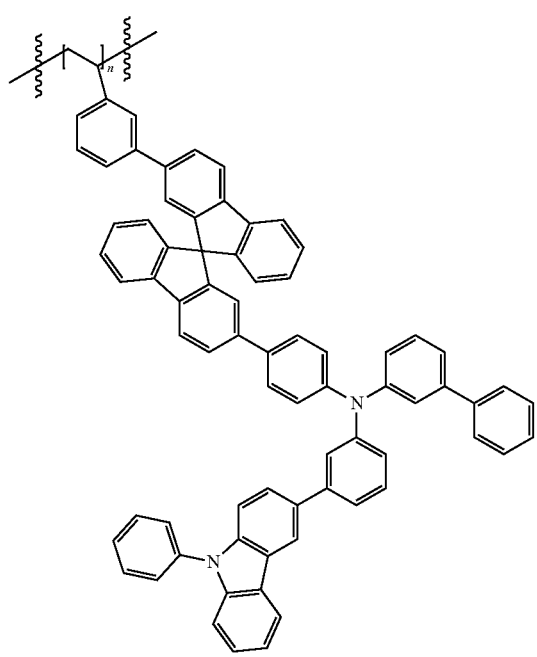
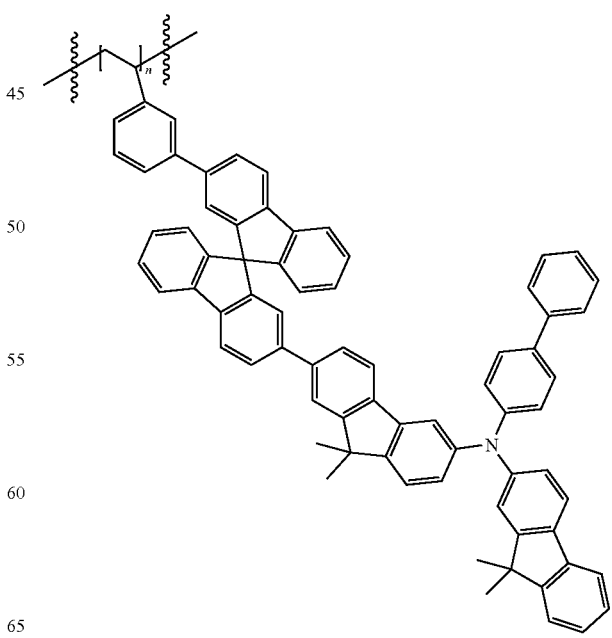

75
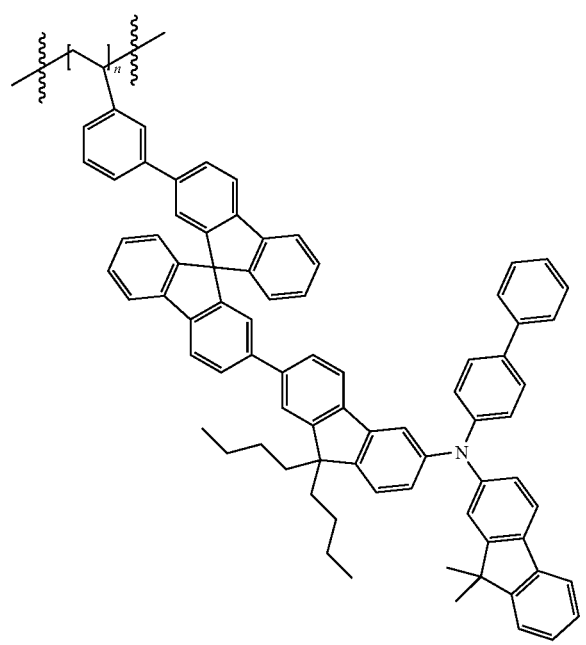
76
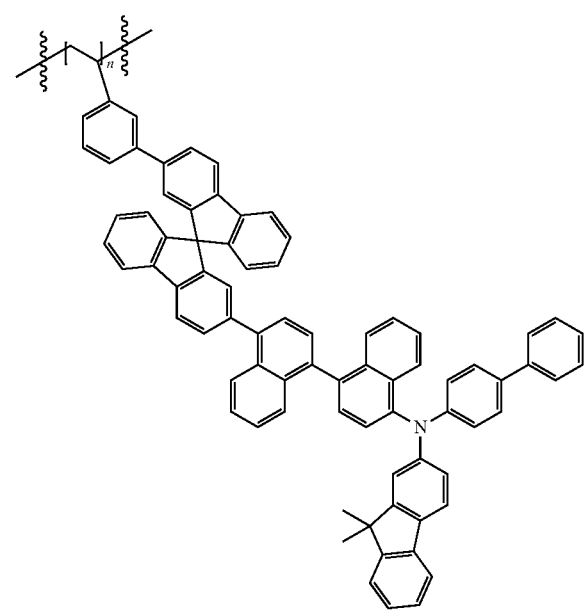
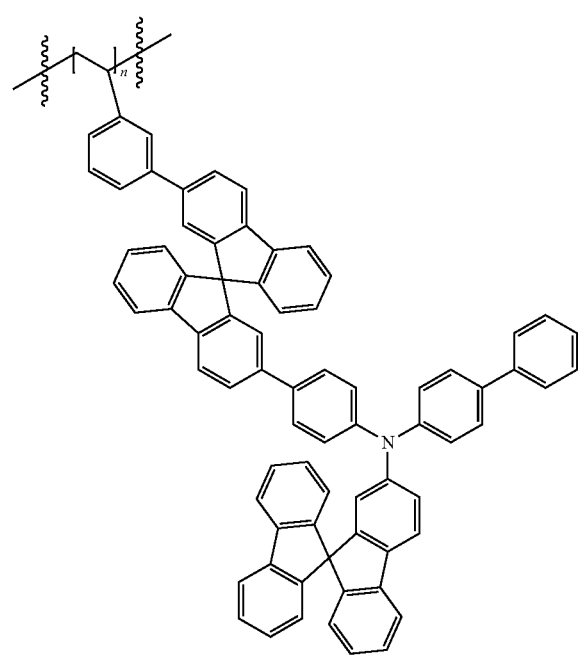
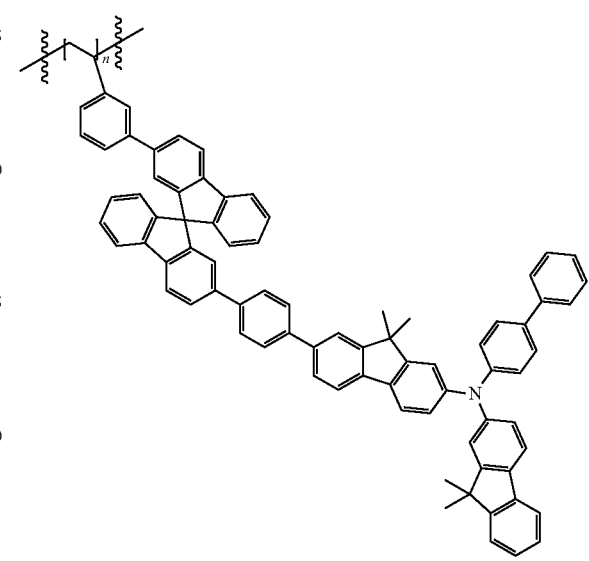

77
-continued
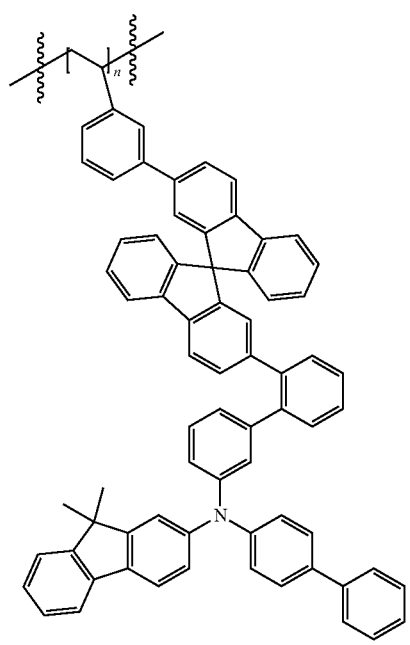
78
-continued
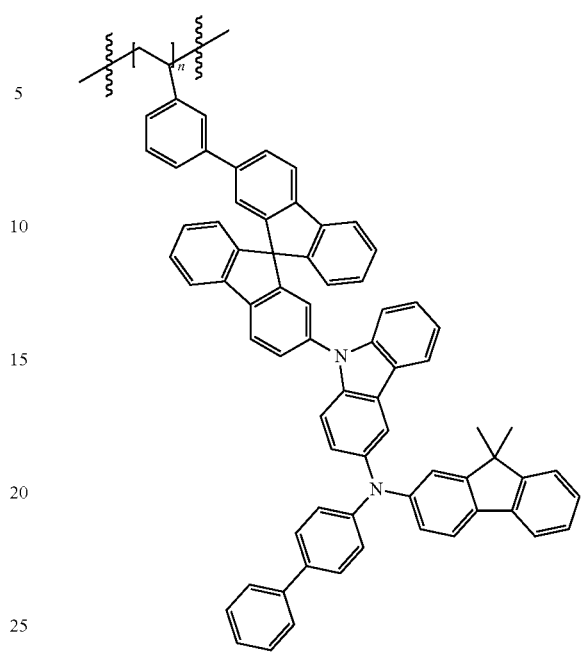
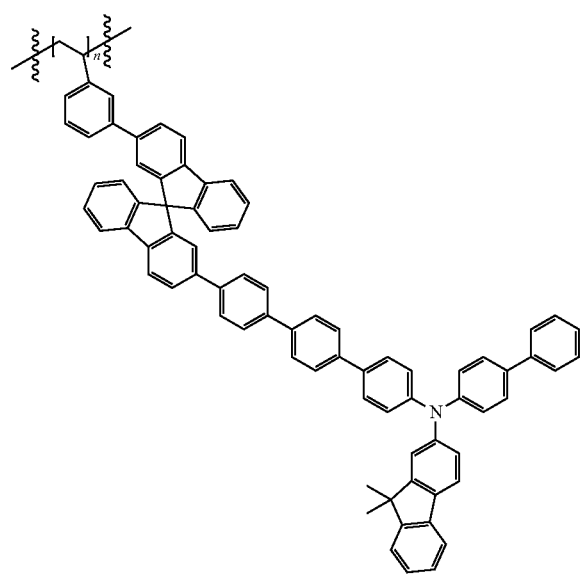
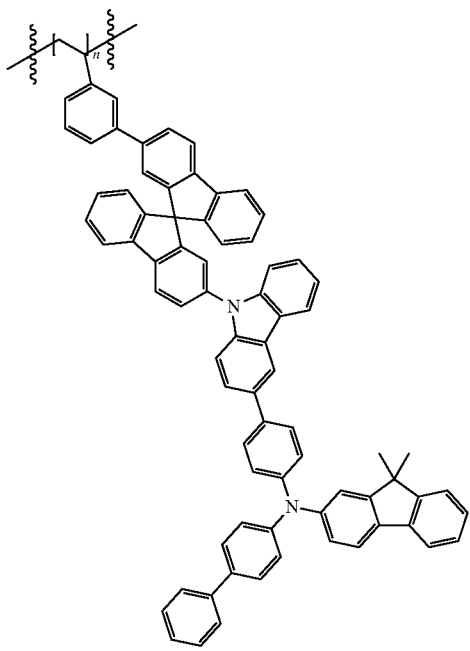

79
-continued
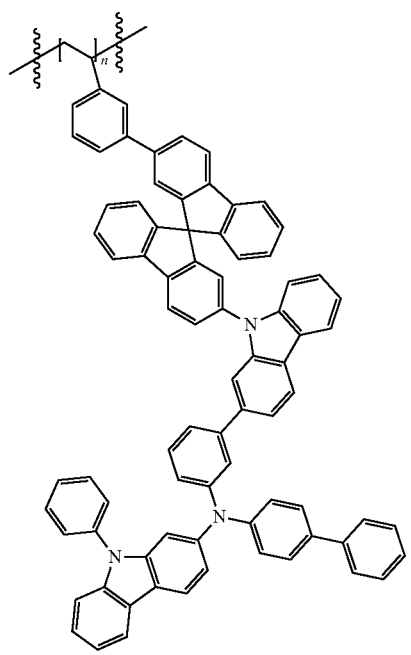
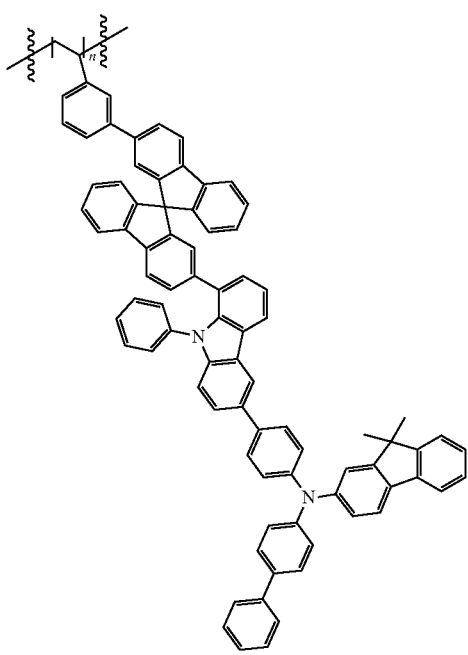
80
-continued
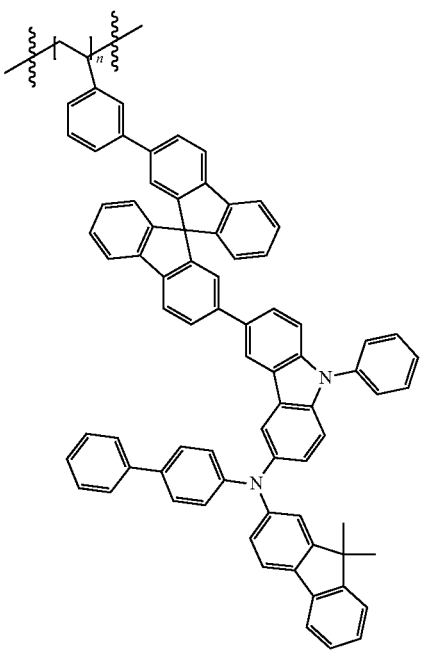
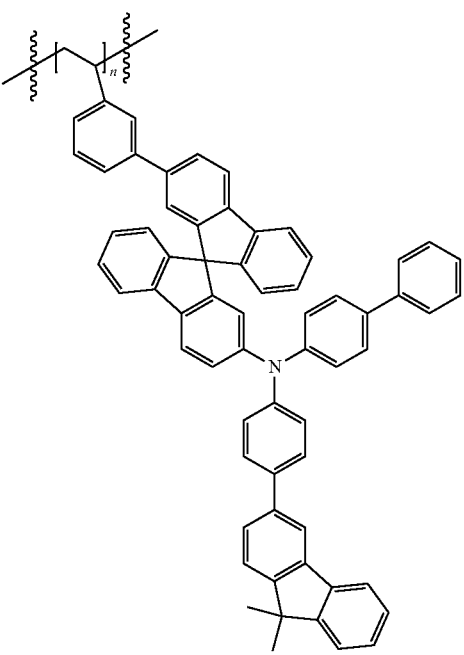

81
-continued
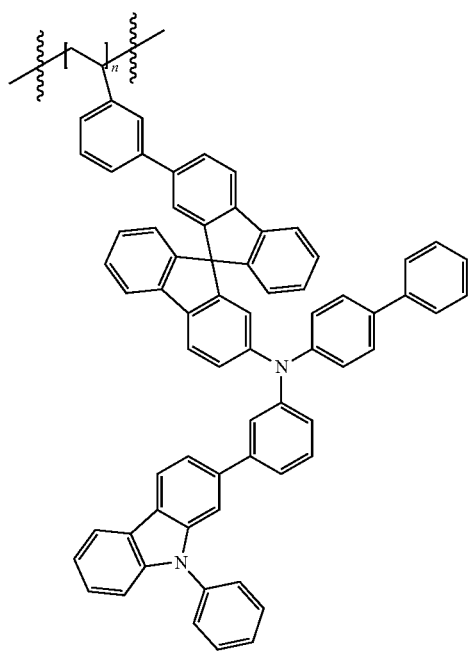
82
-continued
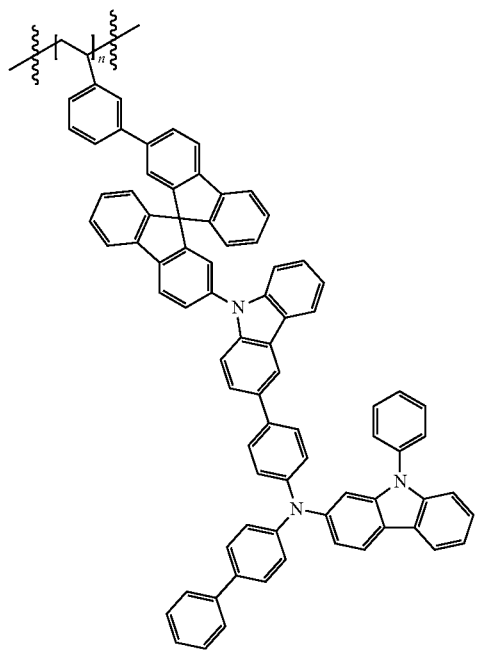
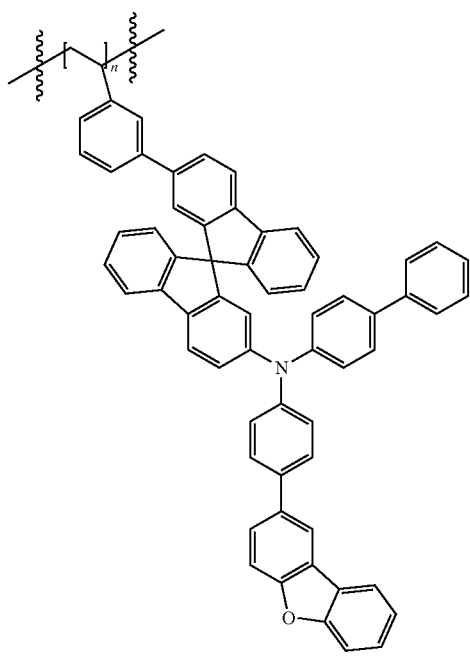
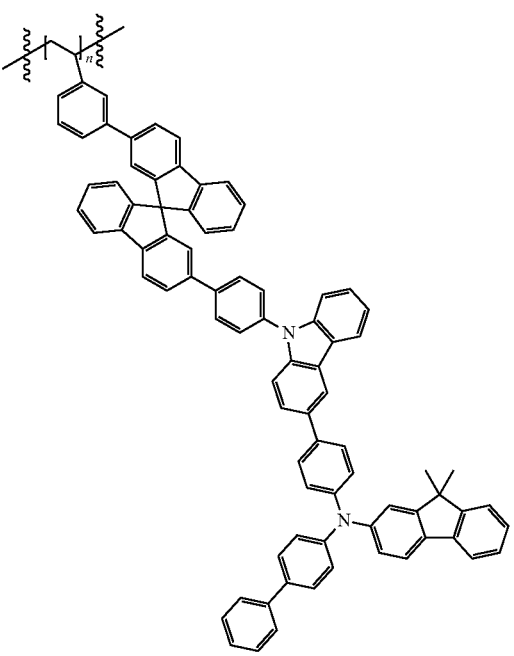

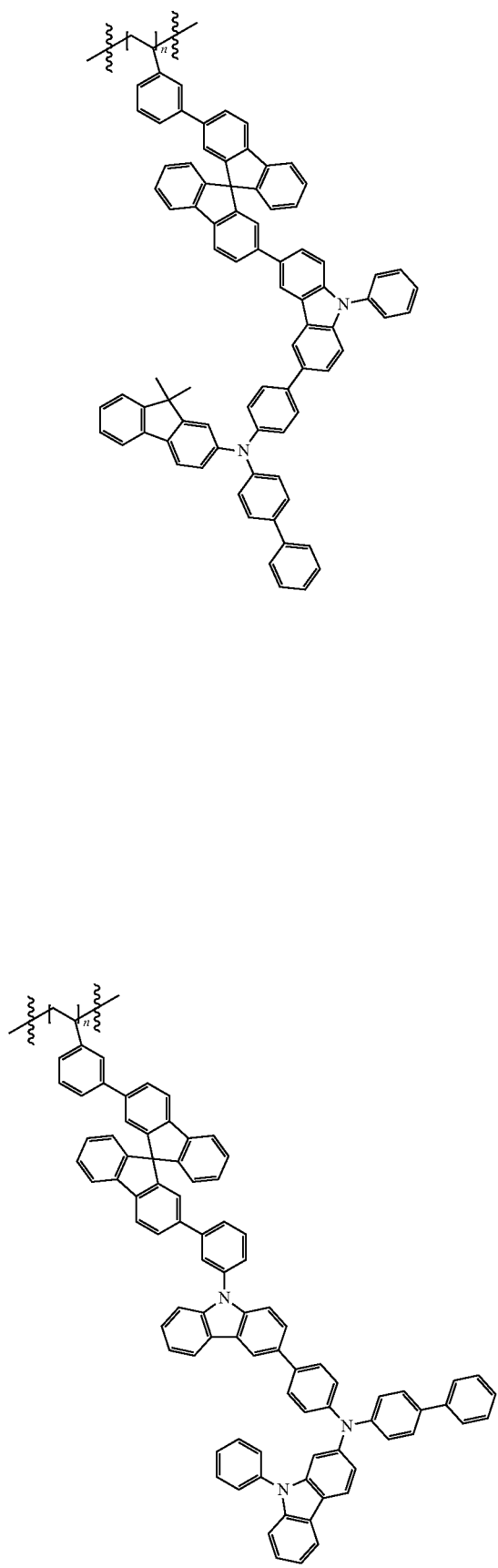
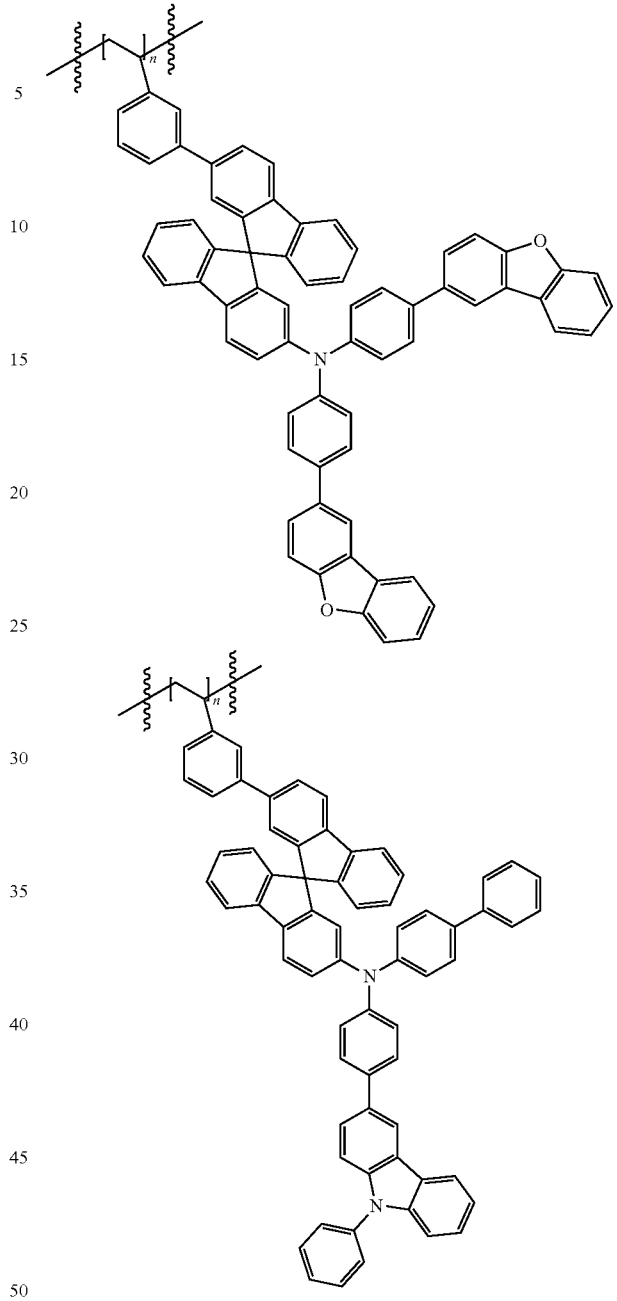

In the structures, n has the same definition as in Chemical Formula 1.

In the present specification, an end group of the polymer may be hydrogen, but is not limited thereto.

In one embodiment of the present specification, the polymer comprising the unit represented by Chemical Formula 1 has a number average molecular weight of 5,000 g/mol to 1,000,000 g/mol, and more preferably 10,000 g/mol to 300,000 g/mol. When the polymer comprising the unit represented by Chemical Formula 1 has a number average molecular weight of less than 5000 g/mol, performance of a device aimed in the present disclosure is difficult to obtain, and the number average molecular weight being greater than 1,000,000 g/mol has a problem of reducing solubility of the polymer for a solvent, and therefore, it is preferred to have the molecular weight in the above-mentioned range.

In one embodiment of the present specification, n is, as a repetition number, an integer of 4 to 200.

In one embodiment of the present specification, n is, as a repetition number, an integer of 4 to 150.

In one embodiment of the present specification, n is, as a repetition number, an integer of 4 to 100.

In one embodiment of the present specification, the polymer may have molecular weight distribution of 1 to 10. Preferably, the polymer has molecular weight distribution of 1 to 3.

In the present specification, the terms number average molecular weight (Mn) and weight average molecular weight (Mw) mean a converted molecular weight for standard polystyrene measured using gel permeation chromatography (GPC). In the present specification, the molecular weight distribution means a number obtained by dividing the weight average molecular weight (Mw) by the number average molecular weight (Mn), that is, weight average molecular weight (Mw)/number average molecular weight (Mn).

The number average molecular weight (Mn) and the molecular weight distribution may be measured as follows using gel permeation chromatography (GPC). First, the target for analysis is placed in a 5 mL vial, and diluted in tetrahydrofuran (THF) so as to have a concentration of approximately 1 mg/mL. After that, a standard sample for calibration and the sample to analyze are filtered through a syringe filter (pore size=0.45 μm), GPC is measured thereon.

As the analysis program, ChemStation of Agilent Technologies may be used, and after obtaining each of the weight average molecular weight (Mw) and the number average molecular weight (Mn) by comparing an elution time of the sample with the calibration curve, the molecular weight distribution (PDI) may be calculated from the ratio (Mw/Mn). Measurement conditions of the GPC may be as follows.

Instrument: 1200 series of Agilent Technologies
Column: use two PLgel mixed B of Polymer Laboratories
Solvent: THF
Column temperature: 40° C.
Sample concentration: 1 mg/mL, inject 100 L
Standard sample: polystyrene (Mp: 3900000, 723000, 316500, 52200, 31400, 7200, 3940, 485)

One embodiment of the present specification provides a coating composition comprising the polymer.

According to one embodiment of the present specification, the coating composition may further comprise a solvent.

In one embodiment of the present specification, the coating composition may be a liquid phase. The "liquid phase" means being in a liquid state at room temperature and atmospheric pressure.

In one embodiment of the present specification, examples of the solvent may comprise chlorine-based solvents such as chloroform, methylene chloride, 1,2-dichloroethane, 1,1,2-trichloroethane, chlorobenzene or o-dichlorobenzene; ether-based solvents such as tetrahydrofuran or dioxane; aromatic hydrocarbon-based solvents such as toluene, xylene, trimethylbenzene or mesitylene; aliphatic hydrocarbon-based solvents such as cyclohexane, methylcyclohexane, n-pentane, n-hexane, n-heptane, n-octane, n-nonane or n-decane; ketone-based solvents such as acetone, methyl ethyl ketone or cyclohexanone; ester-based solvents such as ethyl acetate, butyl acetate or ethyl cellosolve acetate; polyalcohols such as ethylene glycol, ethylene glycol monobutyl ether, ethylene glycol monoethyl ether, ethylene glycol monomethyl ether, dimethoxyethane, propylene glycol, diethoxymethane, triethylene glycol monoethyl ether, glycerin or 1,2-hexanediol, and derivatives thereof; alcohol-based solvents such as methanol, ethanol, propanol, isopropanol or cyclohexanol; sulfoxide-based solvents such as dimethyl sulfoxide; amide-based solvents such as N-methyl-2-pyrrolidone or N,N-dimethylformamide; benzoate-based solvents such as methyl benzoate, butyl benzoate or 3-phenoxybenzoate; tetraline, and the like, however, the solvent is not limited thereto as long as it is a solvent capable of dissolving or dispersing the compound according to one embodiment of the present specification.

In another embodiment, the solvent may be used either alone as one type, or as a mixture mixing two or more solvent types.

In another embodiment, viscosity of the single or mixed solvent is preferably from 1 cP to 10 cP and more preferably from 3 cP to 8 cP, but is not limited thereto.

In another embodiment, the content of the polymer comprising the unit represented by Chemical Formula 1 in the coating composition is preferably from 0.1 wt/v % to 20 wt/v % and more preferably from 0.5 wt/v % to 5 wt/v %, but is not limited thereto.

In another embodiment, the content of the monomer represented by Chemical Formula 2 in the coating composition is preferably from 0.1 wt/v % to 20 wt/v % and more preferably from 0.5 wt/v % to 5 wt/v %, but is not limited thereto.

In one embodiment of the present specification, the coating composition may further comprise one, two or more types of additives selected from the group consisting of a thermal polymerization initiator and a photopolymerization initiator.

Examples of the thermal polymerization initiator may comprise peroxides such as methyl ethyl ketone peroxide, methyl isobutyl ketone peroxide, acetylacetone peroxide, methylcyclohexanone peroxide, cyclohexanone peroxide, isobutyryl peroxide, 2,4-dichlorobenzoyl peroxide, bis-3,5,5-trimethyl hexanoyl peroxide, lauryl peroxide, benzoyl peroxide, dicumyl peroxide, 2,5-dimethyl-2,5-(t-butyloxy)-hexane, 1,3-bis(t-butylperoxy-isopropyl)benzene, t-butyl cumyl peroxide, di-t-butyl peroxide, 2,5-dimethyl-2,5-(di-t-butylperoxy)hexane, tris-(t-butylperoxy)triazine, 1,1-di-t-butylperoxy-3,3,5-trimethylcyclohexane, 1,1-di-t-butylperoxycyclohexane, 2,2-di(t-butylperoxy)butane, 4,4-di-t-butylperoxy valeric acid n-butyl ester, 2,2-bis(4,4-t-butylperoxycyclohexyl)propane, t-butyl peroxyisobutyrate, di-t-butyl peroxyhexahydroterephthalate, t-butylperoxy-3,5,5-trimethylhexate, t-butyl peroxybenzoate or di-t-butyl peroxytrimethyl adipate; or azo-based such as azobis isobutylnitrile, azobis dimethylvaleronitrile or azobis cyclohexyl nitrile, but are not limited thereto.

Examples of the photopolymerization initiator may comprise acetophenone-based or ketal-based photopolymerization initiators such as diethoxyacetophenone, 2,2-dimethoxy-1,2-diphenyl ethan-1-one, 1-hydroxy-cyclohexyl-phenyl-ketone, 4-(2-hydroxyethoxy)phenyl-(2-hydroxy-2-propyl)ketone, 2-benzyl-2-dimethylamino-1-(4-morpholinophenyl)butanone-1,2-hydroxy-2-methyl-1-phenylpropan-1-one, 2-methyl-2-morpholino(4-methylthiophenyl)propan-1-one or 1-phenyl-1,2-propanedion-2-(o-ethoxycarbonyl)oxime; benzoin ether-based photopolymerization initiators such as benzoin, benzoin methyl ether, benzoin ethyl ether, benzoin isobutyl ether or benzoin isopropyl ether; benzophenone-based photopolymerization initiators such as benzophenone, 4-hydroxybenzophenone, 2-benzoylnaphthalene, 4-benzoylbiphenyl, 4-benzoyl phenyl ether, acrylated benzophenone or 1,4-benzoylbenzene; and thioxanthone-based photopolymerization initiators such as 2-isopropylthioxanthone, 2-chlorothioxanthone, 2,4-dimethylthioxanthone, 2,4-diethylthioxanthone or 2,4-dichlorothioxanthone; and, as other photopolymerization initiators, ethyl anthraquinone, 2,4,6-trimethylbenzoyldiphenylphosphine oxide, 2,4,6-trimethylbenzoylphenylethoxyphosphine oxide, bis(2,4,6-trimethylbenzoyl)phenylphosphine oxide, bis(2,4-dimethoxybenzoyl)-2,4,4-trimethylpentylphosphine oxide, methylphenylglyoxyester, 9,10-phenanthrene, acridine-based compounds, triazine-based compounds, imidazole-based compounds, and the like, but are not limited thereto.

In one embodiment, the coating composition may further comprise a photopolymerization accelerator. Using the photopolymerization accelerator together with the photopolymerization initiator may increase a polymerization reaction rate. Examples of the photopolymerization accelerator may comprise triethanolamine, methyldiethanolamine, ethyl 4-dimethylaminobenzoate, isoamyl 4-dimethylaminobenzoate, (2-dimethylamino)ethyl benzoate, 4,4'-dimethylaminobenzophenone and the like, but are not limited thereto.

One embodiment of the present specification provides a coating composition comprising the polymer comprising the unit represented by Chemical Formula 1.

Another embodiment of the present specification provides a coating composition comprising the monomer represented by Chemical Formula 2.

In one embodiment of the present specification, the coating composition may further comprise a p-doping material.

In one embodiment of the present specification, the p-doping material comprises at least one selected from the group consisting of $F_4TCNQ$; and a boron anion.

In one embodiment of the present specification, the boron anion comprises a halogen group.

In one embodiment of the present specification, the boron anion comprises F.

In one embodiment of the present specification, the p-doping material is one, two or more types selected from among the following structural formulae.

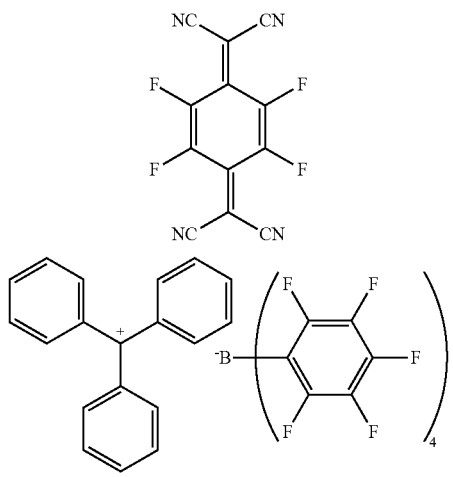

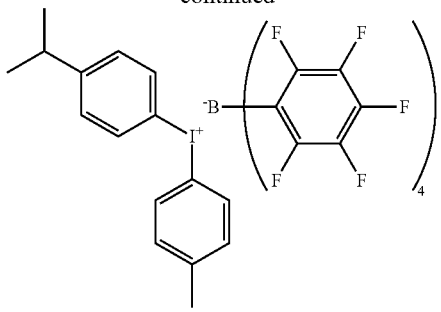

In one embodiment of the present specification, when the coating composition comprises the p-doping material, the polymer comprising the unit represented by Chemical Formula 1 and the p-doping material in the coating composition may have a weight ratio of 99:1 to 70:30, and more preferably 90:10 to 70:30.

In one embodiment of the present specification, when the coating composition comprises the p-doping material, the monomer represented by Chemical Formula 2 and the p-doping material in the coating composition may have a weight ratio of 99:1 to 70:30, and more preferably 90:10 to 70:30.

In addition, one embodiment of the present specification provides an organic light emitting device formed using the coating composition.

One embodiment of the present specification provides an organic light emitting device comprising a first electrode; a second electrode; and an organic material layer provided between the first electrode and the second electrode, wherein the organic material layer comprises the polymer comprising the unit represented by Chemical Formula 1 described above.

In one embodiment of the present specification, the first electrode is a cathode, and the second electrode is an anode.

In another embodiment, the first electrode is an anode, and the second electrode is a cathode.

In one embodiment of the present specification, the organic material layer comprising the polymer comprising the unit represented by Chemical Formula 1 is an electron blocking layer; a hole transfer layer; a hole injection layer; or a layer carrying out hole transfer and hole injection at the same time.

In another embodiment of the present specification, the organic material layer comprising the polymer comprising the unit represented by Chemical Formula 1 is a hole blocking layer; an electron transfer layer; an electron injection layer; or a layer carrying out electron transfer and electron injection at the same time.

In one embodiment of the present specification, the organic material layer may further comprise one, two or more layers selected from the group consisting of a hole injection layer; a hole transfer layer; a light emitting layer; an electron transfer layer; an electron injection layer; an electron blocking layer; and a hole blocking layer.

In another embodiment, the organic light emitting device may be an organic light emitting device having a structure in a normal direction in which an anode, one or more organic material layers and a cathode are consecutively laminated on a substrate (normal type).

In another embodiment, the organic light emitting device may be an organic light emitting device having a structure in a reverse direction in which a cathode, one or more organic material layers and an anode are consecutively laminated on a substrate (inverted type).

The organic material layer of the organic light emitting device of the present specification may be formed in a single layer structure, but may also be formed in a multilayer structure in which two or more organic material layers are laminated. For example, the organic light emitting device of the present specification may have a structure comprising a hole injection layer, a hole transfer layer, a light emitting layer, an electron transfer layer, an electron injection layer and the like as the organic material layer.

For example, a structure of the organic light emitting device according to one embodiment of the present specification is illustrated in the FIGURE.

The FIGURE illustrates a structure of the organic light emitting device in which a first electrode (201), a hole injection layer (301), a hole transfer layer (401), a light emitting layer (501), a layer carrying out electron transfer and electron injection at the same time (601) and a second electrode (701) are consecutively laminated on a substrate (101).

In one embodiment of the present specification, the hole injection layer (301) or the hole transfer layer (401) of the FIGURE may be formed using the coating composition comprising the polymer comprising the unit represented by Chemical Formula 1, or may be formed using the coating composition comprising the monomer represented by Chemical Formula 2.

In one embodiment of the present specification, the hole injection layer (301) of the FIGURE may be formed using the coating composition comprising the polymer comprising the unit represented by Chemical Formula 1, or may be formed using the coating composition comprising the monomer represented by Chemical Formula 2.

In one embodiment of the present specification, the hole transfer layer (401) of the FIGURE may be formed using the coating composition comprising the polymer comprising the unit represented by Chemical Formula 1, or may be formed using the coating composition comprising the monomer represented by Chemical Formula 2.

The FIGURE illustrates the organic light emitting device, however, the organic light emitting device is not limited thereto.

When the organic light emitting device comprises a plurality of organic material layers, the organic material layers may be formed with materials the same as or different from each other.

The organic light emitting device of the present specification may be manufactured using materials and methods known in the art, except that one or more layers of the organic material layers are formed using the coating composition according to one embodiment of the present disclosure.

For example, the organic light emitting device of the present specification may be manufactured by consecutively laminating an anode, an organic material layer and a cathode on a substrate. Herein, the organic light emitting device may be manufactured by forming an anode on a substrate by depositing a metal, a metal oxide having conductivity, or an alloy thereof using a physical vapor deposition (PVD) method such as sputtering or e-beam evaporation, forming an organic material layer comprising a hole injection layer, a hole transfer layer, a light emitting layer and an electron transfer layer thereon, and then depositing a material capable of being used as a cathode thereon. In addition to such a method, the organic light emitting device may also be manufactured by consecutively depositing a cathode material, an organic material layer and an anode material on a substrate.

Another embodiment of the present specification provides a method for manufacturing an organic light emitting device formed using the coating composition. Herein, the coating composition means the coating composition comprising the polymer comprising the unit represented by Chemical Formula 1; or the coating composition comprising the monomer represented by Chemical Formula 2.

Specifically, one embodiment of the present specification provides a method for manufacturing an organic light emitting device, the method comprising preparing a first electrode; forming one or more organic material layers on the first electrode; and forming a second electrode on the organic material layer, wherein the forming of one or more organic material layers comprises forming the organic material layer using the coating composition comprising the polymer comprising the unit represented by Chemical Formula 1 described above or the coating composition comprising the monomer represented by Chemical Formula 2 described above, and the forming of the organic material layer using the coating composition comprises coating the coating composition on the first electrode; and heat treating or light treating the coated coating composition.

In one embodiment of the present specification, the organic material layer formed using the coating composition is formed using spin coating or inkjet coating.

In another embodiment, the organic material layer formed using the coating composition is formed using a printing method.

In an embodiment of the present specification, examples of the printing method comprise inkjet printing, nozzle printing, offset printing, transfer printing, screen printing or the like, but are not limited thereto.

The coating composition according to one embodiment of the present specification is suited for a solution process due to its structural properties and may be formed using a printing method, and therefore, is economically effective in terms of time and costs when manufacturing a device.

In one embodiment of the present specification, the forming of the organic material layer using the coating composition comprises coating the coating composition on the first electrode; and heat treating or light treating the coated coating composition.

In one embodiment of the present specification, in the heat treating or light treating, the time of the heat treating is preferably within 1 hour and more preferably within 30 minutes.

In one embodiment of the present specification, in the heat treating or light treating, the atmosphere of the heat treating is preferably an inert gas atmosphere such as argon or nitrogen.

In one embodiment, when using the coating composition comprising the polymer comprising the unit represented by Chemical Formula 1 as the coating composition, the heat treating or light treating of the coated coating composition may include removing the solvent from the coated coating composition.

In one embodiment, when using the coating composition comprising the monomer represented by Chemical Formula 2 as the coating composition, the heat treating or light treating of the coated coating composition may include removing the solvent while an alkenyl group of the monomer represented by Chemical Formula 2 participates in the polymerization and forms the polymer comprising the unit represented by Chemical Formula 1.

In the forming of the organic material layer using the coating composition, the organic material layer formed through the heat treating or light treating may have a structure in which the coating composition described above is thin filmed.

In this case, the organic material layer formed using the coating composition may not be dissolved by the solvent of the organic material layer deposited on the surface, may not be morphologically influenced, or may not be decomposed.

Accordingly, the organic material layer formed using the coating composition has resistance for a specific solvent, and a multilayer may be formed by repeatedly performing a solution deposition method using the specific solvent. In this case, lifetime properties of a device are also enhanced due to increased stability of the organic material layer.

In one embodiment of the present specification, the coating composition comprising the polymer comprising the unit represented by Chemical Formula 1; or the monomer represented by Chemical Formula 2 may further comprise a polymer binder.

In one embodiment of the present specification, as the polymer binder, those that do not extremely inhibit charge transfer are preferred, and those that do not have strong absorption for visible light are preferably used. Examples of the polymer binder may comprise poly(N-vinylcarbazole), polyaniline and derivatives thereof, polythiophene and derivatives thereof, poly(p-phenylenevinylene) and derivatives thereof, poly(2,5-thienylenevinylene) and derivatives thereof, polycarbonate, polyacrylate, polymethyl acrylate, polymethyl methacrylate, polystyrene, polyvinyl chloride, polysiloxane and the like.

In addition, the organic material layer according to one embodiment of the present specification may comprise the polymer comprising the unit represented by Chemical Formula 1 alone, but may also further comprise other monomers or other polymers.

As the anode material, materials having large work function are normally preferred so that hole injection to an organic material layer is smooth. Specific examples of the anode material usable in the present specification comprise metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or SnO2:Sb; conductive polymers such as poly(3-methylthiophene), poly[3,4-(ethylene-1,2-dioxy)thiophene] (PEDOT), polypyrrole and polyaniline, and the like, but are not limited thereto.

As the cathode material, materials having small work function are normally preferred so that electron injection to an organic material layer is smooth. Specific examples of the cathode material comprise metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

The hole injection layer is a layer that injects holes from an electrode, and the hole injection material is preferably a compound that has an ability to transfer holes and thereby has a hole injection effect in an anode and an excellent hole injection effect for a light emitting layer or a light emitting material, prevents excitons generated in the light emitting layer from moving to an electron injection layer or an electron injection material, and in addition thereto, has an excellent thin film forming ability. The highest occupied molecular orbital (HOMO) of the hole injection material is preferably in between the work function of an anode material and the HOMO of surrounding organic material layers. Specific examples of the hole injection material comprise metal porphyrins, oligothiophene, arylamine-based organic materials, hexanitrile hexaazatriphenylene-based organic materials, quinacridone-based organic materials, perylene-based organic materials, anthraquinone, and polyaniline- and polythiophene-based conductive polymers, and the like, but are not limited thereto.

The hole transfer layer is a layer that receives holes from a hole injection layer and transfers the holes to a light emitting layer, and, when the organic light emitting device comprises an additional hole transfer layer in addition to the hole transfer layer comprising the polymer comprising the unit represented by Chemical Formula 1, materials capable of receiving holes from an anode or a hole injection layer, moving the holes to a light emitting layer, and having high mobility for the holes are suited as the hole transfer material. Specific examples thereof comprise arylamine-based organic materials, conductive polymers, block copolymers having conjugated parts and non-conjugated parts together, and the like, but are not limited thereto.

The electron blocking layer is a layer capable of enhancing device lifetime and efficiency by preventing electrons injected from an electron injection layer from entering a hole injection layer after passing through a light emitting layer, and as necessary, may be formed in a proper part between the light emitting layer and the hole injection layer using known materials.

The light emitting material is a material capable of emitting light in a visible light region by receiving holes and electrons from a hole transfer layer and an electron transfer layer, respectively, and binding the holes and the electrons, and is preferably a material having favorable quantum efficiency for fluorescence or phosphorescence. Specific examples thereof comprise 8-hydroxyquinoline aluminum complexes (Alq3); carbazole-based compounds; dimerized styryl compounds; BAlq; 10-hydroxybenzoquinoline-metal compounds; benzoxazole-, benzothiazole- and benzimidazole-based compounds; poly(p-phenylenevinylene) (PPV)-based polymers; spiro compounds; polyfluorene, rubrene, or the like, but are not limited thereto.

The light emitting layer may comprise a host material and a dopant material. The host material comprises fused aromatic ring derivatives, heteroring-containing compounds or the like. Specifically, the fused aromatic ring derivative comprises anthracene derivatives, pyrene derivatives, naphthalene derivatives, pentacene derivatives, phenanthrene compounds, fluoranthene compounds and the like, and the heteroring-containing compound comprises carbazole derivatives, dibenzofuran derivatives, ladder-type furan compounds, pyrimidine derivatives and the like, however, the material is not limited thereto.

The dopant material comprises aromatic amine derivatives, styrylamine compounds, boron complexes, fluoranthene compounds, metal complexes and the like. Specifically, the aromatic amine derivative is a fused aromatic ring derivative having a substituted or unsubstituted arylamine group and comprises arylamine group-including pyrene, anthracene, chrysene, peryflanthene and the like, and the styrylamine compound is a compound in which substituted or unsubstituted arylamine is substituted with at least one arylvinyl group, and compounds in which one, two or more substituents selected from the group consisting of an aryl group, a silyl group, an alkyl group, a cycloalkyl group and an arylamine group are substituted or unsubstituted may be used. Specifically, styrylamine, styryldiamine, styryltriamine, styryltetramine or the like is included, however, the styrylamine compound is not limited thereto. In addition, the metal complex comprises iridium complexes, platinum complexes or the like, but is not limited thereto.

The electron transfer layer is a layer that receives electrons from an electron injection layer and transfers the electrons to a light emitting layer, and as the electron transfer material, materials capable of favorably receiving electrons from a cathode, moving the electrons to a light emitting layer, and having high mobility for the electrons are suited. Specific examples thereof comprise Al complexes of 8-hydroxyquinoline; complexes comprising Alq3; organic radical compounds; hydroxyflavon-metal complexes, or the like, but are not limited thereto. The electron transfer layer may be used together with any desired cathode material as used in the art. Particularly, examples of the suitable cathode material comprise common materials that have small work function, and in which an aluminum layer or a silver layer follows. Specifically, the cathode material comprises cesium, barium, calcium, ytterbium and samarium, and in each case, an aluminum layer or a silver layer follows.

The electron injection layer is a layer that injects electrons from an electrode, and the electron injection material is preferably a compound that has an ability to transfer electrons, has an electron injection effect from a cathode, has an excellent electron injection effect for a light emitting layer or a light emitting material, prevents excitons generated in the light emitting layer from moving to a hole injection layer, and in addition thereto, has an excellent thin film forming ability. Specific examples thereof comprise fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, metal complex compounds, nitrogen-containing 5-membered ring derivatives, and the like, but are not limited there.

The metal complex compound comprises 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato) gallium, bis(10-hydroxybenzo[h]quinolinato)beryllium, bis(10-hydroxybenzo[h]quinolinato) zinc, bis(2-methyl-8-quinolinato) chlorogallium, bis(2-methyl-8-quinolinato) (o-cresolato) gallium, bis(2-methyl-8-quinolinato) (1-naphtholato)aluminum, bis(2-methyl-8-quinolinato) (2-naphtholato)gallium and the like, but is not limited thereto.

In the present specification, as the material of the layer carrying out electron transfer and electron injection at the same time, the materials of the electron injection layer and the electron transfer layer described above may be used without limit.

In the present specification, as the material of the layer carrying out hole transfer and hole injection at the same time, the materials of the hole injection layer and the hole transfer layer described above may be used without limit.

The hole blocking layer is a layer blocking holes from reaching a cathode, and specific examples of the hole blocking layer material comprise oxadiazole derivatives or triazole derivatives, phenanthroline derivatives, aluminum complexes and the like, but are not limited thereto.

The organic light emitting device according to the present specification may be a top-emission type, a bottom-emission type or a dual-emission type depending on the materials used.

Hereinafter, the present specification will be described in detail with reference to examples in order to specifically describe the present specification. However, examples according to the present specification may be modified to various different forms, and the scope of the present specification is not to be construed as being limited to the examples described below. Examples of the present specification are provided in order to more fully describe the present specification to those having average knowledge in the art.

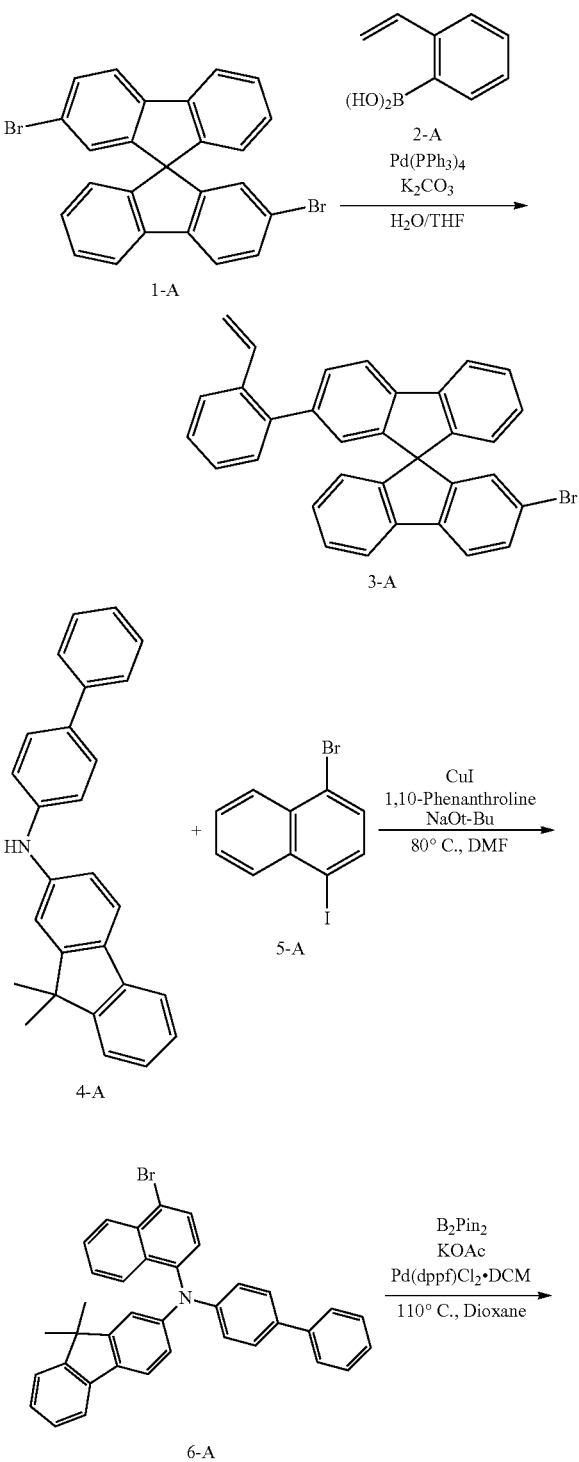

Synthesis of Monomer 1

-continued

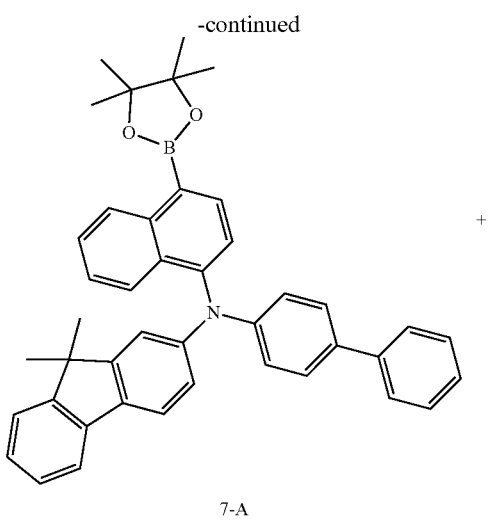

7-A

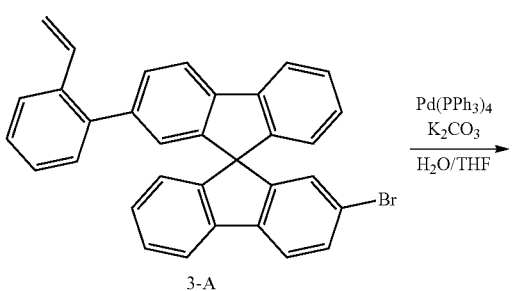

3-A

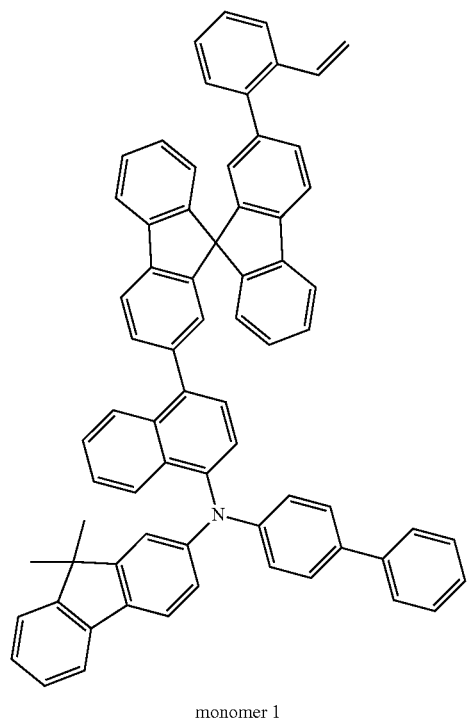

monomer 1

Synthesis of Compound 3-A

Compound 1-A (50 g, 105.4 mmol, 1 eq.) and Compound 2-A (31.2 g, 211 mmol, 2 eq.) were dissolved in tetrahydrofuran (THF) (300 g), and stirred for 10 minutes in a 80° C. silicone bath. $K_2CO_3$ (37.89 g, 274 mmol, 2.6 eq.) dissolved in water (300 mL) was added dropwise thereto for 10 minutes. A Pd catalyst (3.66 g, 3.2 mmol, 0.03 eq.) was introduced thereto under reflux. The result was stirred for 2 hours, then washed with ethyl acetate (EA)/$H_2O$ to separate the organic layer, and the solvent was vacuum dried. The result was purified by column chromatography through n-hexane (n-Hex) and ethyl acetate (EA), and then recrystallized with tetrahydrofuran (THF) and ethanol to obtain white solid Compound 3-A.

Synthesis of Compound 6-A

Compound 4-A (17.24 g, 47.7 mmol, 1.0 eq.), Compound 5-A (19.07 g, 57.26 mmol, 1.2 eq.) NaOt-Bu (6.42 g, 66.8 mmol, 1.4 eq.) and 1,10-phenanthroline (1.72 g, 9.54 mmol, 0.2 eq.) were dissolved in DMF (140 mL), and stirred for 10 minutes in a 80° C. silicone bath. CuI (0.91 g, 4.77 mmol, 10 mol %) was introduced thereto, and the result was stirred for 12 hours. The result was washed with ethyl acetate (EA)/$H_2O$ to separate the organic layer, and the solvent was vacuum dried. The result was purified by medium pressure liquid chromatography (MPLC) through n-hexane (n-Hex) and ethyl acetate (EA), and then recrystallized with n-hexane (n-Hex) to obtain Compound 6-A.

Synthesis of Compound 7-A

Compound 6-A (11.90 g, 21 mmol, 1.0 eq.) and $B_2Pin_2$ (13.3 g, 52.4 mmol, 2.5 eq.) were dissolved in 1,4-dioxane (300 mL), and stirred for 10 minutes in a 80° C. silicone bath. KOAc (8.86 g, 90.3 mmol, 4.3 eq.) and Pd (pddf) $Cl_2 \cdot DCM$ (1.38 g, 1.89 mmol, 0.09 eq.) were introduced thereto. The result was stirred for 12 hours in a 110° C. silicone bath, then washed with ethyl acetate (EA)/$H_2O$ to separate the organic layer, and the solvent was vacuum dried. The result was purified by medium pressure liquid chromatography (MPLC) through n-hexane (n-Hex) and dichloromethane (DCM), and then recrystallized with n-hexane (n-Hex) to obtain Compound 7-A.

Synthesis of Monomer 1

Compound 3-A (2.49 g, 5 mmol, 1 eq.) and Compound 7-A (3.68 g, 6 mmol, 1.2 eq.) were dissolved in tetrahydrofuran (THF) (20 ml), and stirred for 30 minutes in a 80° C. silicone bath. $K_2CO_3$ (5.1 g, 37 mmol, 1.75 eq.) dissolved in water (40 mL) was added dropwise thereto for 10 minutes while maintaining an inner temperature of the solution at 65° C. A Pd catalyst (0.077 g, 0.15 mmol, 0.03 eq.) was introduced thereto under reflux. The result was stirred for 1 hour, then washed with ethyl acetate (EA)/$H_2O$ to separate the organic layer, and the solvent was vacuum dried. The result was purified by column chromatography through n-hexane (n-Hex) and dichloromethane (DCM), and then recrystallized with n-hexane (n-Hex) to obtain Monomer 1 (4.01 g, MS: $[M+H]^+=903$).

Synthesis of Monomer 2

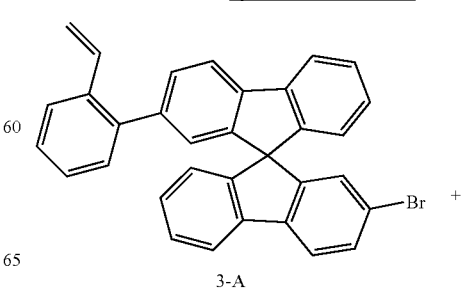

3-A

-continued

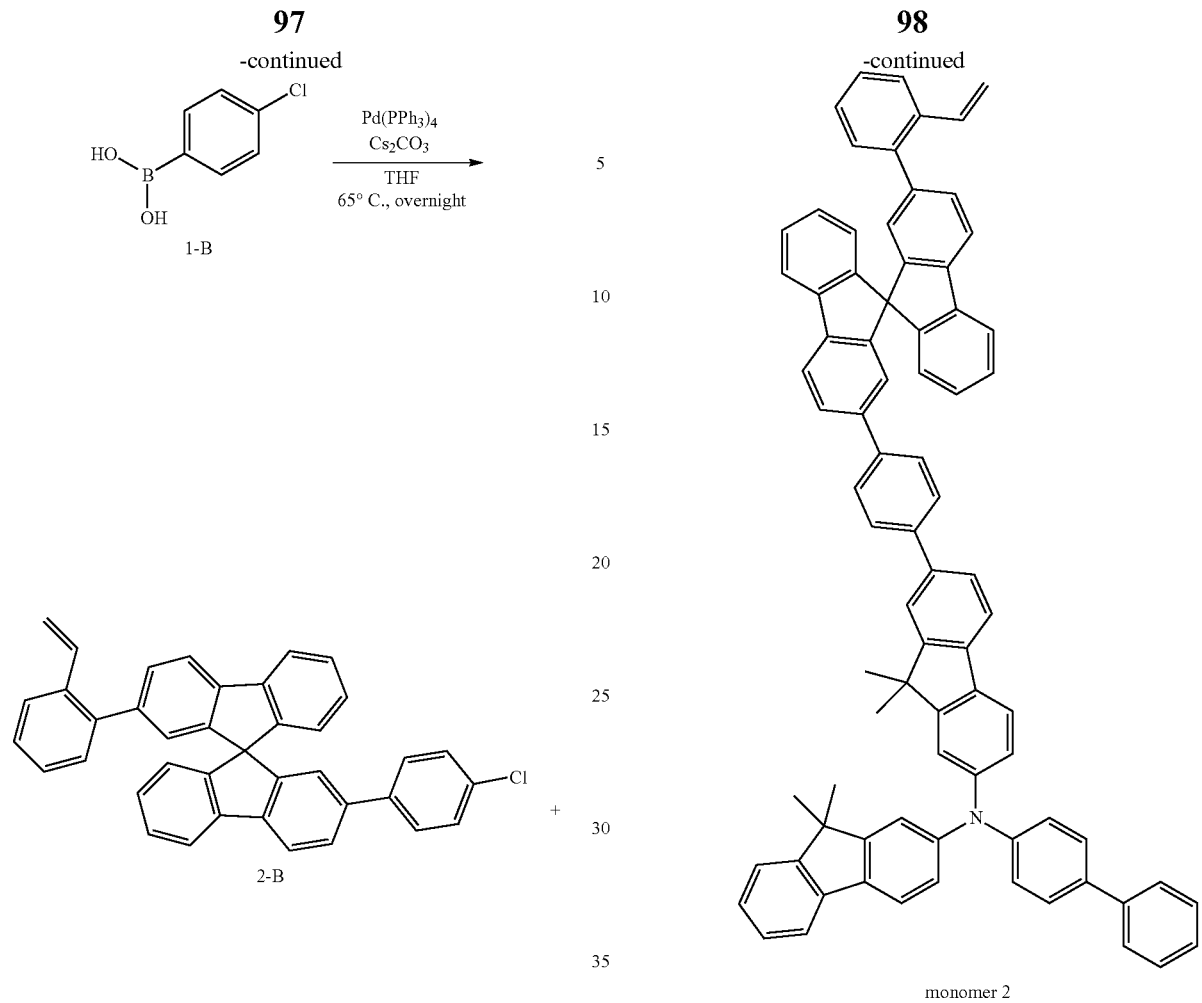

monomer 2

Synthesis of Compound 2-B

Compound 3-A (13.2 g, 26.6 mmol, 1.0 eq.) and Compound 1-B (4.58 g, 29.3 mmol, 1.1 eq.) were dissolved in tetrahydrofuran (THF) (100 mL), and stirred for 10 minutes in a 80° C. silicone bath. $Cs_2CO_3$ (43.4 g, 133 mmol, 5.0 eq.) dissolved in water (90 mL) was added dropwise thereto for 10 minutes. $Pd(PPh_3)_4$ (1.54 g, 1.33 mol, 0.05 eq.) was introduced thereto under reflux. The result was stirred for 12 hours in a 65° C. silicone bath, then washed with ethyl acetate (EA)/$H_2O$ to separate the organic layer, and the solvent was vacuum dried. The result was purified by medium pressure liquid chromatography (MPLC) through n-hexane (n-Hex) and ethyl acetate (EA), and then recrystallized with n-hexane (n-Hex) to obtain Compound 2-B.

Synthesis of Monomer 2

Compound 2-B (3.6 g, 6 mmol, 1 eq.) and Compound 3-B (4.49 g, 6.6 mmol, 1.1 eq.) were dissolved in tetrahydrofuran (THF) (36 ml), and stirred for 10 minutes in a 80° C. silicone bath. $K_2CO_3$ (2.15 g, 15 mmol, 2.6 eq.) dissolved in water (30 mL) was added dropwise thereto for 10 minutes. A Pd catalyst (0.092 g, 0.18 mmol, 0.03 eq.) was introduced thereto under reflux. The result was stirred for 6 hours, then washed with ethyl acetate (EA)/$H_2O$ to separate the organic layer, and the solvent was vacuum dried. The result was purified by column chromatography through n-hexane (n-Hex) and dichloromethane (DCM), and then recrystallized with n-hexane (n-Hex) to obtain white solid Monomer 2 (4.2 g, MS: $[M+H]^+$=1045).

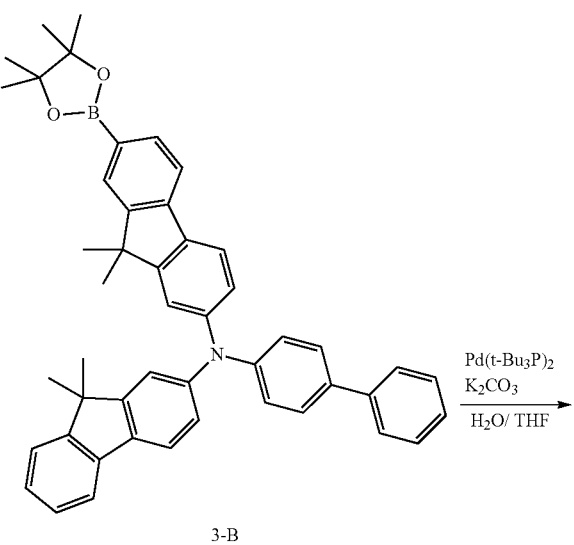

Synthesis of Monomer 3

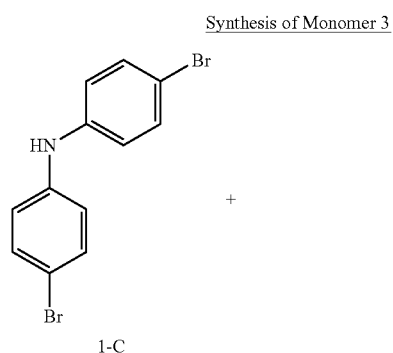

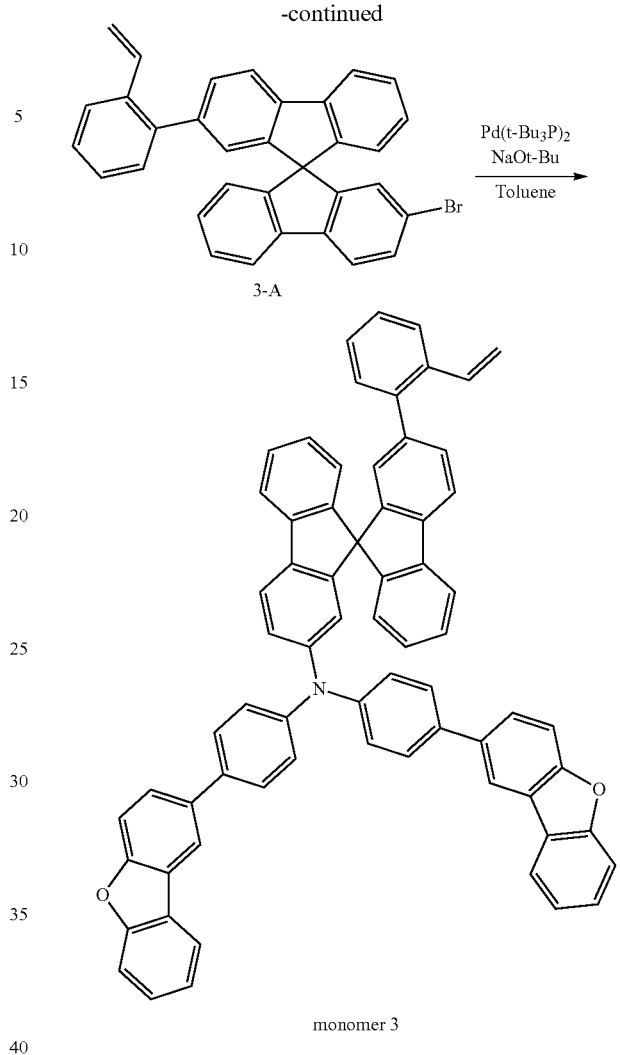

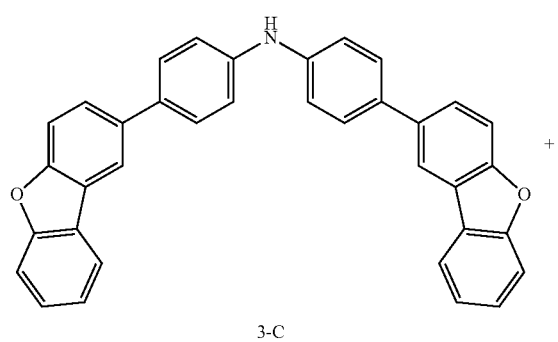

Synthesis of Compound 3-C

Compound 1-C (19.93 g, 60.95 mmol, 1.0 eq.) and Compound 2-C (37.65 g, 128 mmol, 2.10 eq.) were dissolved in tetrahydrofuran (THF) (200 mL), and stirred for 10 minutes in a 80° C. silicone bath. $K_2CO_3$ (21.9 g, 158 mmol, 2.6 eq.) dissolved in water (87 mL) was added dropwise thereto for 10 minutes. A Pd catalyst (2.11 g, 1.8 mmol, 0.03 eq.) was introduced thereto under reflux. The result was stirred for 12 hours, then washed with ethyl acetate (EA)/$H_2O$ to separate the organic layer, and the solvent was vacuum dried. The result was purified by medium pressure liquid chromatography (MPLC) through n-hexane (n-Hex) and ethyl acetate (EA), and then recrystallized with n-hexane (n-Hex) to obtain Compound 3-C.

Synthesis of Monomer 3

Compound 3-C (3.01 g, 6 mmol, 1 eq.) and Compound 3-A (3.28 g, 6.6 mmol, 1.1 eq.) were dissolved in anhydrous toluene (15 g), and stirred for 10 minutes in a 130° C. silicone bath. Sodium tert-butoxide (NaOt-Bu) (1.45 g, 15 mmol, 2.5 eq.) was introduced thereto. A Pd catalyst (0.077 g, 0.15 mmol, 0.03 eq.) was introduced thereto under reflux. The result was stirred for 1 hour, then washed with ethyl acetate (EA)/$H_2O$ to separate the organic layer, and the solvent was vacuum dried. The result was purified by column chromatography through n-hexane (n-Hex) and dichloromethane (DCM), and then recrystallized with n-hexane (n-Hex) to obtain white solid Monomer 3 (5.3 g, MS: [M+H]⁺=917).

Synthesis of Monomer 4

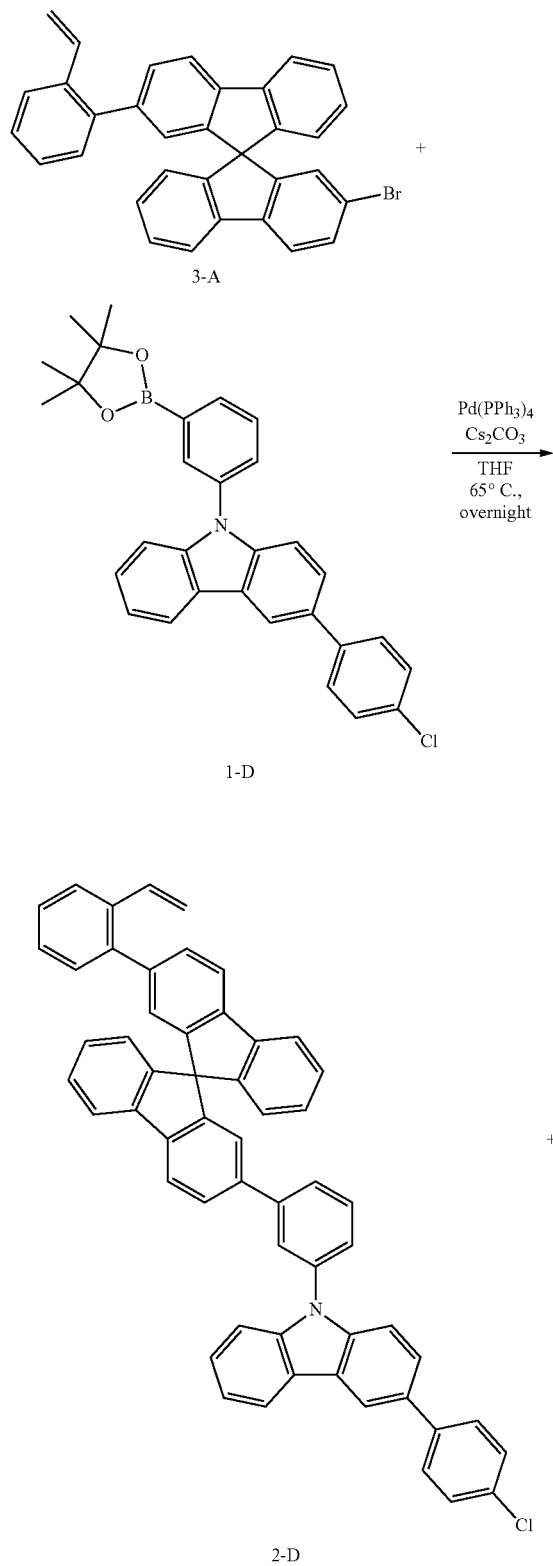

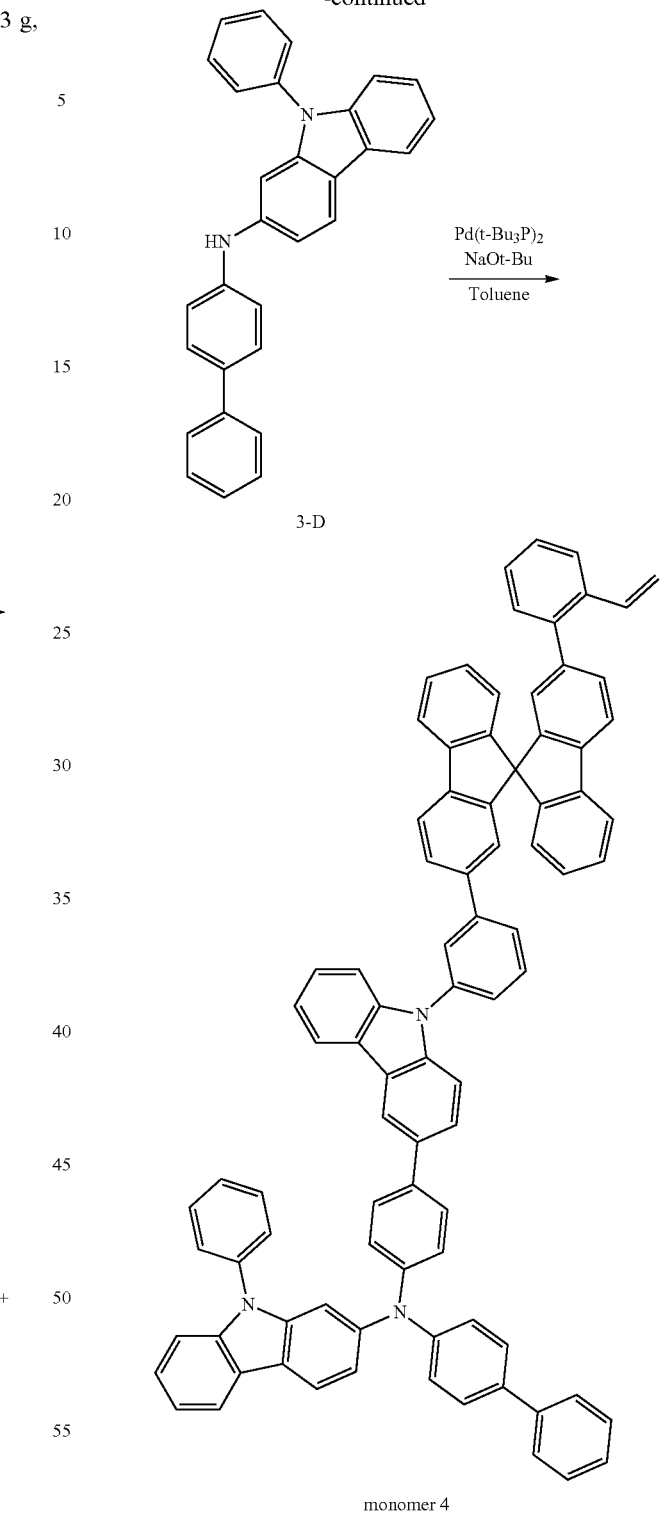

Synthesis of Compound 2-D

Compound 3-A (13.2 g, 26.6 mmol, 1.0 eq.) and Compound 1-D (14.06 g, 29.3 mmol, 1.1 eq.) were dissolved in tetrahydrofuran (THF) (100 mL), and stirred for 10 minutes in a 80° C. silicone bath. $Cs_2CO_3$ (43.4 g, 133 mmol, 5.0 eq.) dissolved in water (90 mL) was added dropwise thereto for 10 minutes. $Pd(PPh_3)_4$ (1.54 g, 1.33 mol, 0.05 eq.) was introduced thereto under reflux. The result was stirred for 12 hours in a 65° C. silicone bath, then washed with ethyl acetate (EA)/H₂O to separate the organic layer, and the solvent was vacuum dried. The result was purified by medium pressure liquid chromatography (MPLC) through n-hexane (n-Hex) and ethyl acetate (EA), and then recrystallized with n-hexane (n-Hex) to obtain Compound 2-D.

Synthesis of Monomer 4

Compound 3-D (2.5 g, 6 mmol, 1 eq.) and Compound 2-D (5.08 g, 6.6 mmol, 1.1 eq.) were dissolved in anhydrous toluene (36 ml), and stirred for 10 minutes in a 130° C. silicone bath. Sodium tert-butoxide (NaOt-Bu) (1.45 g, 15 mmol, 2.5 eq.) was introduced thereto. A Pd catalyst (0.15 g, 0.3 mmol, 0.05 eq.) was introduced thereto under reflux. The result was stirred for 1 hour, then washed with ethyl acetate (EA)/H₂O to separate the organic layer, and the solvent was vacuum dried. The result was purified by column chromatography through n-hexane (n-Hex) and dichloromethane (DCM), and then recrystallized with n-hexane (n-Hex) to obtain white solid Monomer 4 (6.1 g, MS: [M+H]$^+$=1143).

Synthesis of Monomer 5

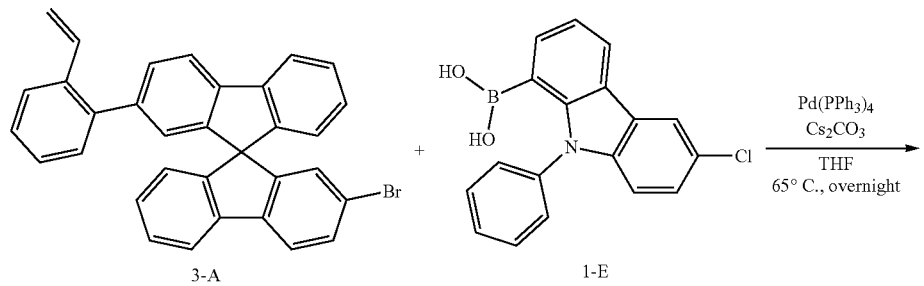

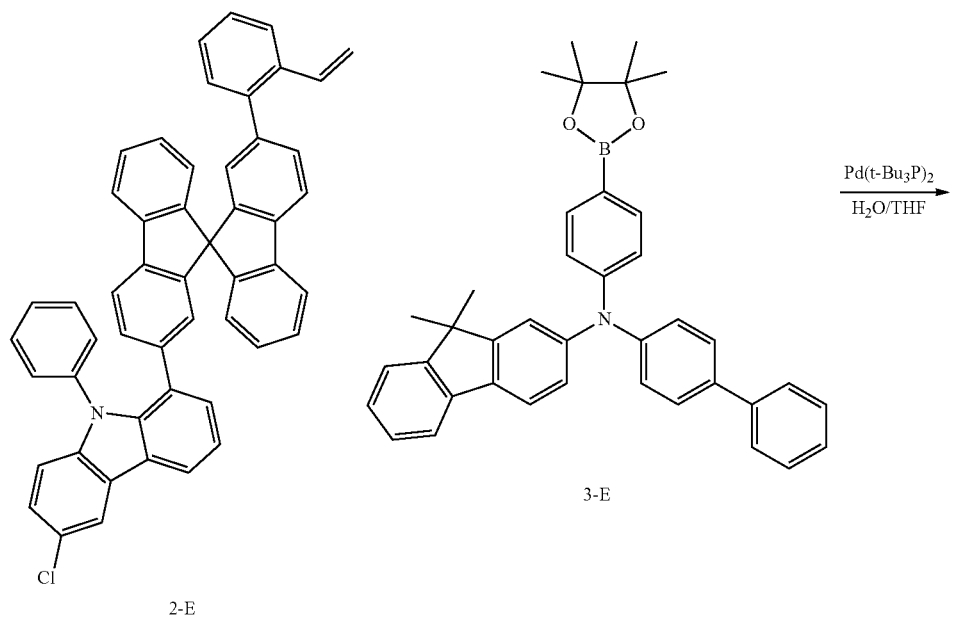

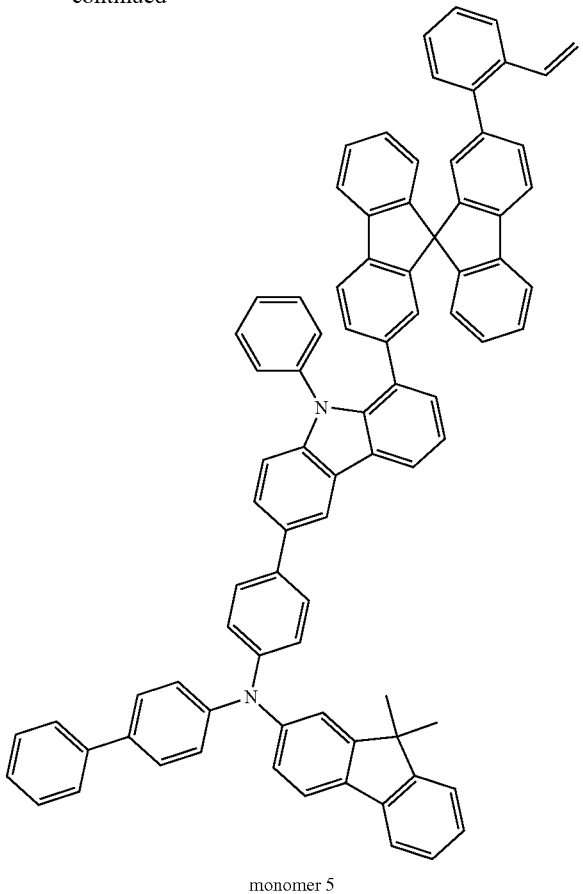

monomer 5

Synthesis of Compound 2-E

Compound 3-A (13.2 g, 26.6 mmol, 1.0 eq.) and Compound 1-E (9.42 g, 29.3 mmol, 1.1 eq.) were dissolved in tetrahydrofuran (THF) (100 mL), and stirred for 10 minutes in a 80° C. silicone bath. $Cs_2CO_3$ (43.4 g, 133 mmol, 5.0 eq.) dissolved in water (90 mL) was added dropwise thereto for 10 minutes. $Pd(PPh_3)_4$ (1.54 g, 1.33 mol, 0.05 eq.) was introduced thereto under reflux. The result was stirred for 12 hours in a 65° C. silicone bath, then washed with ethyl acetate (EA)/$H_2O$ to separate the organic layer, and the solvent was vacuum dried. The result was purified by medium pressure liquid chromatography (MPLC) through n-hexane (n-Hex) and ethyl acetate (EA), and then recrystallized with n-hexane (n-Hex) to obtain Compound 2-E.

Synthesis of Monomer 5

Compound 2-E (3.47 g, 5 mmol, 1 eq.) and Compound 3-E (3.10 g, 5.5 mmol, 1.1 eq.) were dissolved in tetrahydrofuran (THF) (20 ml), and stirred for 30 minutes in a 70° C. silicone bath. $K_2CO_3$ (5.1 g, 37 mmol, 1.75 eq.) dissolved in water (40 mL) was added dropwise thereto for 10 minutes while maintaining an inner temperature of the solution at 45° C. or higher. A Pd catalyst (0.077 g, 0.15 mmol, 0.03 eq.) was introduced thereto under reflux. The result was stirred for 3 hours, then washed with ethyl acetate (EA)/$H_2O$ to separate the organic layer, and the solvent was vacuum dried. The result was purified by column chromatography through n-hexane (n-Hex) and dichloromethane (DCM), and then recrystallized with n-hexane (n-Hex) to obtain Monomer 5 (4.2 g, MS: $[M+H]^+$=1094).

Synthesis of Monomer 6

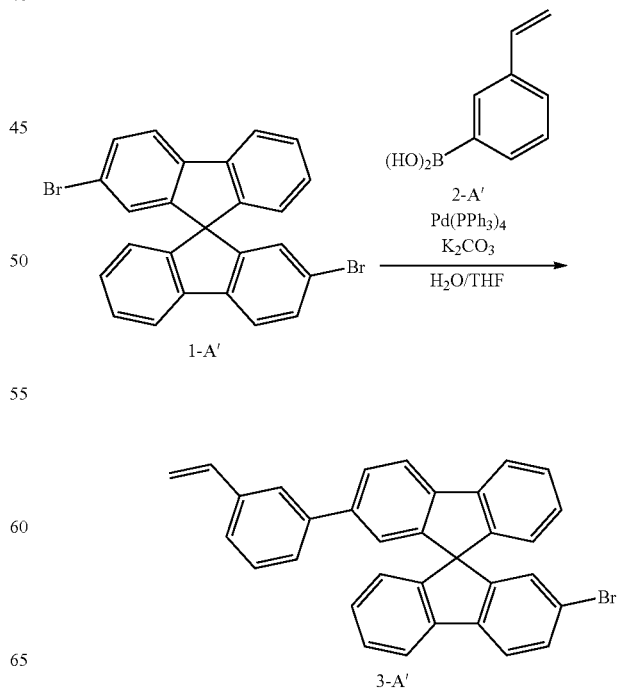

-continued

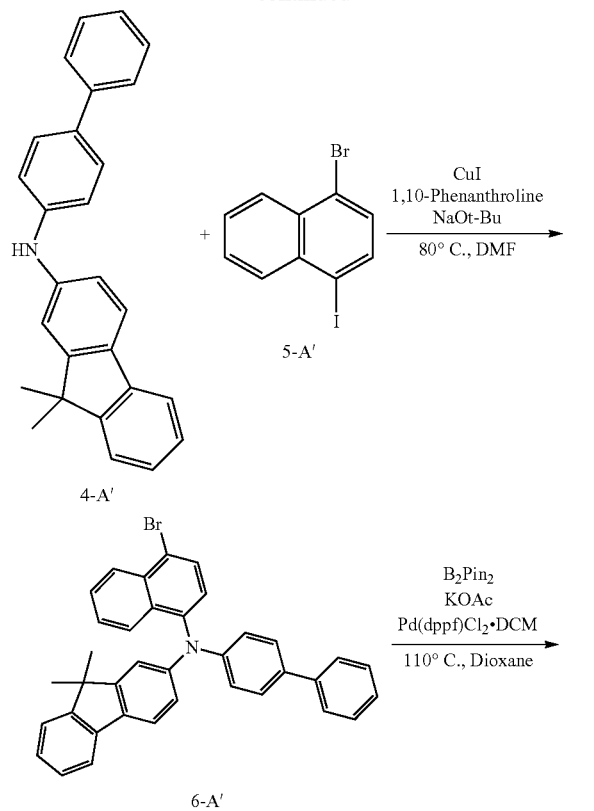

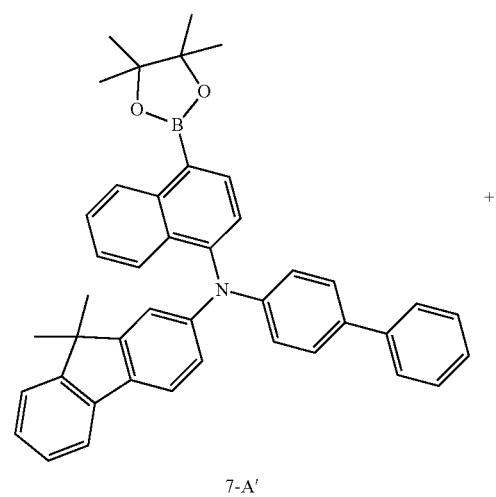

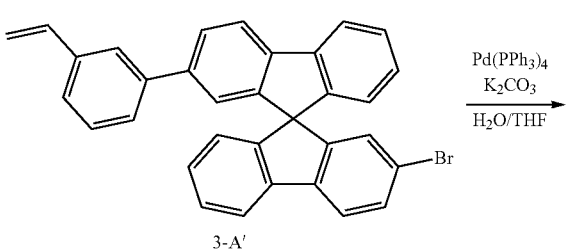

-continued

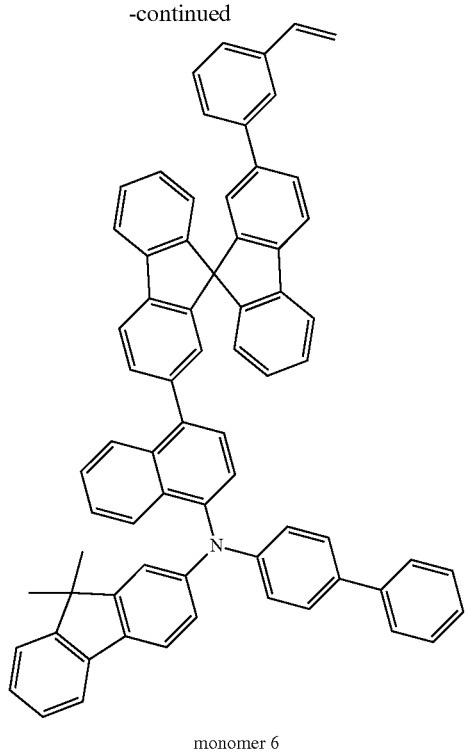

monomer 6

Synthesis of Compound 3-A'

Compound 1-A' (50 g, 105.4 mmol, 1 eq.) and Compound 2-A' (31.2 g, 211 mmol, 2 eq.) were dissolved in tetrahydrofuran (THF) (300 g), and stirred for 10 minutes in a 80° C. silicone bath. $K_2CO_3$ (37.89 g, 274 mmol, 2.6 eq.) dissolved in water (300 mL) was added dropwise thereto for 10 minutes. A Pd catalyst (3.66 g, 3.2 mmol, 0.03 eq.) was introduced thereto under reflux. The result was stirred for 2 hours, then washed with ethyl acetate (EA)/$H_2O$ to separate the organic layer, and the solvent was vacuum dried. The result was purified by column chromatography through n-hexane (n-Hex) and ethyl acetate (EA), and then recrystallized with tetrahydrofuran (THF) and ethanol to obtain white solid Compound 3-A'.

Synthesis of Compound 6-A'

Compound 4-A' (17.24 g, 47.7 mmol, 1.0 eq.), Compound 5-A' (19.07 g, 57.26 mmol, 1.2 eq.), NaOt-Bu (6.42 g, 66.8 mmol, 1.4 eq.) and 1,10-phenanthroline (1.72 g, 9.54 mmol, 0.2 eq.) were dissolved in DMF (140 mL), and stirred for 10 minutes in a 80° C. silicone bath. CuI (0.91 g, 4.77 mmol, 10 mol %) was introduced thereto, and the result was stirred for 12 hours. The result was washed with ethyl acetate (EA)/$H_2O$ to separate the organic layer, and the solvent was vacuum dried. The result was purified by medium pressure liquid chromatography (MPLC) through n-hexane (n-Hex) and ethyl acetate (EA), and then recrystallized with n-hexane (n-Hex) to obtain Compound 6-A'.

Synthesis of Compound 7-A'

Compound 6-A' (11.90 g, 21 mmol, 1.0 eq.) and $B_2Pin_2$ (13.3 g, 52.4 mmol, 2.5 eq.) were dissolved in 1,4-dioxane (300 mL), and stirred for 10 minutes in a 80° C. silicone bath. KOAc (8.86 g, 90.3 mmol, 4.3 eq.) and Pd (pddf) $Cl_2$·DCM (1.38 g, 1.89 mmol, 0.09 eq.) were introduced thereto. The result was stirred for 12 hours in a 110° C. silicone bath, then washed with ethyl acetate (EA)/$H_2O$ to separate the organic layer, and the solvent was vacuum dried. The result was purified by medium pressure liquid chromatography (MPLC) through n-hexane (n-Hex) and dichloromethane (DCM), and then recrystallized with n-hexane (n-Hex) to obtain Compound 7-A'.

Synthesis of Monomer 6

Compound 3-A' (2.49 g, 5 mmol, 1 eq.) and Compound 7-A' (3.68 g, 6 mmol, 1.2 eq.) were dissolved in tetrahydrofuran (THF) (20 ml), and stirred for 30 minutes in a 80° C. silicone bath. $K_2CO_3$ (5.1 g, 37 mmol, 1.75 eq.) dissolved in water (40 mL) was added dropwise thereto for 10 minutes while maintaining an inner temperature of the solution at 65° C. A Pd catalyst (0.077 g, 0.15 mmol, 0.03 eq.) was introduced thereto under reflux. The result was stirred for 1 hour, then washed with ethyl acetate (EA)/$H_2O$ to separate the organic layer, and the solvent was vacuum dried. The result was purified by column chromatography through n-hexane (n-Hex) and dichloromethane (DCM), and then recrystallized with n-hexane (n-Hex) to obtain Monomer 6 (4.16 g, MS: $[M+H]^+=903$).

Synthesis of Monomer 7

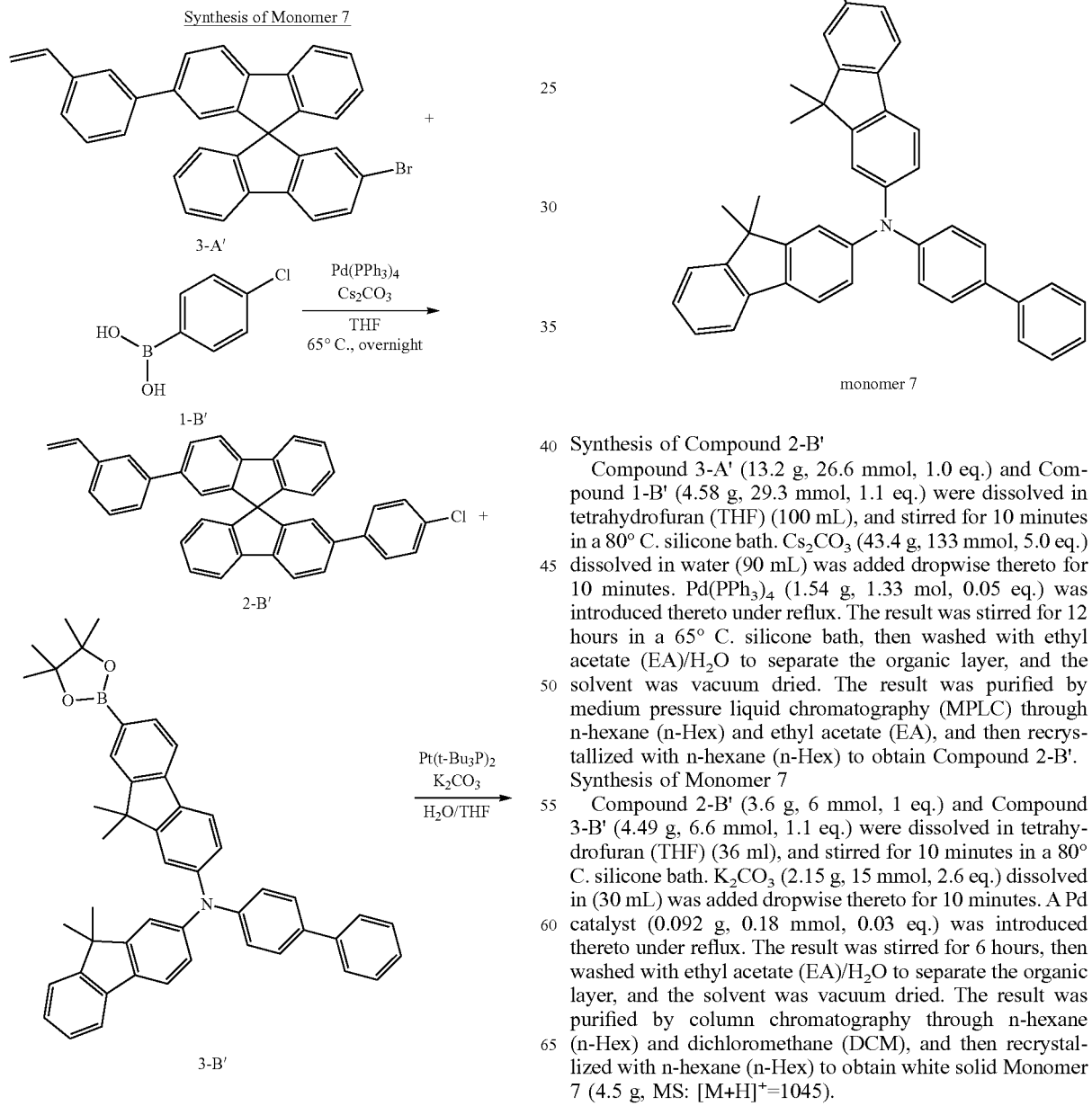

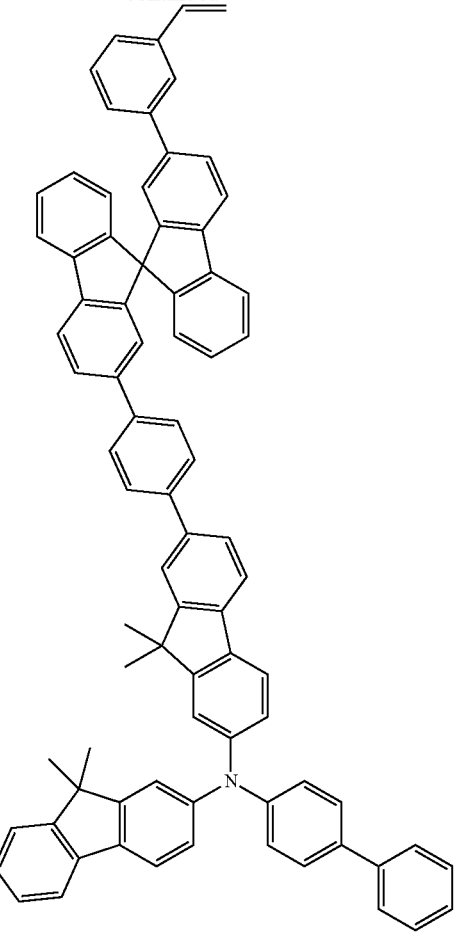

monomer 7

Synthesis of Compound 2-B'

Compound 3-A' (13.2 g, 26.6 mmol, 1.0 eq.) and Compound 1-B' (4.58 g, 29.3 mmol, 1.1 eq.) were dissolved in tetrahydrofuran (THF) (100 mL), and stirred for 10 minutes in a 80° C. silicone bath. $Cs_2CO_3$ (43.4 g, 133 mmol, 5.0 eq.) dissolved in water (90 mL) was added dropwise thereto for 10 minutes. $Pd(PPh_3)_4$ (1.54 g, 1.33 mol, 0.05 eq.) was introduced thereto under reflux. The result was stirred for 12 hours in a 65° C. silicone bath, then washed with ethyl acetate (EA)/$H_2O$ to separate the organic layer, and the solvent was vacuum dried. The result was purified by medium pressure liquid chromatography (MPLC) through n-hexane (n-Hex) and ethyl acetate (EA), and then recrystallized with n-hexane (n-Hex) to obtain Compound 2-B'.

Synthesis of Monomer 7

Compound 2-B' (3.6 g, 6 mmol, 1 eq.) and Compound 3-B' (4.49 g, 6.6 mmol, 1.1 eq.) were dissolved in tetrahydrofuran (THF) (36 ml), and stirred for 10 minutes in a 80° C. silicone bath. $K_2CO_3$ (2.15 g, 15 mmol, 2.6 eq.) dissolved in (30 mL) was added dropwise thereto for 10 minutes. A Pd catalyst (0.092 g, 0.18 mmol, 0.03 eq.) was introduced thereto under reflux. The result was stirred for 6 hours, then washed with ethyl acetate (EA)/$H_2O$ to separate the organic layer, and the solvent was vacuum dried. The result was purified by column chromatography through n-hexane (n-Hex) and dichloromethane (DCM), and then recrystallized with n-hexane (n-Hex) to obtain white solid Monomer 7 (4.5 g, MS: $[M+H]^+=1045$).

Synthesis of Monomer 8

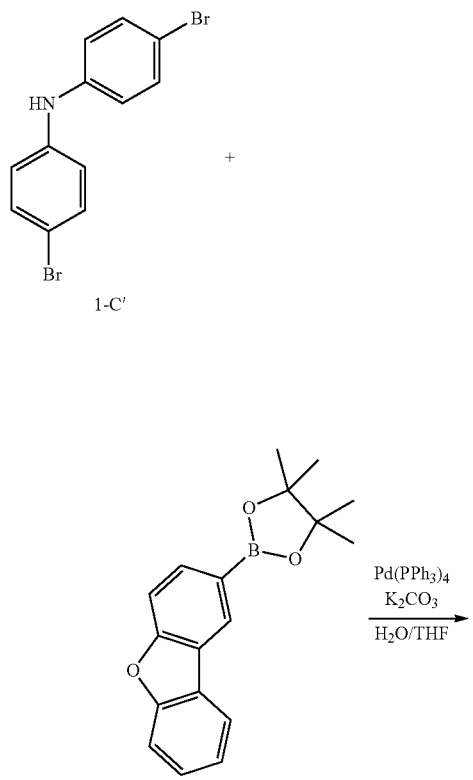

1-C'

2-C'

3-C'

3-A

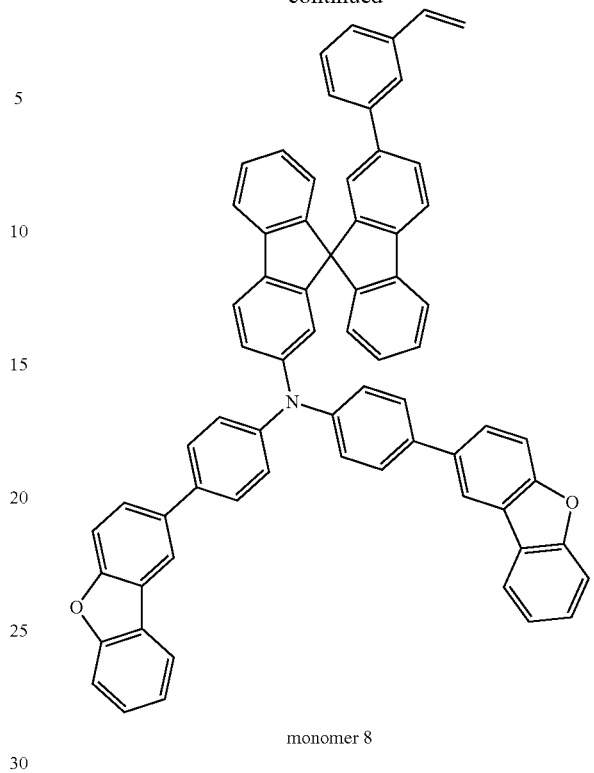

monomer 8

Synthesis of Compound 3-C'

Compound 1-C' (19.93 g, 60.95 mmol, 1.0 eq.) and Compound 2-C' (37.65 g, 128 mmol, 2.10 eq.) were dissolved in tetrahydrofuran (THF) (200 mL), and stirred for 10 minutes in a 80° C. silicone bath. $K_2CO_3$ (21.9 g, 158 mmol, 2.6 eq.) dissolved in water (87 mL) was added dropwise thereto for 10 minutes. A Pd catalyst (2.11 g, 1.8 mmol, 0.03 eq.) was introduced thereto under reflux. The result was stirred for 12 hours, then washed with ethyl acetate (EA)/$H_2O$ to separate the organic layer, and the solvent was vacuum dried. The result was purified by medium pressure liquid chromatography (MPLC) through n-hexane (n-Hex) and ethyl acetate (EA), and then recrystallized with n-hexane (n-Hex) to obtain Compound 3-C'.

Synthesis of Monomer 8

Compound 3-C' (3.01 g, 6 mmol, 1 eq.) and Compound 3-A' (3.28 g, 6.6 mmol, 1.1 eq.) were dissolved in anhydrous toluene (15 g), and stirred for 10 minutes in a 130° C. silicone bath. Sodium tert-butoxide (NaOt-Bu) (1.45 g, 15 mmol, 2.5 eq.) was introduced thereto. A Pd catalyst (0.077 g, 0.15 mmol, 0.03 eq.) was introduced thereto under reflux. The result was stirred for 1 hour, then washed with ethyl acetate (EA)/$H_2O$ to separate the organic layer, and the solvent was vacuum dried. The result was purified by column chromatography through n-hexane (n-Hex) and dichloromethane (DCM), and then recrystallized with n-hexane (n-Hex) to obtain white solid Monomer 8 (5.07 g, MS: $[M+H]^+$=917).

Synthesis of Monomer 9
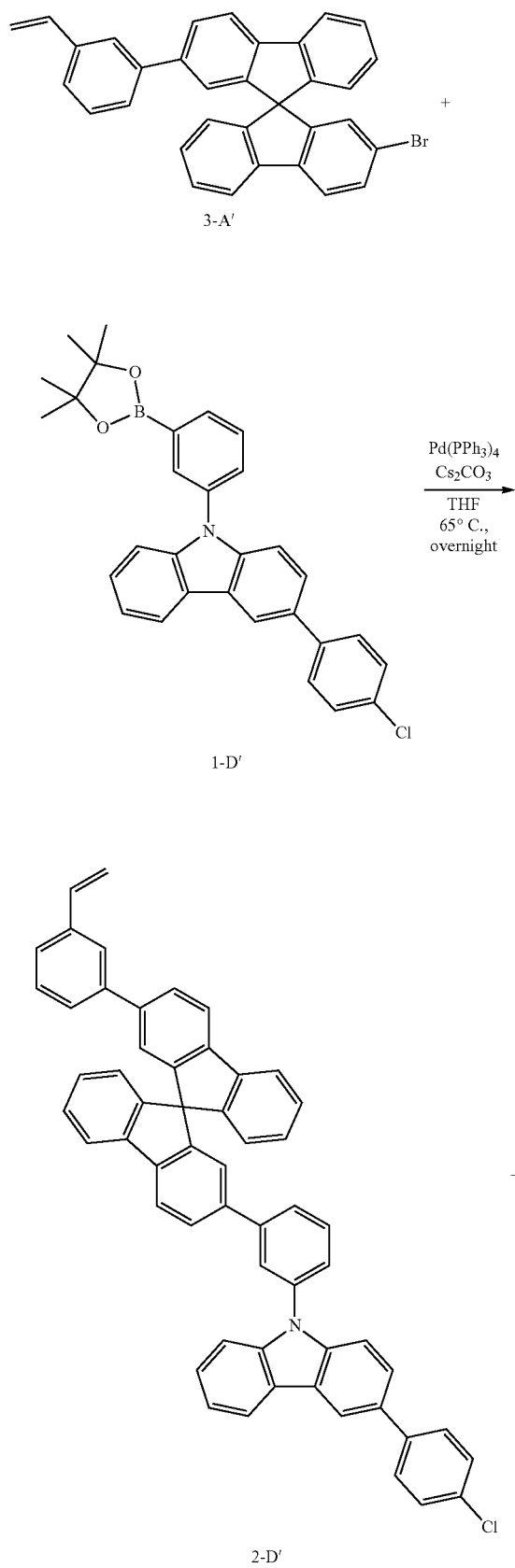
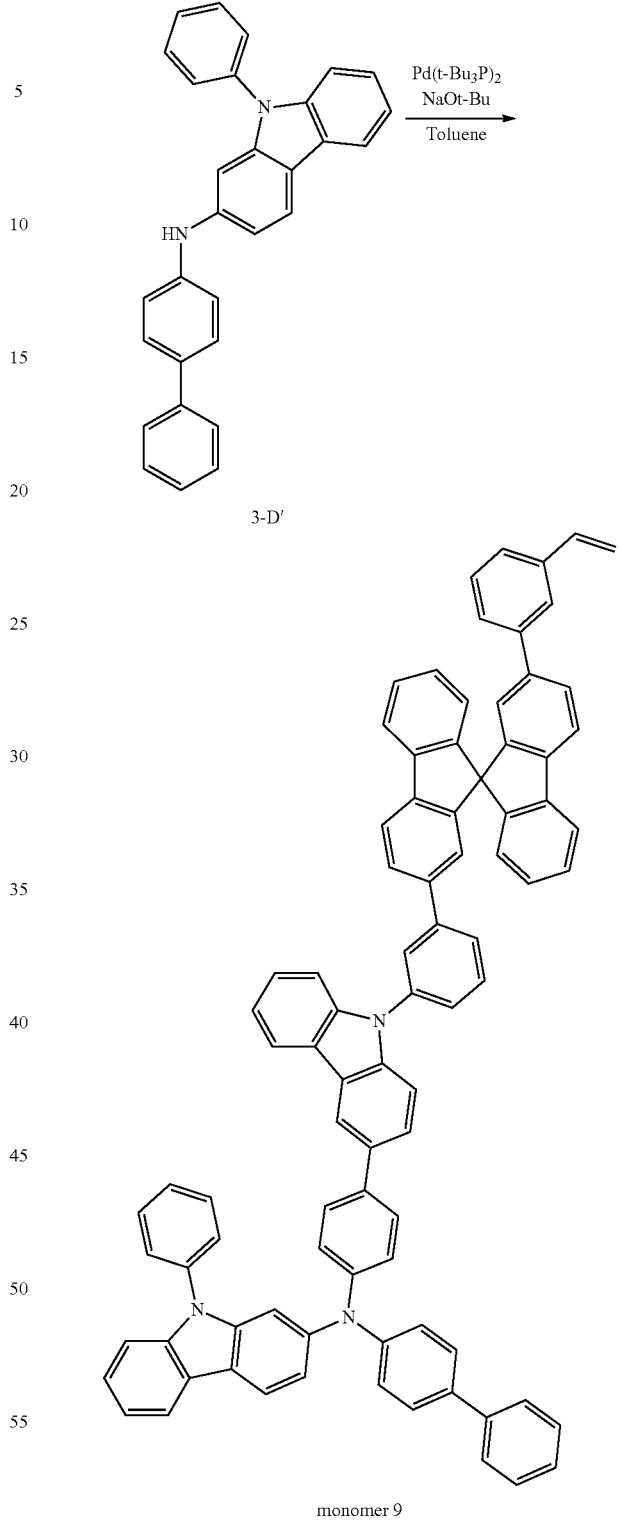
Synthesis of Compound 2-D'
Compound 3-A' (13.2 g, 26.6 mmol, 1.0 eq.) and Compound 1-D' (14.06 g, 29.3 mmol, 1.1 eq.) were dissolved in tetrahydrofuran (THF) (100 mL), and stirred for 10 minutes in a 80° C. silicone bath. Cs$_2$CO$_3$ (43.4 g, 133 mmol, 5.0 eq.) dissolved in water (90 mL) was added dropwise thereto for 10 minutes. Pd(PPh$_3$)$_4$ (1.54 g, 1.33 mol, 0.05 eq.) was introduced thereto under reflux. The result was stirred for 12 hours in a 65° C. silicone bath, then washed with ethyl acetate (EA)/H₂O to separate the organic layer, and the solvent was vacuum dried. The result was purified by medium pressure liquid chromatography (MPLC) through n-hexane (n-Hex) and ethyl acetate (EA), and then recrystallized with n-hexane (n-Hex) to obtain Compound 2-D'.

Synthesis of Monomer 9

Compound 3-D' (2.5 g, 6 mmol, 1 eq.) and Compound 2-D' (5.08 g, 6.6 mmol, 1.1 eq.) were dissolved in anhydrous toluene (36 ml), and stirred for 10 minutes in a 130° C. silicone bath. Sodium tert-butoxide (NaOt-Bu) (1.45 g, 15 mmol, 2.5 eq.) was introduced thereto. A Pd catalyst (0.15 g, 0.3 mmol, 0.05 eq.) was introduced thereto under reflux. The result was stirred for 1 hour, then washed with ethyl acetate (EA)/H₂O to separate the organic layer, and the solvent was vacuum dried. The result was purified by column chromatography through n-hexane (n-Hex) and dichloromethane (DCM), and then recrystallized with n-hexane (n-Hex) to obtain white solid Monomer 9 (5.72 g, MS: [M+H]⁺=1143).

Synthesis of Monomer 10

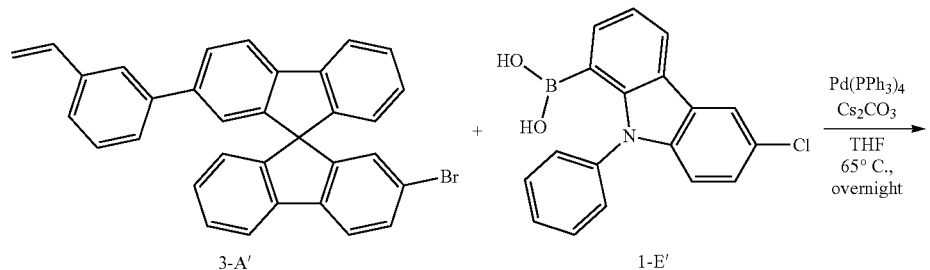

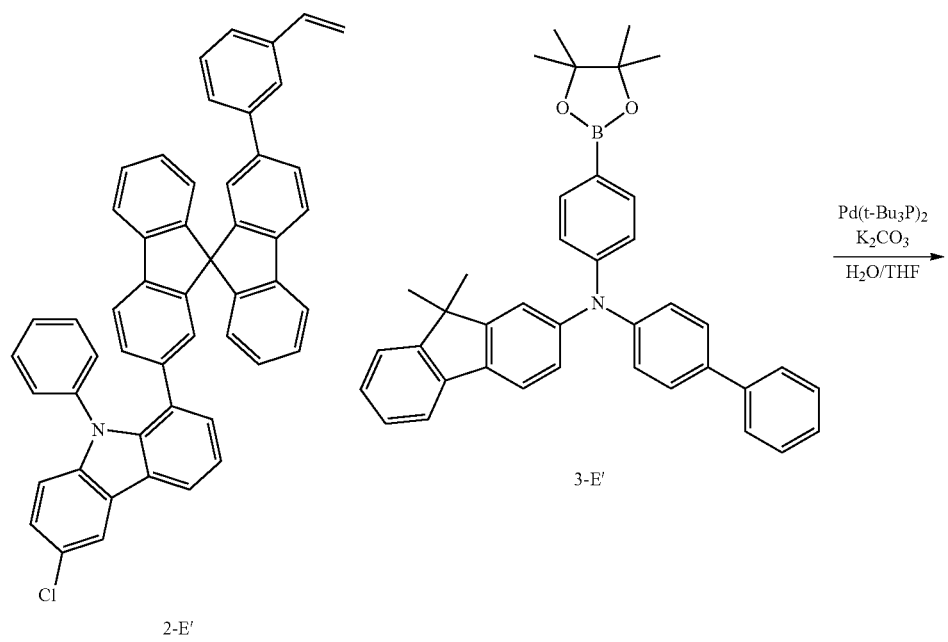

-continued

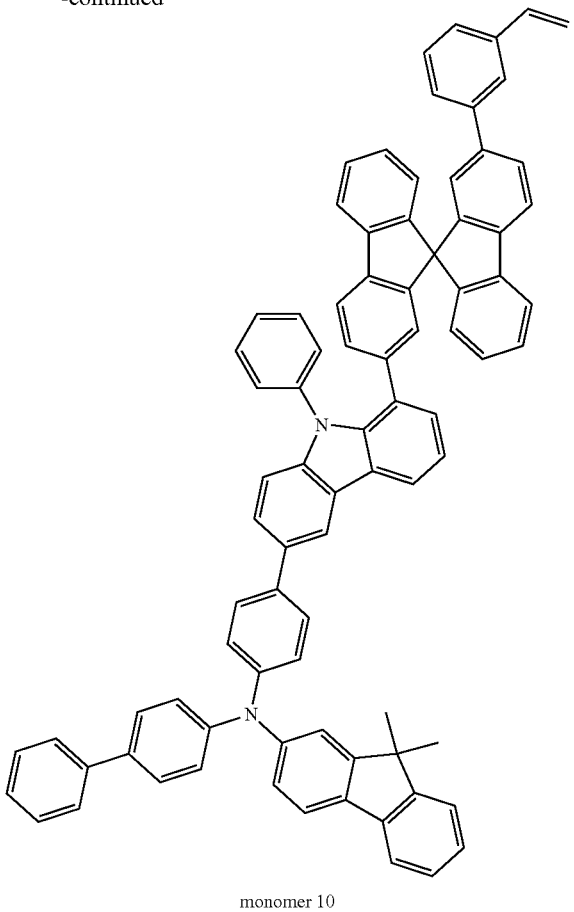

monomer 10

Synthesis of Compound 2-E'

Compound 3-A' (13.2 g, 26.6 mmol, 1.0 eq.) and Compound 1-E' (9.42 g, 29.3 mmol, 1.1 eq.) were dissolved in tetrahydrofuran (THF) (100 mL), and stirred for 10 minutes in a 80° C. silicone bath. $Cs_2CO_3$ (43.4 g, 133 mmol, 5.0 eq.) dissolved in water (90 mL) was added dropwise thereto for 10 minutes. $Pd(PPh_3)_4$ (1.54 g, 1.33 mol, 0.05 eq.) was introduced thereto under reflux. The result was stirred for 12 hours in a 65° C. silicone bath, then washed with ethyl acetate (EA)/$H_2O$ to separate the organic layer, and the solvent was vacuum dried. The result was purified by medium pressure liquid chromatography (MPLC) through n-hexane (n-Hex) and ethyl acetate (EA), and then recrystallized with n-hexane (n-Hex) to obtain Compound 2-E'.

Synthesis of Monomer 10

Compound 2-E' (3.47 g, 5 mmol, 1 eq.) and Compound 3-E' (3.10 g, 5.5 mmol, 1.1 eq.) were dissolved in tetrahydrofuran (THF) (20 ml), and stirred for 20 minutes in a 70° C. silicone bath. $K_2CO_3$ (5.1 g, 37 mmol, 1.75 eq.) dissolved in water (40 mL) was added dropwise thereto for 10 minutes while maintaining an inner temperature of the solution at 45° C. or higher. A Pd catalyst (0.077 g, 0.15 mmol, 0.03 eq.) was introduced thereto under reflux. The result was stirred for 3 hours, then washed with ethyl acetate (EA)/$H_2O$ to separate the organic layer, and the solvent was vacuum dried. The result was purified by column chromatography through n-hexane (n-Hex) and dichloromethane (DCM), and then recrystallized with n-hexane (n-Hex) to obtain Monomer 10 (4.38 g, MS: $[M+H]^+$=1094).

Synthesis of Monomer 11

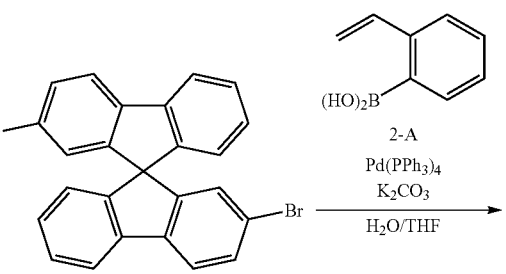

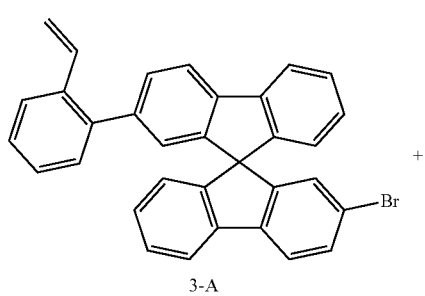

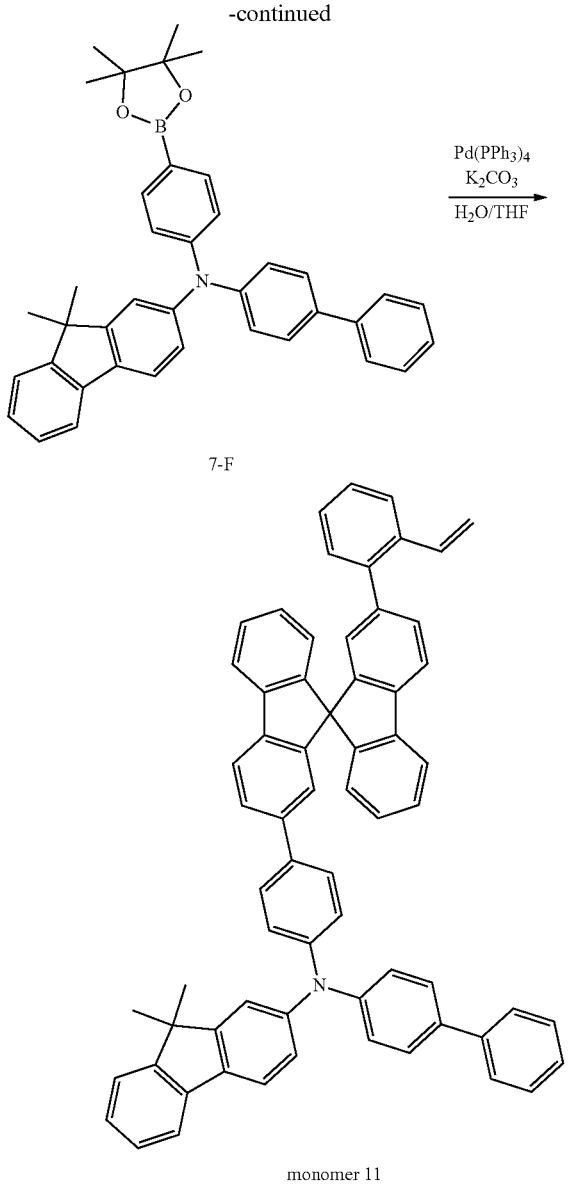

7-F monomer 11

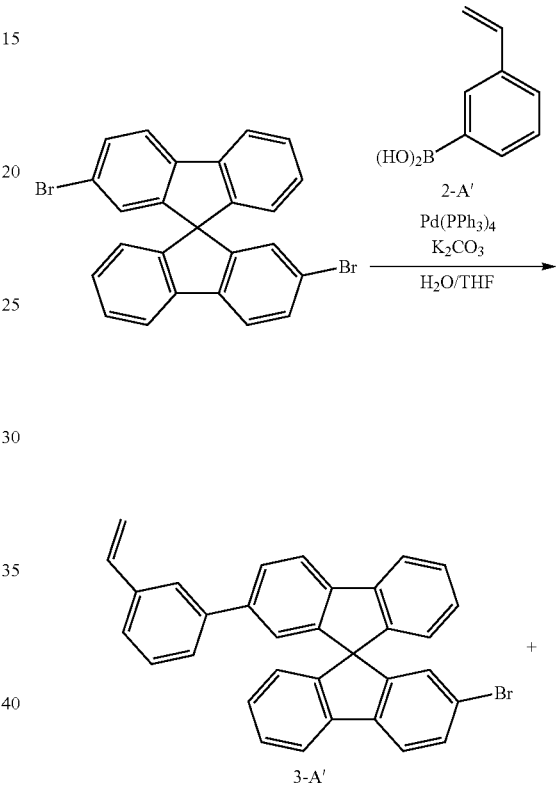

2-A'

3-A'

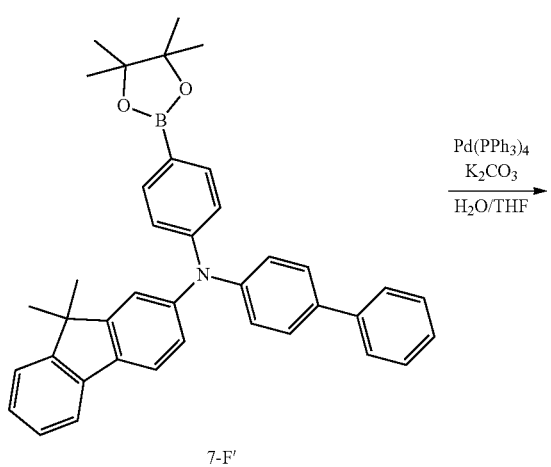

7-F' maintaining an inner temperature of the solution at 65° C. A Pd catalyst (0.077 g, 0.15 mmol, 0.03 eq.) was introduced thereto under reflux. The result was stirred for 1 hour, then washed with ethyl acetate (EA)/H₂O to separate the organic layer, and the solvent was vacuum dried. The result was purified by column chromatography through n-hexane (n-Hex) and dichloromethane (DCM), and then recrystallized with n-hexane (n-Hex) to obtain Monomer 11 (3.61 g, MS: $[M+H]^+=853$).

Synthesis of Monomer 12

Synthesis of Compound 3-A

Compound 1-A (50 g, 105.4 mmol, 1 eq.) and Compound 2-A (31.2 g, 211 mmol, 2 eq.) were dissolved in tetrahydrofuran (THF) (300 g), and stirred for 10 minutes in a 80° C. silicone bath. K₂CO₃ (37.89 g, 274 mmol, 2.6 eq.) dissolved in water (300 mL) was added dropwise thereto for 10 minutes. A Pd catalyst (3.66 g, 3.2 mmol, 0.03 eq.) was introduced thereto under reflux. The result was stirred for 2 hours, then washed with ethyl acetate (EA)/H₂O to separate the organic layer, and the solvent was vacuum dried. The result was purified by column chromatography through n-hexane (n-Hex) and ethyl acetate (EA), and then recrystallized with tetrahydrofuran (THF) and ethanol to obtain white solid Compound 3-A.

Synthesis of Monomer 11

Monomer 3-A (2.49 g, 5 mmol, 1 eq.) and Compound 7-F (3.38 g, 6 mmol, 1.2 eq.) were dissolved in tetrahydrofuran (THF) (20 ml), and stirred for 30 minutes in a 80° C. oil bath. K₂CO₃ (5.1 g, 37 mmol, 1.75 eq.) dissolved in water (40 mL) was added dropwise thereto for 10 minutes while -continued

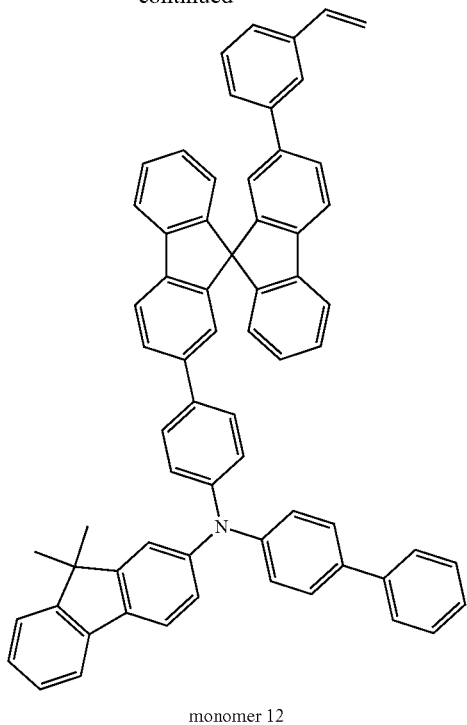 [SMILES: C=Cc1cccc(-c2ccc3c(c2)C2(c4ccccc4-c4ccc(-c5ccc(N(c6ccc(-c7ccccc7)cc6)c6ccc7c(c6)C(C)(C)c6ccccc6-7)cc5)cc42)c2ccccc2-3)c1]

monomer 12

Synthesis of Compound 3-A'

Compound 1-A (50 g, 105.4 mmol, 1 eq.) and Compound 2-A' (31.2 g, 211 mmol, 2 eq.) were dissolved in tetrahydrofuran (THF) (300 g), and stirred for 10 minutes in a 80° C. silicone bath. $K_2CO_3$ (37.89 g, 274 mmol, 2.6 eq.) dissolved in water (300 mL) was added dropwise thereto for 10 minutes. A Pd catalyst (3.66 g, 3.2 mmol, 0.03 eq.) was introduced thereto under reflux. The result was stirred for 2 hours, then washed with ethyl acetate (EA)/$H_2O$ to separate the organic layer, and the solvent was vacuum dried. The result was purified by column chromatography through n-hexane (n-Hex) and ethyl acetate (EA), and then recrystallized with tetrahydrofuran (THF) and ethanol to obtain white solid Compound 3-A'.

Synthesis of Monomer 12

Monomer 3-A' (2.49 g, 5 mmol, 1 eq.) and Compound 7-F' (3.38 g, 6 mmol, 1.2 eq.) were dissolved in tetrahydrofuran (THF) (20 ml), and stirred for 30 minutes in a 80° C. oil bath. $K_2CO_3$ (5.1 g, 37 mmol, 1.75 eq.) dissolved in water (40 mL) was added dropwise thereto for 10 minutes while maintaining an inner temperature of the solution at 65° C. A Pd catalyst (0.077 g, 0.15 mmol, 0.03 eq.) was introduced thereto under reflux. The result was stirred for 1 hour, then washed with ethyl acetate (EA)/$H_2O$ to separate the organic layer, and the solvent was vacuum dried. The result was purified by column chromatography through n-hexane (n-Hex) and dichloromethane (DCM), and then recrystallized with n-hexane (n-Hex) to obtain Monomer 12 (3.68 g, MS: $[M+H]^+$=853).

Preparation of Polymer 1

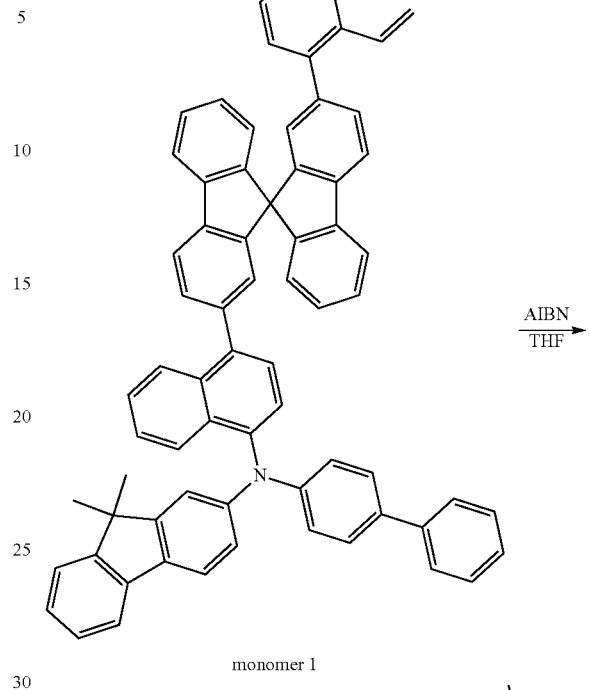

monomer 1

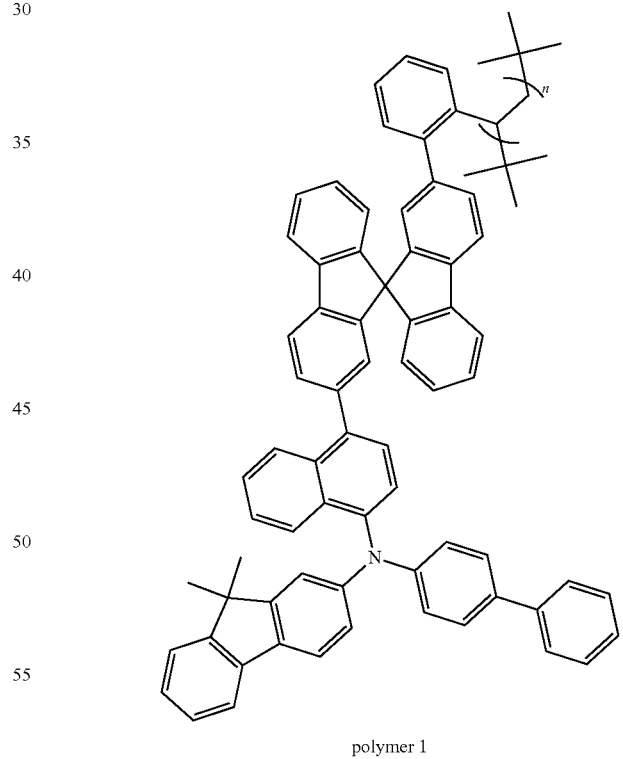

polymer 1

Monomer 1 (0.5 g, 0.53 mmol) and AIBN (3.0 mg, 0.02 mmol) were introduced to a Schlenk reaction flask and dissolved in THF (1.5 mL). Then, freeze-evacuate-thaw was repeated three times, and the result was stirred for 7 hours at 80° C. Ethyl acetate was added thereto to dissolve an unreacted monomer and to precipitate a polymer, and as a result, Polymer 1 was prepared.

Preparations of Polymers 2 to 12

Polymers 2 to 12 were prepared in the same manner as in Preparation of Polymer 1 except that monomers of the following Table 1 were used instead of Monomer 1.

Preparation of Polymer P1

Polymer P1 was prepared in the same manner as in Preparation of Polymer 1 except that a monomer of the following C1 was used instead of Monomer 1.

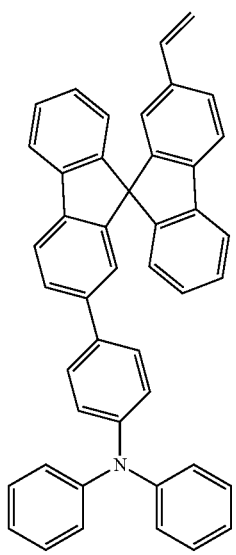

C1

Preparations of Polymers P3 to P7

Polymers P3 to P7 were prepared in the same manner as in Preparation of Polymer 1 except that monomers of the following Table 1 were used instead of Monomer 1.

TABLE 1

| Polymer | Monomer | Mn (g/mol) |
|---------|---------|------------|
| 1 | 1 | 15500 |
| 2 | 2 | 13600 |
| 3 | 3 | 22300 |
| 4 | 4 | 18500 |
| 5 | 5 | 14900 |
| 6 | 6 | 21400 |
| 7 | 7 | 18600 |
| 8 | 8 | 31200 |
| 9 | 9 | 23600 |
| 10 | 10 | 48800 |
| 11 | 11 | 16100 |
| 12 | 12 | 21900 |
| P1 | C1 | 48800 |
| P3 | C3 | 16600 |
| P4 | C4 | 12400 |
| P5 | C5 | 51200 |
| P6 | C6 | 32500 |
| P7 | C7 | 11300 |

TABLE 1-continued

| Polymer | Monomer | Mn (g/mol) |
|---------|---------|------------|

C3

C4

TABLE 1-continued

| Polymer | Monomer | Mn (g/mol) |
|---|---|---|
| C5 | | |
| C6 | 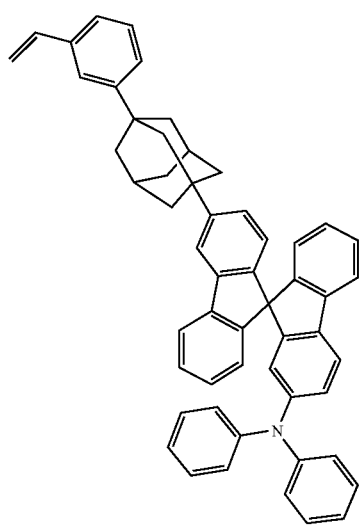 [SMILES: C=Cc1cccc(C23CC4CC(C2)CC(c2ccc5c(c2)-c2ccccc2C52c5ccccc5-c5ccc(N(c6ccccc6)c6ccccc6)cc52)(C4)C3)c1] | |
| C7 | | |

Example 1

A glass substrate on which indium tin oxide (ITO) was coated as a thin film to a thickness of 150 nm was placed in detergent-dissolved distilled water and ultrasonic cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol and acetone, then dried, cleaned for 5 minutes, and then transferred to a glove box.

On the transparent ITO electrode, a coating composition obtained by dissolving Compound A and Compound B (weight ratio of 8:2) in cyclohexanone in 2 wt/v % was spin coated (4000 rpm), and heat treated (cured) for 30 minutes at 230° C. to form a hole injection layer having a thickness of 40 nm. On the hole injection layer, a composition obtained by dissolving Polymer 1 in toluene in 2 wt % was spin coated, and heat treated for 30 minutes at 230° C. to form a hole transfer layer having a thickness of 20 nm. On the hole transfer layer, a coating composition obtained by dissolving the following Compound C and the following Compound D in a weight ratio of 92:8 in cyclohexanone in 2 wt/v % was spin coated (4000 rpm), and heat treated for 30 minutes at 150° C. to form a light emitting layer having a thickness of 25 nm. After the result was transferred to a vacuum deposition apparatus, a layer carrying out electron transfer and electron injection at the same time was formed by vacuum depositing the following Compound E on the light emitting layer to a thickness of 35 nm. On the layer carrying out electron transfer and electron injection at the same time, LiF and aluminum were consecutively deposited to a thickness of 1 nm and a thickness of 100 nm, respectively, to form a cathode.

A

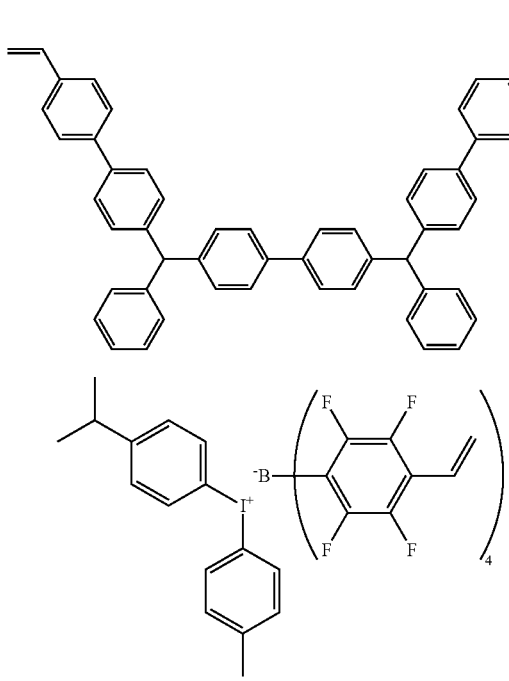

B

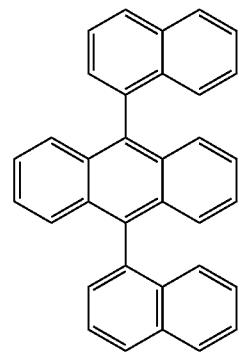

C

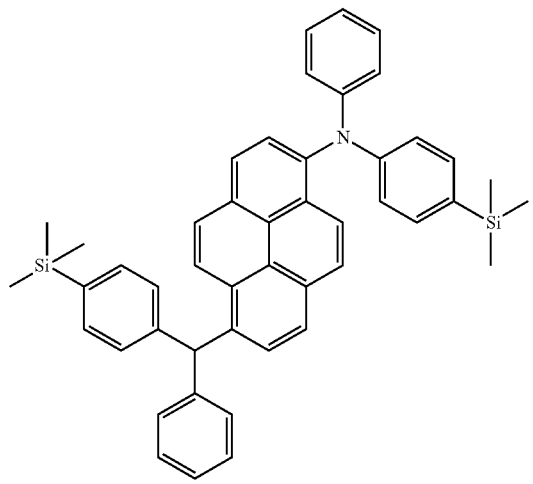

D

E

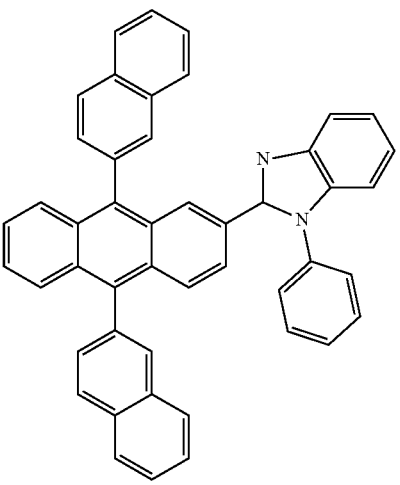

In the above-mentioned process, the deposition rates of the organic materials were maintained at 0.04 nm/sec to 0.07 nm/sec, the deposition rates of the LiF and the aluminum were maintained at 0.03 nm/sec and 0.2 nm/sec, respectively, and the degree of vacuum during the deposition was maintained at $2\times10^{-7}$/torr to $5\times10^{-6}$ torr.

Examples 2 to 12

Organic light emitting devices of Examples 2 to 12 were manufactured in the same manner as in Example 1 except that polymers of the following Table 2 were used instead of Polymer 1.

Comparative Examples 1 and 2

Organic light emitting devices of Comparative Examples 1 and 2 were manufactured in the same manner as in Example 1 except that a polymer or a compound of the following Table 2 was used instead of Polymer 1.

Compound P2 used in Comparative Example 2 is as follows.

P2

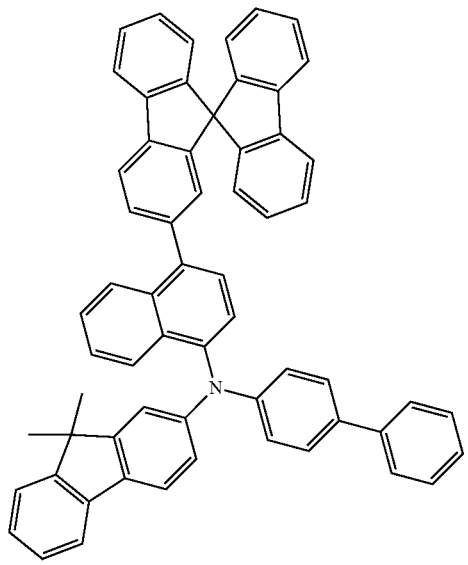

Comparative Example 3 to 7

Organic light emitting devices of Comparative Examples 3 to 7 were manufactured in the same manner as in Example 1 except that polymers of the following Table 2 were used instead of Polymer 1.

Evaluation on Device

For the organic light emitting devices manufactured in the examples and the comparative examples, results of measuring driving voltage, external quantum efficiency (EQE), luminance and lifetime at current density of 10 mA/cm$^2$ are shown in the following Table 2. The external quantum efficiency was obtained by (the number of emitted photons)/(the number of injected charge carriers). T90 means time taken for luminance to decrease to 90% from initial luminance (500 nit).

TABLE 2

|  | Compound | Driving Voltage (V) | EQE (%) | T90 (hr) |
| --- | --- | --- | --- | --- |
| Example 1 | Polymer 1 | 4.22 | 6.8 | 236 |
| Example 2 | Polymer 2 | 4.13 | 6.7 | 251 |
| Example 3 | Polymer 3 | 4.15 | 6.8 | 216 |
| Example 4 | Polymer 4 | 4.26 | 6.8 | 225 |
| Example 5 | Polymer 5 | 4.2 | 6.5 | 244 |
| Example 6 | Polymer 6 | 4.49 | 6.8 | 241 |
| Example 7 | Polymer 7 | 4.30 | 6.6 | 244 |
| Example 8 | Polymer 8 | 4.33 | 6.7 | 221 |
| Example 9 | Polymer 9 | 4.46 | 6.9 | 231 |
| Example 10 | Polymer 10 | 4.26 | 6.6 | 233 |
| Example 11 | Polymer 11 | 4.21 | 6.8 | 239 |
| Example 12 | Polymer 12 | 4.39 | 6.8 | 242 |
| Comparative Example 1 | Polymer P1 | 4.74 | 6.1 | 211 |
| Comparative Example 2 | Compound P2 | Impossible to Measure | Impossible to Measure | Impossible to Measure |
| Comparative Example 3 | Polymer P3 | 4.55 | 6.7 | 121 |
| Comparative Example 4 | Polymer P4 | 4.31 | 6.6 | 126 |
| Comparative Example 5 | Polymer P5 | 4.27 | 6.1 | 209 |
| Comparative Example 6 | Polymer P6 | 4.41 | 6.2 | 211 |
| Comparative Example 7 | Polymer P7 | 4.35 | 6.1 | 208 |

The polymer according to one embodiment of the present specification had excellent solubility for organic solvents, and a coating composition was readily prepared. From the results of Table 2, it was identified that a uniform coating layer was able to be formed when using the composition comprising the polymer of the present disclosure, and superior performance was obtained in the organic light emitting device by having excellent film stability.

In addition, it was identified that, from the device examples of the examples, the organic material layer comprising the polymer comprising the unit of Chemical Formula 1 according to one embodiment of the present disclosure had tolerance for a cyclohexanone solvent. In other words, forming an organic material layer with the polymer comprising the unit of Chemical Formula 1 according to one embodiment of the present disclosure has an advantage in that other organic material layers may be formed on the organic material layer using a solution process.

When comparing the examples with Comparative Example 1, it was identified that, when spirobifluorene was connected to a main chain of the polymer through an o-phenylene group or an m-phenylene group, the device had a lower driving voltage, higher external quantum efficiency, and particularly, significantly enhanced lifetime properties compared to when phenylene did not bond.

In the device of Comparative Example 2, the hole transfer layer was formed using a monomer of Compound P2. However, when spin coating the cyclohexanone composition on the hole transfer layer formed using Compound P2, Compound P2 was dissolved in the cyclohexanone solvent making it difficult to form the light emitting layer, and the device was not able to be manufactured. Accordingly, data values of Comparative Example 2 of Table 2 were not able to measure.

In the devices of Comparative Examples 3 and 4, the hole transfer layer was formed using a polymer having fluorene bonding to the spirobifluorene position. Comparative Examples 5 to 7 used a polymer having spirobifluorene connected to a main chain of the polymer through phenylene-adamantane.

The invention claimed is:

1. A polymer comprising a unit represented by the following Chemical Formula 1:

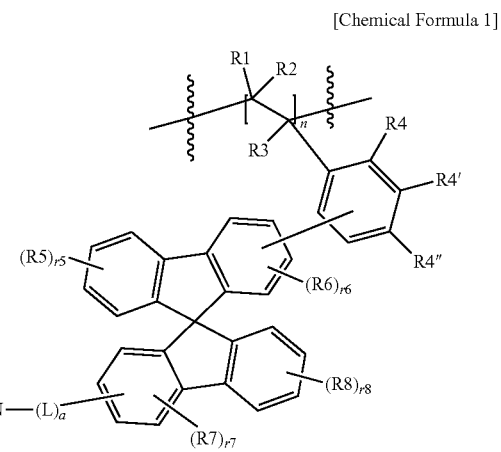

[Chemical Formula 1]

wherein, in Chemical Formula 1,

L is a direct bond; a substituted or unsubstituted arylene group; or a substituted or unsubstituted heteroarylene group;

a is an integer of 0 to 3, and when a is 2 or greater, Ls are the same as or different from each other;

Ar1 and Ar2 are the same as or different from each other, and each independently a substituted or unsubstituted aryl group; or a substituted or unsubstituted heteroaryl group;

R1 to R4, R4' and R4" are the same as or different from each other, and each independently hydrogen; deuterium; a halogen group; a hydroxyl group; a cyano group; a substituted or unsubstituted alkyl group; a substituted or unsubstituted cycloalkyl group; a substituted or unsubstituted alkoxy group; a substituted or unsubstituted aryl group; or a substituted or unsubstituted heteroaryl group;

R5 to R8 are the same as or different from each other, and each independently deuterium; a halogen group; a hydroxyl group; a cyano group; a substituted or unsubstituted alkyl group; a substituted or unsubstituted cycloalkyl group; a substituted or unsubstituted alkoxy group; a substituted or unsubstituted aryl group; or a substituted or unsubstituted heteroaryl group;

r6 and r7 are the same as or different from each other, and each independently an integer of 0 to 3, and when r6 is 2 or 3, R6s are the same as or different from each other, and when r7 is 2 or 3, R7s are the same as or different from each other;

r5 and r8 are the same as or different from each other, and each independently an integer of 0 to 4, and when r5 is 2 to 4, R5s are the same as or different from each other, and when r8 is 2 to 4, R8s are the same as or different from each other; and n is, as a repetition number of the unit, an integer of 2 to 10,000, wherein the polymer is a homopolymer.

2. The polymer of claim 1, wherein the unit is represented by Chemical Formula 1-1:

[Chemical Formula 1-1]

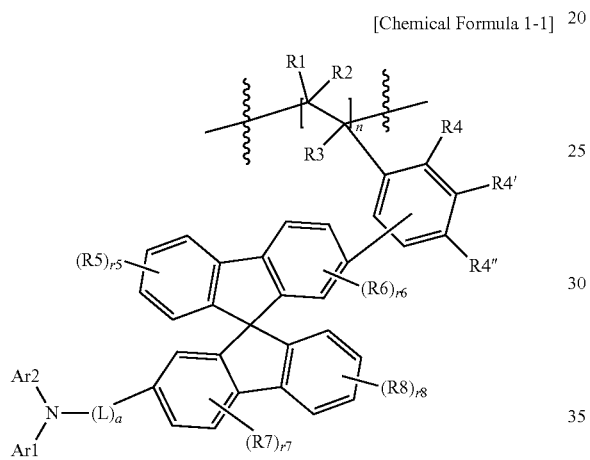

in Chemical Formula 1-1,

R1 to R8, R4', R4", L, Ar1, Ar2, r5 to r8, n and a have the same definitions as in Chemical Formula 1.

3. The polymer of claim 1, wherein L is a direct bond; or any one selected from among the following structures:

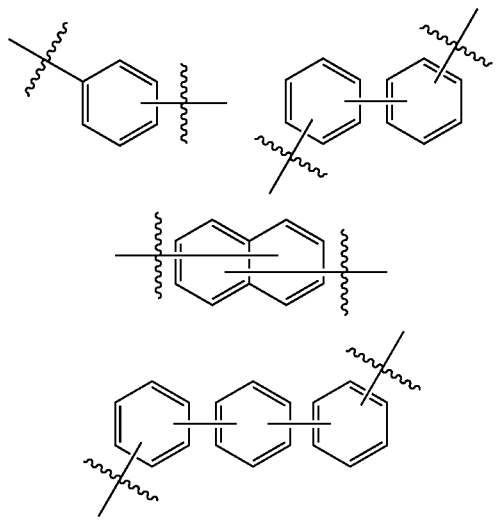

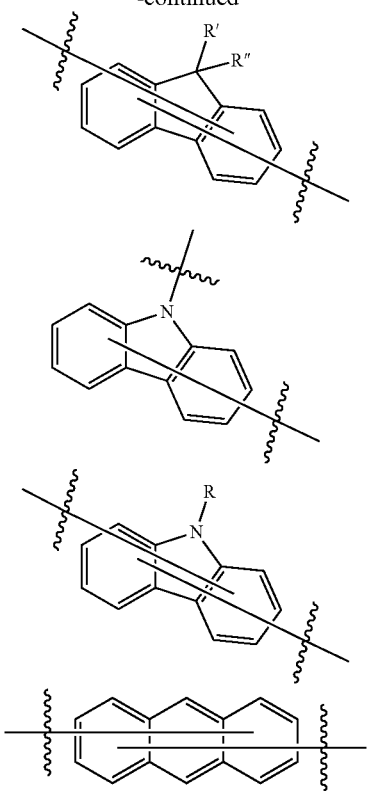

in the structures,
R is an aryl group;
R' and R" are the same as or different from each other, and each independently hydrogen; or an alkyl group; and
the structures are each optionally further substituted with an alkyl group.

4. The polymer of claim 1, wherein Ar1 and Ar2 are the same as or different from each other, and each independently an aryl group unsubstituted or substituted with an aryl group; an aryl group substituted with a heteroaryl group; an aryl group substituted with an alkyl group; an aryl group substituted with an aryl group substituted with an alkyl group; an aryl group substituted with a heteroaryl group substituted with an aryl group; or a heteroaryl group unsubstituted or substituted with an aryl group.

5. A coating composition comprising the polymer of claim 1.

6. The coating composition of claim 5, wherein a content of the polymer comprising the unit represented by Chemical Formula 1 in the coating composition is from 0.1 wt/v % to 20 wt/v %.

7. A method for manufacturing an organic light emitting device, the method comprising:
preparing a first electrode;
forming an organic material layer on the first electrode; and
forming a second electrode on the organic material layer,
wherein the forming of an organic material layer comprises forming the organic material layer using the coating composition of claim 5; and
the forming of the organic material layer using the coating composition comprises coating the coating composition on the first electrode; and heat treating or light treating the coated coating composition.

8. An organic light emitting device comprising:
a first electrode;
a second electrode; and
an organic material layer provided between the first electrode and the second electrode,
wherein the organic material layer comprises the polymer of claim 1.

9. The organic light emitting device of claim 8, wherein the organic material layer comprising the polymer is an electron blocking layer; a hole transfer layer; a hole injection layer; or a layer carrying out hole transfer and hole injection at the same time.

10. The organic light emitting device of claim 8, wherein the organic material layer comprising the polymer is a hole blocking layer; an electron transfer layer; an electron injection layer; or a layer carrying out electron transfer and electron injection at the same time.

11. The organic light emitting device of claim 8, wherein the organic material layer comprising the polymer has solubility of 0.05 wt % or less for cyclohexanone.

12. A method for manufacturing an organic light emitting device, the method comprising:
preparing a first electrode;
forming an organic material layer on the first electrode; and
forming a second electrode on the organic material layer,
wherein the forming of the organic material layer comprises forming the organic material layer using the coating composition comprising the polymer of claim 1; and
the forming of the organic material layer using the coating composition comprises coating the coating composition on the first electrode; and heat treating or light treating the coated coating composition.

13. The polymer of claim 1, wherein the polymer has a number average molecular weight of 5,000 g/mol to 1,000,000 g/mol.

14. A coating composition comprising a monomer represented by Chemical Formula 2 and a solvent:

[Chemical Formula 2]

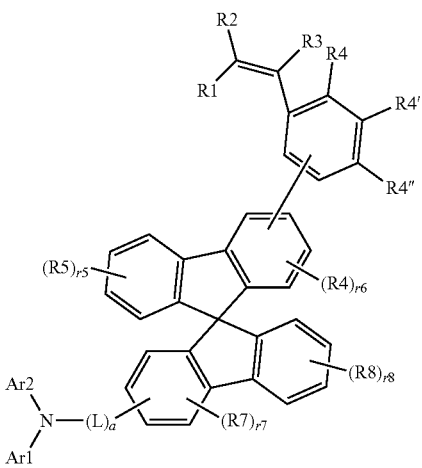

wherein, in Chemical Formula 2,
L is a direct bond; a substituted or unsubstituted arylene group; or a substituted or unsubstituted heteroarylene group;
a is an integer of 0 to 3, and when a is 2 or greater, Ls are the same as or different from each other;
Ar1 and Ar2 are the same as or different from each other, and each independently a substituted or unsubstituted aryl group; or a substituted or unsubstituted heteroaryl group;

R1 to R4, R4' and R4'' are the same as or different from each other, and each independently hydrogen; deuterium; a halogen group; a hydroxyl group; a cyano group; a substituted or unsubstituted alkyl group; a substituted or unsubstituted cycloalkyl group; a substituted or unsubstituted alkoxy group; a substituted or unsubstituted aryl group; or a substituted or unsubstituted heteroaryl group;

R5 to R8 are the same as or different from each other, and each independently deuterium; a halogen group; a hydroxyl group; a cyano group; a substituted or unsubstituted alkyl group; a substituted or unsubstituted cycloalkyl group; a substituted or unsubstituted alkoxy group; a substituted or unsubstituted aryl group; or a substituted or unsubstituted heteroaryl group;

r6 and r7 are the same as or different from each other, and each independently an integer of 0 to 3, and when r6 is 2 or 3, R6s are the same as or different from each other, and when r7 is 2 or 3, R7s are the same as or different from each other; and r5 and r8 are the same as or different from each other, and each independently an integer of 0 to 4, and when r5 is 2 to 4, R5s are the same as or different from each other, and when r8 is 2 to 4, R8s are the same as or different from each other, wherein the solvent is at least one of chloroform, methylene chloride, 1,2-dichloroethane, 1,1,2-trichloroethane, tetrahydrofuran, cyclohexane, methylcyclohexane, n-pentane, n-hexane, n-heptane, n-octane, n-nonane, n-decane, acetone, methyl ethyl ketone, cyclohexanone, ethyl acetate, butyl acetate, ethyl cellosolve acetate, ethylene glycol, ethylene glycol monobutyl ether, ethylene glycol monoethyl ether, ethylene glycol monomethyl ether, dimethoxyethane, propylene glycol, diethoxymethane, triethylene glycol monoethyl ether, glycerin, 1,2-hexanediol, methanol, ethanol, propanol, isopropanol, cyclohexanol, dimethyl sulfoxide, methyl benzoate, butyl benzoate, 3-phenoxybenzoate, or tetraline.

15. The coating composition of claim 14, wherein the monomer is any one selected from among the following structures:

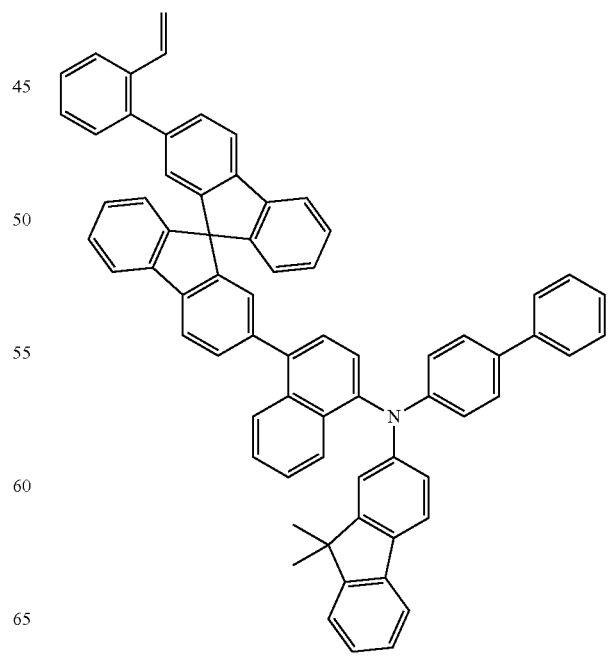

135
-continued
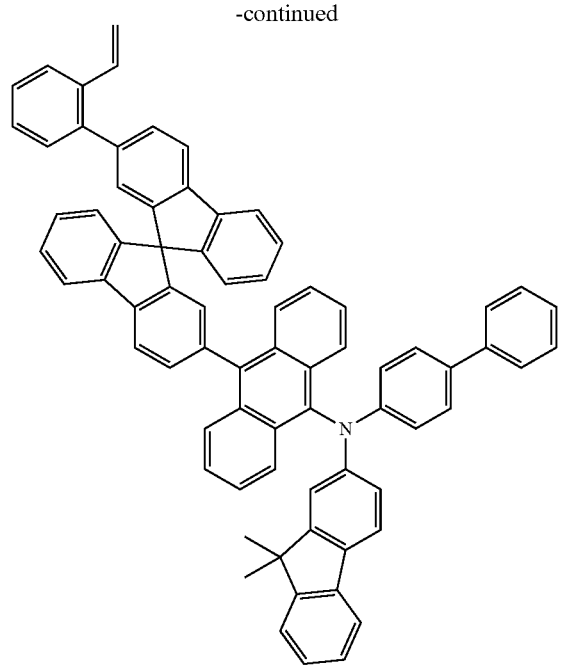
136
-continued
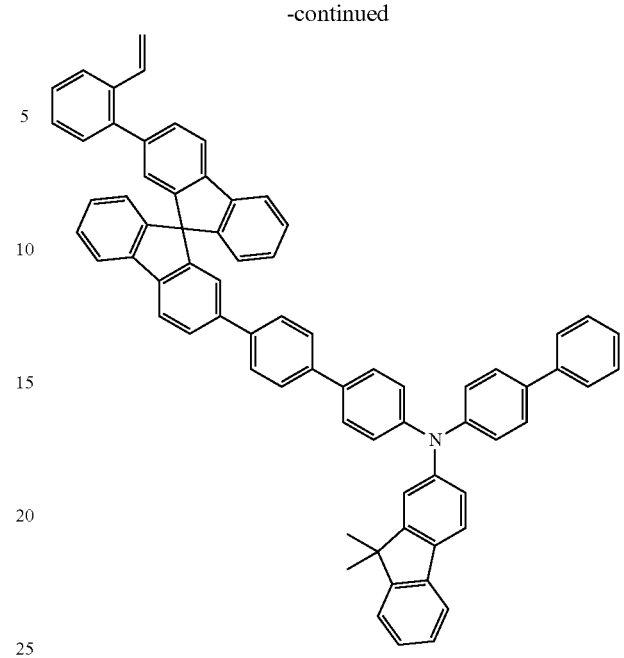

137
-continued
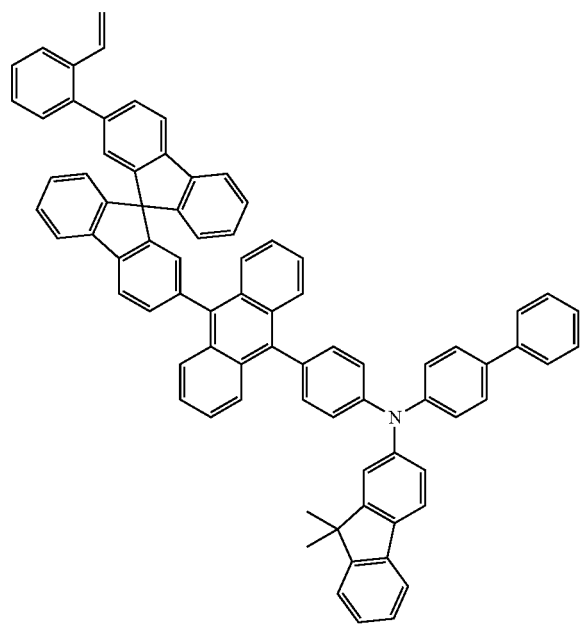
138
-continued
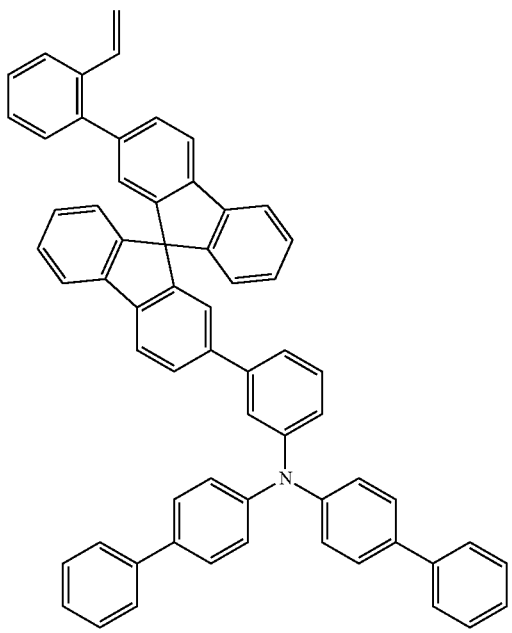
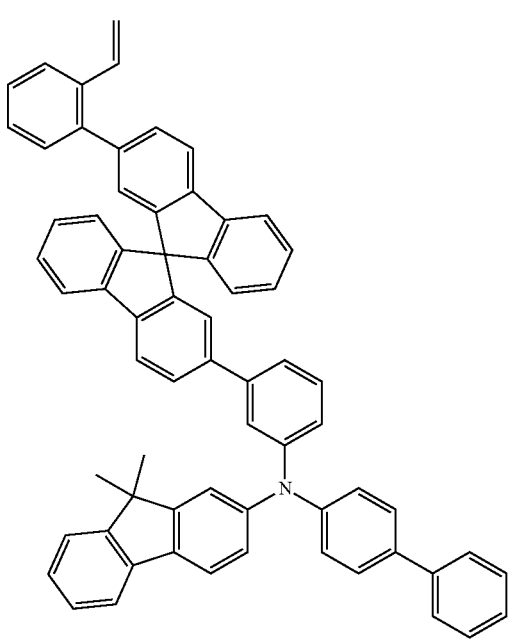
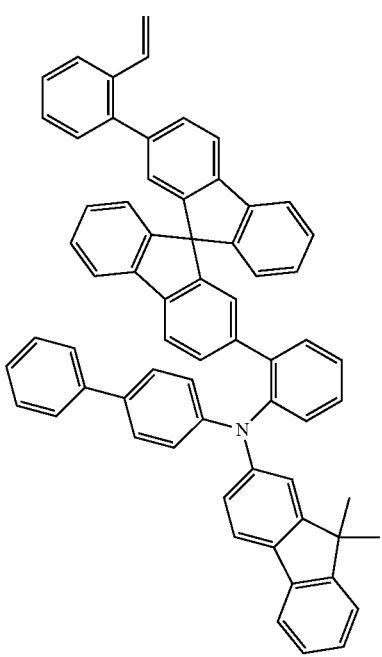

139
-continued
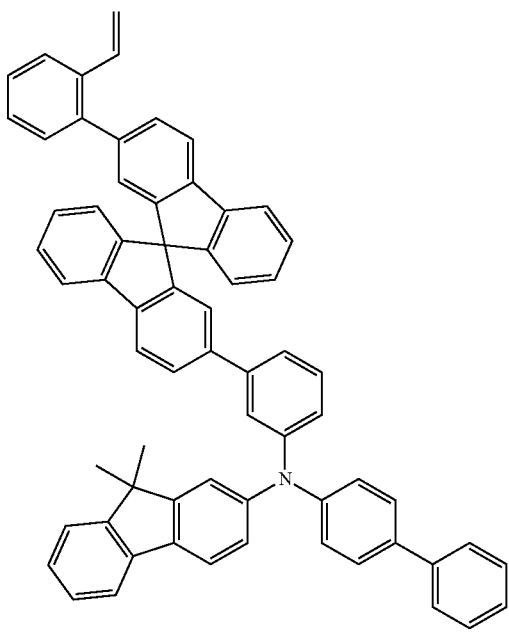
140
-continued
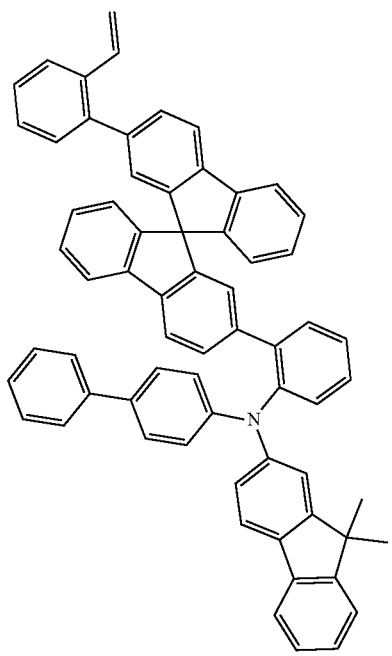
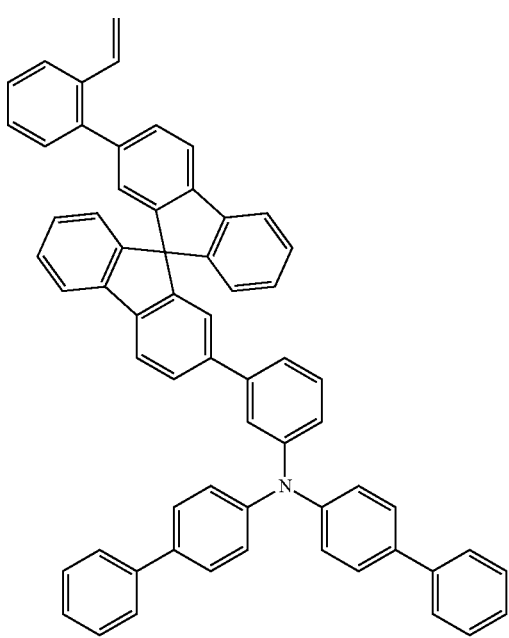
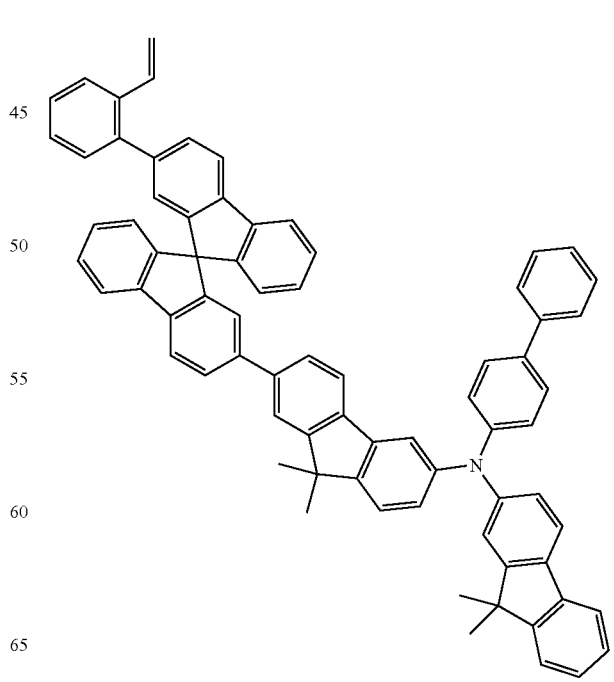

141
-continued
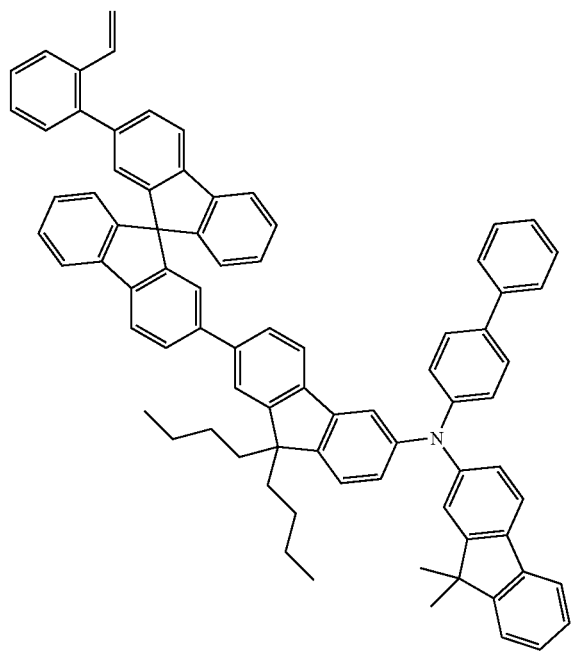
142
-continued
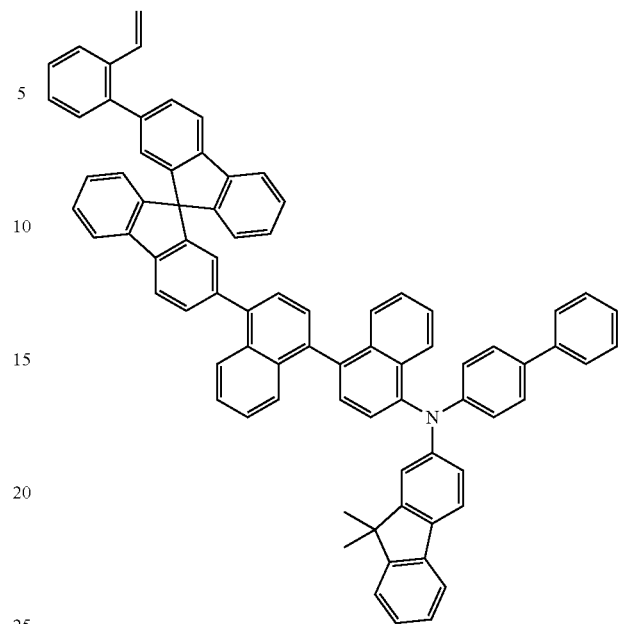
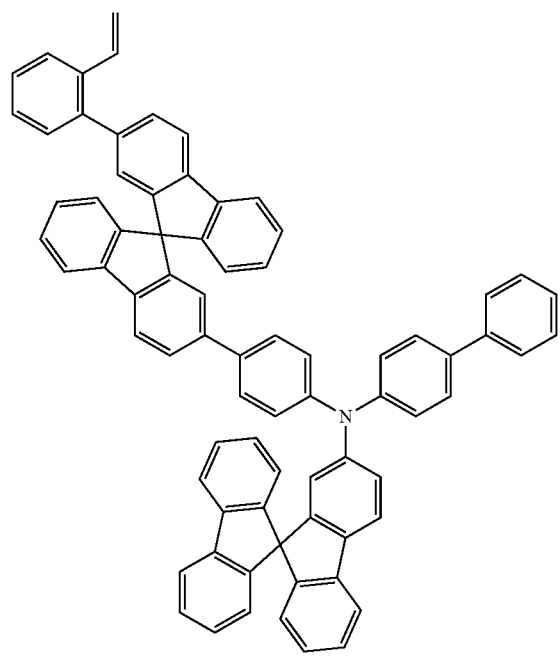
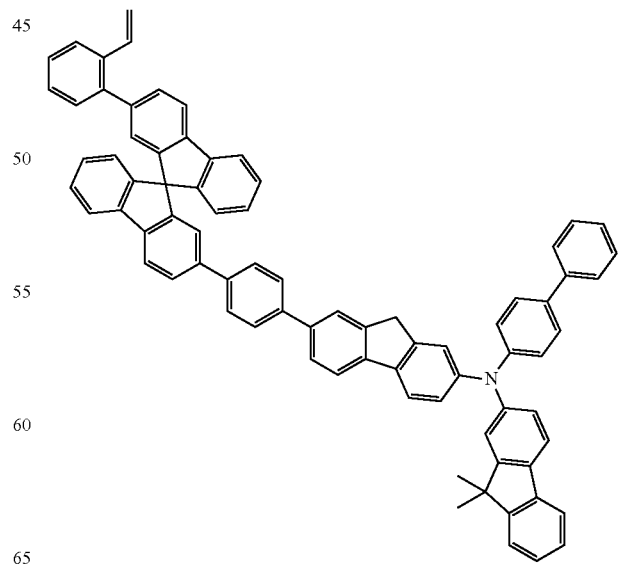

143
-continued
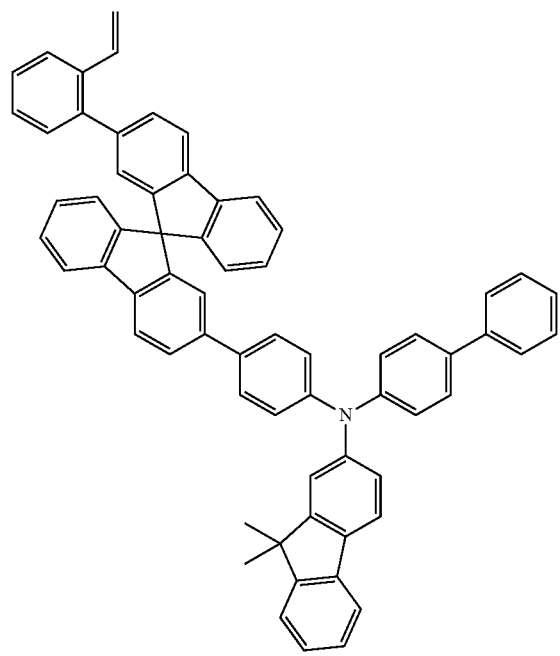
144
-continued
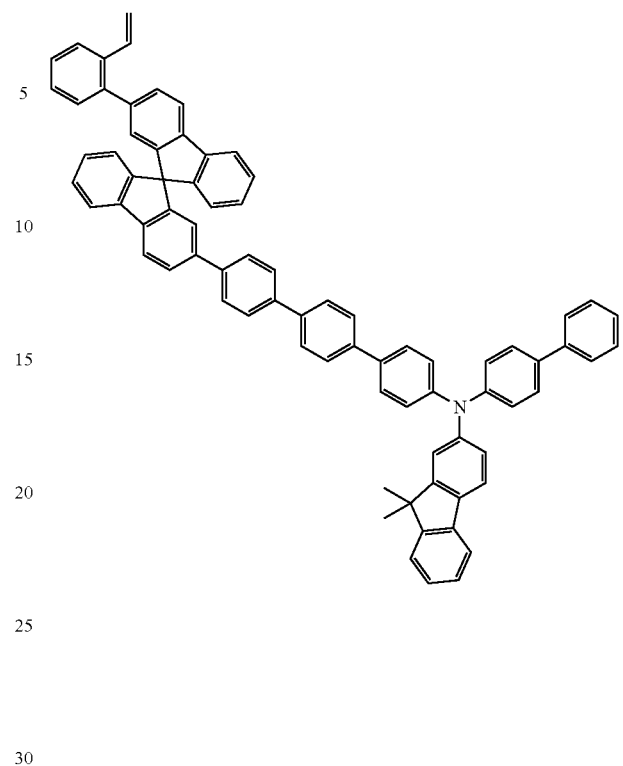
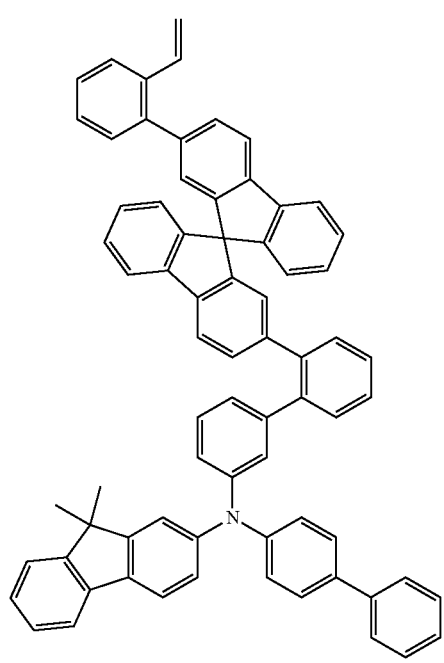
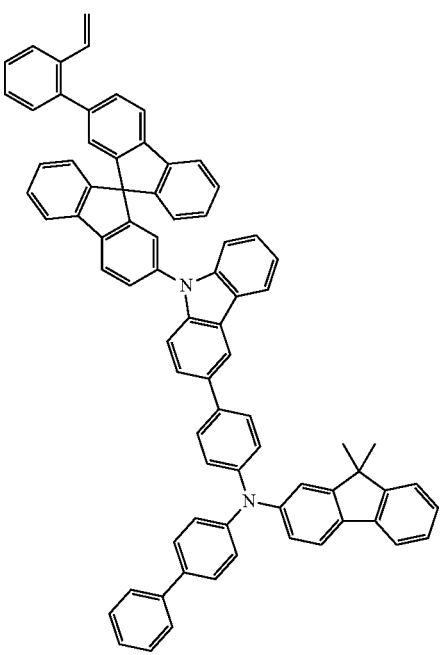

145
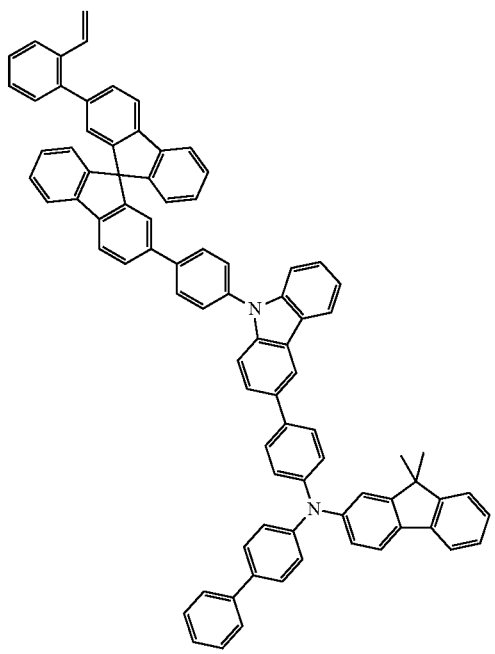
146
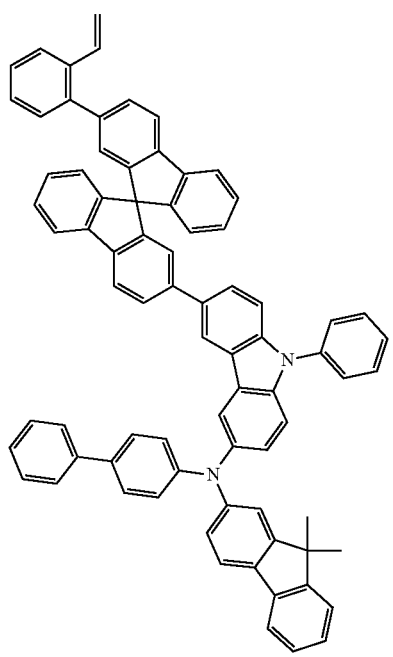
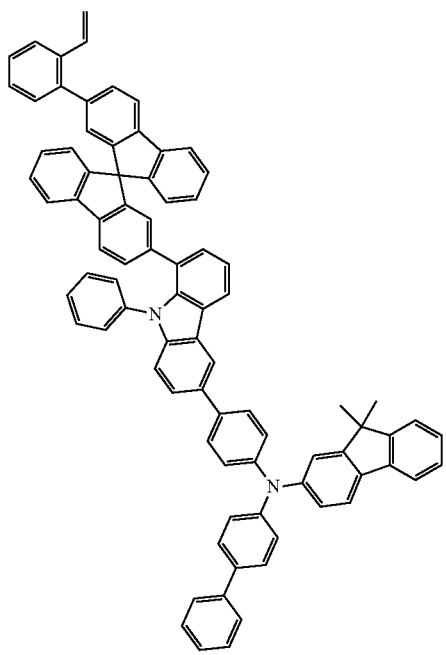 [SMILES: C=Cc1ccccc1-c1ccc2c(c1)C1(c3ccccc3-2)c2ccccc2-c2ccc(-c3cccc4c5cc(-c6ccc(N(c7ccc(-c8ccccc8)cc7)c7ccc8c(c7)C(C)(C)c7ccccc7-8)cc6)ccc5n(-c5ccccc5)c34)cc21]
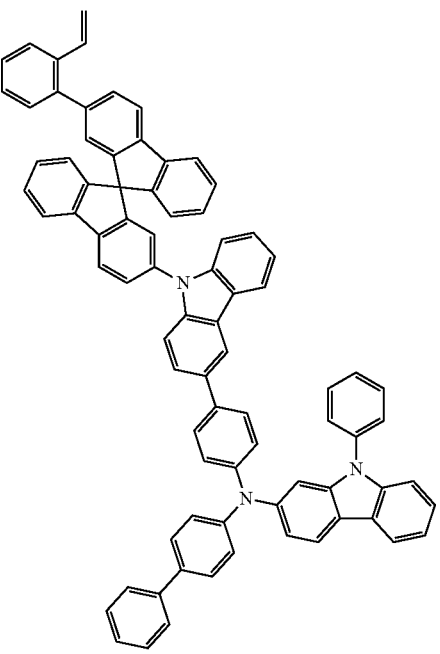

147
-continued
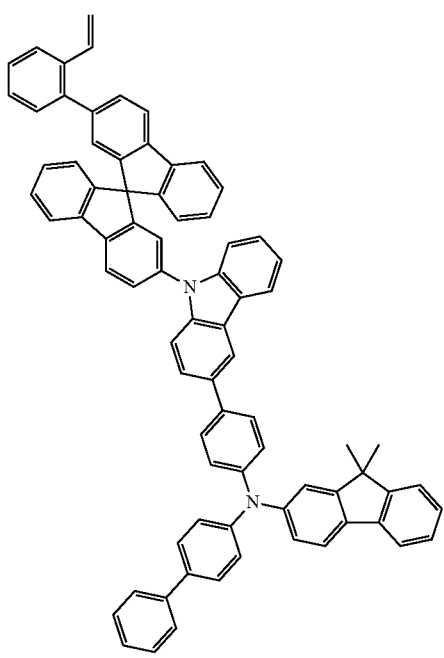
148
-continued
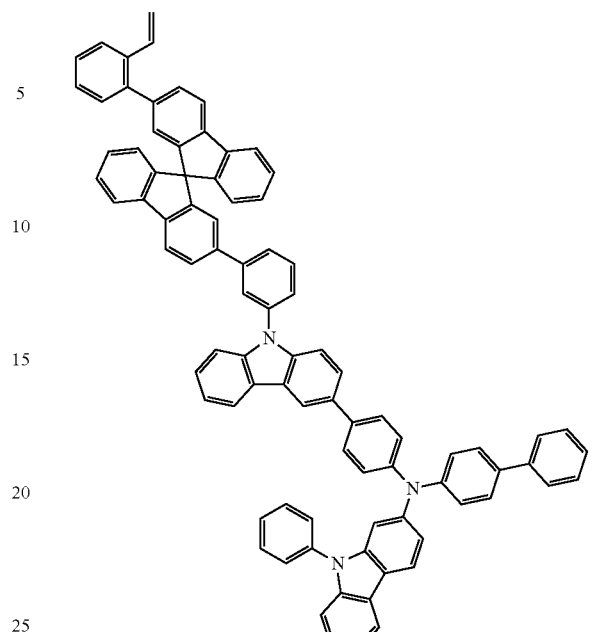
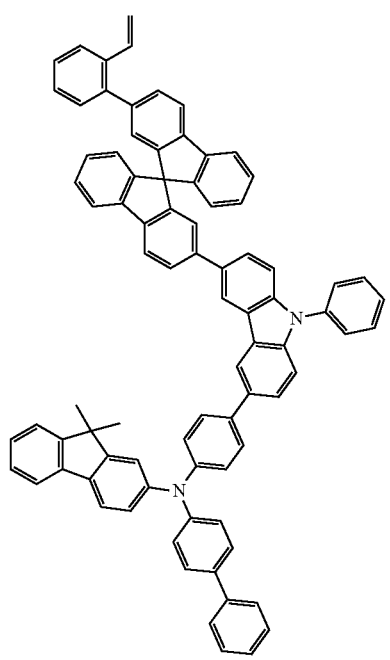
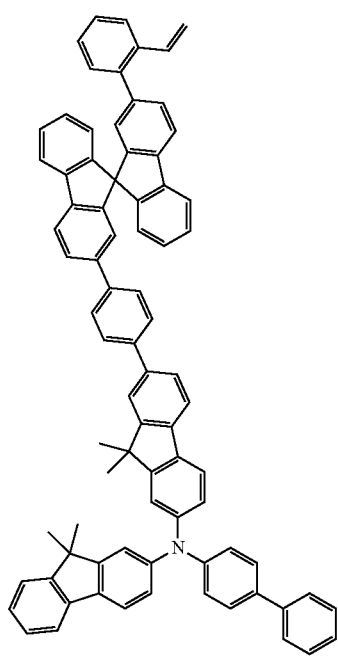

149
-continued
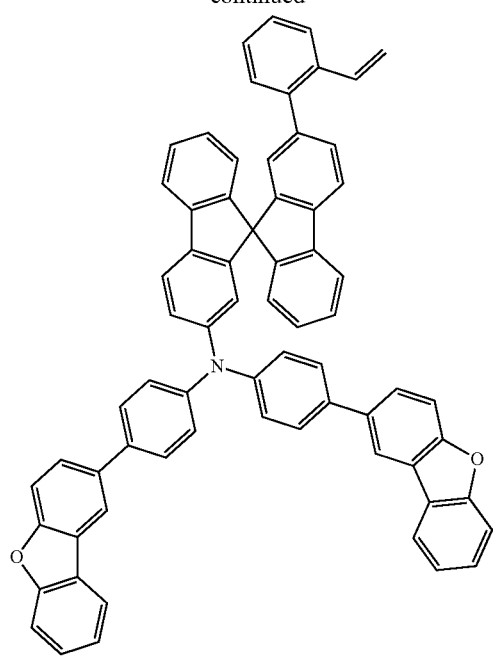
150
-continued
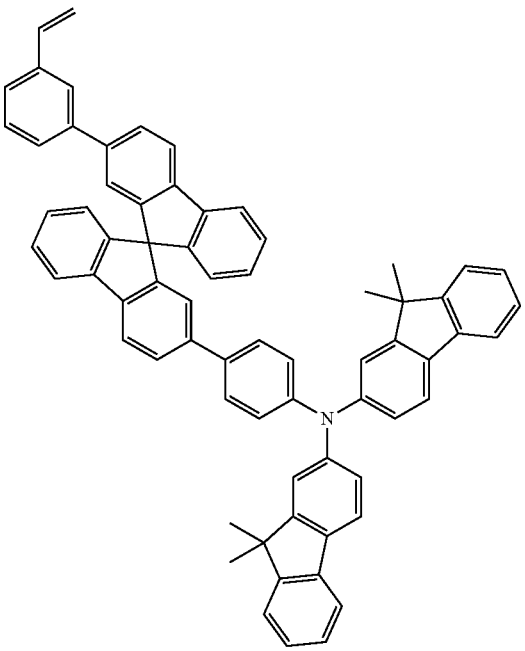
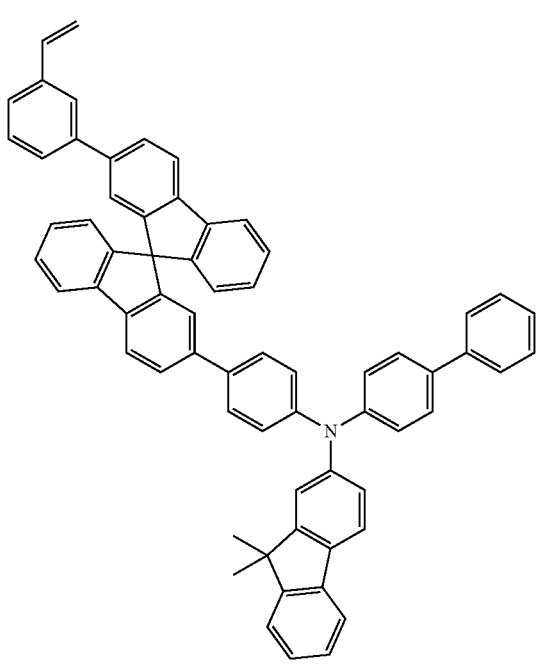
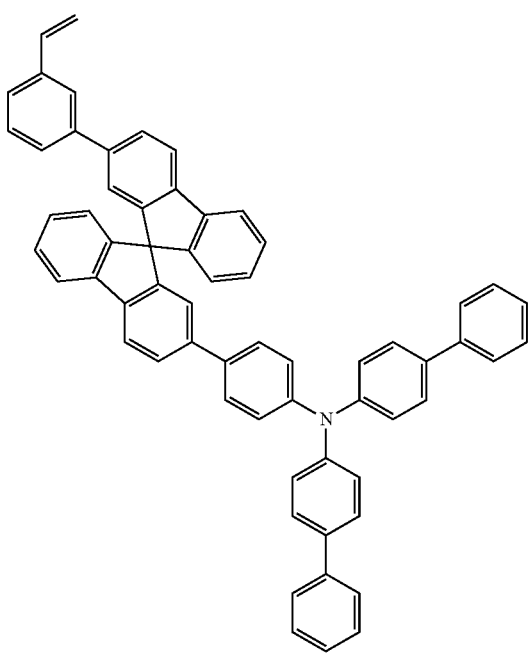

151
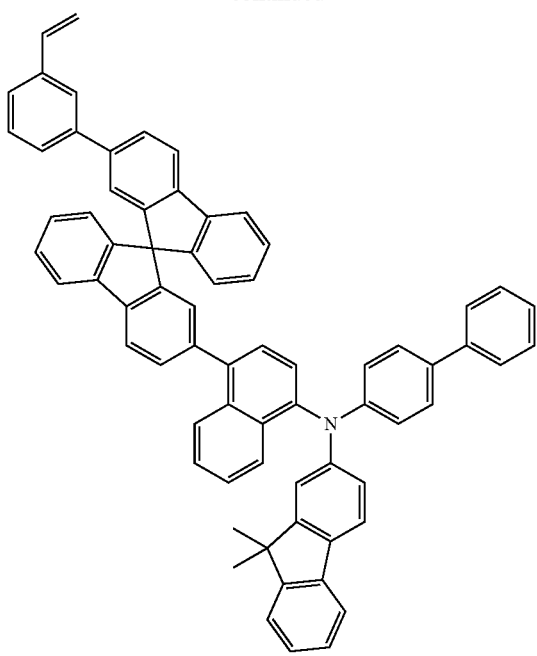
152
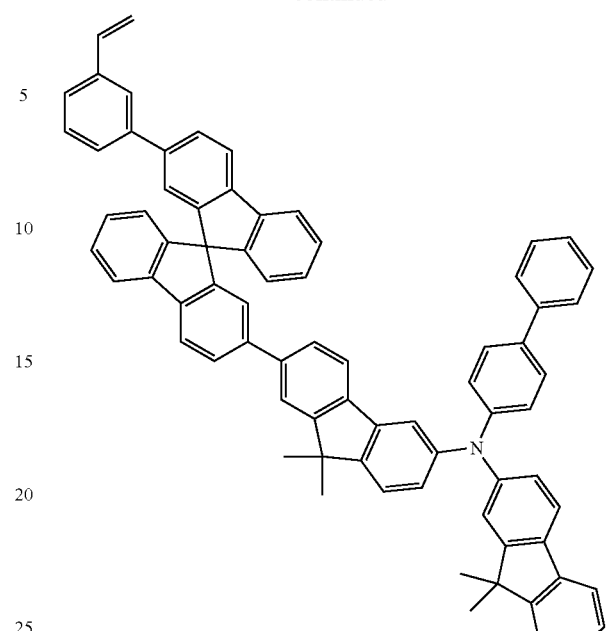
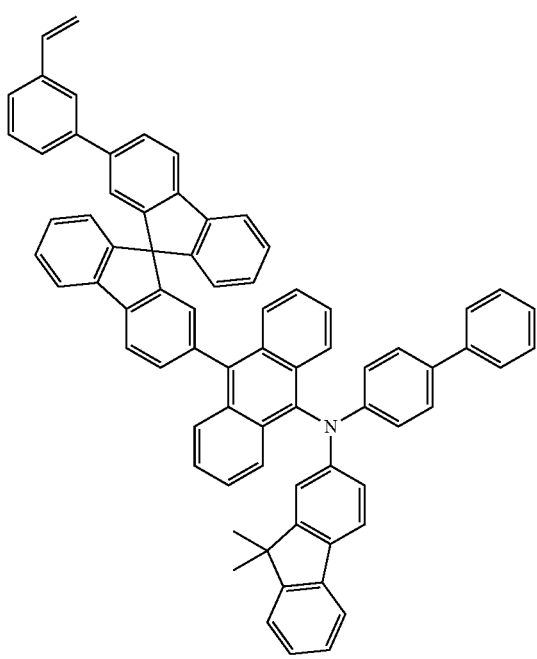
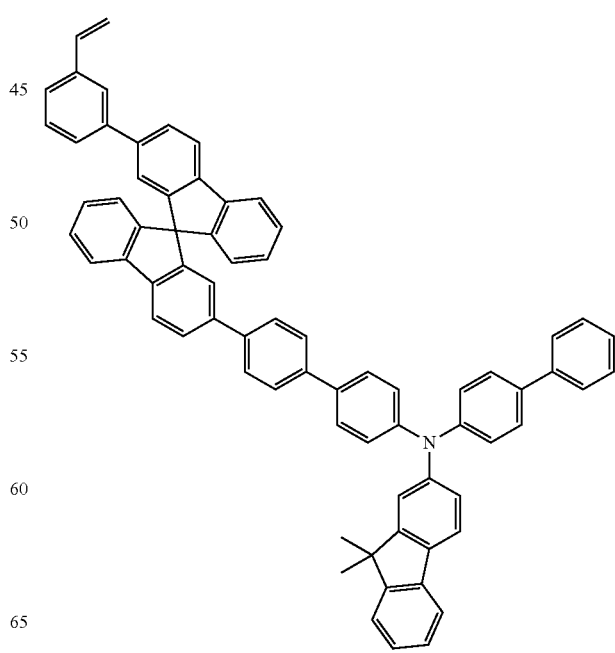

153
-continued
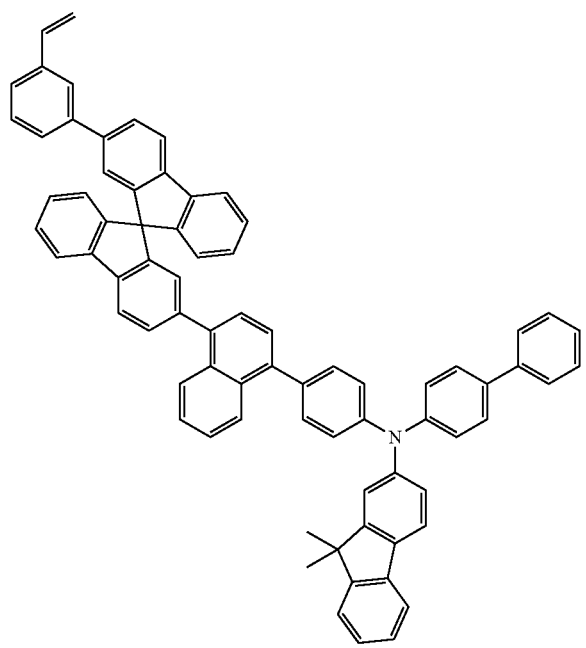
154
-continued
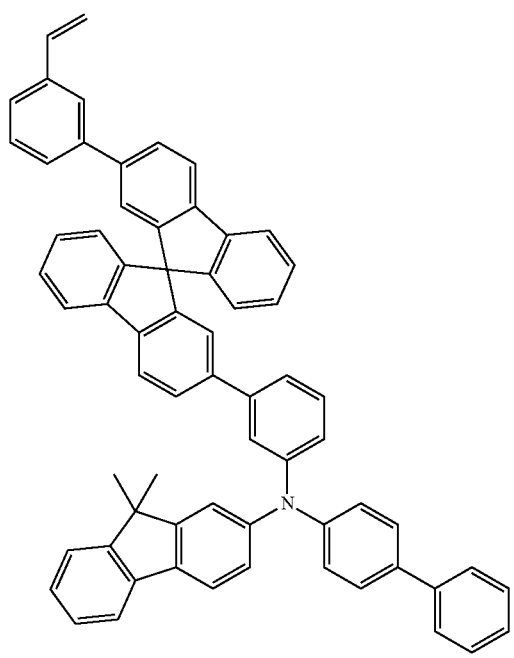
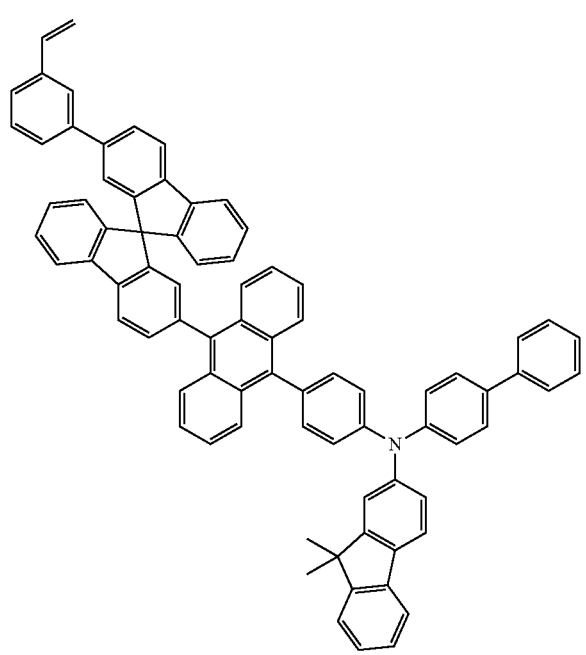 [SMILES: C=Cc1cccc(-c2ccc3c(c2)C2(c4ccccc4-3)c3ccccc3-c3ccc(-c4c5ccccc5c(-c5ccc(N(c6ccc(-c7ccccc7)cc6)c6ccc7c(c6)C(C)(C)c6ccccc6-7)cc5)c5ccccc45)cc32)c1]
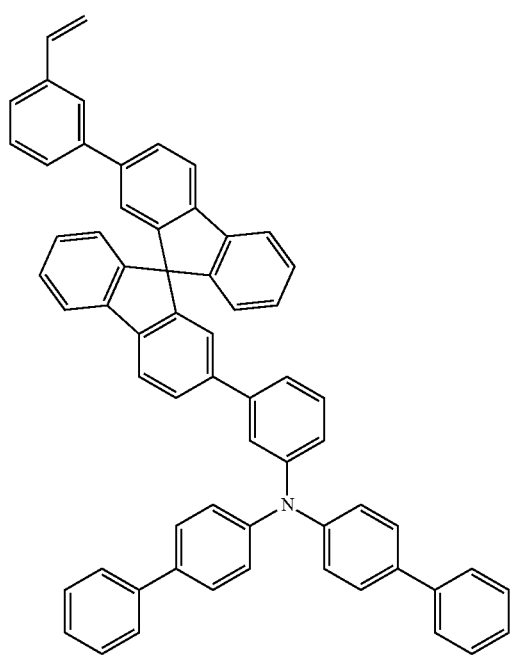

155
-continued
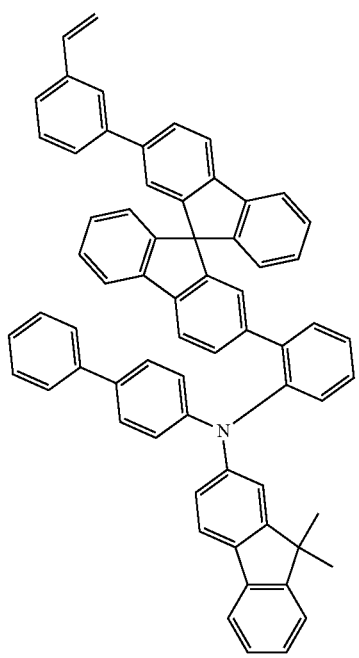 [SMILES: C=Cc1cccc(-c2ccc3c(c2)C2(c4ccccc4-3)c3ccccc3-c3ccc(-c4ccccc4N(c4ccc(-c5ccccc5)cc4)c4ccc5c(c4)C(C)(C)c4ccccc4-5)cc32)c1]
156
-continued
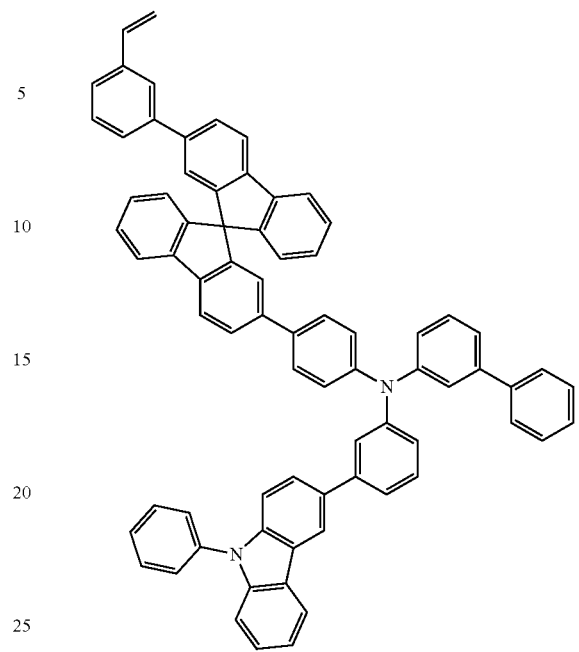
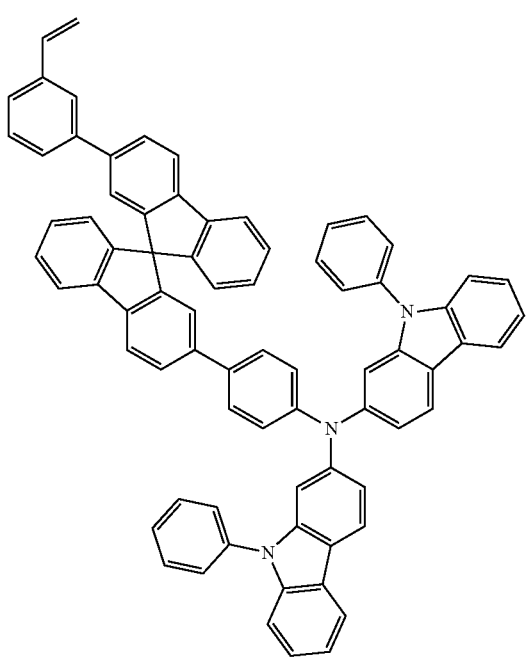
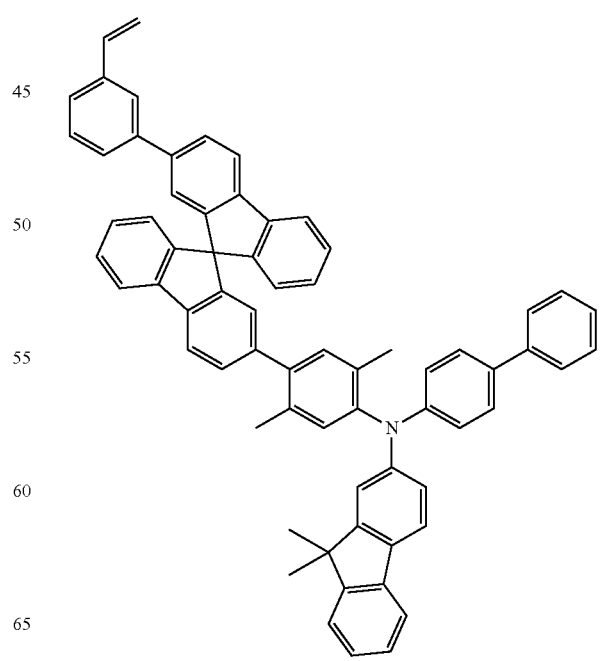

157
-continued
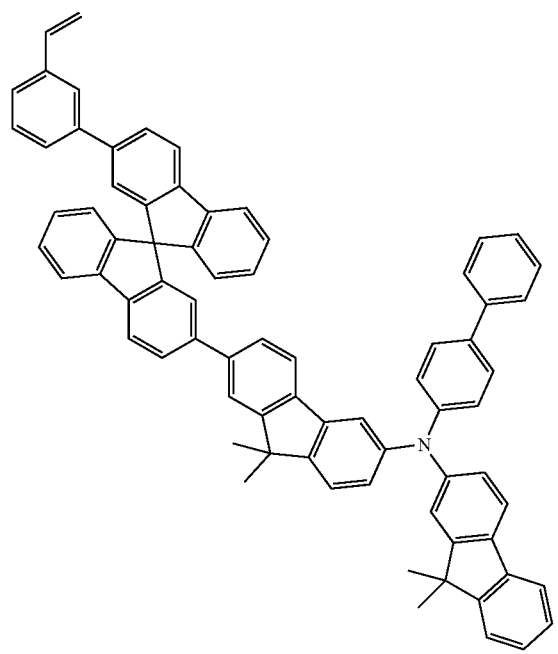
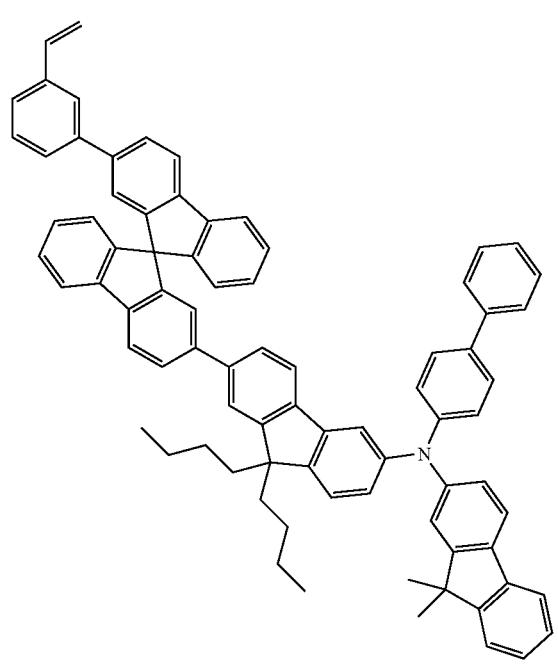
158
-continued
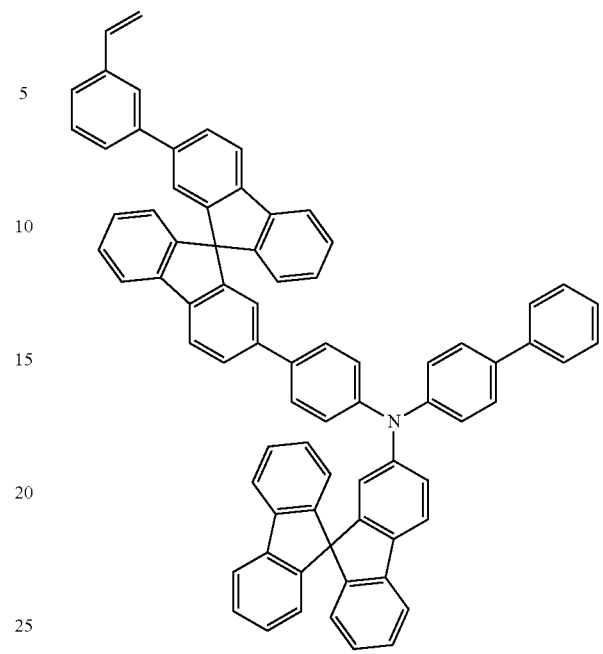
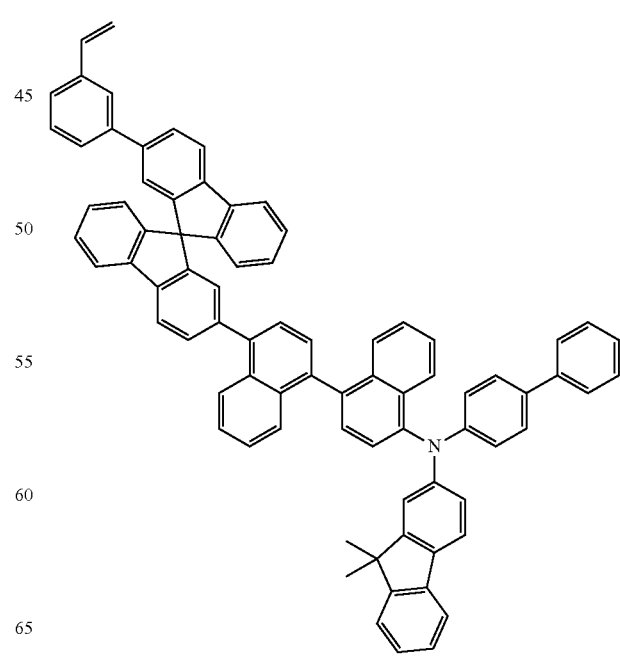

159
-continued
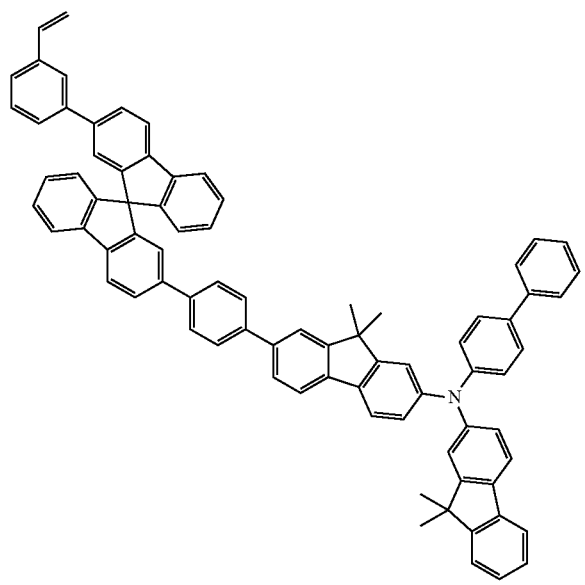
160
-continued
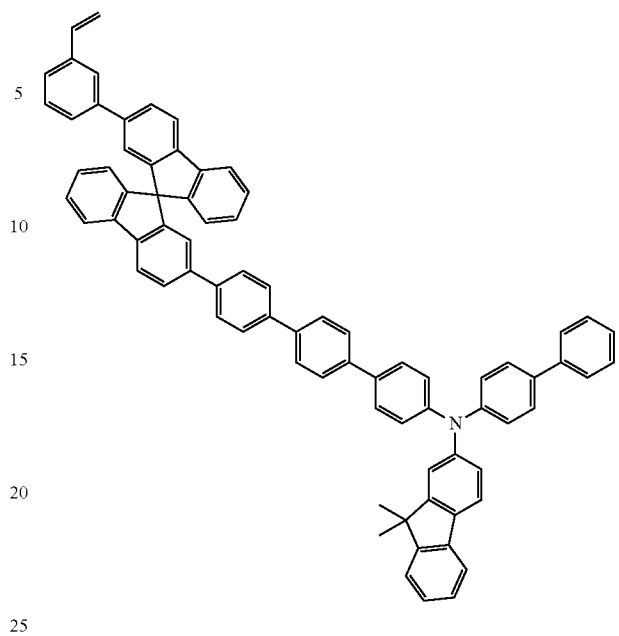
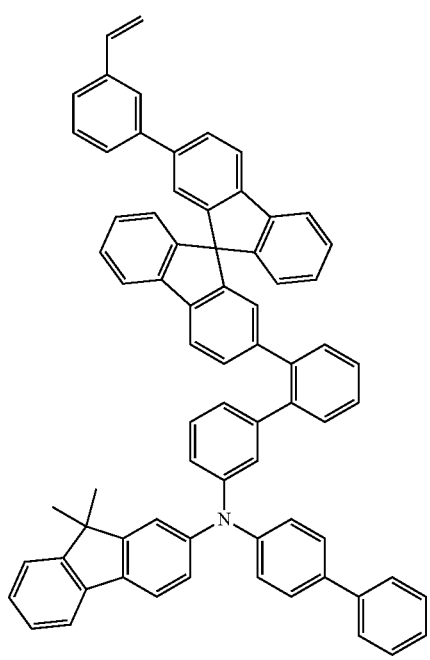
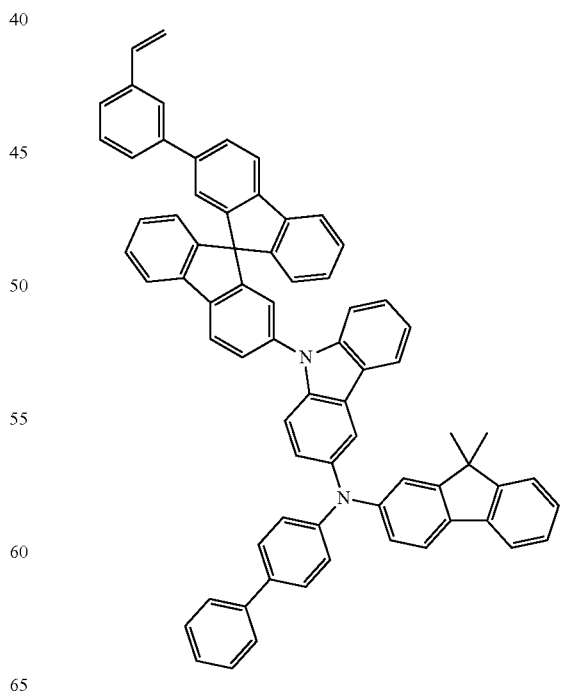

161
-continued
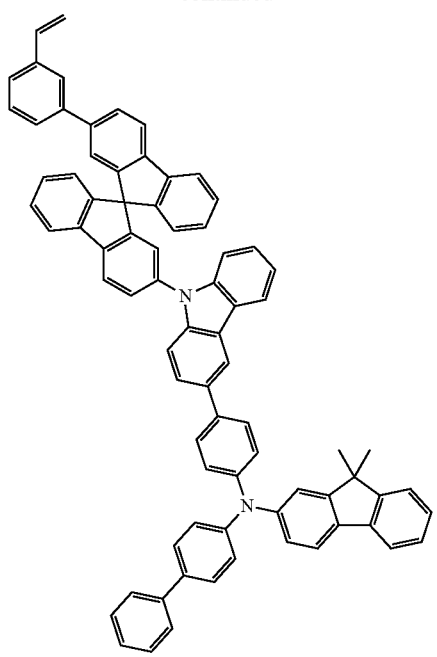
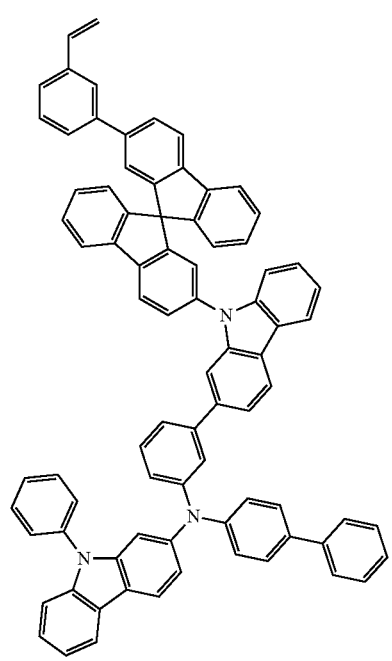
162
-continued
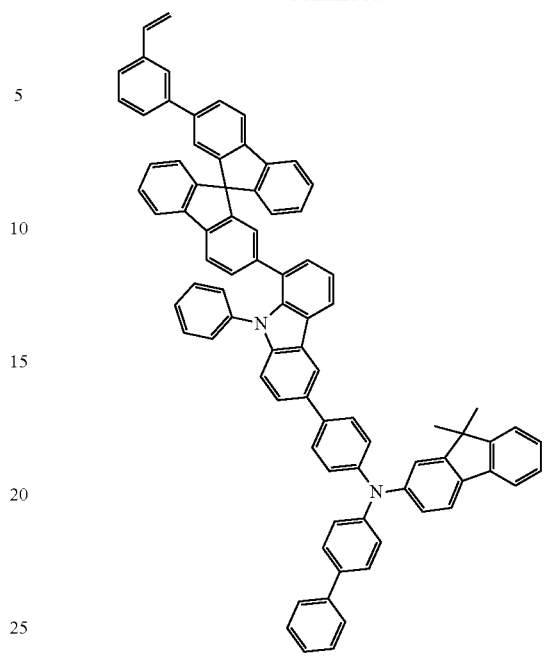
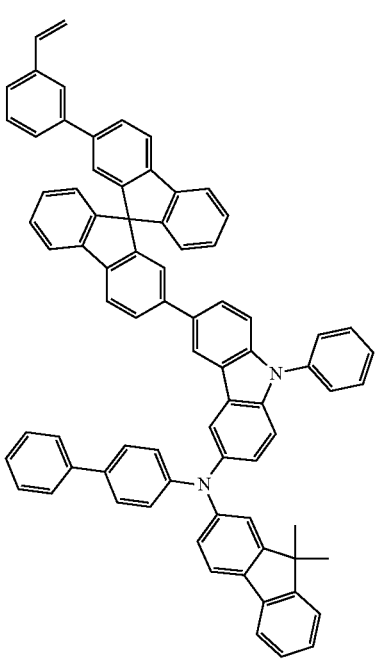

163
-continued
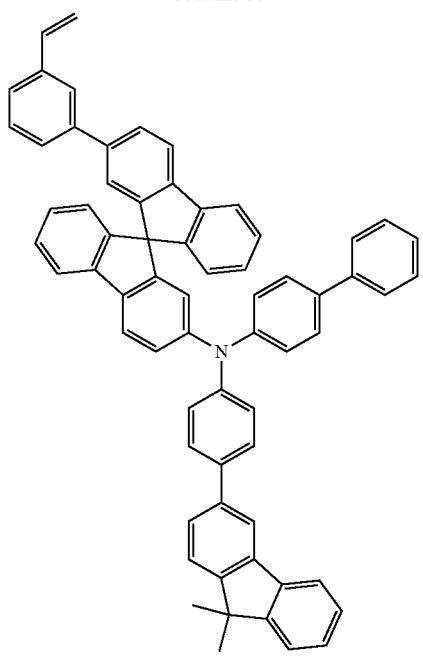
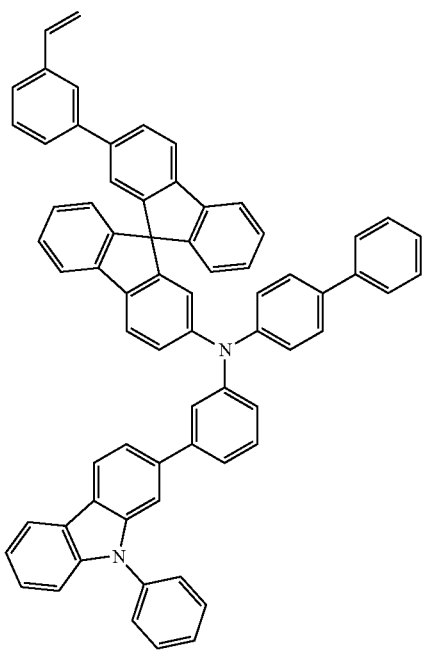
164
-continued
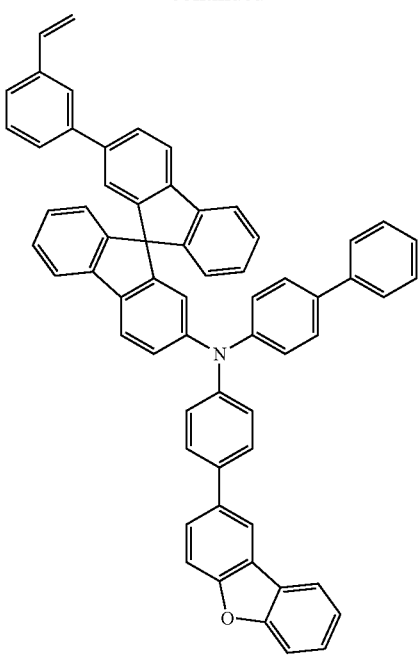
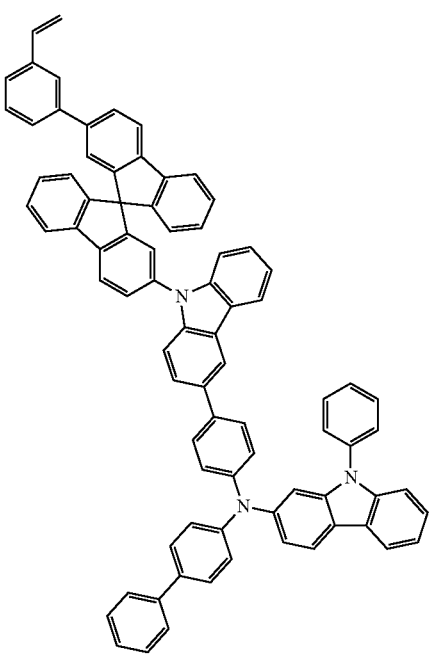

165
-continued
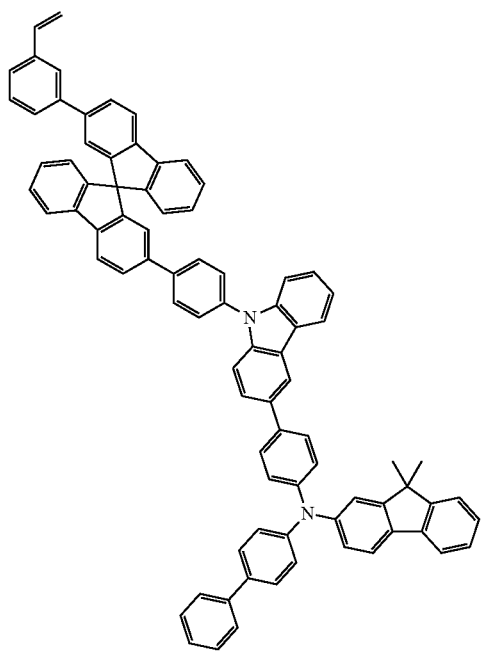
166
-continued
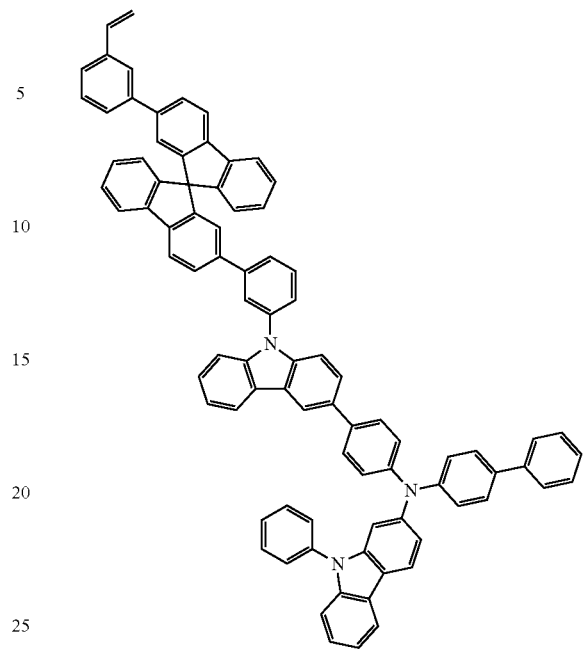
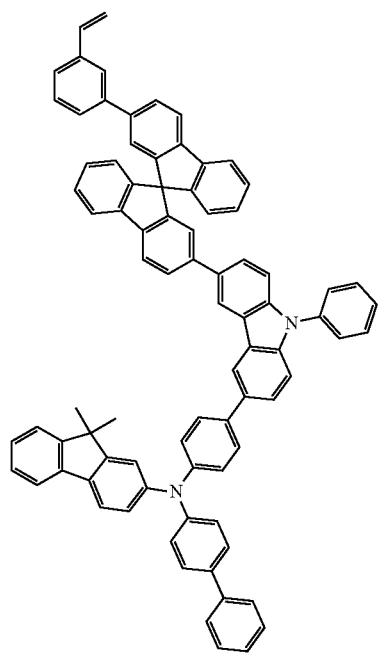
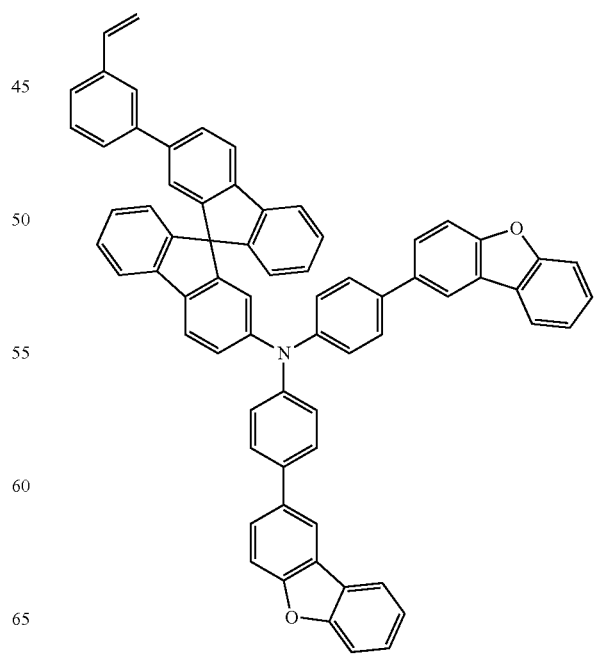

167
-continued
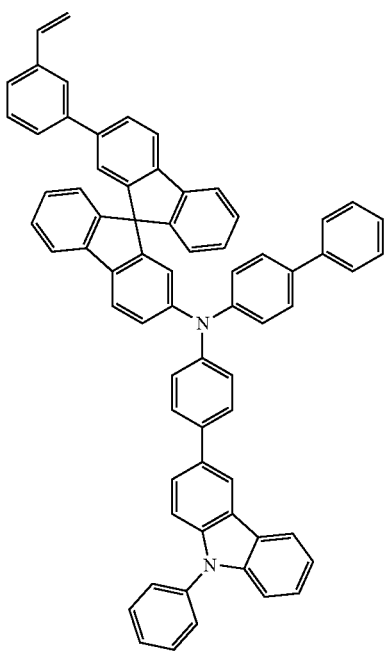
168
-continued
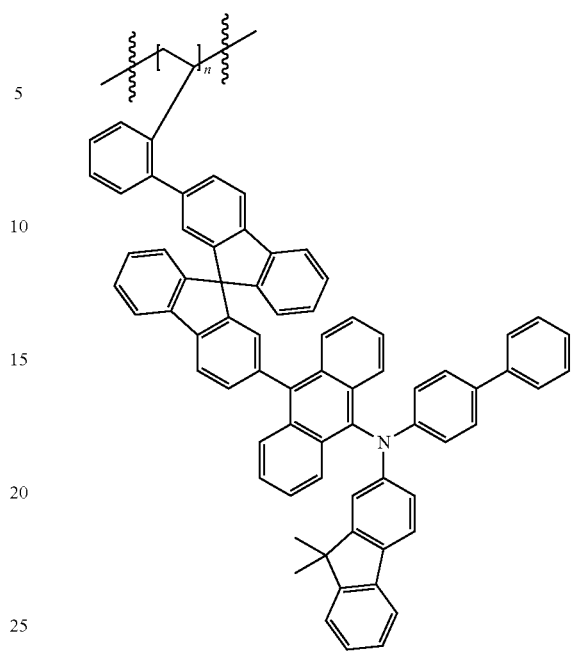
16. A coating composition comprising the monomer of claim 15.
17. The coating composition of claim 14, wherein a content of the monomer represented by Chemical Formula 2 in the coating composition is from 0.1 wt/v % to 20 wt/v %.
18. A homopolymer comprising a unit of any one selected from among the following structures:
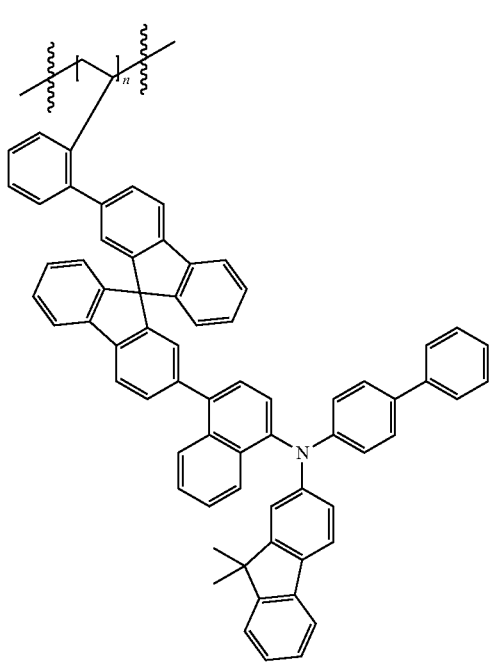
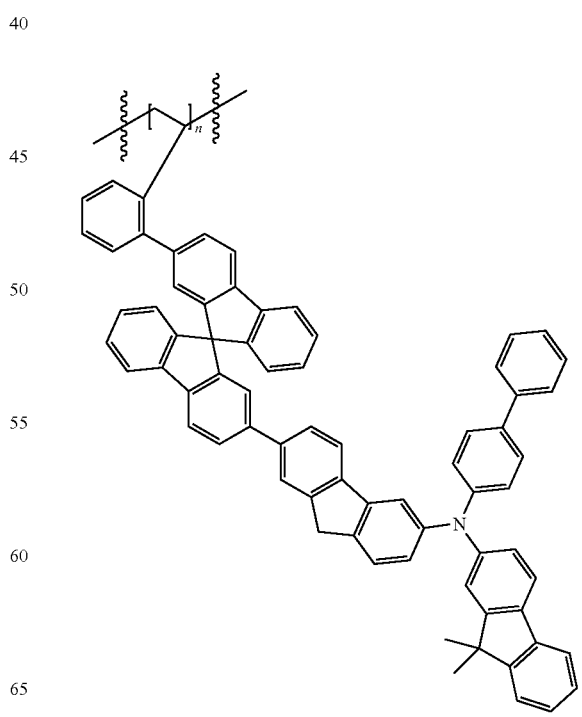

169
-continued
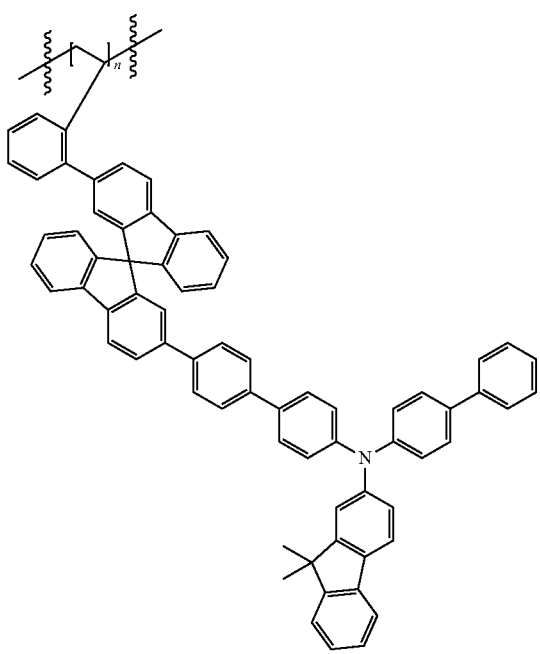
170
-continued
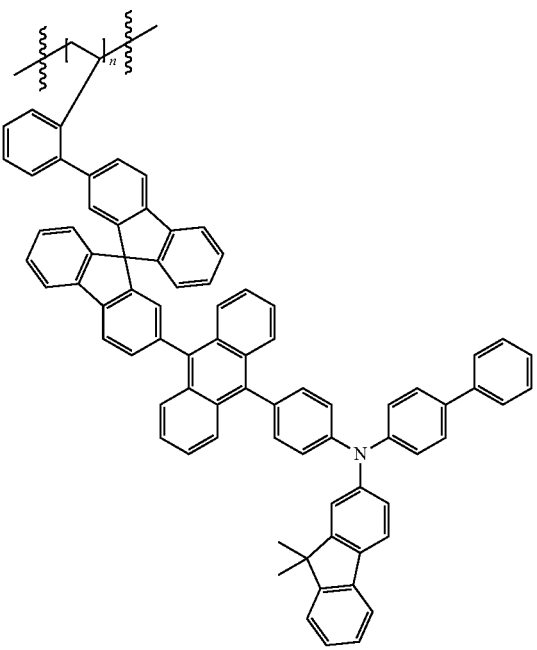
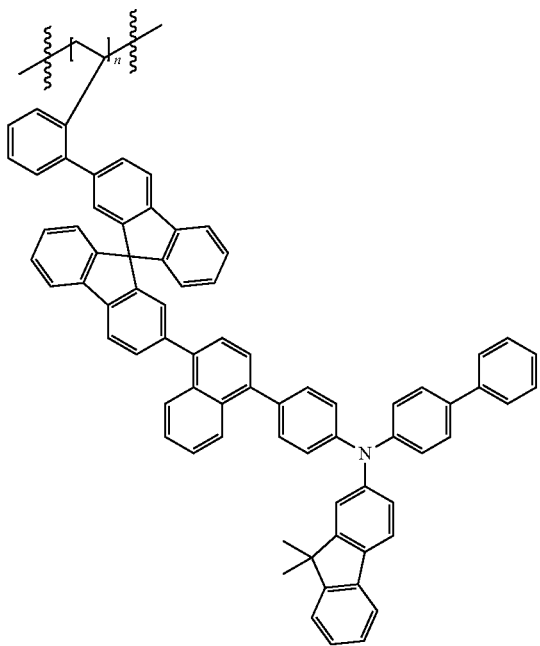
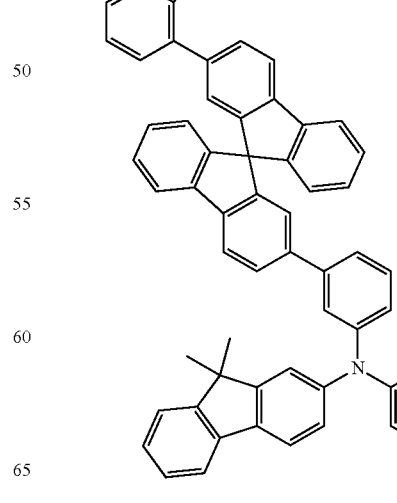

171
-continued
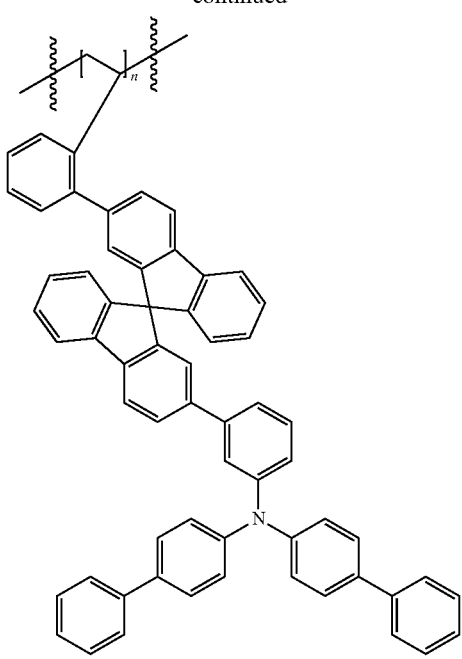
172
-continued
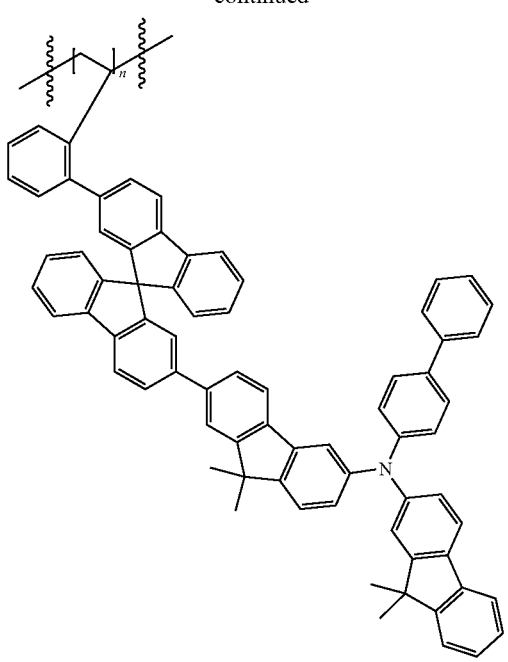
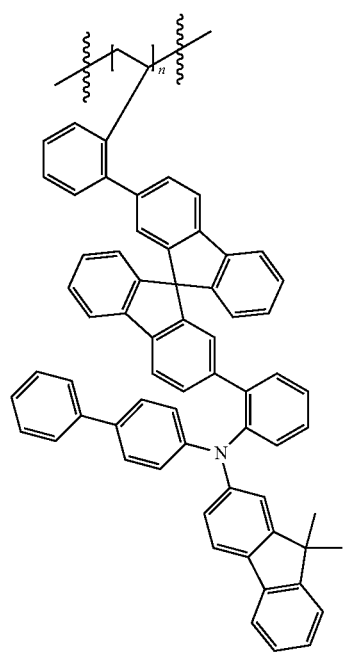
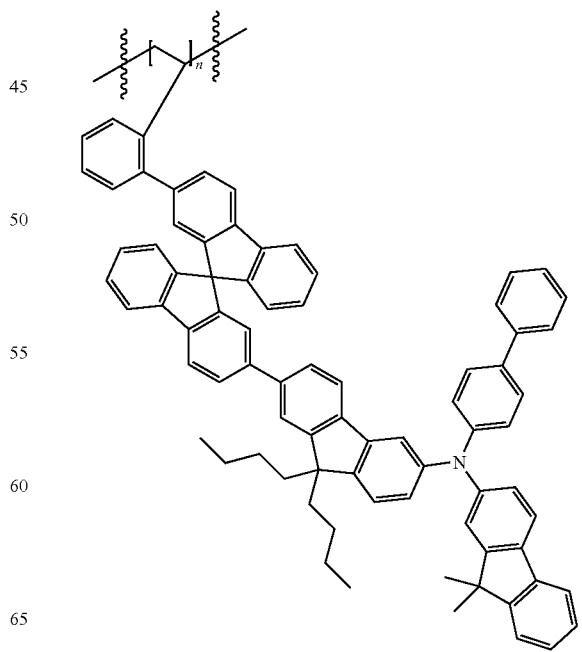

173
-continued
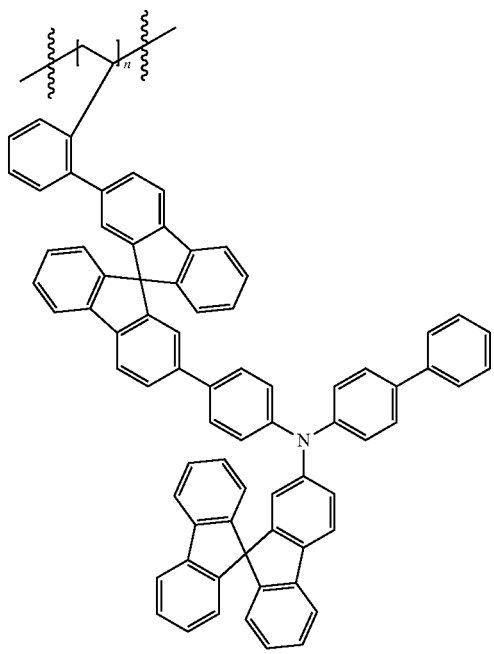
174
-continued
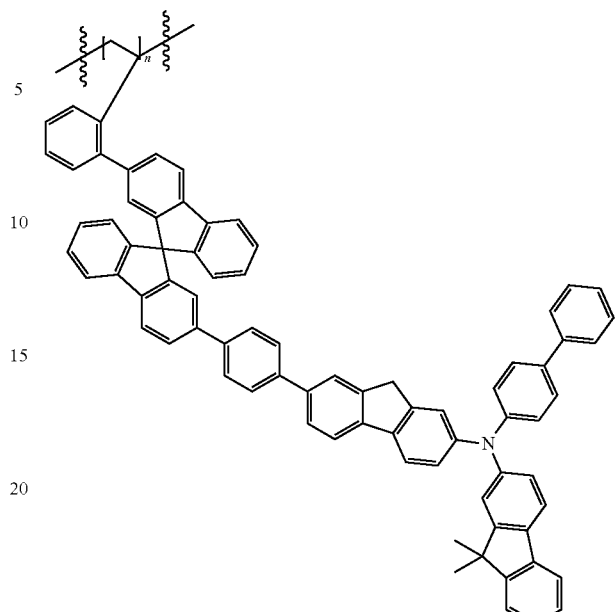
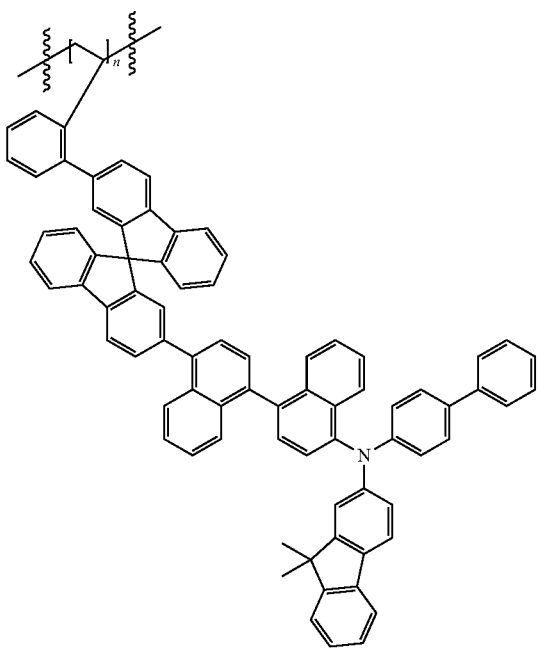
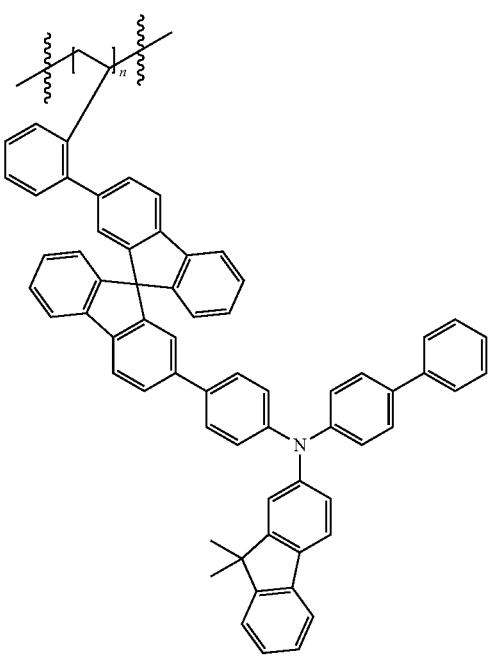

175
-continued
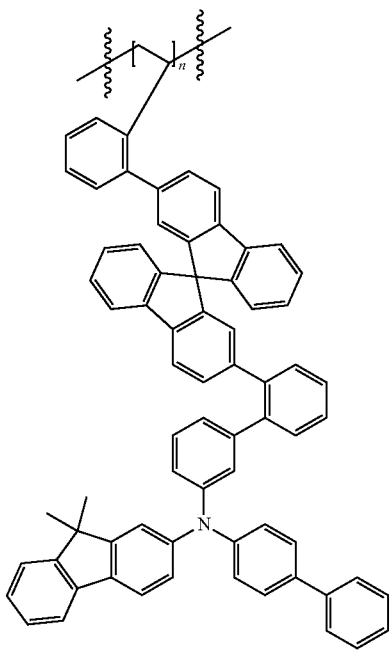
176
-continued
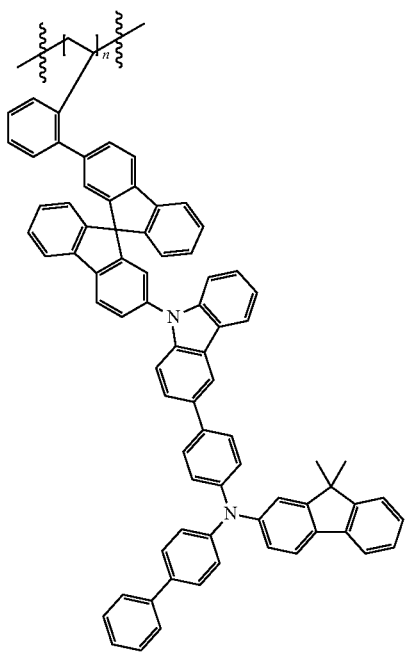
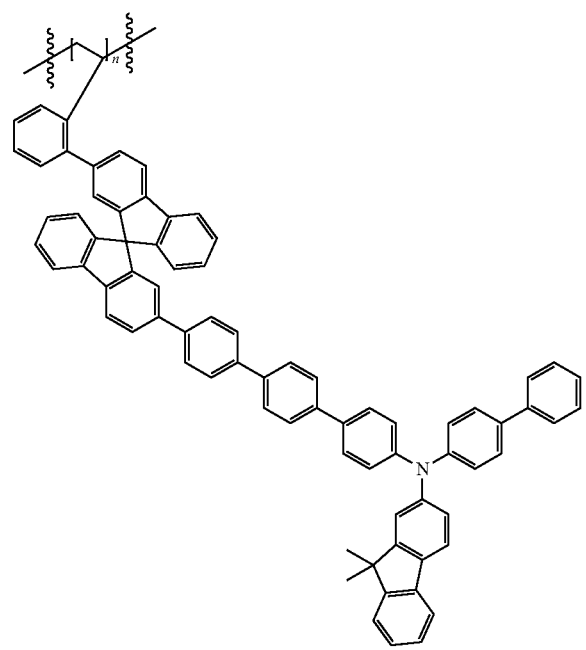
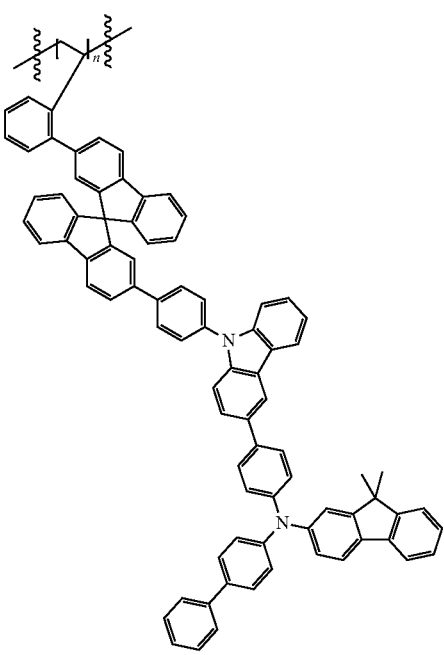

177
-continued
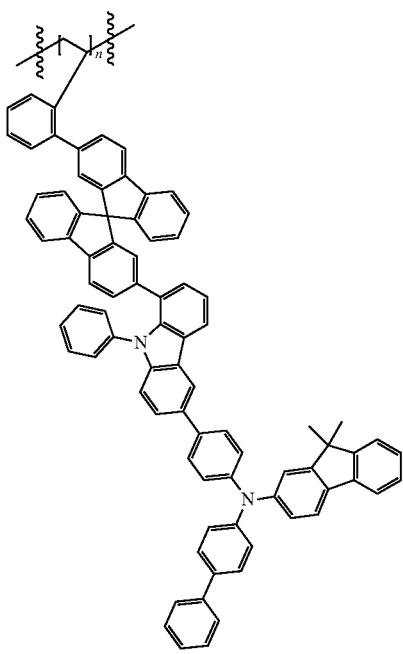
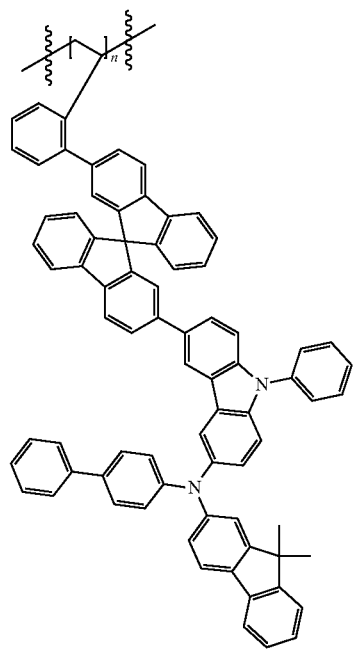
178
-continued
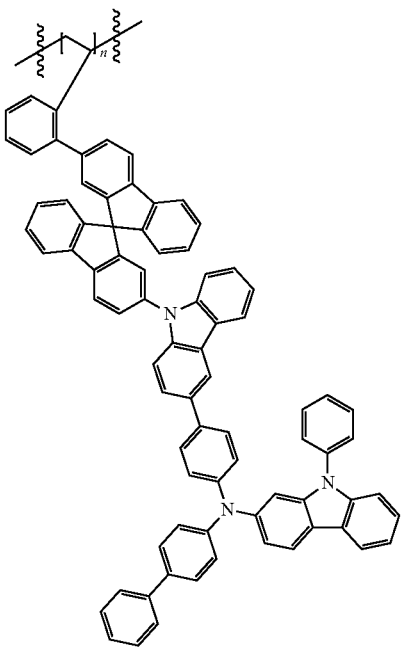
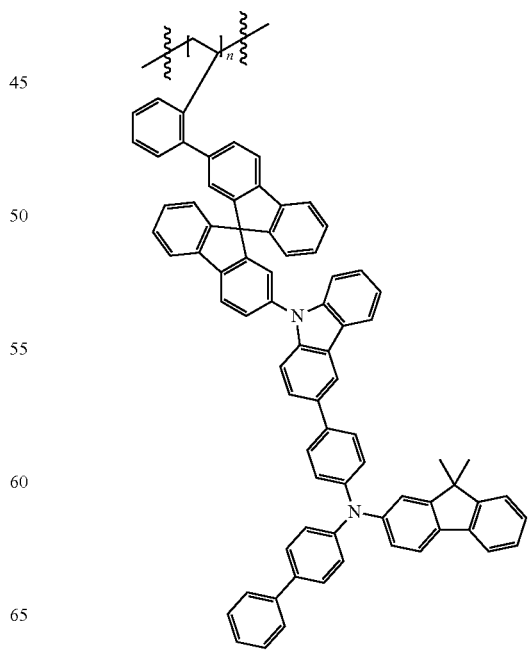

| 179 -continued | 180 -continued |
|---|---|
| 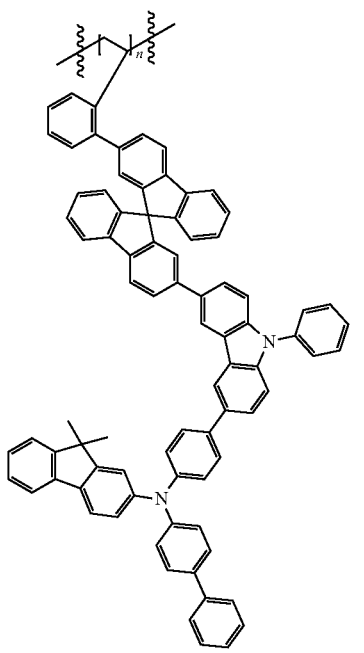 | 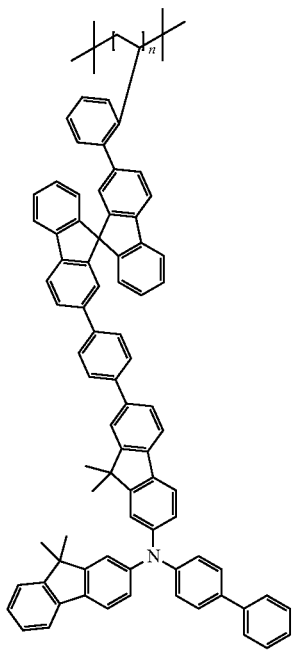 |
| 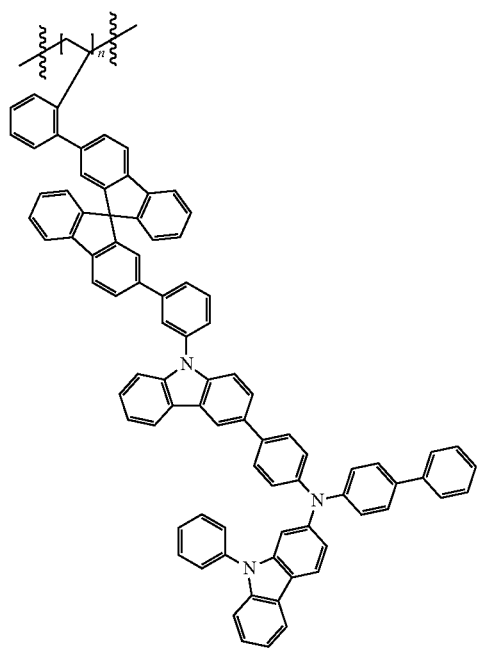 | 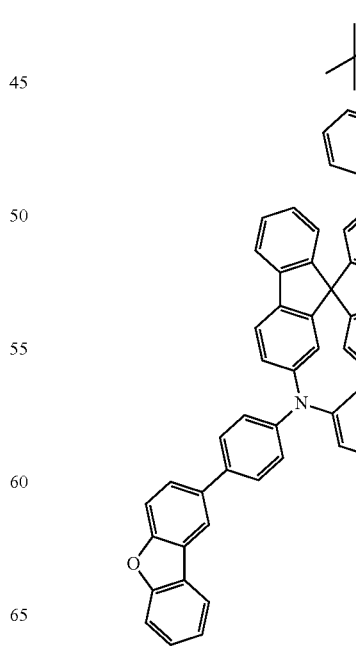 |

181
-continued
182
-continued
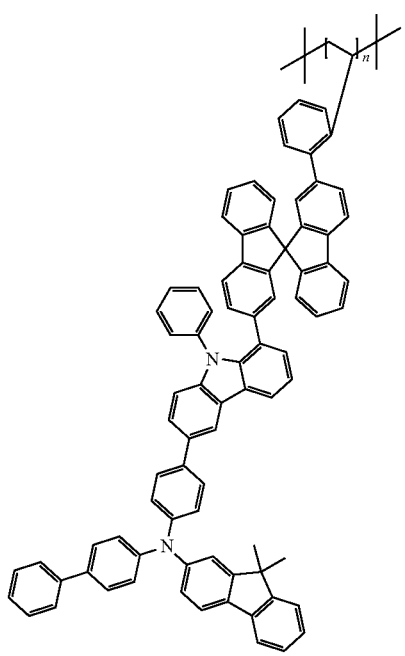
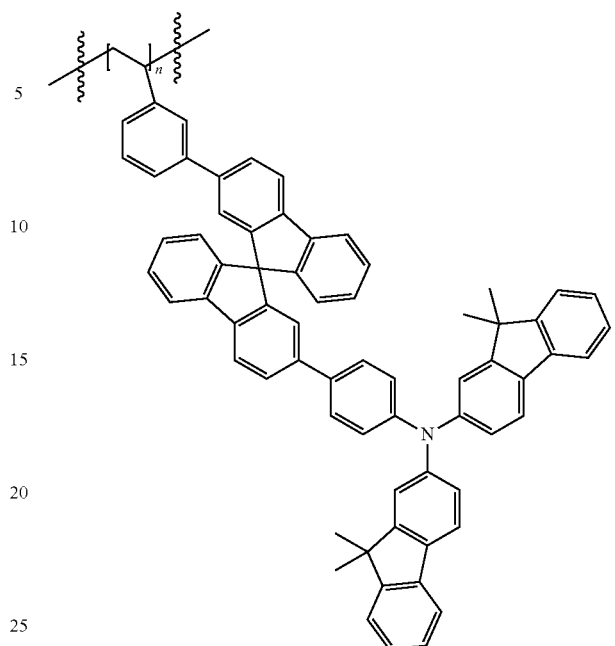
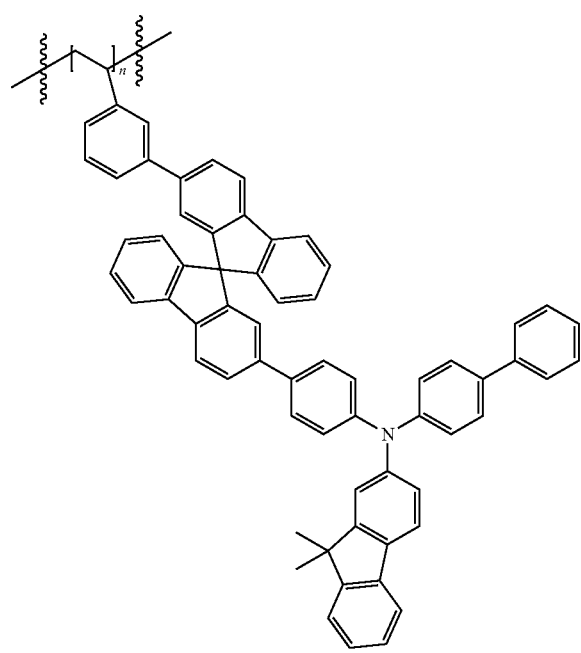
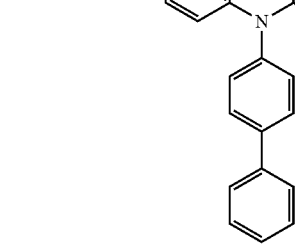

183
-continued
184
-continued
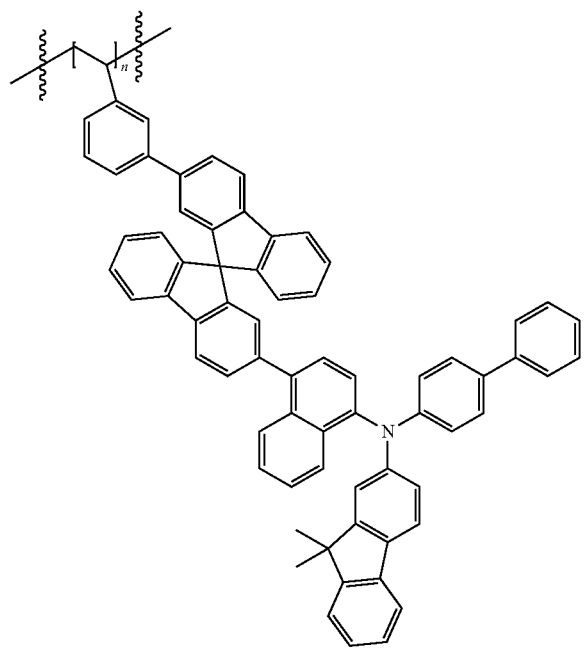
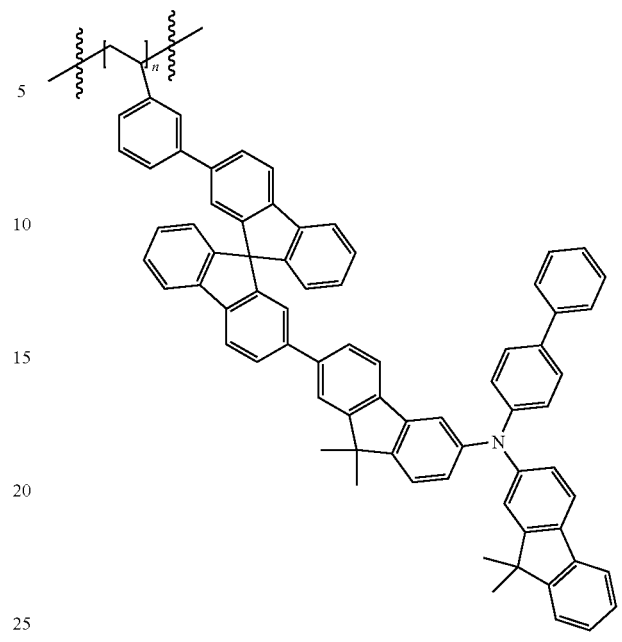
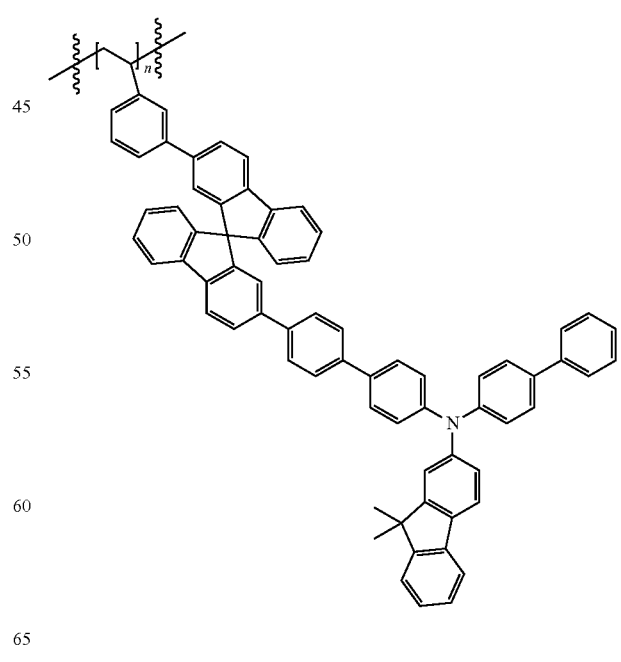

185
-continued
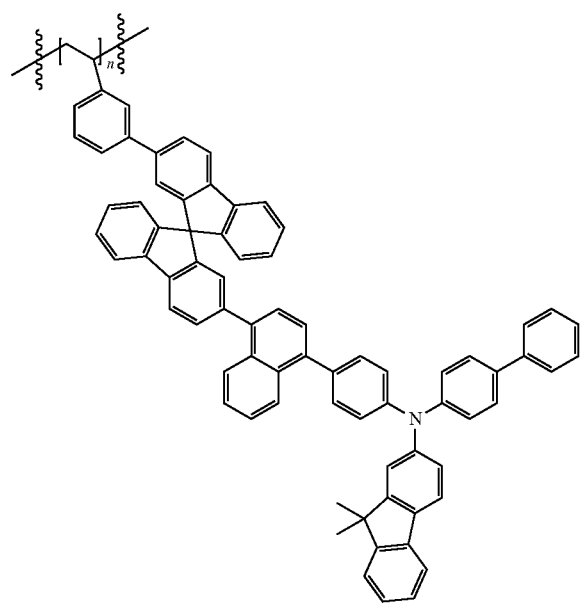
186
-continued
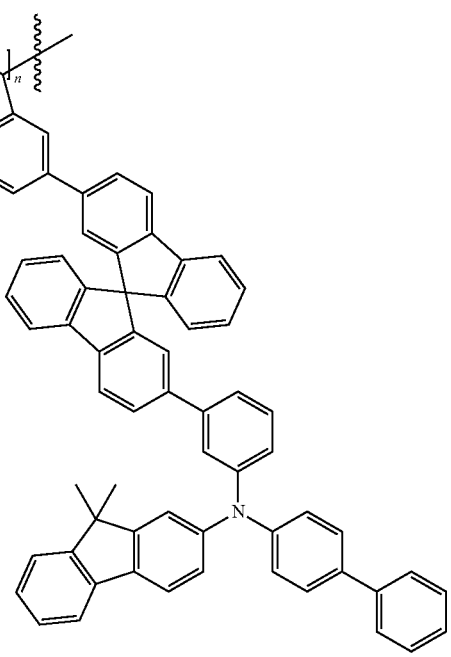
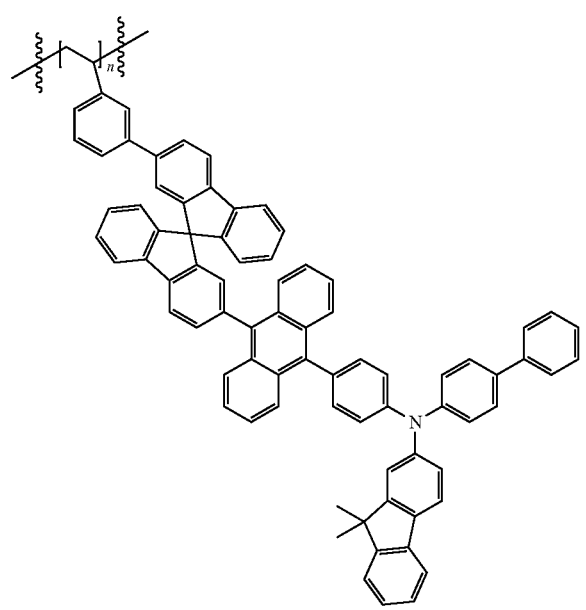
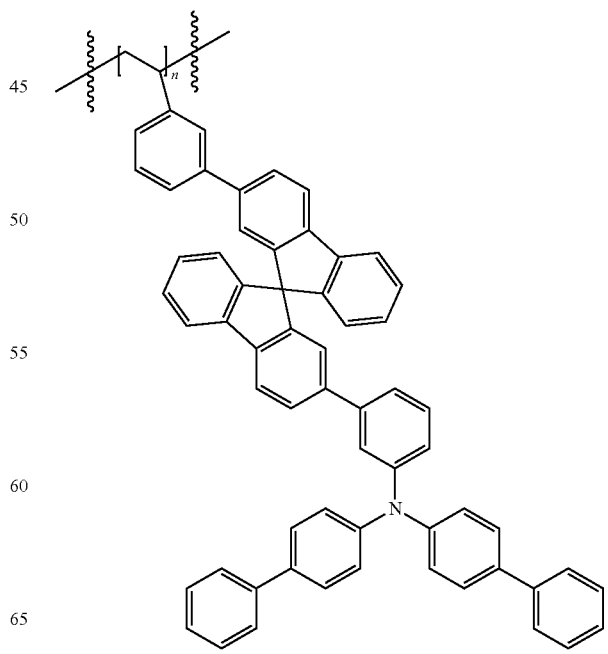

187
-continued
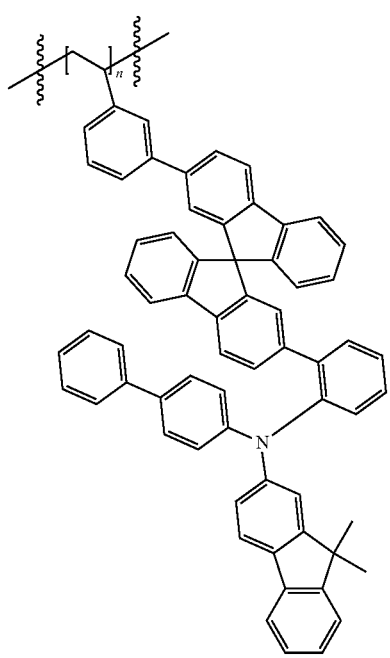
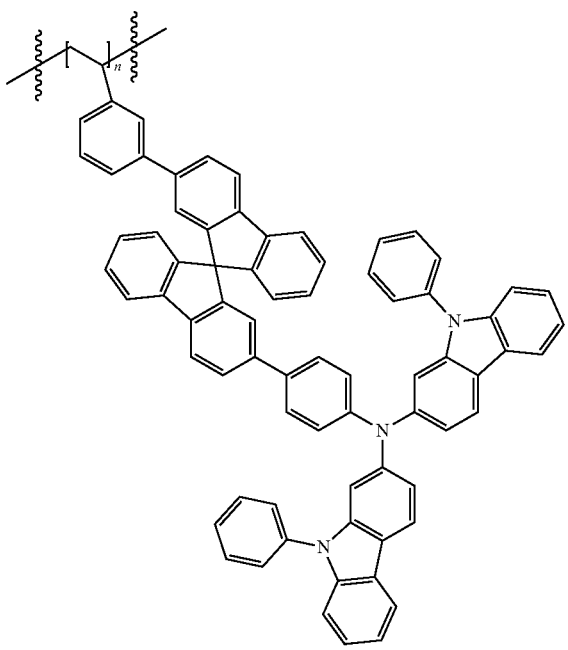
188
-continued
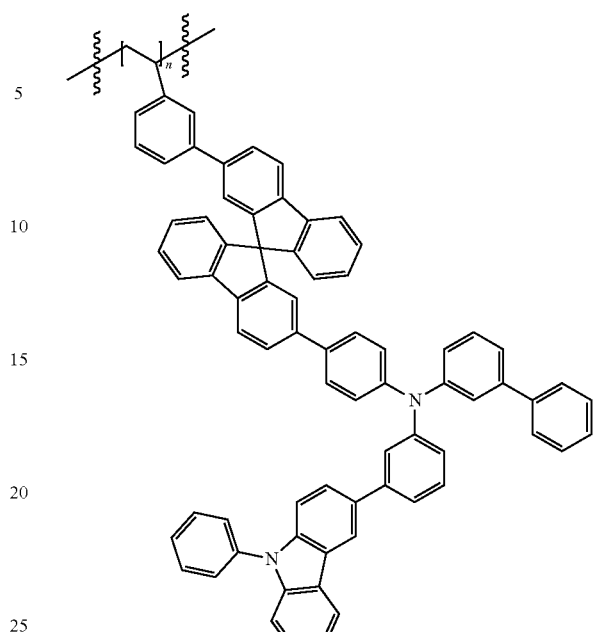
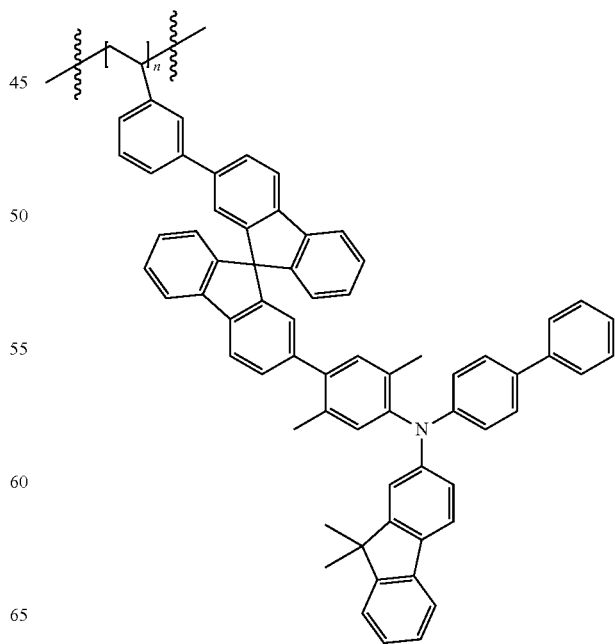

189
-continued
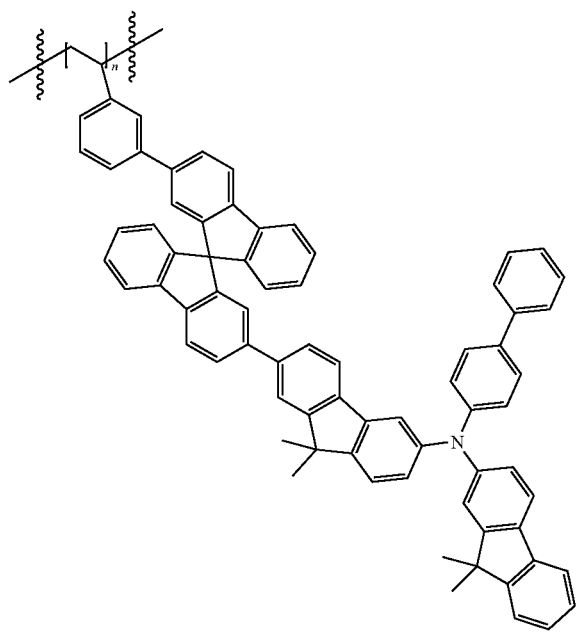
190
-continued
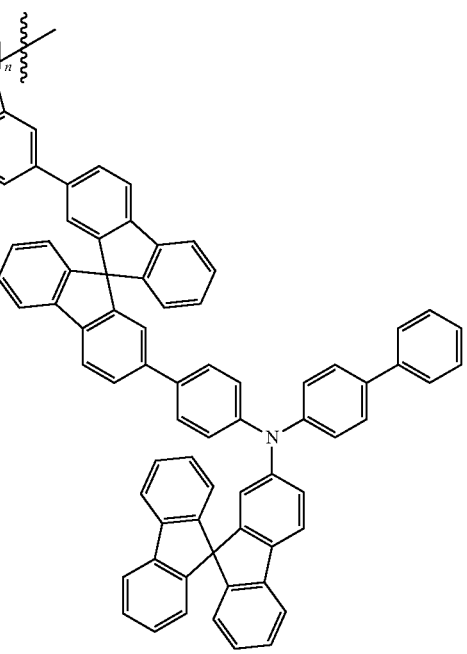
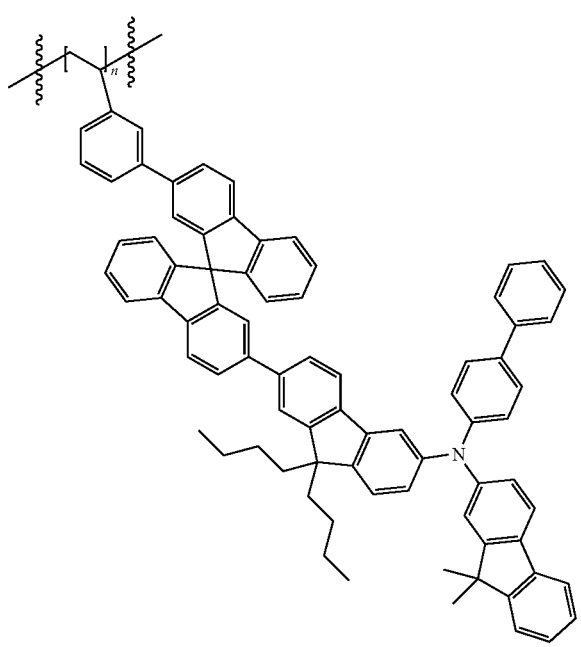
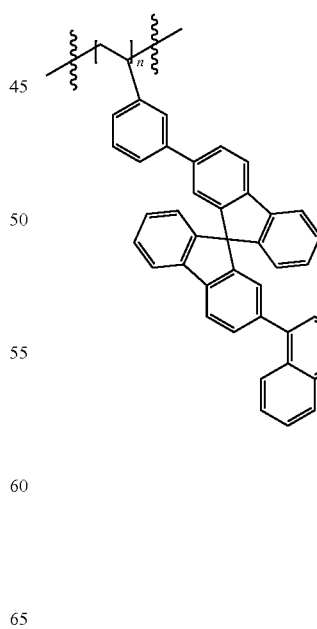

191
-continued
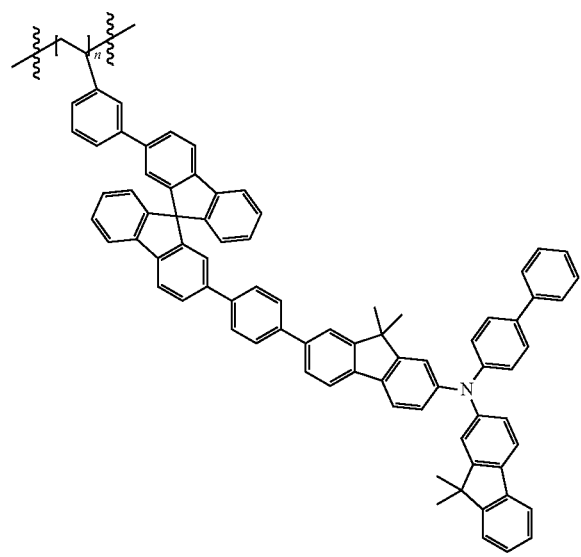
192
-continued
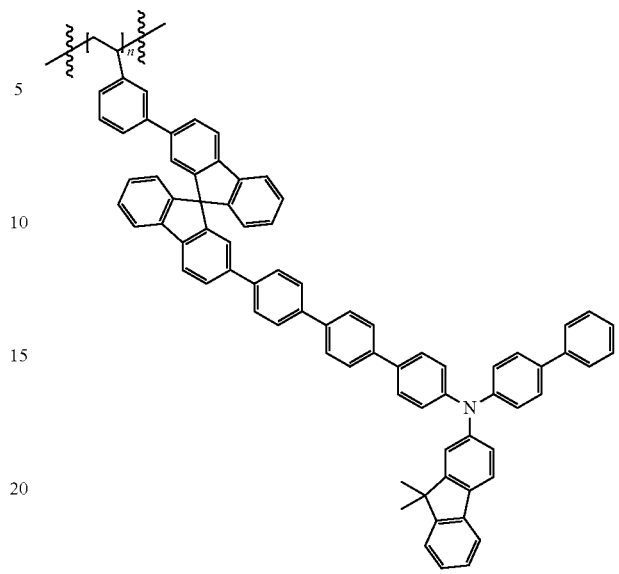
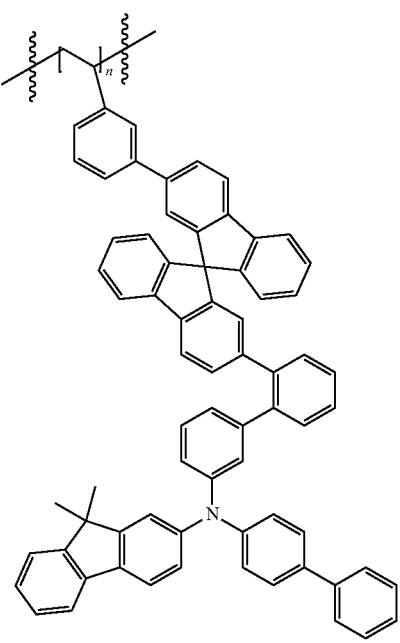
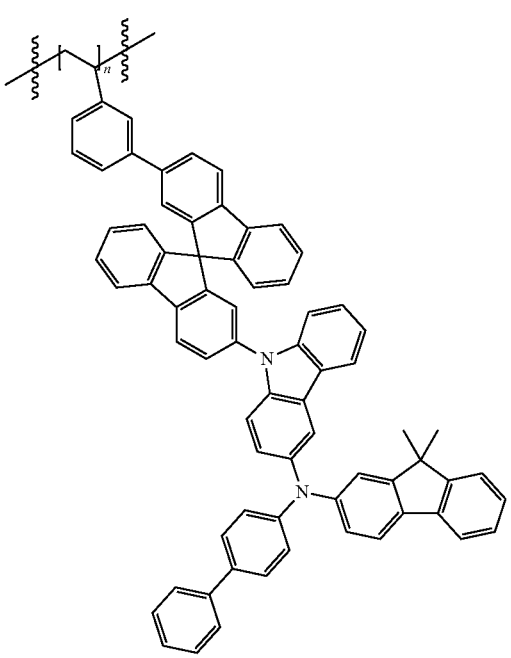

193
-continued
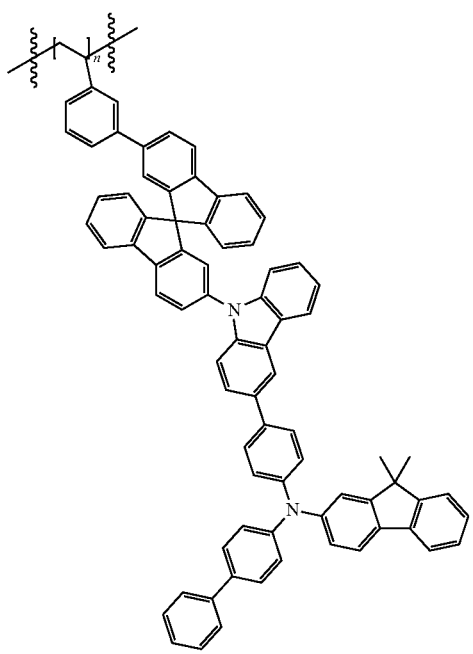
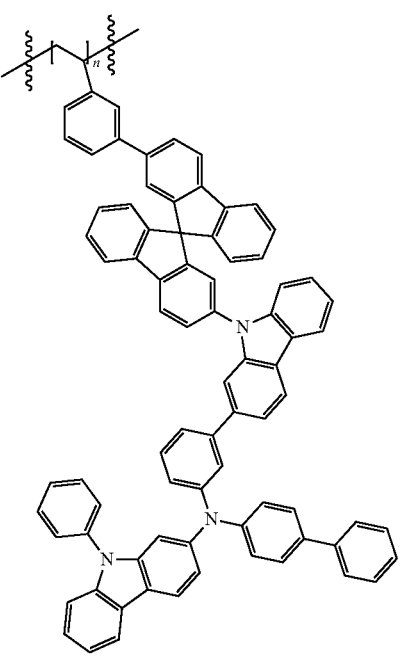
194
-continued
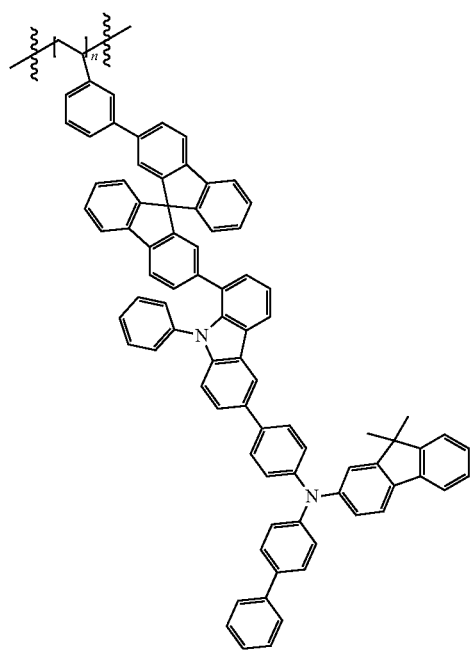
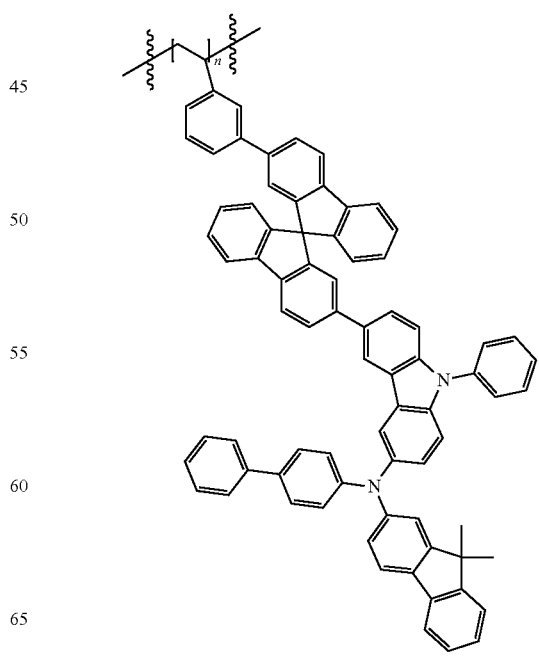

195
-continued
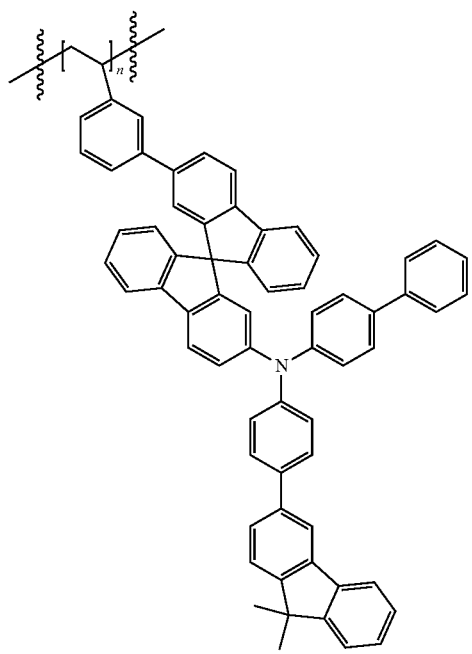
196
-continued
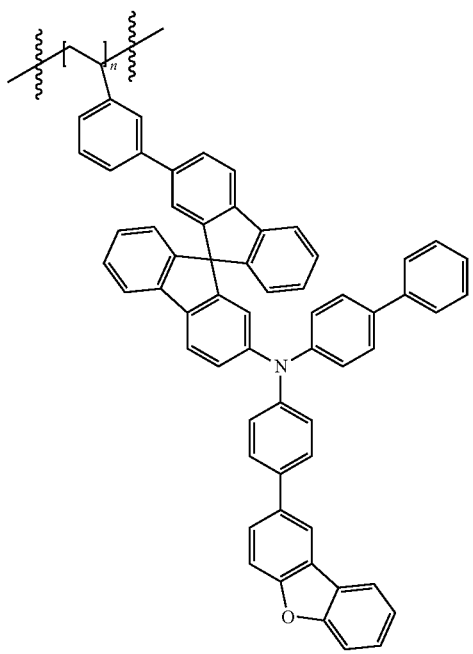
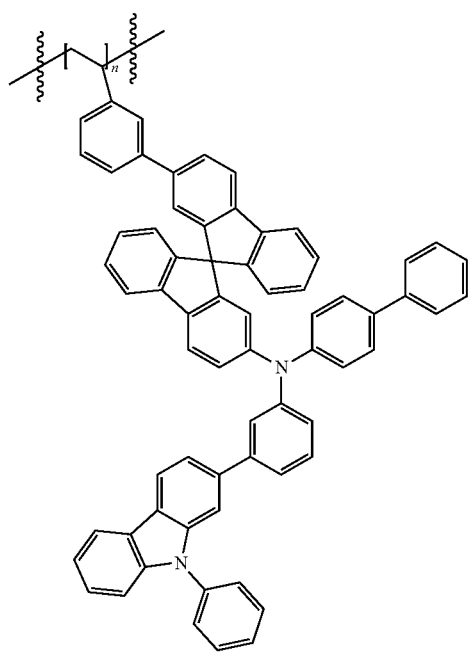
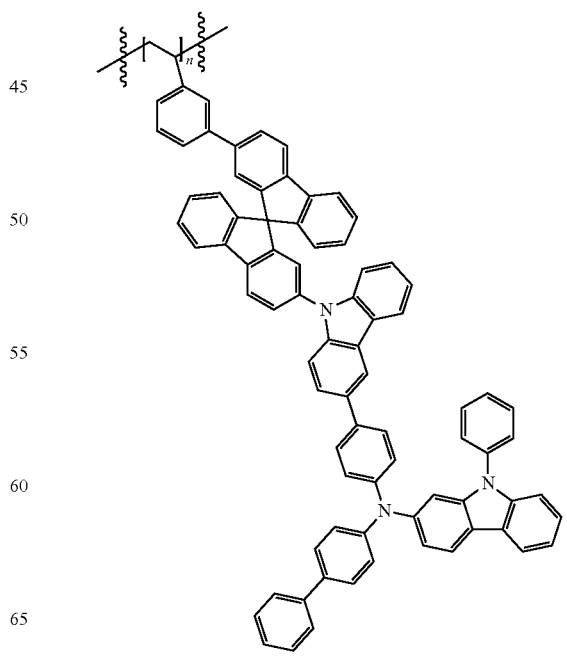

197
-continued
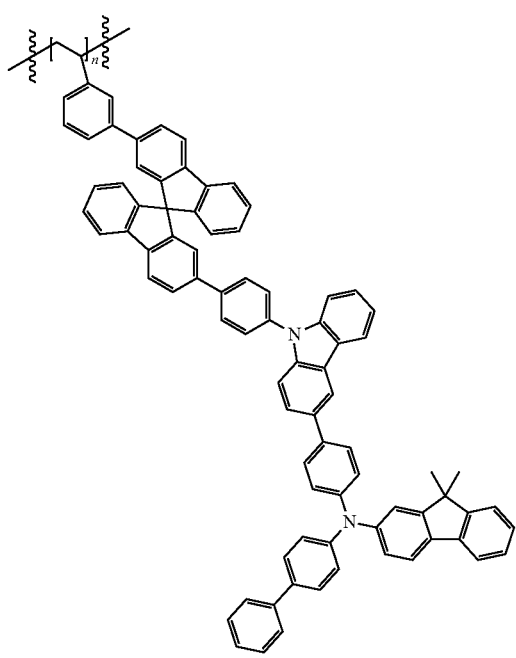
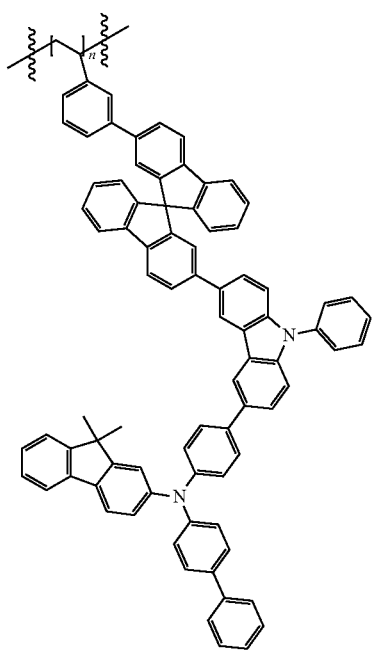
198
-continued
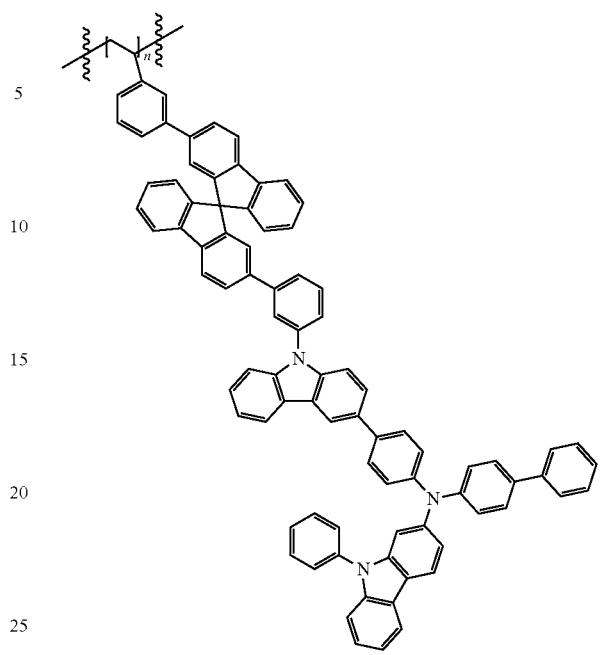
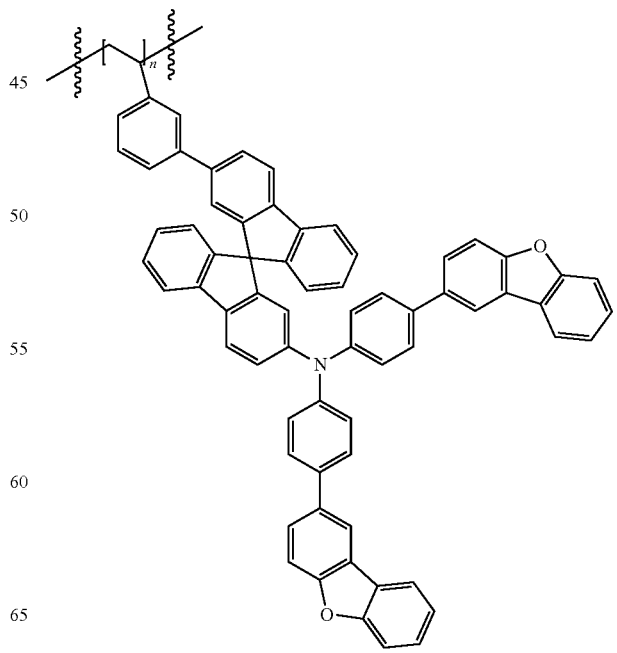

-continued
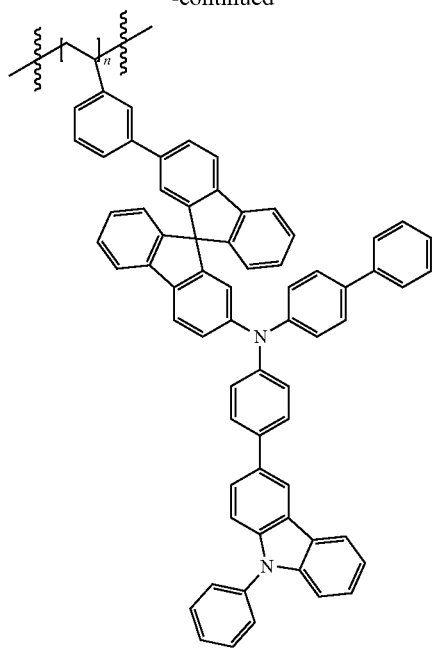
wherein n has the same definition as in Chemical Formula 1.
* * * * *